US012440486B2

(12) United States Patent
Petrukhin et al.

(10) Patent No.: US 12,440,486 B2
(45) Date of Patent: Oct. 14, 2025

(54) RBP4 ANTAGONISTS FOR TREATMENT AND PREVENTION OF NON-ALCOHOLIC FATTY LIVER DISEASE AND GOUT

(71) Applicant: The Trustees of Columbia University in the City of New York, New York, NY (US)

(72) Inventors: Konstantin Petrukhin, New Windsor, NY (US); Boglarka Racz, Brooklyn, NY (US); Andras Varadi, Brooklyn, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 1048 days.

(21) Appl. No.: 17/261,851

(22) PCT Filed: Aug. 1, 2019

(86) PCT No.: PCT/US2019/044754

§ 371 (c)(1),
(2) Date: Jan. 20, 2021

(87) PCT Pub. No.: WO2020/028723

PCT Pub. Date: Feb. 6, 2020

(65) Prior Publication Data

US 2023/0241049 A1 Aug. 3, 2023

Related U.S. Application Data

(60) Provisional application No. 62/713,288, filed on Aug. 1, 2018.

(51) Int. Cl.

*A61K 31/4545* (2006.01)
*A61K 31/506* (2006.01)
(Continued)

(52) U.S. Cl.

CPC ........ *A61K 31/4545* (2013.01); *A61K 31/506* (2013.01); *A61P 1/16* (2018.01); *A61P 19/06* (2018.01)

(58) Field of Classification Search

None
See application file for complete search history.

(56) References Cited

U.S. PATENT DOCUMENTS

| | | | | |
|---|---|---|---|---|
| 9,777,010 | B2 * | 10/2017 | Petrukhin | A61P 27/02 |
| 10,273,243 | B2 * | 4/2019 | Petrukhin | C07D 401/06 |

(Continued)

FOREIGN PATENT DOCUMENTS

| | | | | |
|---|---|---|---|---|
| EP | 3210973 A1 | 8/2017 | | |
| WO | WO-2014152013 A1 * | 9/2014 | | A61K 31/437 |

(Continued)

OTHER PUBLICATIONS

Cronstein (Cronstein et al., Arthritis Res Ther 8 (Suppl 1), S3 (2006)) (Year: 2006).*

(Continued)

*Primary Examiner* — Jeffrey S Lundgren
*Assistant Examiner* — Anthony Joseph Seitz
(74) *Attorney, Agent, or Firm* — Gary J. Gershik

(57) ABSTRACT

The subject invention provides a method for treating a non-alcoholic fatty liver disease (NAFLD) disease in a subject afflicted therewith comprising administering to the subject a pharmaceutical composition comprising an amount of a compound which is a non-retinoid retinol-binding protein 4 (RBP4) antagonist effective to treat the subject, thereby treating the subject.

The subject invention provides a method for treating gout in a subject afflicted therewith comprising administering to the subject a pharmaceutical composition comprising an amount (Continued)

of a compound which is a retinol-binding protein 4 (RBP4) antagonist effective to treat the subject, thereby treating the subject.

22 Claims, 18 Drawing Sheets

(51) Int. Cl.

| | |
|---|---|
| ***A61P 1/16*** | (2006.01) |
| ***A61P 19/06*** | (2006.01) |

(56) References Cited

U.S. PATENT DOCUMENTS

| | | | | |
|---|---|---|---|---|
| 10,913,746 | B2 * | 2/2021 | Petrukhin ............... | A61P 27/02 |
| 11,649,240 | B2 * | 5/2023 | Petrukhin ............ | C07D 487/04<br>546/184 |
| 2011/0123421 | A1 | 5/2011 | Monia et al. | |
| 2011/0123521 | A1 | 5/2011 | Monia et al. | |
| 2014/0066420 | A1 | 3/2014 | Kasai et al. | |
| 2016/0046648 | A1 | 2/2016 | Petrukhin et al. | |
| 2023/0312585 | A1 * | 10/2023 | Petrukhin ............ | C07D 471/04<br>546/184 |

FOREIGN PATENT DOCUMENTS

| | | | |
|---|---|---|---|
| WO | WO 2018/232150 | A1 | 12/2018 |
| WO | WO 2018/232154 | A1 | 12/2018 |
| WO | WO 2020/028723 | A1 | 2/2020 |

OTHER PUBLICATIONS

Nair (Nair et al., J Basic Clin Pharm. Mar. 2016;7(2):27-31) (Year: 2016).*

Haig A. The Formation and Excretion of Uric Acid. Chic Med J Exam. Sep. 1888;57(3):171-176 (Year: 1888).*

Brown, Bioisosteres in Medicinal Chemistry, 2012, p. 17, Classical Bioisosteres (Year: 2012).*

Deng et al., Serum retinol-binding protein 4 levels are elevated but do not contribute to insulin resistance in newly diagnosed Chinese hypertensive patients. Diabetol Metab Syndr. Jun. 11, 2014;6:72 (Year: 2014).*

Chen (Chen et al., Metabolism, vol. 58, Issue 12, 2009, pp. 1812-1816) (Year: 2009).*

Li et al., Retinol-binding protein 4 as a novel risk factor for cardiovascular disease in patients with coronary artery disease and hyperinsulinemia. Am J Med Sci. Dec. 2014;348(6):474-9 (Year: 2014).*

International Search Report issued Nov. 27, 2019 in connection with PCT International Application No. PCT/US2019/044754.

Written Opinion of the International Searching Authority issued Nov. 27, 2019 in connection with PCT International Application No. PCT/US2019/044754.

International Preliminary Report on Patentability issued Feb. 2, 2021, including Written Opinion of the International Searching Authority, issued Nov. 27, 2019 in connection with PCT International Application No. PCT/US2019/044754.

Tan, Yi et al., "Suppression of retinol-binding protein 4 with RNA oligonucleotide prevents high-fat diet-induced metabolic syndrome and non-alcoholic fatty liver disease in mice", Department of Medical & Molecular BioScience, Oct. 1, 2011.

Yang, Jin et al., "Berberine ameliorates non-alcoholic steatohepatitis in ApoE$^{-/-}$mice", Center for Translational Medicine, Mar. 17, 2017.

Zhang, Wei et al., "Anti-diabetic effects of cinnamaldehyde and berberine and their impacts on retinol-binding protein 4 expression in rats with type 2 diabetes mellitus", Chinese Medical Association, Jun. 8, 2022.

Bluher, Mattias et al., "Does Retinol-Binding Protein 4 Cause or Reflect Fatty Liver Disease," Hepatology, 2008.

Jun. 21, 2022 European Extended Search Report issued in connection with European Patent Application No. EP 19845117.1-1112.

Oct. 23, 2023 Communication Pursuant to Article 94(3) EPC issued in connection with European Patent Application No. EP 19845117.1-1112.

English Translation of the Dec. 18, 2023 First Office Action issued in connection with Chinese Patent Application No. CN 201980051205.3.

Atti, Alan et al., "Adipocyte metabolism and obesity", Journal of Lipid Research, Supplement Apr. 2009, p. S395-S399.

Balagopal, Prabhakaran et al., "Reduction of elevated serum retinol binding protein in obese children by lifestyle intervention: association with subclinical inflammation", Journal of Clinical Endocrinology and Metabolism, May 2007 vol. 92, p. 1971-1974.

Esteve, Eduardo et al., "Adipocytokines and insulin resistance: the possible role of lipocalin-2, retinol binding protein-4, and adiponectin" Diabetes Care, Nov. 2009, vol. 32, supplement 2, p. S362-S367.

Gavi, Shai et al., "Reitnol-binding protein 4 is associated with insulin resistance and body fat distribution in nonobese subject without type 2 diabetes", Journal of Clinical Endocrinology and Metabolism, May 2007 vol. 92, p. 1886-1890.

Jung, Un et al., "Obesity and its metabolic complications: the role of adipokines and the relationship between obesity, inflammation, insulin resistance, dyslipidemia and nonalcoholic fatty liver disease", International Journal of Molecular Sciences, Apr. 2014 vol. 15, p. 6184-6223.

Klöting, Nora et al., "Serum retinol-binding protein is more highly expressed in visceral than in subcutaneous adipose tissue and is a marker of intra-abdominal fat mass", Cell Metabolism, Jul. 2007 vol. 6, p. 79-87.

Li, Jia-Ying et al., "Elevated RBP4 plasma levels were associated with diabetic retinopathy in type 2 diabetes", Bioscience Reports, 2018 vol. 38, iss. 5.

Moraes-Vieira, Pedro et al., "RBP4 activates antigen-presenting cells leading to tissue inflammation and systemic insulin resistance", Cell Metabolism, Mar. 2014 vol. 19, p. 512-526.

Nair, Anup et al. "Case-control analysis of SNPs in GLUT4, RBP4 and STRA6: association of SNPs in STRA6 with type 2 diabetes in a south Indian population", PLoS One, Jul. 2010 vol. 5, iss. 7 e11444.

Öst, Anita et al. "Retinol binding protein 4 attenuates insulin-induced phosphorylation of IRS1 and ERK½ in primary human adipocytes", The FASB Journal, Nov. 2007 vol. 21, p. 3696-3704.

Samaras, Katherine et al. "Subcutaneous and visceral adipose tissue gene expression of serum adipokines that predict type 2 diabetes", Obesity, Mar. 2010 vol. 18, p. 884-889.

Takebayashi, Kohzo et al. "Retinol binding protein-4 levels and clinical features of type 2 diabetes patients", Journal of Clinical Endocrinology and Metabolism, Jul. 2007 vol. 92, p. 2712-2719.

Yang, Qin et al. "Serum retinol binding protein 4 contributes to insulin resistance in obesity and type 2", Nature, Jul. 2005 vol. 436, p. 356-362.

* cited by examiner

| rt. | species | CL[a] (mL/h/kg) | $C_{max}$[b] (ng/mL) | $T_{max}$[b] (h) | $T_{1/2}$[a] (h) | $V_{ss}$[a] (mL/kg) | $AUC_{inf}$[a] (h·ng/mL) | %F[a] |
|---|---|---|---|---|---|---|---|---|
| Cpd 3 | mouse[c] | 163.3 | 1590 | 2.00 | 4.7 | 1113 | 18402 | 53.7 |
| | rat[b] | 755 ± 49 | 410 ± 165 | 1.00 ± 0.0 | 6.8 ± 0.5 | 2203 ± 479 | 2815 ± 908 | 42.6 ± 13.7 |
| Cpd 1 | mouse[c] | 390 | 617 | 4 | 6.2 | 2964 | 8721 | 61.6 |
| | rat[c] | 1134 | 176 | 1.6 | 10.53 | 4281 | 1771 | 42.0 |

Fig. 16A-D

RBP4 ANTAGONISTS FOR TREATMENT AND PREVENTION OF NON-ALCOHOLIC FATTY LIVER DISEASE AND GOUT

CROSS-REFERENCE TO RELATED APPLICATIONS

This application is a § 371 national stage of PCT International Application No. PCT/US2019/044754, filed Aug. 1, 2019, claiming the benefit of U.S. Provisional Application No. 62/713,288, filed Aug. 1, 2018, the entire contents of each of which are hereby incorporated by reference into the subject application.

This invention was made with government support under Grant numbers NS074476 and EY027027 awarded by the National Institutes of Health. The government has certain rights in the invention.

Throughout this application, certain publications are referenced in parentheses. Full citations for these publications may be found immediately preceding the claims. The disclosures of these publications in their entireties are hereby incorporated by reference into this application in order to describe more fully the state of the art to which this invention relates.

BACKGROUND OF THE INVENTION

Non-Alcoholic Fatty Liver Disease (NAFLD)

Non-alcoholic fatty liver disease (NAFLD) encompasses a spectrum of conditions associated with lipid deposition in hepatocytes of the liver. Hepatic steatosis refers to accumulation of lipids in the liver. NAFLD is characterized by hepatic steatosis due to causes other than excessive alcohol use. Clinically, hepatic steatosis is defined as a hepatic triglyceride content that exceed 5% of total liver weight. While simple hepatic steatosis is on the least extreme side of the NAFLD spectrum, it can progress to more severe conditions of the NAFLD spectrum such as mild hepatic steatosis and nonalcoholic steatohepatitis (NASH). NASH is the extreme form of NAFLD which is characterized by lipid accumulation in the liver combined with inflammation and hepatocellular injury or fibrosis. NASH frequently leads to severe liver complications such as cirrhosis and hepatocellular carcinoma.

NAFLD is the most common form of chronic liver disease in the United States, affecting an estimated 75 to 100 million people. There is no currently approved pharmacotherapy for any form of NAFLD. Developing of a drug therapy for NAFLD is of extreme importance.

Gouty Arthritis

Gouty arthritis (Gout) is the most common form of inflammatory arthritis and affects more than 8 million people in the Unites States (Lawrence, R. C. et al. 2008). Uric acid is a metabolic product resulting from the metabolism of purines, which are found in many foods and in human tissue (Terkeltaub, R. A. 2001; Burns, C. et al. 2013). Gout is caused by excess uric acid levels in the blood, which lead to the deposition of monosodium urate crystals in tissue. These crystals are formed when concentration of uric acid in tissues and in circulation exceeds the solubility limit, leading to gout flares. Risk factors for gout include being overweight or obese, having hypertension, alcohol intake, diuretic use, a diet rich in meat and seafood, excessive consumption of fructose, and poor kidney function (Choi, H. K. et al. 2004a; Choi, H. K. 2004b; Krishnan, E. 2012).

Acute flares occur when urate crystals in the joint causes acute inflammation. A flare is characterized by pain, redness, swelling, and warmth lasting days to weeks. Pain may be mild or excruciating. Most initial attacks occur in lower extremities. The typical presentation in the metatarsophalageal joint of the great toe (podagra) is the presenting joint for 50% of people with gout. Chronic gout is characterized by chronic arthritis, with soreness and aching of joints. People with gout may also get tophi or lumps of urate crystals deposited in soft tissue. Clinically inactive (intercritical) segments between gout flares occur after an acute flare has subsided. The person with gout continues to have hyperuricemia, which results in continued deposition of urate crystals in tissues and resulting damage. Intercritical segments become shorter as the disease progresses.

Uric acid is synthesized from its precursor, xanthine, by the enzyme called xanthine oxidase (XO). Accordingly, XO inhibitors (e.g., allopurinol and febuxostat) dominate the market (Stamp, L. K. et al. 2015; Love, B. L. et al. 2010). However, elevated levels of circulating uric acid most commonly result from undersecretion of uric acid in the kidneys. Marginally effective probenecid and recently approved lesinurad are the treatments that increase the renal secretion of uric acid.

The incidence and prevalence of gout is rising. This is due to factors such as an increase in the aged population, many of whom take thiazide diuretics and prophylactic aspirin that promote hyperuricemia and lifestyle factors characterized by diets that include excessive fructose and alcohol intake, physical inactivity and abdominal fat accumulation which favor hyperuricemia (Burns, C. et al. 2013; Choi, H. K. et al. 2004a).

Significant unmet clinical need remains in the treatment of gout. Of the 8 million of patients with gout, over 3 million are on urate-lowering therapy (mainly XO inhibitors). Despite this fact, 1 million patients continue to experience 3 or more flares per year indicating the need for better urate-lowering therapy.

SUMMARY OF THE INVENTION

The subject invention provides a method for treating a non-alcoholic fatty liver disease (NAFLD) disease in a subject afflicted therewith comprising administering to the subject a pharmaceutical composition comprising an amount of a compound which is a non-retinoid retinol-binding protein 4 (RBP4) antagonist effective to treat the subject, thereby treating the subject.

The subject invention provides a method for treating gout in a subject afflicted therewith comprising administering to the subject a pharmaceutical composition comprising an amount of a compound which is a retinol-binding protein 4 (RBP4) antagonist effective to treat the subject, thereby treating the subject.

The subject invention further provides a method for treating a non-alcoholic fatty liver disease (NAFLD) or gout in a subject afflicted therewith comprising administering to the subject a pharmaceutical composition comprising an amount of a compound effective to treat the subject, thereby treating the subject, wherein compound has the structure

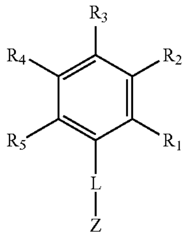

wherein L is a linking group having the structure:

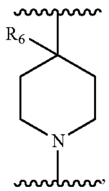, 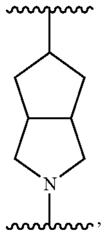, 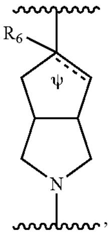, 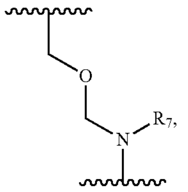 or

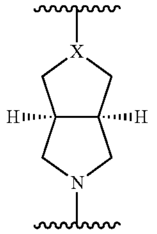

and Z is a group having the structure:

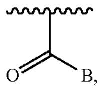, 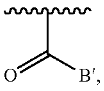, 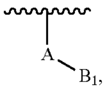, or 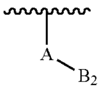

wherein $R_1$, $R_2$, $R_3$, $R_4$, and $R_5$ are each independently H, halogen, $CF_3$ or $C_1$-$C_4$ alkyl;

$R_6$ is H, OH, or halogen or absent;

ψ is absent or present, and when present is a bond;

B is a substituted or unsubstituted heterobicycle, pyridazine, pyrazole, pyrazine, thiadiazole, or triazole, wherein the heterobicycle is other than chloro substituted indole; and the pyrazole, when substituted, is substituted with other than trifluoromethyl;

B' is a substituted or unsubstituted phenyl, pyridine, pyrimidine, benzyl, pyrrolidine, sulfolane, oxetane, $CO_2H$ or ($C_1$-$C_4$ alkyl)-$CO_2H$, wherein the substituted phenyl is substituted with other than trifluoromethyl or 3-(methyl carboxylate), the substituted pyridine is substituted with other than trifluoromethyl and the substituted pyrrolidine is substituted with other than hydroxamic acid, and the substituted or unsubstituted pyrrolidine is bound to the carbonyl through a carbon-carbon bond;

A is absent or present, and when present is

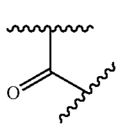 or 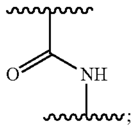;

$B_1$ is substituted or unsubstituted monocycle, bicycle, heteromonocycle, heterobicycle, benzyl, $CO_2H$ or ($C_1$-$C_4$ alkyl)-$CO_2H$, wherein when $B_1$ is $CO_2H$, then A is present and is

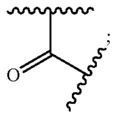;

$R_7$ is alkyl;

X is N or $CR_8$, wherein $R_8$ is H, OH, or halogen;

$B_2$ has the structure:

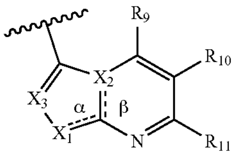

wherein

α and β are each a bond that is present or absent;

$X_1$ is N, NH or $NR_{99}$, wherein $R_{99}$ is alkyl, alkenyl or alkynyl;

$X_2$ is C or N;

$X_3$ is CH or N;

$R_9$, $R_{10}$ and $R_{11}$ are each, independently, H, halogen, alkyl, alkenyl, alkynyl, alkyl-OH, alkyl-$NH_2$, alkyl-OAc alkyl-O(CO)-alkyl, alkyl-O-alkyl, haloalkyl, cycloalkyl, O-alkyl, NH-alkyl, C(O)OH, C(O)—$NH_2$, C(O)—$N(CH_3)_2$, C(O)—$NHCH_3$, NHC(O)—$N(CH_3)_2$, CN or $CF_3$, wherein $X_1$, $X_2$ and $X_3$ are each N, α is present and β is absent; or $X_1$ is NH, $X_2$ is C, $X_3$ is CH, α is absent and β is present; or $X_1$ is N, $X_2$ is N, $X_3$ is CH, α is present and β is absent; or $X_1$ is NH or $NR_{99}$, $X_2$ is C, $X_3$ is N, α is absent and β is present, wherein when $X_1$ is NH, $X_2$ is C, $X_3$ is N, α is absent and β is present, then one of $R_9$, $R_{10}$ and $R_{11}$ is other than H, or $B_2$ has the structure:

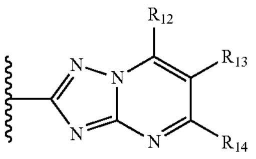

wherein $R_{12}$, $R_{13}$ and $R_{14}$ are each, independently, H, halogen, alkyl, alkenyl, alkynyl alkyl-OH, alkyl-$NH_2$, alkyl-Oac, alkyl-O(CO)-alkyl, alkyl-O-alkyl, haloalkyl, cycloalkyl, O-alkyl, NH-alkyl, C(O)OH, C(O)—$NH_2$, C(O)—$N(CH_3)_2$, C(O)—$NHCH_3$, NHC(O)—$N(CH_3)_2$, CN or $CF_3$, or a pharmaceutically acceptable salt thereof.

Compound 1

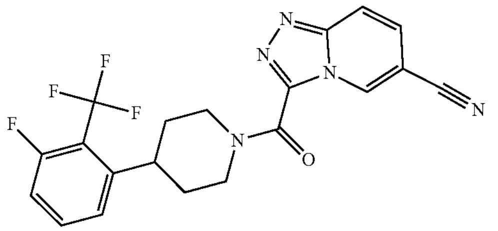

Determination of the RBP4 level was conducted in plasma samples collected at baseline and at 10 timepoints after administration of Compound 1. Three groups of mice were used in the oral and intravenous dosing experiments (Mouse Group 1, Mouse Group 2 and Mouse Group 3). Each mouse group consisted of 5 animals. Plasma RBP4 levels were determined using the RBP4 (mouse/rat) dual ELISA kit (AdipoGen, Switzerland) following the manufacturer's instructions.

Figure 2:
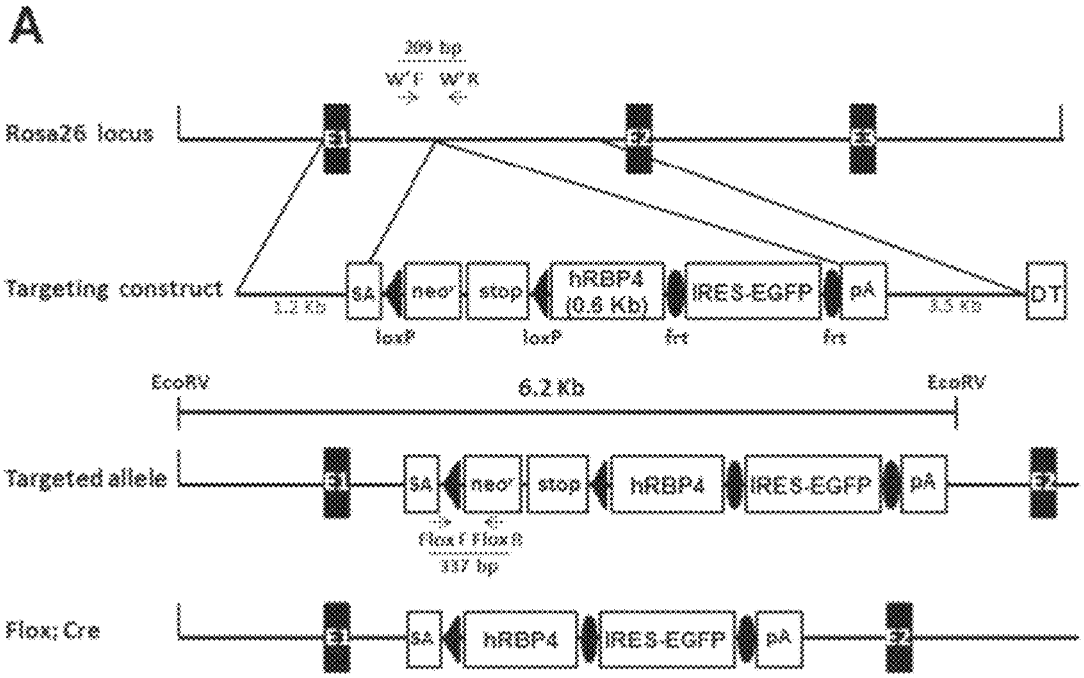

FIG. 2: Generation of the adi-hRBP4 transgenic mouse model as described by Lee 2016. A human hRBP4 transgene was introduced into ROSA26 locus. The human transgene contains loxP-flanked stop cassette which prevents expression. These mice are bred with mice expressing adiponectin-Cre and thus the stop cassette is removed only in adipocytes. Accordingly, in this model, human RBP4 is expressed specifically in adipose tissue.

Figure 3:
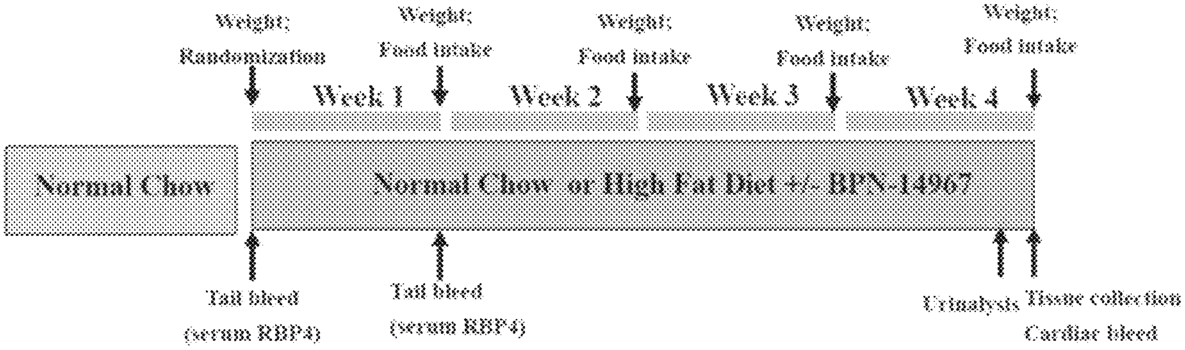

FIG. 3: Experimental Design for evaluation of Compound 1 efficacy in the adi-hRBP4 genetic model of hepatic steatosis.

Figure 4:
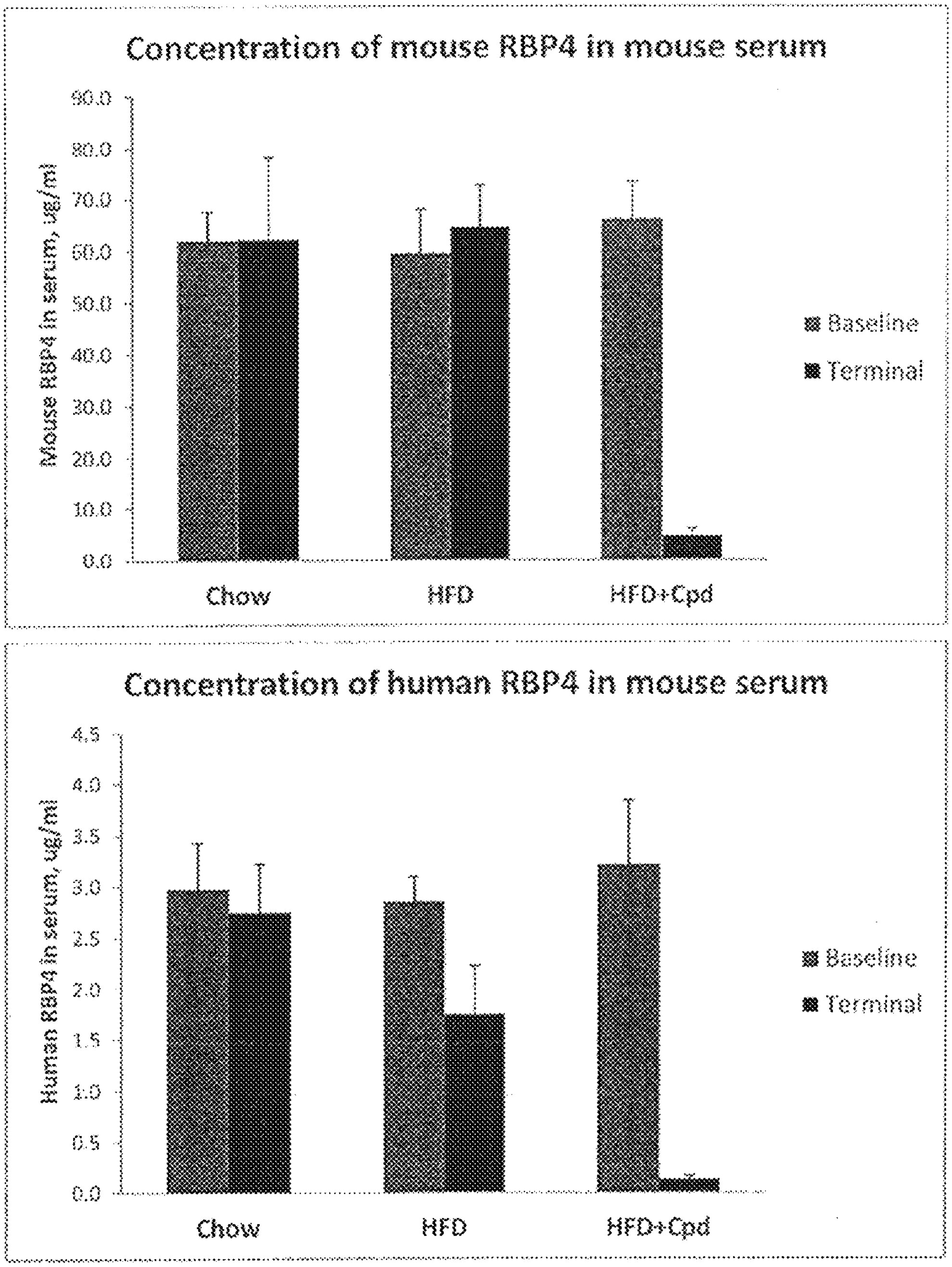

FIG. 4: Compound 1 induced reduction in serum levels of both human and mouse RBP4 in the transgenic mouse strain. The left bar in each pair of bars is a lighter shade of gray and represents the baseline data. The right bar in each pair of bars is a darker shade of gray and represent serum levels of human and mouse RBP4 at the end of the study.

Figure 5:
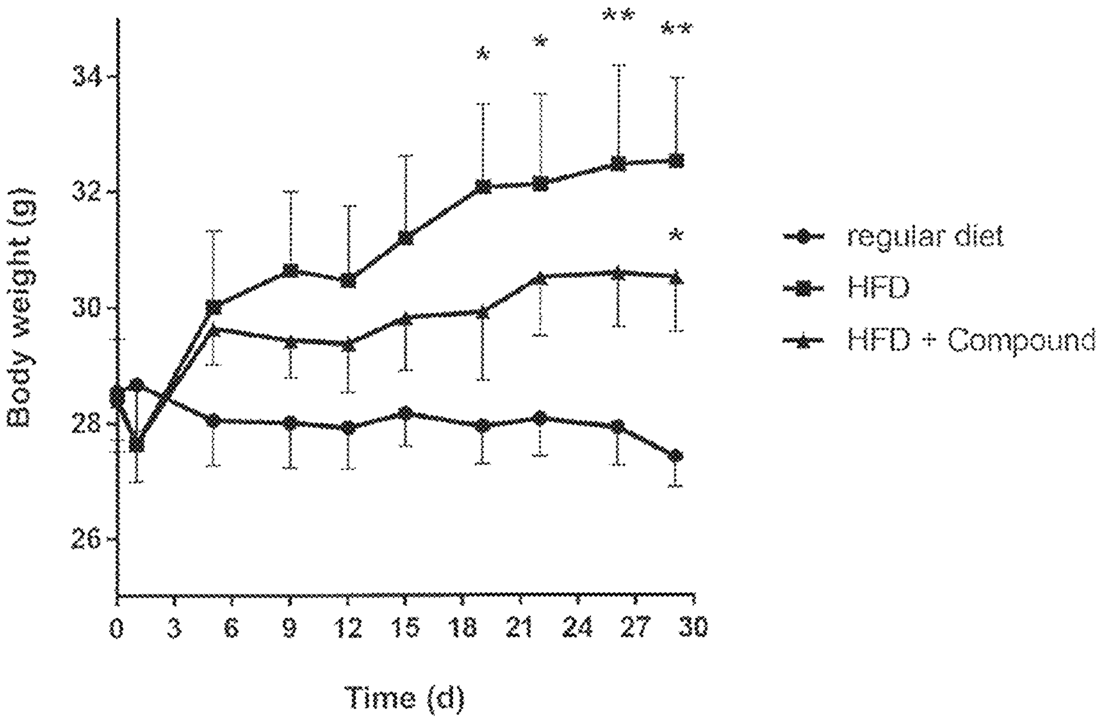

FIG. 5: Dynamics of body weight changes in the three groups of transgenic animals: Both high-fat diet (HFD) groups accumulate more weight than the control chow group. There was significant body weight gain in the HFD group compared to the standard chow group (*$P<0.05$; **$P<0.01$; 2-way RM ANOVA with Holm-Sidak post hoc test).

Figure 6:
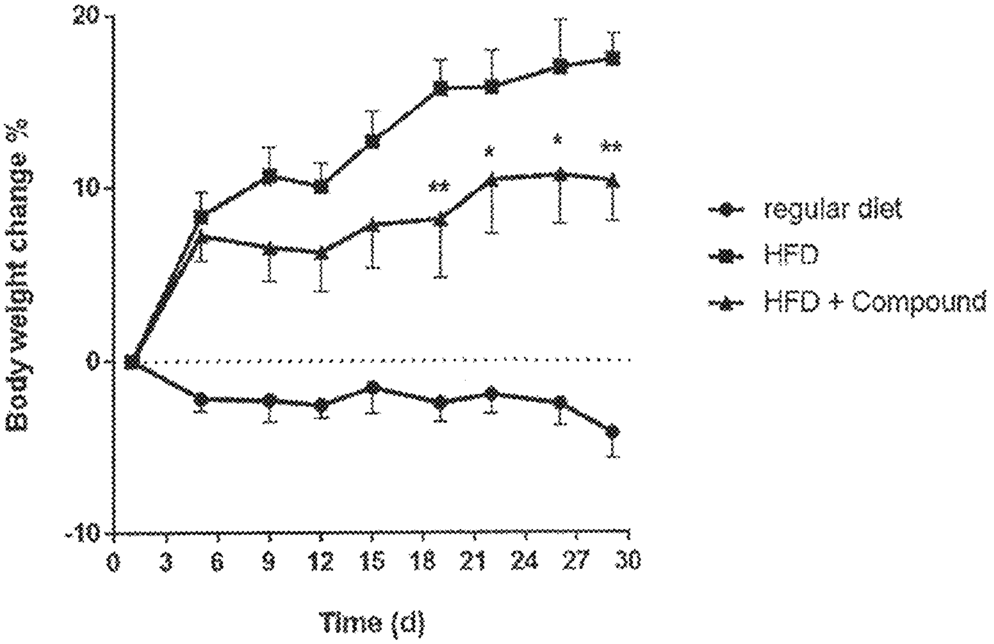

FIG. 6: Significance between HFD and HFD+ compound. Compound 1 treatment significantly reduced HFD-induced body weight gain at several timepoints. A significant body weight difference was detected between the HFD only group and the treatment (HFD plus Compound 1) group (*$P<0.05$; **$P<0.01$; 2-way RM ANOVA with Holm-Sidak post hoc test).

Figure 7:
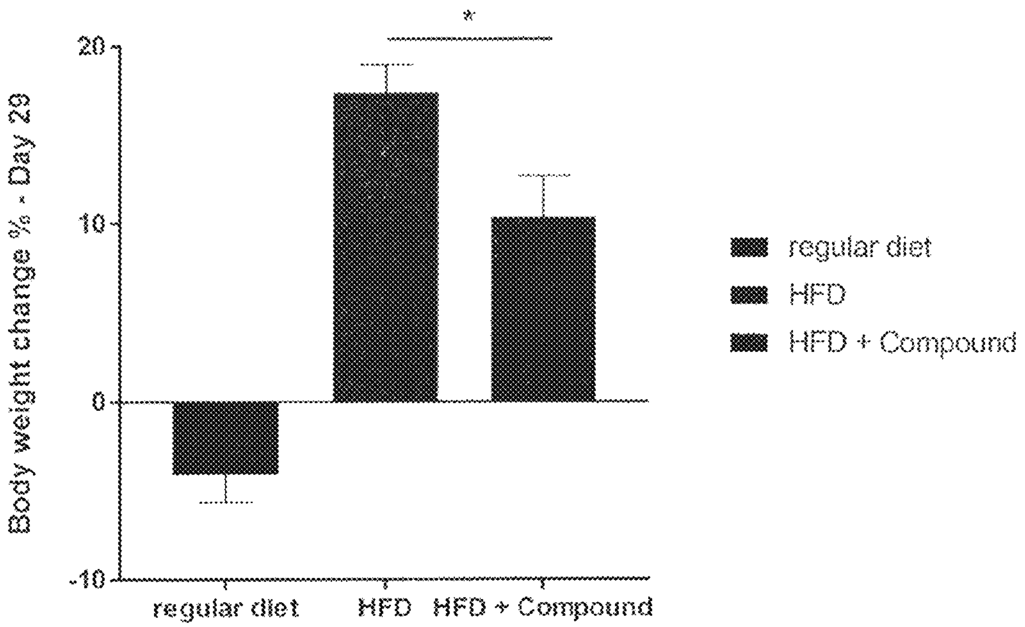

FIG. 7: Treatment with Compound 1 significantly decreased body weight at the end of the 29-day treatment period as shown by the comparison between the treatment (HFD plus Compound 1) group and the HFD only group. A significant difference between the HFD group and the treatment (HFD plus Compound 1) group was observed ($P=0.0153$; 1-way RM ANOVA with Holm-Sidak post hoc test).

Figure 8:
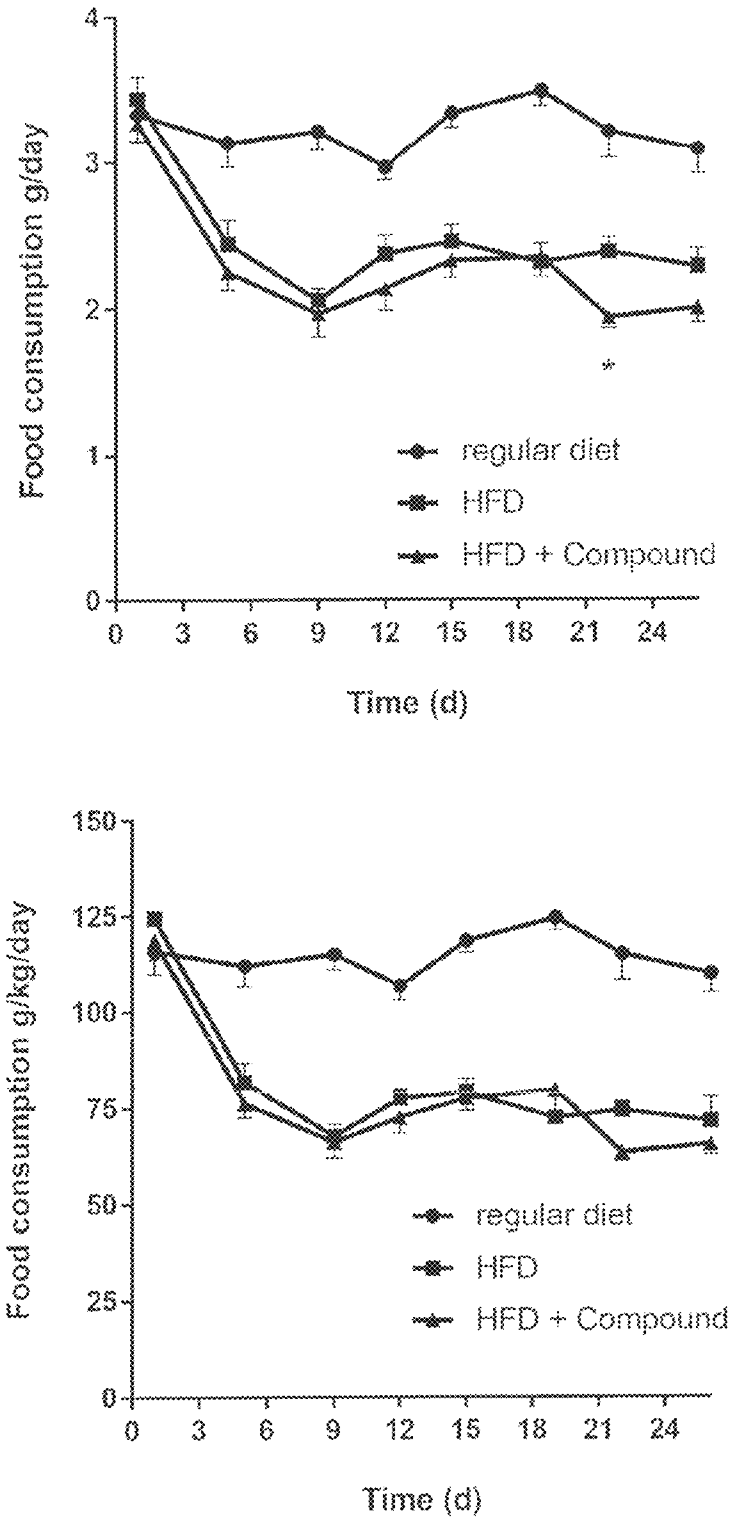

FIG. 8: There was no difference in food intake between the treatment (HFD plus Compound 1) group and the HFD only group (2-way RM ANOVA with Holm-Sidak post hoc test).

Figure 9:
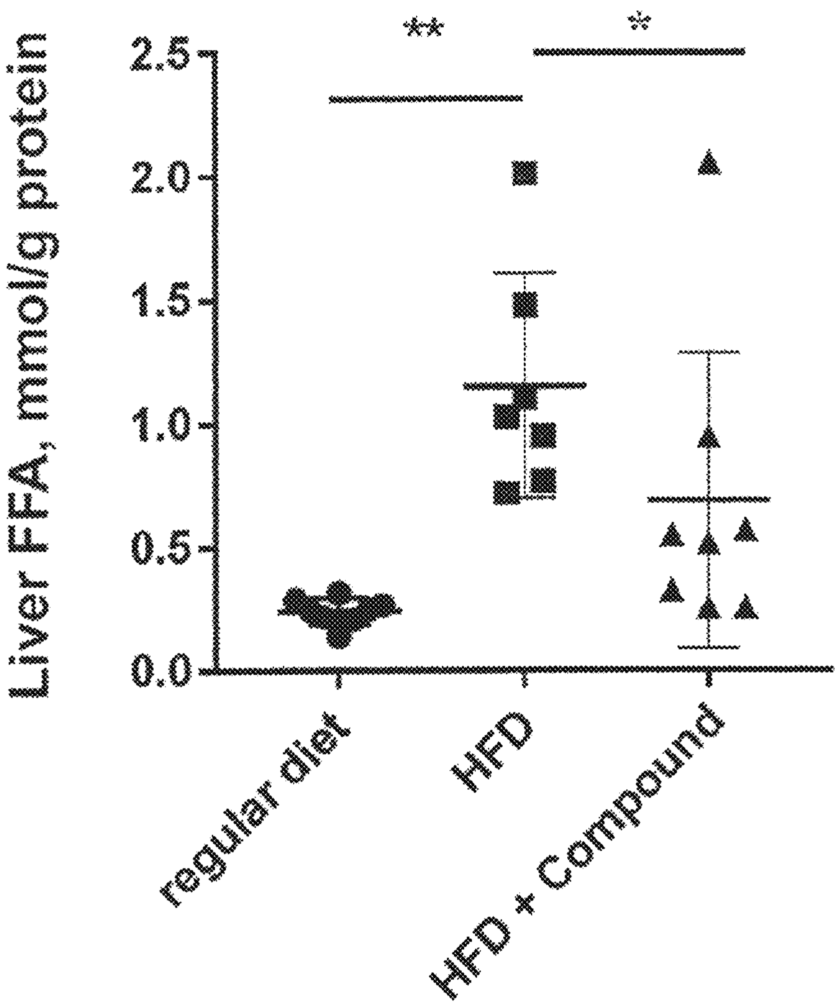

FIG. 9: Compound 1 significantly reduces hepatic free fatty acid concentration. There was a significant difference between the HFD only group and the treatment (HFD plus Compound 1) group at the end of the 29 day study ($P=0.011$; 1-way ANOVA with Holm-Sidak post hoc test). Data shown was determined at the end of the 29 day study.

Figure 10:
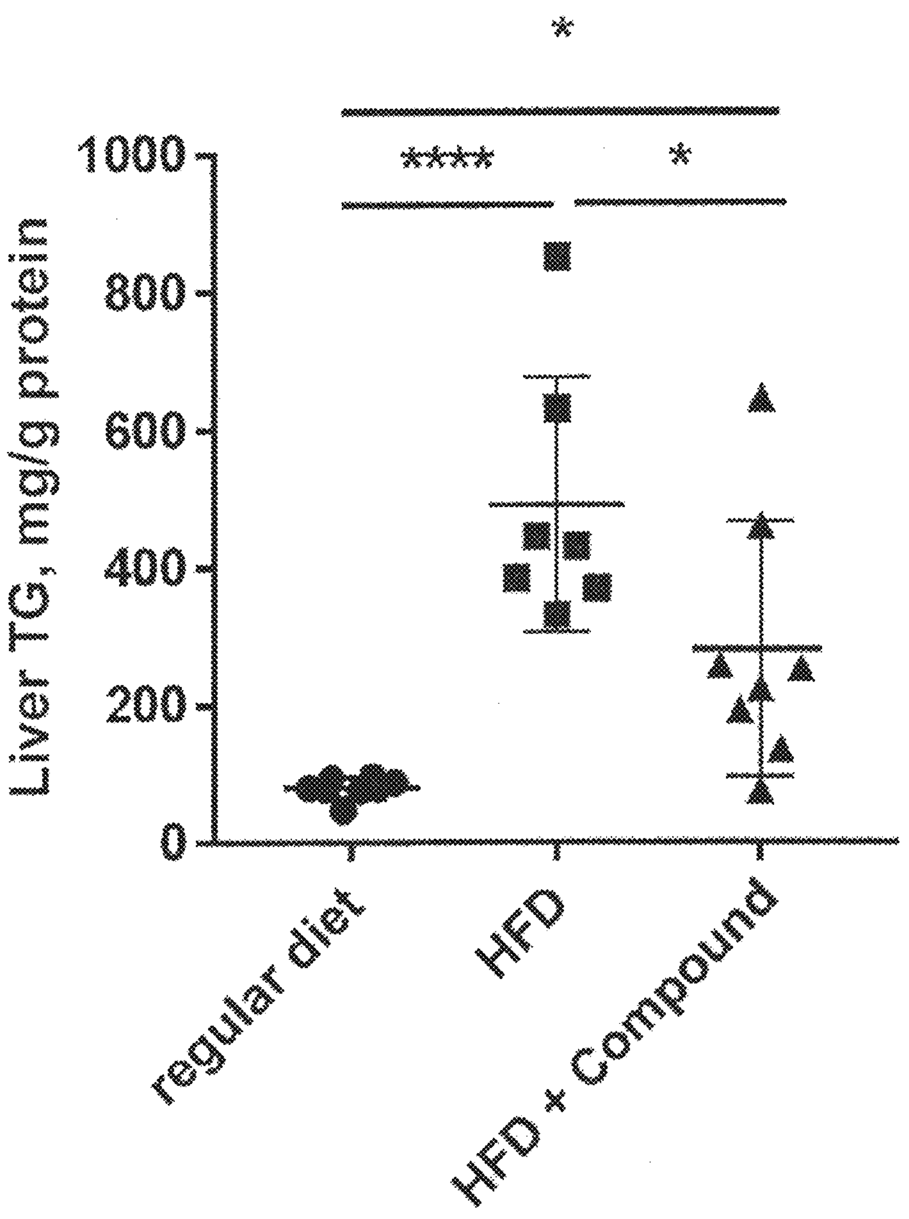

FIG. 10: Compound 1 significantly reduced liver triglycerides. There was a significant difference between the HFD only group and the treatment (HFD plus Compound 1) group ($P=0.01$; 1-way ANOVA with Holm-Sidak post hoc test). Data shown was determined at the end of the 29 day study.

Figure 11:
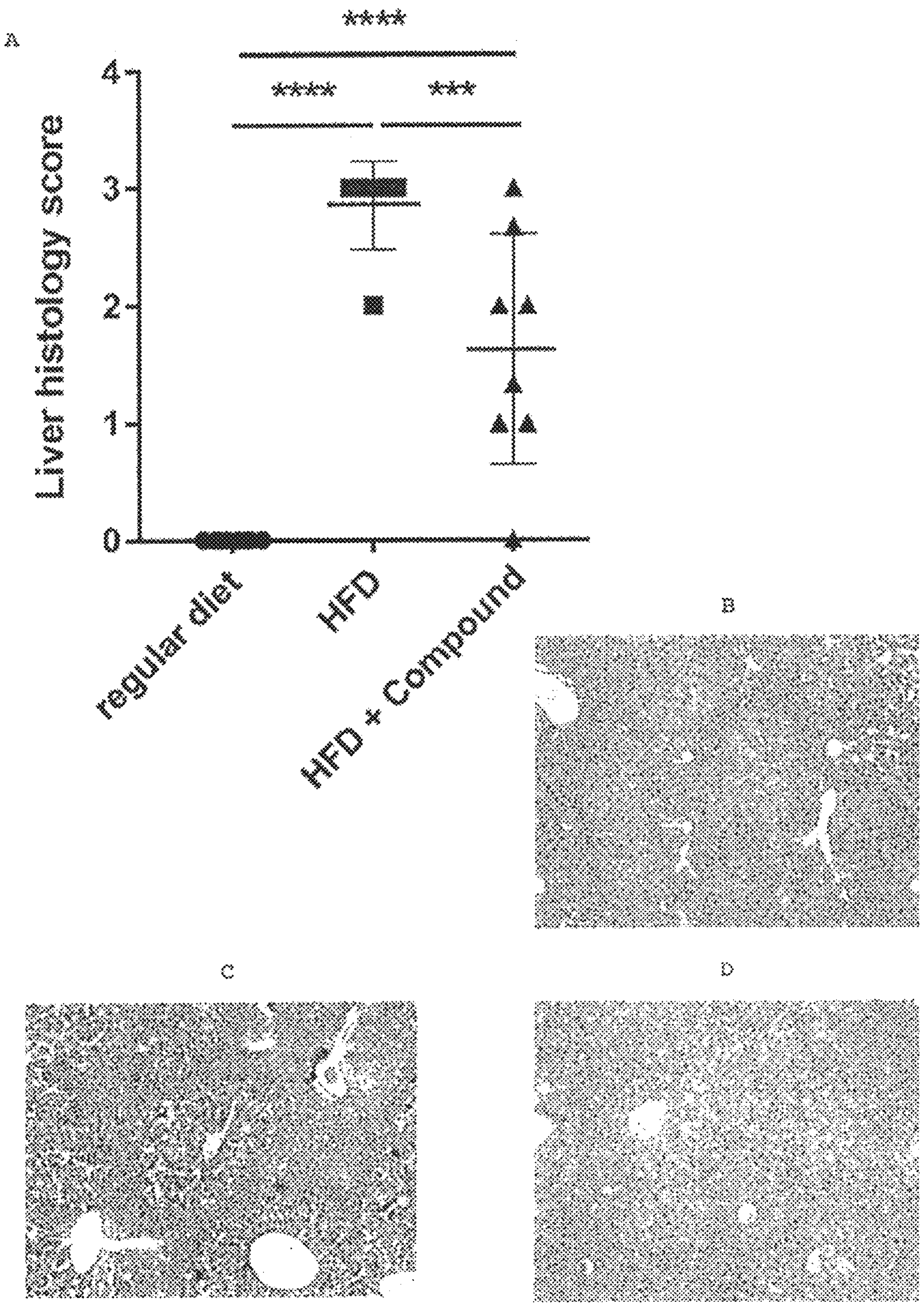

FIG. 11: Compound 1 significantly reduces lipid deposition in liver of treated animals. A. Liver histology Score.

FIG. 11B: Compound 1 significantly reduces lipid deposition in liver of treated animals. B. the normal chow group had an average score 0.

FIG. 11C: Compound 1 significantly reduces lipid deposition in liver of treated animals. C. the HFD only group had an average score of 2.9.

FIG. 11D: Compound 1 significantly reduces lipid deposition in liver of treated animals. D. the treatment (HFD plus Compound 1) group had an average score of 1.6. A significant difference was observed between the HFD only group and the treatment (HFD plus Compound 1) group ($P<0.001$; 1-way ANOVA with Holm-Sidak post hoc test). Data shown was determined at the end of the 29 day study.

Figure 12:
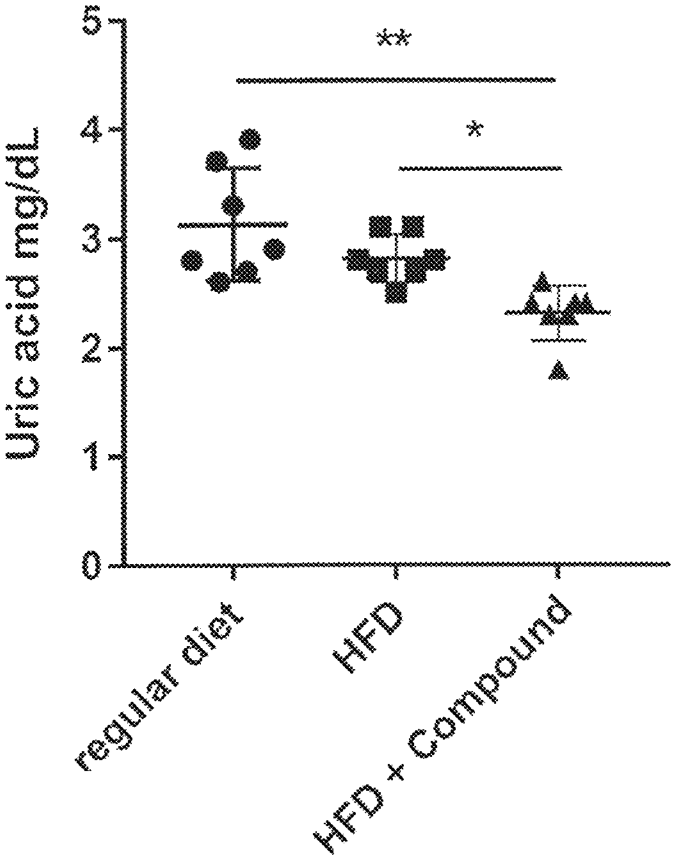

FIG. 12: Compound 1 significantly reduced serum uric acid. There was a significant difference between the HFD only group and the treatment group (HFD plus Compound 1) ($P=0.03$; 1-way ANOVA with Holm-Sidak post hoc test). However, there was no statistically significant difference between the regular chow group and the HFD only group. Data shown was determined at the end of the 29 day study.

Figure 13:
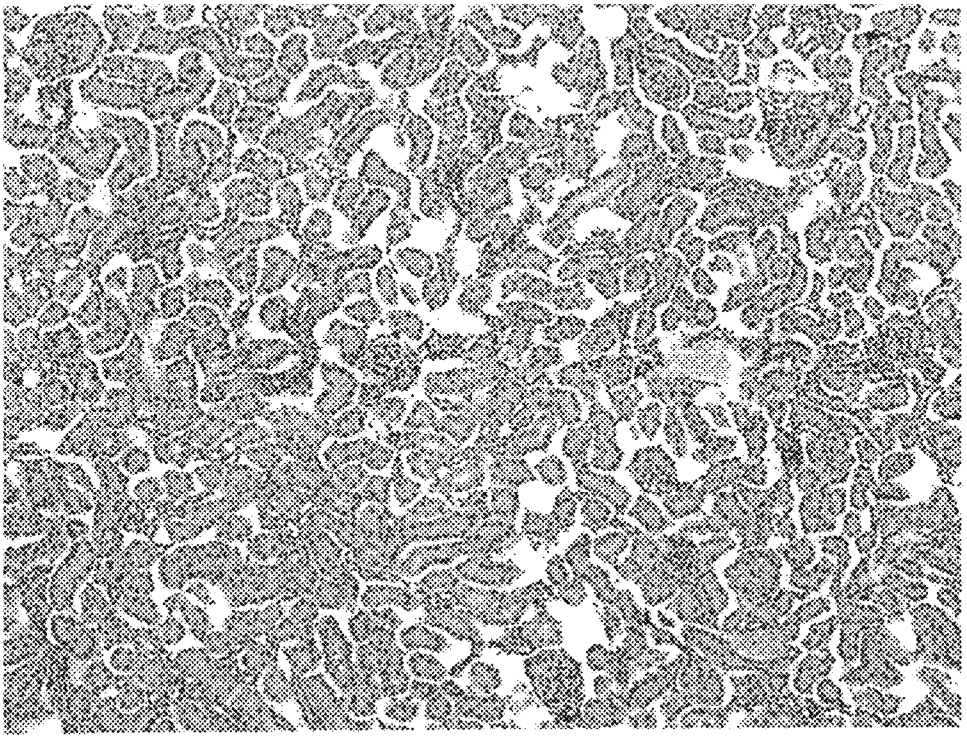

FIG. 13: No steatosis was observed in the kidney of animals on HFD. This figure is a representative image from the HFD only group. No fat droplets were seen in kidney tubules in any of the three experimental groups. Data shown was determined at the end of the 29 day study.

Figure 14:
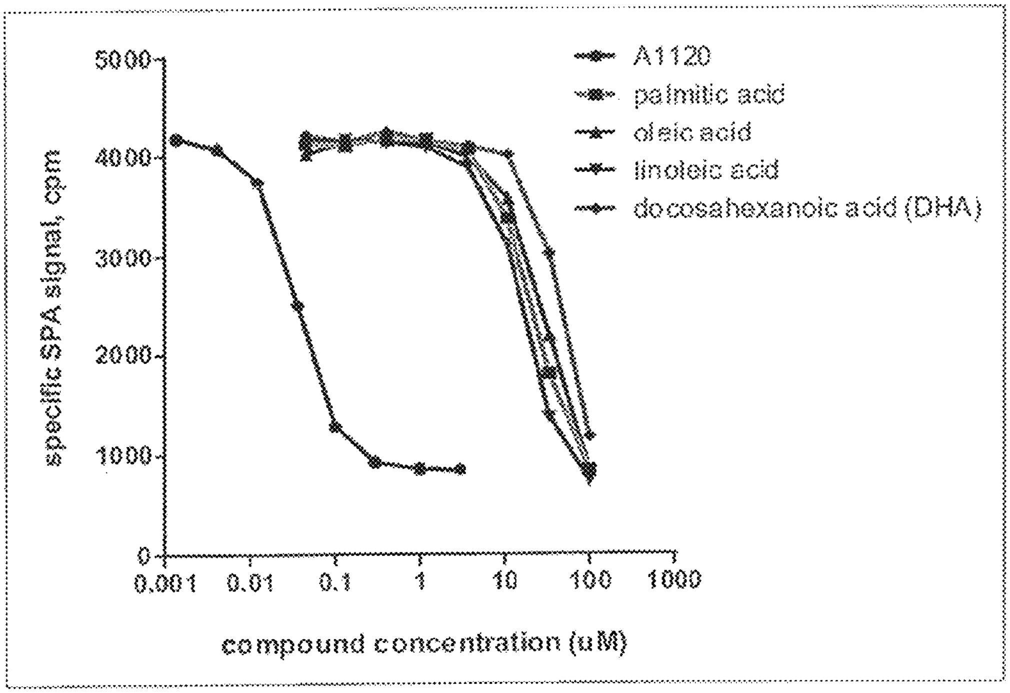

FIG. 14: Representative isotherms of A1120 (positive control) and fatty acid binding to human RBP4. $^3$H-retinol at 10 nM was used as a radioligand. Fatty acids, such as palmitic, oleic and linoleic acids, can displace radioactive retinol from RBP4 indicating that they can bind to the retinol-binding pocket of RBP4. This data implies that RBP4 expressed in adipose tissue may be involved in trafficking of fatty acids from adipose tissue to the liver. Compound 1, as well as other RBP4 antagonists, can inhibit this fatty acid trafficking as they compete for binding to the same retinol-binding pocket in RBP4.

| | A1120 | palmitic acid | oleic acid | linoleic acid | Docosahexanoic acid (DHA) |
|---|---|---|---|---|---|
| IC50 μM | 0.03665 | 22.59 | 33.01 | 17.32 | 49.91 |

Figure 15:
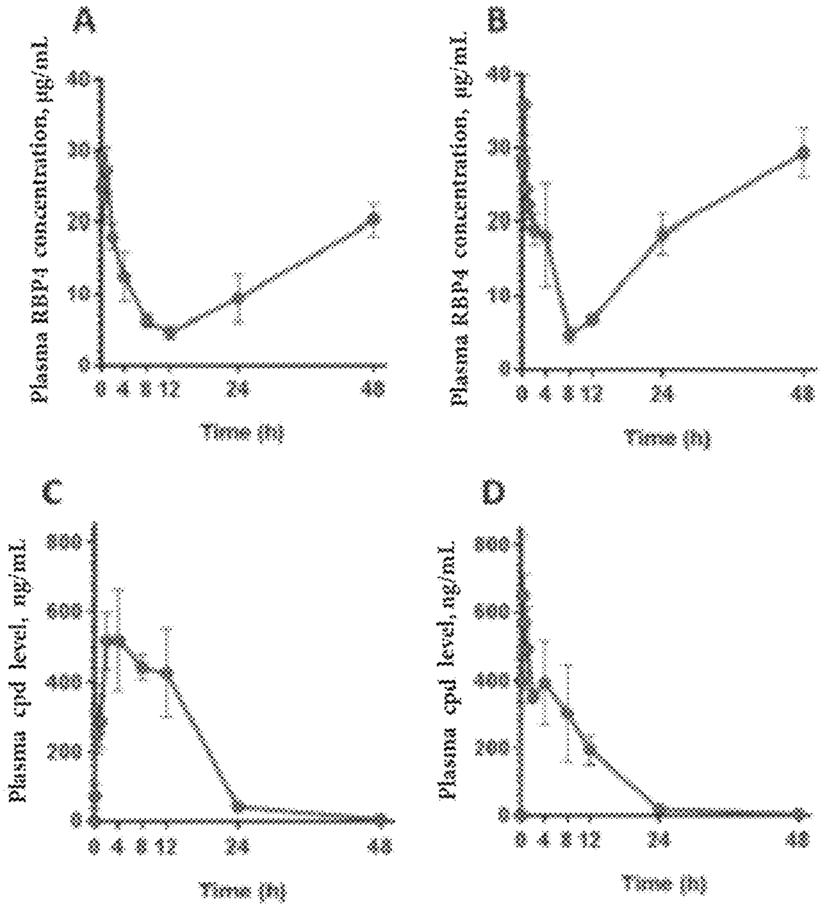

FIG. 15: In Vivo PK Data for Analogues Compound 1 and 2 Following IV and PO Administration in Rodent[a].

[a]Dosing groups consisted of three drug naive male CD-1 mice or adult male Sprague-Dawley rats. Data are represented as mean±SD. [b]Total body clearance. [c]Maximum observed concentration of the compound in plasma. [d]Time of the maximum observed concentration of the compound in plasma after oral administration. [e]Apparent half-life of the terminal phase of elimination of the compound from plasma. [f]Volume of distribution at a steady state. [g]Area under the plasma concentration versus time curve from 0 to the last time point compound was quantifiable in plasma. [h]Bioavailability; F=(AUCINFpo×doseiv)÷(AUCINFiv×dosepo). iIntravenous (IV) formulation=3% dimethacrylate/45% poly (ethylene glycol) 300/12% ethanol/40% sterile water; IV dosing volume=2 mL/kg; orally (PO) formulation=2% Tween 80 in 0.9% saline; PO dosing volume=5 mL/kg. Dosing regimen for Compound 3 in mouse and rat: 2.0 mg/kg IV, 5 mg/kg PO. Dosing regimen for Compound 1 in mouse: 2.0 mg/kg IV, 5 mg/kg PO. Dosing regimen for Compound 1 in rat: 1.0 mg/kg IV, 2.0 mg/kg IV, 5 mg/kg PO.

FIG. 16A: PK/PD properties of Compound 1 in mice. Plasma RBP4 levels in CD-1 mice following a single 5 mg/kg oral administration of Compound 1.

FIG. 16B: PK/PD properties of Compound 1 in mice. Plasma RBP4 levels in CD-1 mice following a single 2 mg/kg intravenous administration of Compound 1.

a 2 mg/kg intravenous dose (D) of Compound 1. Data are represented as the mean±SD. For each time point of blood collection, three mice were used in the study.

FIG. 16C: PK/PD properties of Compound 1 in mice. Plasma compound levels following administration of a single oral 5 mg/kg dose of Compound 1. Data are represented as the mean±SD. For each time point of blood collection, three mice were used in the study.

FIG. 16D: PK/PD properties of Compound 1 in mice. Plasma compound levels following administration of a single 2 mg/kg intravenous dose of Compound 1. Data are represented as the mean±SD. For each time point of blood collection, three mice were used in the study.

FIG. 17A: Effect of oral administration of Compound 1 on circulating levels of serum RBP4 in adi-hRBP4 mice. Serum levels of mouse RBP4 were measured at baseline (black circles) and at the end of the 29 day compound treatment (red squares) with species-specific rodent or human enzyme-linked immunosorbent assay tests. Compared with baseline, statistically significant 90% reduction was seen for both human and mouse RBP4 at the study's end in the Compound 1-treated mice (two-way analysis of variance (ANOVA) with Holm-Šidák post-hoc test, ****P<0.0001). A significant reduction in human and mouse RBP4 concentrations was detected in Compound 1-treated adi-hRBP4 mice in comparison with vehicle-treated knockout controls (two-way ANOVA with Holm-Šidák post-hoc test, P<0.0001). Error bars show SD; graph bars show mean. Each data point on the graph represents a serum RBP4 concentration from an individual animal. The number of male adi-hRBP4 mice per treatment group were 8 for normal chow, 7 for HFD, and 8 for HFD with Compound 1.

FIG. 17B: Effect of oral administration of Compound 1 on circulating levels of serum RBP4 in adi-hRBP4 mice. Serum levels of human RBP4 were measured at baseline (black circles) and at the end of the 29 day compound treatment (red squares) with species-specific rodent or human enzyme-linked immunosorbent assay tests. Compared with baseline, statistically significant 90% reduction was seen for both human and mouse RBP4 at the study's end in the Compound 1-treated mice (two-way analysis of variance (ANOVA) with Holm-Šidák post-hoc test, ****P<0.0001). A significant reduction in human and mouse RBP4 concentrations was detected in Compound 1-treated adi-hRBP4 mice in comparison with vehicle-treated knockout controls (two-way ANOVA with Holm-Šidák post-hoc test, P<0.0001). Error bars show SD; graph bars show mean. Each data point on the graph represents a serum RBP4 concentration from an individual animal. The number of male adi-hRBP4 mice per treatment group were 8 for normal chow, 7 for HFD, and 8 for HFD with Compound 1.

Figure 18:
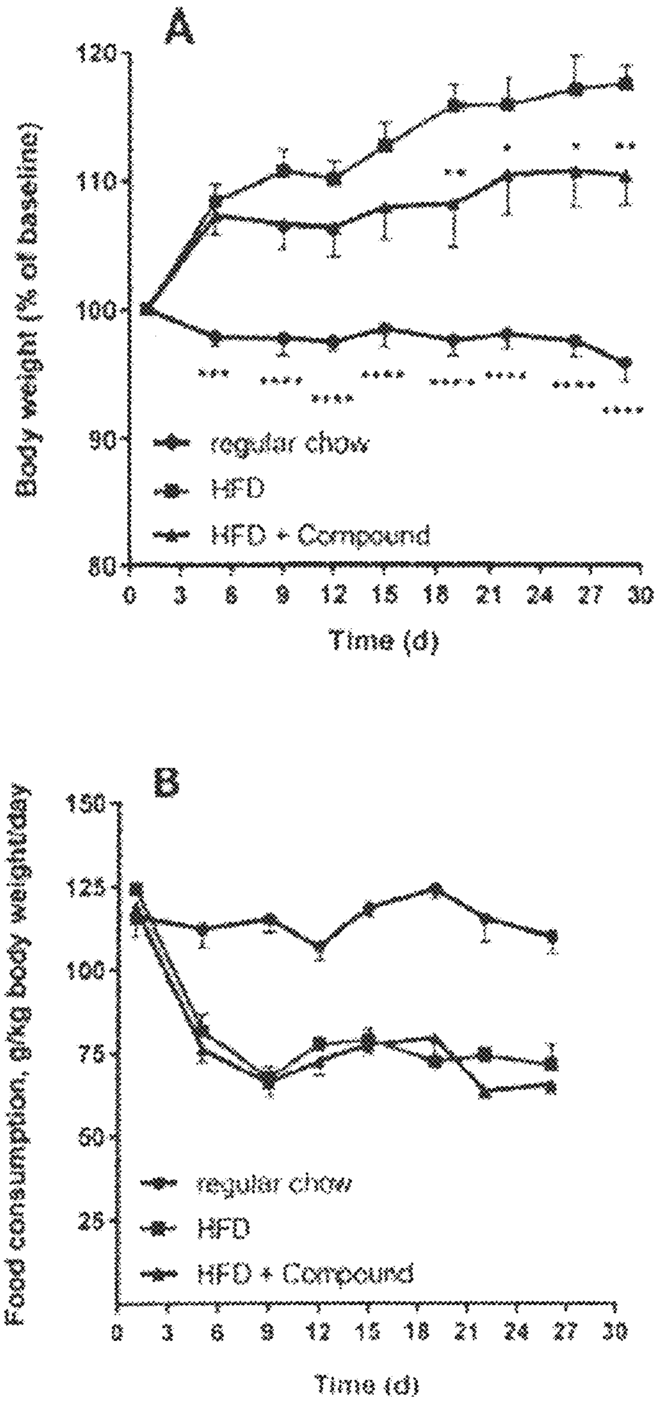

FIG. 18A: Compound 1 partially prevents high-fat diet-induced obesity in adi-hRBP4 mice. Weight gains for male adi-hRBP4 mice fed with normal chow (n=8), HFD (n=7), and HFD with 58 (n=8). In comparison to the untreated HFD group, compound-treated HFD mice registered significantly decreased weight gain at four time points starting from day 19 (two-way repeated measures (RM) ANOVA with Holm-Šidák post-hoc test, *P<0.05; P<0.01). The body weight gain in chow-fed mice was lower than in the HFD group at all time points studied (two-way RM ANOVA with Holm-Šidák post-hoc test, *P<0.001; ****P<0.0001). Values represent mean percent weight change from baseline. Error bars show SD.

FIG. 18B: Compound 1 partially prevents high-fat diet-induced obesity in adi-hRBP4 mice. Daily food consumption normalized to body weight in male adi-hRBP4 mice fed with normal chow, HFD, and HFD with Compound 1. No difference in food consumption between the untreated HFD group and compound-treated HFD mice was detected (two-way RM ANOVA with Holm-Šidák post-hoc test). Values represent mean normalized daily chow consumption. Error bars show SD.

Figure 19:
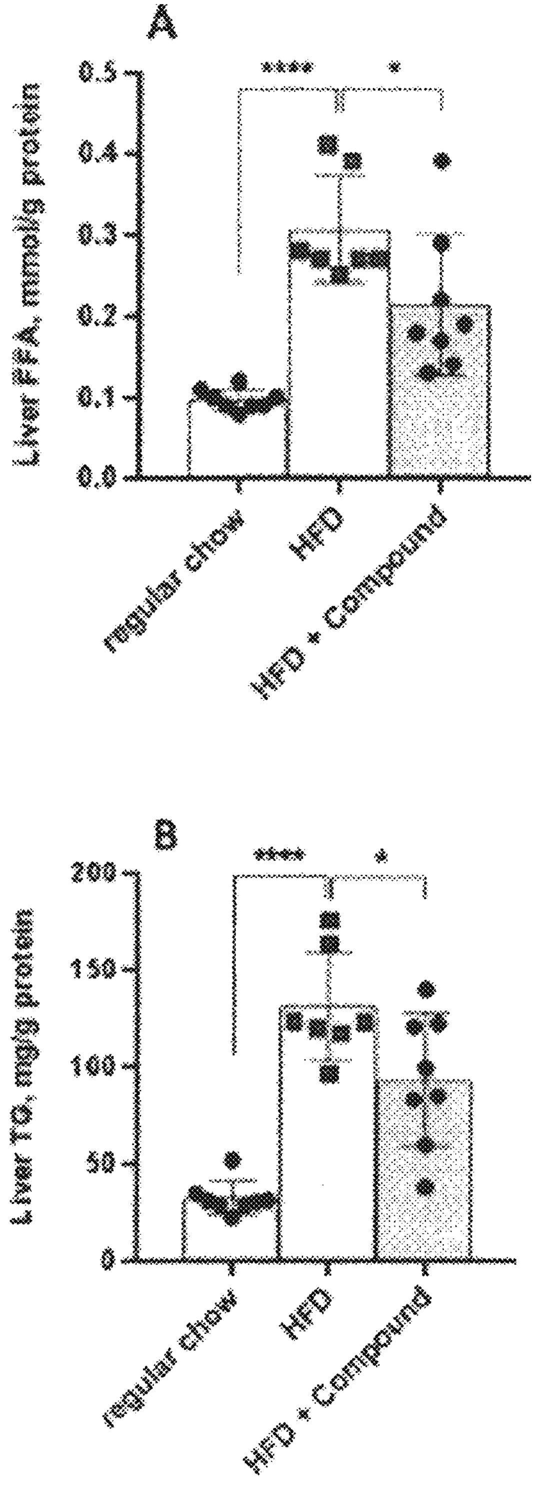

FIG. 19A: Effect of Compound 1 orally administered at the 20 mg/kg dose on hepatic free fatty acid and triglyceride levels in obese adihRBP4 mice. Liver levels of FFA (A) in male adi-hRBP4 mice fed with normal chow (n=8), HFD (n=7), and HFD with Compound 1 (n=8). In comparison with the untreated HFD group, Compound 1-treated HFD mice have significantly decreased hepatic levels of FFA (P=0.0107, one-way ANOVA with Holm-Šidák post-hoc test) and triglycerides (P=0.0104, one-way ANOVA with Holm-Šidák posthoc test). Graph bars show mean; error bars show SD; *P<0.05; ****P<0.0001. Each data point on the graph represents a FFA or TG concentration from an individual animal.

FIG. 19B: Effect of Compound 1 orally administered at the 20 mg/kg dose on hepatic free fatty acid and triglyceride levels in obese adihRBP4 mice. Liver levels of TG (B) in male adi-hRBP4 mice fed with normal chow (n=8), HFD (n=7), and HFD with Compound 1 (n=8). In comparison with the untreated HFD group, Compound 1-treated HFD mice have significantly decreased hepatic levels of FFA (P=0.0107, one-way ANOVA with Holm-Šidák post-hoc test) and triglycerides (P=0.0104, one-way ANOVA with Holm-Šidák posthoc test). Graph bars show mean; error bars show SD; *P<0.05; ****P<0.0001. Each data point on the graph represents a FFA or TG concentration from an individual animal.

Figure 20:
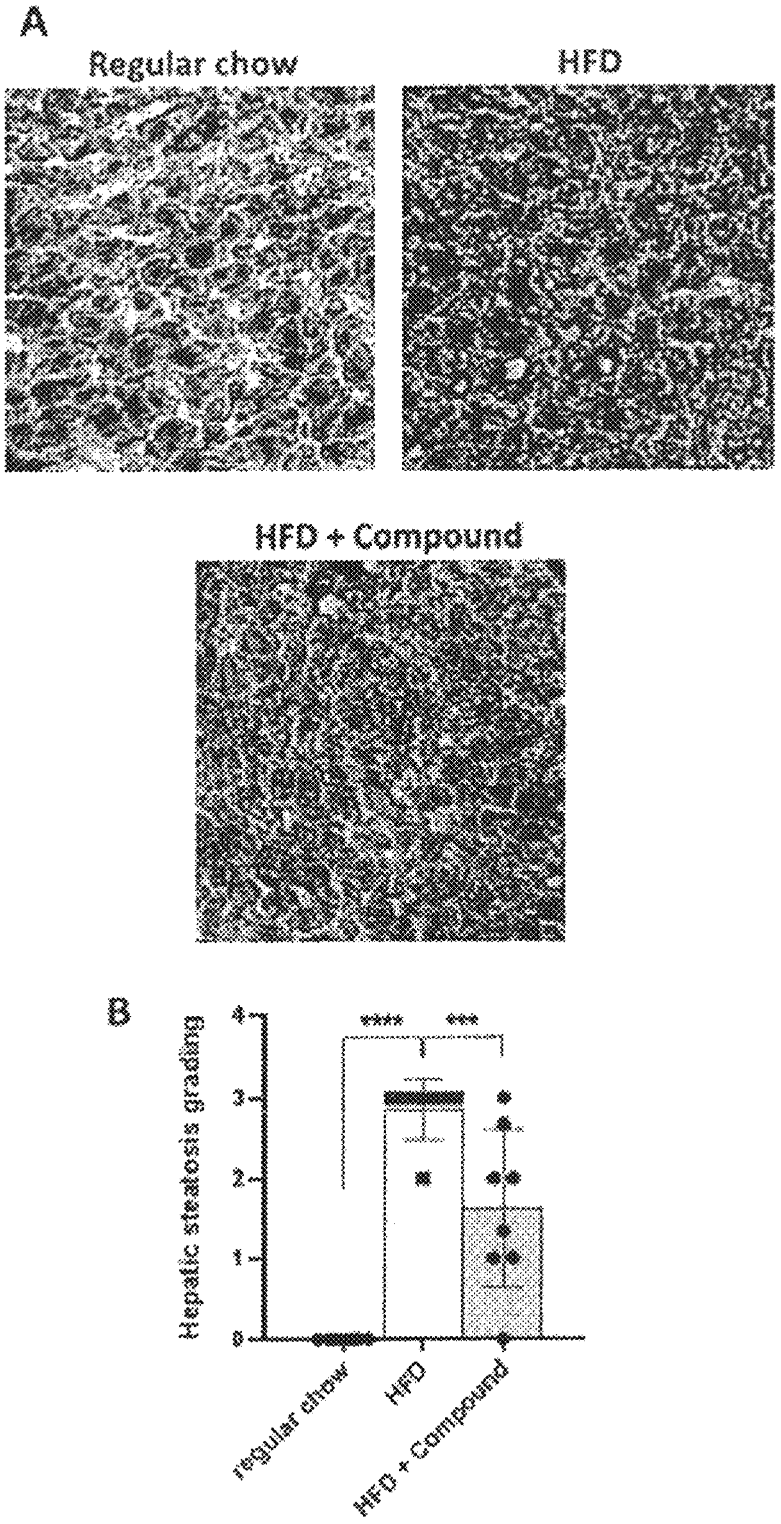

FIG. 20A: Effect of Compound 1 on hepatic lipid disposition in adi-hRBP4 mice. Representative liver cryosections stained with oil red O illustrating fatty liver states in chow-fed, HFD, and Compound 1-treated HFD adi-hRBP4 mice. The compound was orally administered at the 20 mg/kg dose.

FIG. 20B: Effect of Compound 1 on hepatic lipid disposition in adi-hRBP4 mice. Histological scoring of oil red O-stained liver cryosections from chow-fed, HFD, and Compound 1-treated HFD adi-hRBP4 mice. Hepatic steatosis was graded as 0 (0% hepatocytes have macrovesicular steatosis), 1 (<33% hepatocytes have macrovesicular steatosis), 2 (33-66% hepatocytes have macrovesicular steatosis), and 3 (>66% hepatocytes have macrovesicular steatosis). Data was analyzed using one-way ANOVA with Holm-Šidák post-hoc test. Graph bars show mean; error bars show SD; ***P<0.001. Each data point on the graph represents a steatosis histology score from an individual animal. The number of male adi-hRBP4 mice per treatment group were 8 for normal chow, 7 for HFD, and 8 for HFD with Compound 1.

Figure 21:
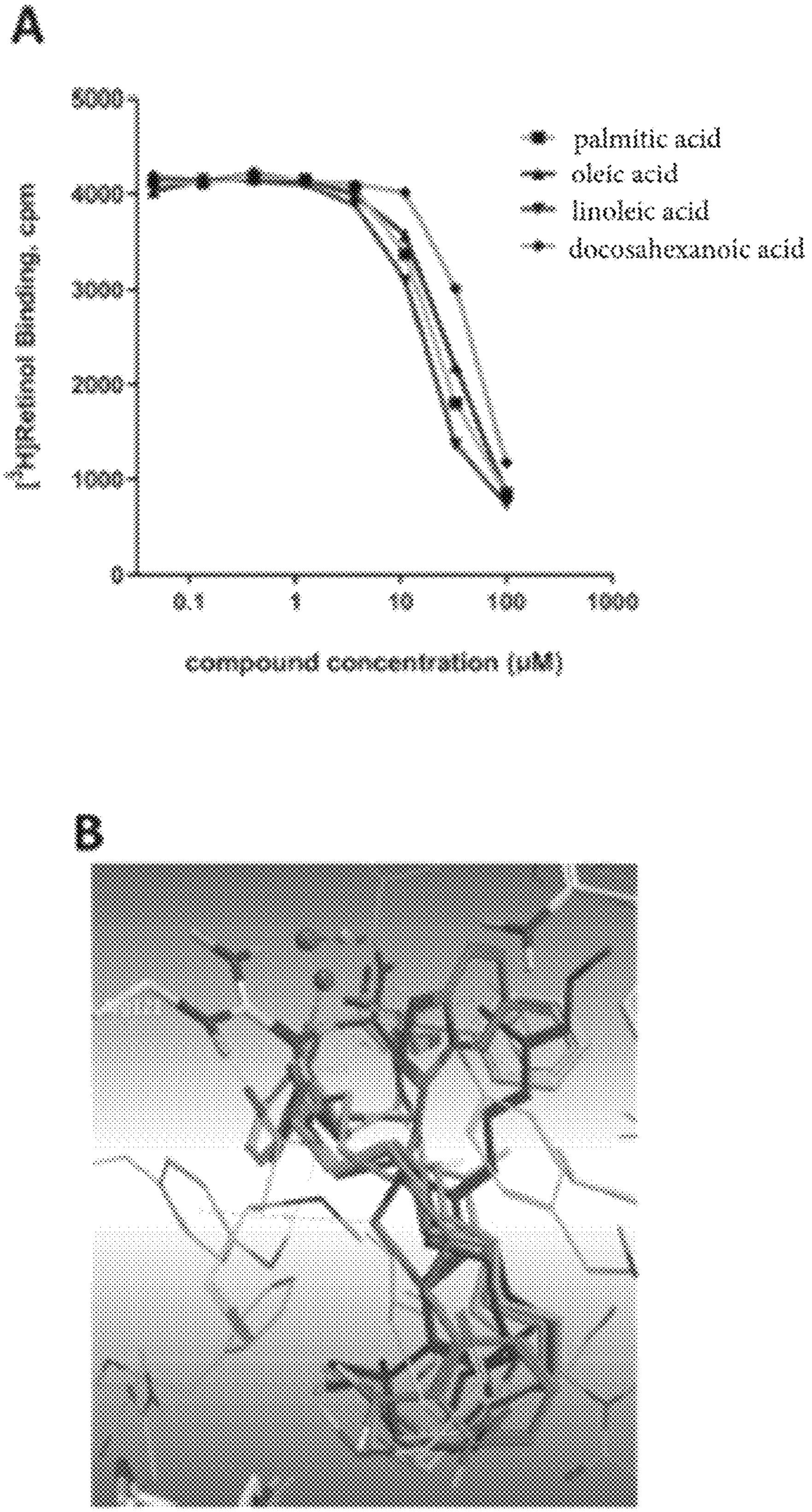

FIG. 21: Binding of fatty acids to RBP4. (A) Isotherms of palmitic acid, oleic acid, linoleic acid, and docosahexaenoic acid binding to human RBP4. 3H-retinol at 10 nM was used as a radioligand. (B) Overlays of minimized bound conformations of retinol (black, 5NU7), antagonist Compound 3 (purple, 3FMZ), and palmitic acid, oleic acid, linoleic acid, and docosahexaenoic acid (orange). Phe36 is dark-green in the 3FMZ (within close proximity to the fatty acid carboxylic acid groups) and light green in the 5NU7 model (within close proximity to the alcohol group of 1). Contacting residues are labeled and illustrated in stick format (MOE, Chemical Computing Group, Inc., Montreal, CA).

DETAILED DESCRIPTION OF THE INVENTION

The subject invention provides a method for treating a non-alcoholic fatty liver disease (NAFLD) disease in a subject afflicted therewith comprising administering to the subject a pharmaceutical composition comprising an amount of a compound which is a non-retinoid retinol-binding protein 4 (RBP4) antagonist effective to treat the subject, thereby treating the subject.

The subject invention provides a method for treating gout in a subject afflicted therewith comprising administering to the subject a pharmaceutical composition comprising an amount of a compound which is a retinol-binding protein 4 (RBP4) antagonist effective to treat the subject, thereby treating the subject.

The subject invention further provides a method for treating a non-alcoholic fatty liver disease (NAFLD) or gout in a subject afflicted therewith comprising administering to the subject a pharmaceutical composition comprising an amount of a compound effective to treat the subject, thereby treating the subject, wherein compound has the structure

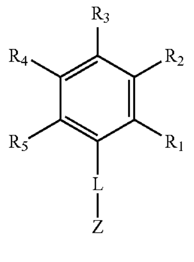

wherein L is a linking group having the structure:

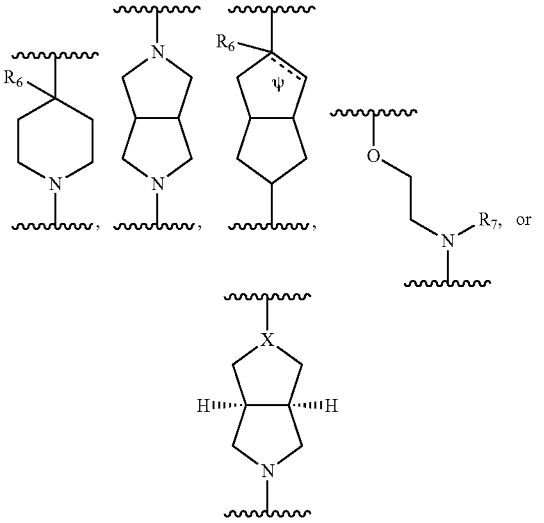

and Z is a group having the structure:

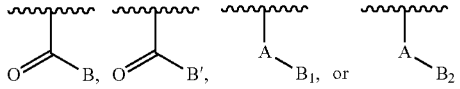

wherein $R_1$, $R_2$, $R_3$, $R_4$, and $R_5$ are each independently H, halogen, $CF_3$ or $C_1$-$C_4$ alkyl;

$R_6$ is H, OH, or halogen or absent;

ψ is absent or present, and when present is a bond;

B is a substituted or unsubstituted heterobicycle, pyridazine, pyrazole, pyrazine, thiadiazole, or triazole, wherein the heterobicycle is other than chloro substituted indole; and the pyrazole, when substituted, is substituted with other than trifluoromethyl;

B' is a substituted or unsubstituted phenyl, pyridine, pyrimidine, benzyl, pyrrolidine, sulfolane, oxetane, $CO_2H$ or ($C_1$-$C_4$ alkyl)-$CO_2H$, wherein the substituted phenyl is substituted with other than trifluoromethyl or 3-(methyl carboxylate), the substituted pyridine is substituted with other than trifluoromethyl and the substituted pyrrolidine is substituted with other than hydroxamic acid, and the substituted or unsubstituted pyrrolidine is bound to the carbonyl through a carbon-carbon bond;

A is absent or present, and when present is

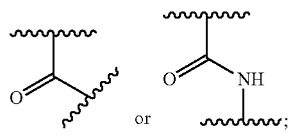

$B_1$ is substituted or unsubstituted monocycle, bicycle, heteromonocycle, heterobicycle, benzyl, $CO_2H$ or ($C_1$-$C_4$ alkyl)-$CO_2H$, wherein when $B_1$ is $CO_2H$, then A is present and is

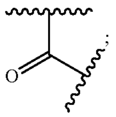

$R_7$ is alkyl;
X is N or $CR_8$, wherein $R_8$ is H, OH, or halogen;
$B_2$ has the structure:

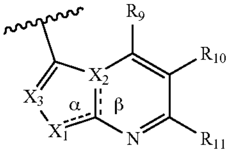

wherein
α and β are each a bond that is present or absent;
$X_1$ is N, NH or $NR_{99}$,
wherein $R_{99}$ is alkyl, alkenyl or alkynyl;
$X_2$ is C or N;
$X_3$ is CH or N;
$R_9$, $R_{10}$ and $R_{11}$ are each, independently, H, halogen, alkyl, alkenyl, alkynyl, alkyl-OH, alkyl-$NH_2$, alkyl-OAc alkyl-O(CO)-alkyl, alkyl-O-alkyl, haloalkyl, cycloalkyl, O-alkyl, NH-alkyl, C(O)OH, C(O)—$NH_2$, C(O)—$N(CH_3)_2$, C(O)—$NHCH_3$, NHC(O)—$N(CH_3)_2$, CN or $CF_3$,
wherein
$X_1$, $X_2$ and $X_3$ are each N, α is present and β is absent; or
$X_1$ is NH, $X_2$ is C, $X_3$ is CH, α is absent and β is present; or
$X_1$ is N, $X_2$ is N, $X_3$ is CH, α is present and β is absent; or
$X_1$ is NH or $NR_{99}$, $X_2$ is C, $X_3$ is N, α is absent and β is present, wherein
when $X_1$ is NH, $X_2$ is C, $X_3$ is N, α is absent and β is present, then one of $R_9$, $R_{10}$ and $R_{11}$ is other than H,
or $B_2$ has the structure:

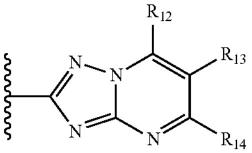

wherein
$R_{12}$, $R_{13}$ and $R_{14}$ are each, independently, H, halogen, alkyl, alkenyl, alkynyl alkyl-OH, alkyl-$NH_2$, alkyl-Oac, alkyl-O(CO)-alkyl, alkyl-O-alkyl, haloalkyl, cycloalkyl, O-alkyl, NH-alkyl, C(O)OH, C(O)—$NH_2$, C(O)—$N(CH_3)_2$, C(O)—$NHCH_3$, NHC(O)—$N(CH_3)_2$, CN or $CF_3$,
or a pharmaceutically acceptable salt thereof.

In one embodiment, the subject is afflicted with a NAFLD disease selected from the group consisting of: hepatic steatosis (fatty liver), nonalcoholic steatohepatitis (NASH), cirrhosis, and hepatocellular carcinoma.

In some embodiments, the method further comprises a step of determining, or having determined, the level of RBP4 in adipose tissue in a subject and administering the pharmaceutical composition if the level of RBP4 in adipose tissue is elevated.

In one embodiment, the method further comprises a step of determining, or having determined, the level of RBP4 in serum in a subject and administering the pharmaceutical composition if the level of RBP4 in serum is elevated.

In an embodiment, the amount of the compound is effective in reducing RBP4 levels in adipose tissue in the subject. In another embodiment the amount of the compound is effective in reducing RBP4 levels in serum in the subject. In another embodiment the amount of the compound is effective in reducing uric acid levels in the serum of the subject. In another embodiment the amount of the compound is effective to normalize the concentration of triglycerides in the liver of the subject.

In an embodiment the amount of the compound is effective to normalize the concentration of free fatty acids in the serum of the subject. In another embodiment the amount of the compound is effective to normalize the concentration of free fatty acids in the liver of the subject. In some embodiments the amount of the compound is effective to prevent trafficking of a fatty acid by RBP4. In additional embodiments the amount of the compound is effective to prevent trafficking of a fatty acid to the liver by RBP4. In an embodiment the amount of the compound is effective to inhibit binding between RBP4 and a fatty acid.

In one embodiment the fatty acid is from adipose tissue.

In an embodiment, the subject does not have elevated serum RBP4 levels. In another embodiment, the subject has elevated serum RBP4 levels. In some embodiments the serum RBP4 level is elevated by more than 3 microgram per ml.

In some embodiments, the NAFLD is a hepatic steatosis selected from simple hepatic steatosis and mild hepatic steatosis.

In one embodiment the compound is not a ligand for nuclear receptor RAR. In another embodiment the RBP4 antagonist is a non-retinoid antagonist. In an additionally embodiment, the RBP4 antagonist is not fenretinide.

In some embodiments, L is

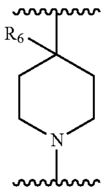

and Z is

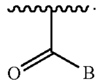

In additional embodiments, L is

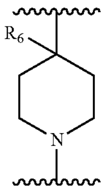

and Z is

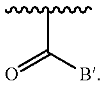

In further embodiments, L is

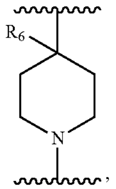

Z is

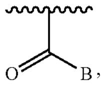

two or more of $R_1$, $R_2$, $R_3$, $R_4$, or $R_5$ are other than H, and when $R_1$ is $CF_3$, $R_2$ is H, $R_3$ is F, $R_4$ is H, and $R_5$ is H, or $R_1$ is H, $R_2$ is $CF_3$, $R_3$ is H, $R_4$ is $CF_3$, and $R_5$ is H, or $R_1$ is Cl, $R_2$ is H, $R_3$ is H, $R_4$ is F, and $R_5$ is H, or $R_1$ is $CF_3$, $R_2$ is H, $R_3$ is F, $R_4$ is H, and $R_5$ is H, or $R_1$ is $CF_3$, $R_2$ is F, $R_3$ is H, $R_4$ is H, and $R_5$ is H, or $R_1$ is Cl, $R_2$ is F, $R_3$ is H, $R_4$ is H, and $R_5$ is H, then B is other than

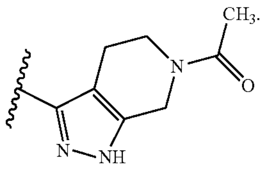 [SMILES: *c1n[nH]c2c1CCN(C(C)=O)C2]

In some embodiments, L is

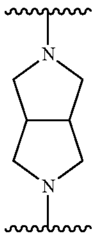 [SMILES: *N1CC2CN(*)CC2C1]

and Z is

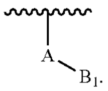

is

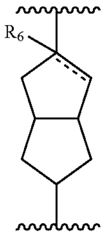

Z is

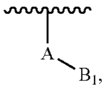

and $R_6$ is absent or present, and when present is H, OH, or halogen and when $\psi$ is present, then $R_6$ is absent and when $\psi$ is absent, then $R_6$ is present.

In some embodiments, L is

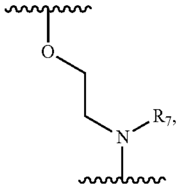

and

Z is

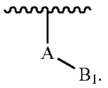

In some embodiments, L is

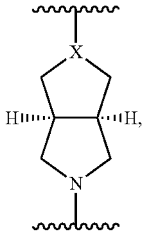

and

Z is

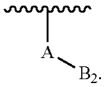

In some embodiments, L is
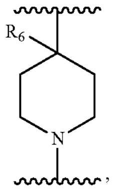
Z is
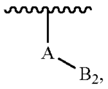
$R_6$ is H, and A is
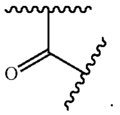 [SMILES: *C(*)=O]
In some embodiments, L is
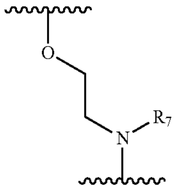
and Z is
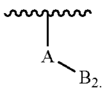
In some embodiments, the compound is
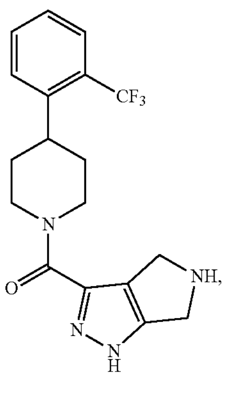
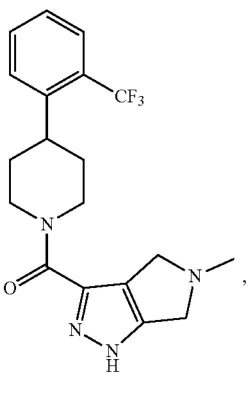
-continued
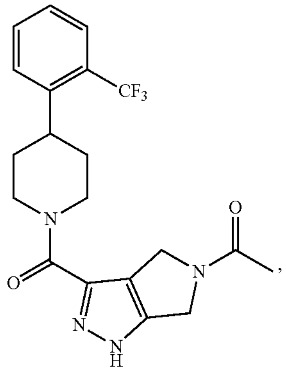
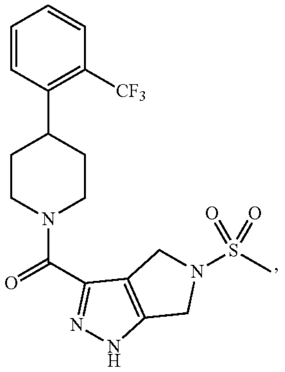
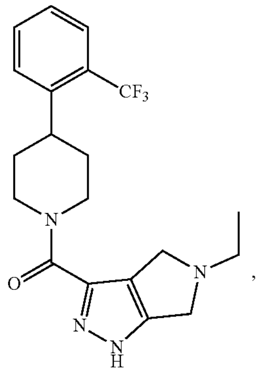
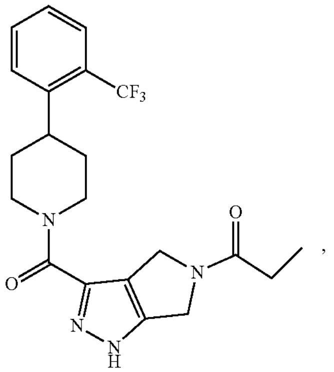
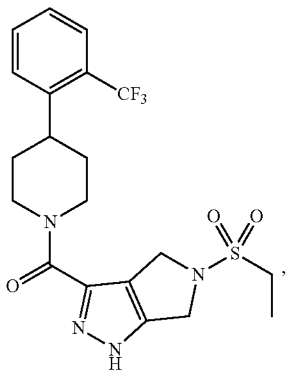

-continued
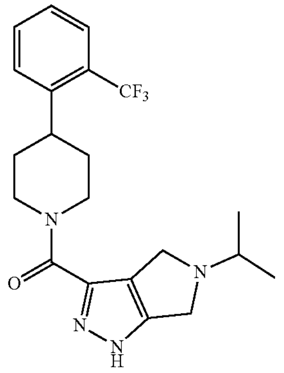
,
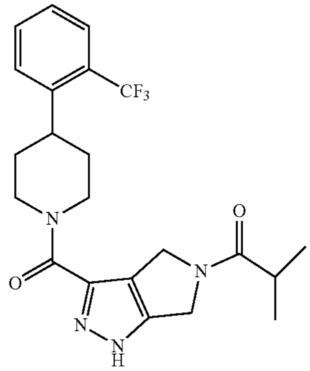
,
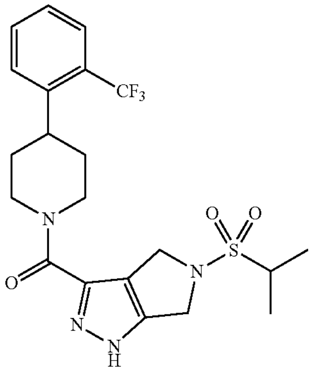
,
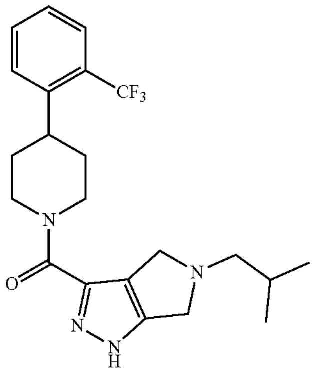
,
-continued
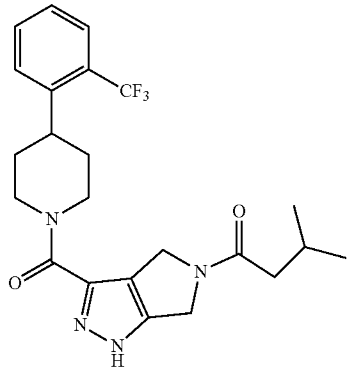
,
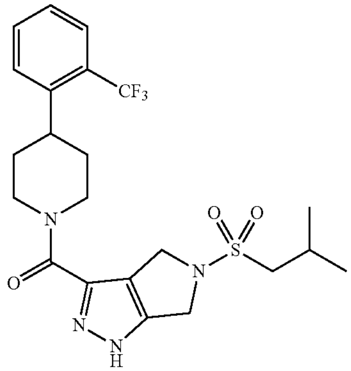
,
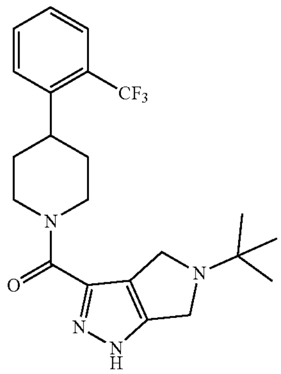
,
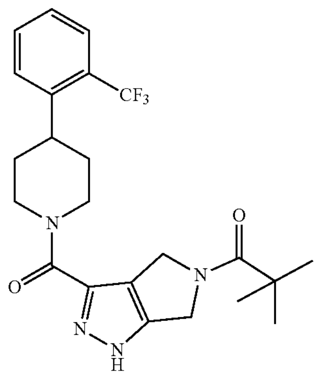
, -continued
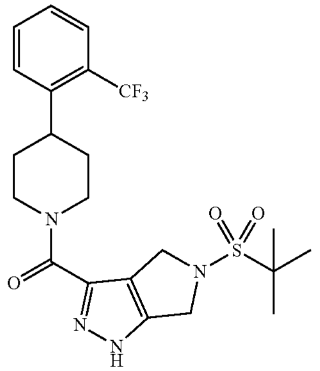
,
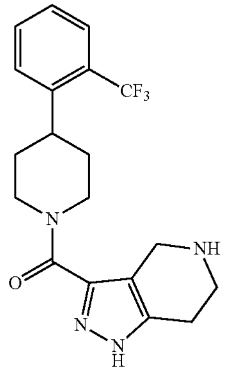
,
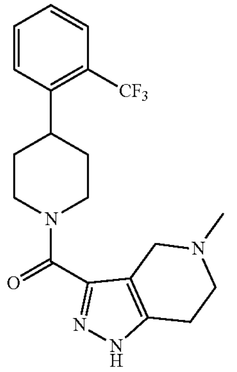
,
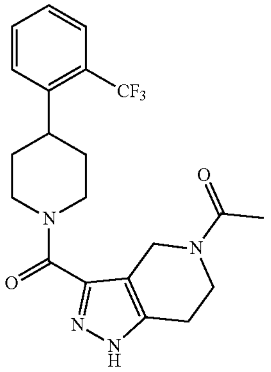
,
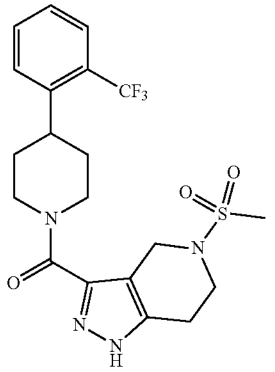
,
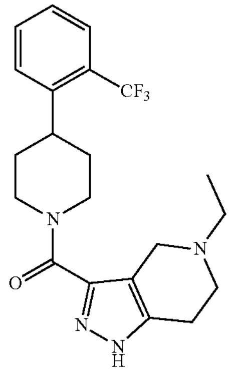
,
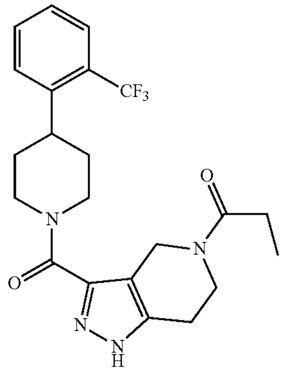
,
-continued
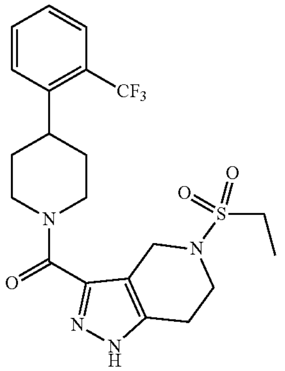
,
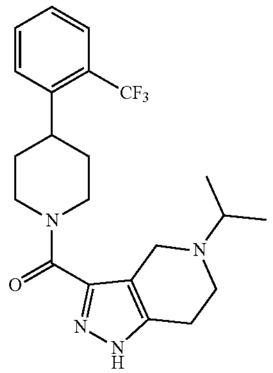
,
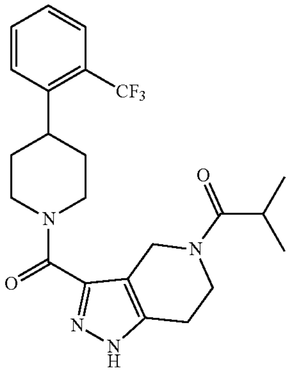
,
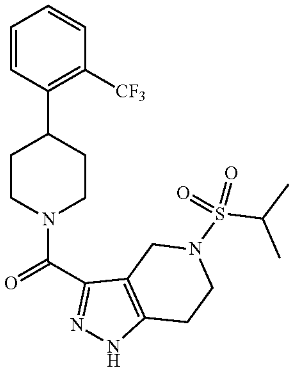
, -continued
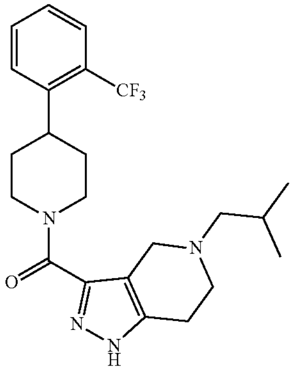
,
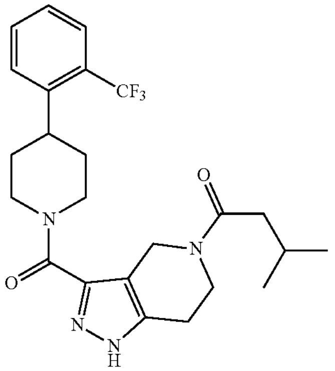
,
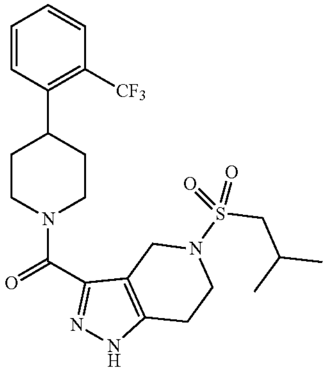
,
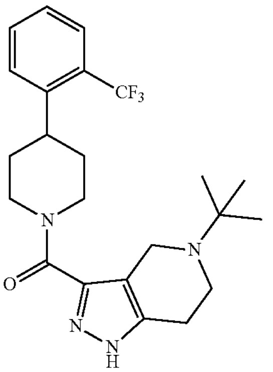
,
-continued
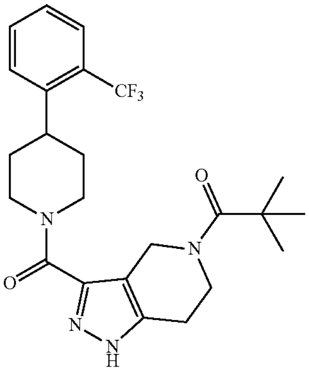
,
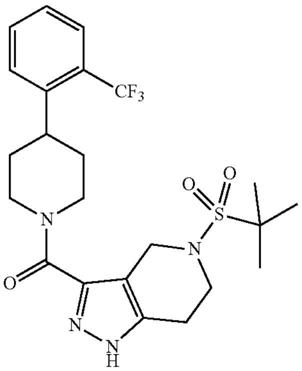
,
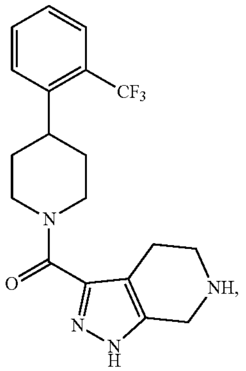
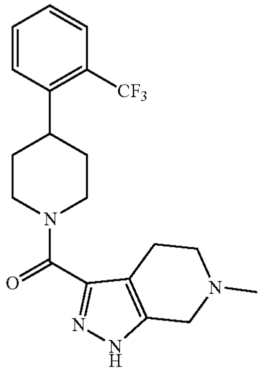
, -continued
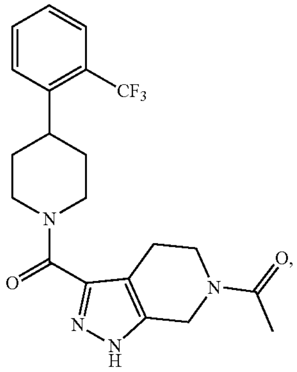
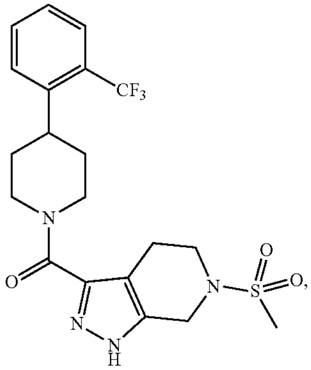
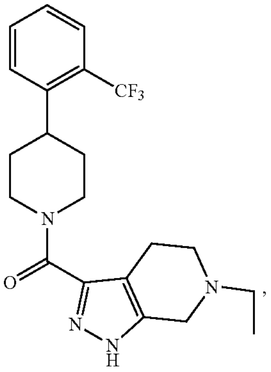
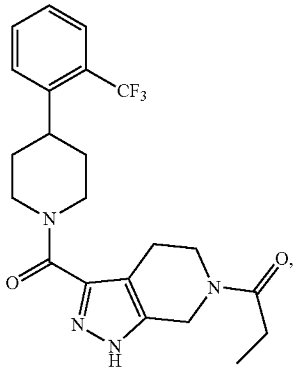
-continued
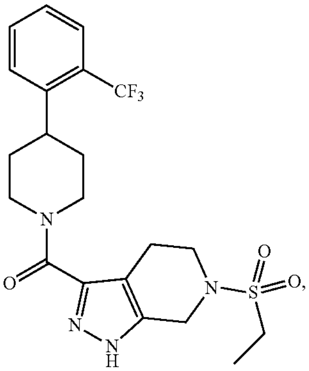
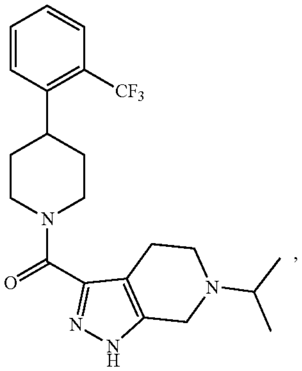
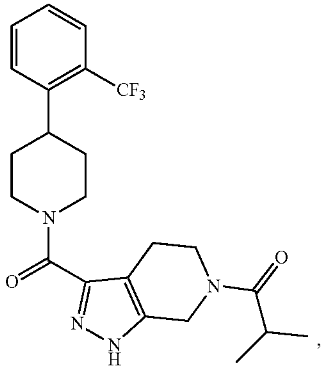
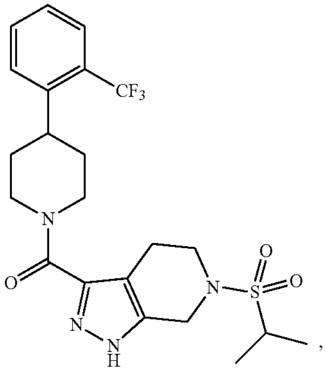

-continued
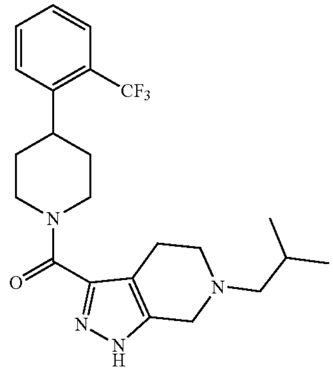
,
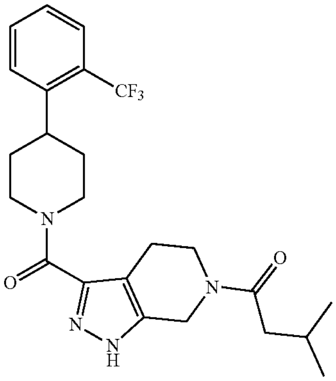
,
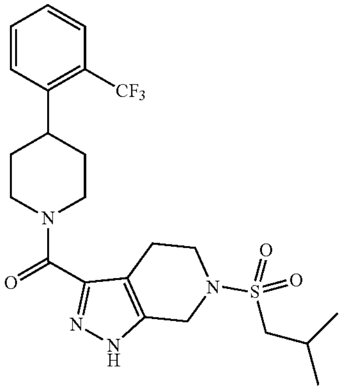
,
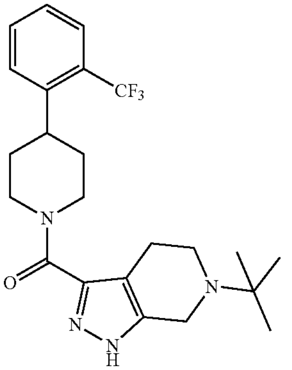
,
-continued
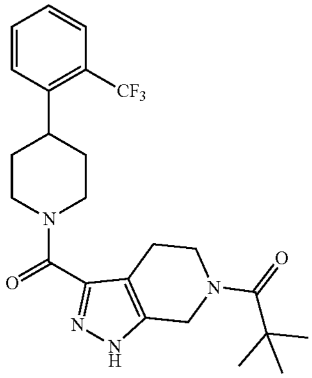
,
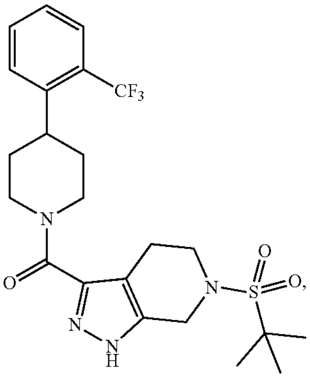
,
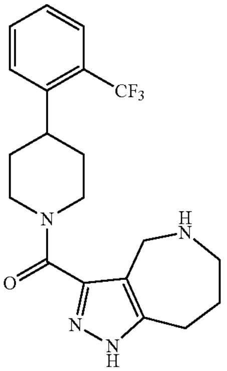
,
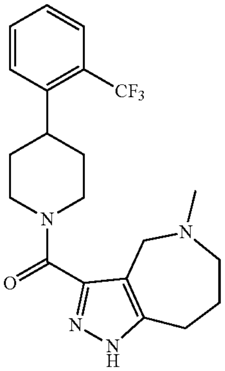
,
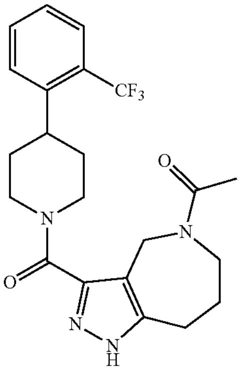
,
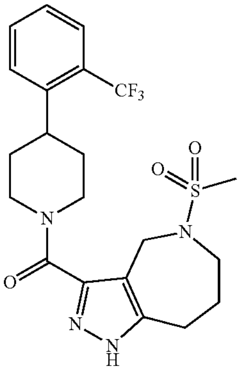
, -continued
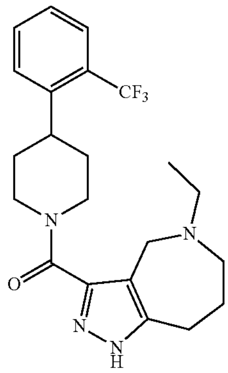
,
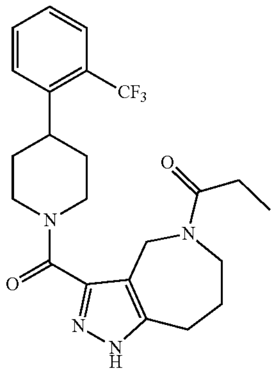
,
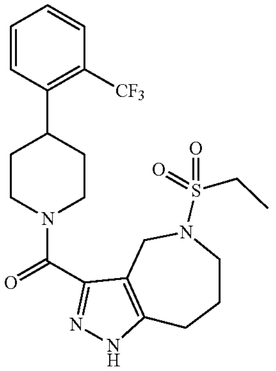
,
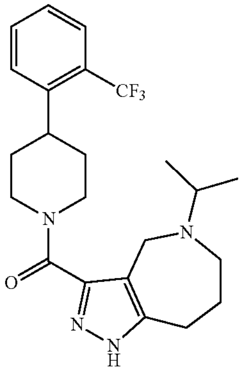
,
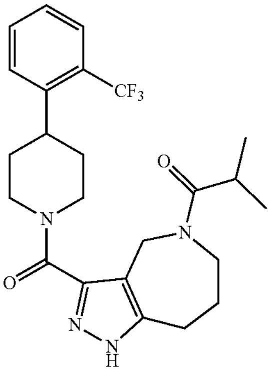
,
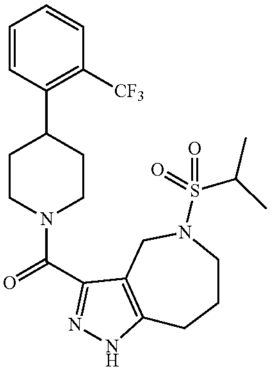
,
-continued
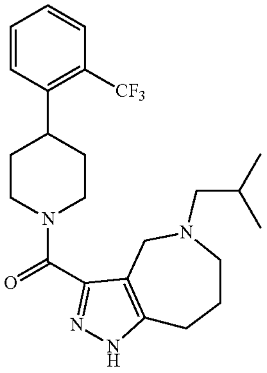
,
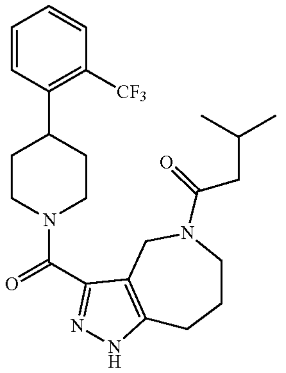
,
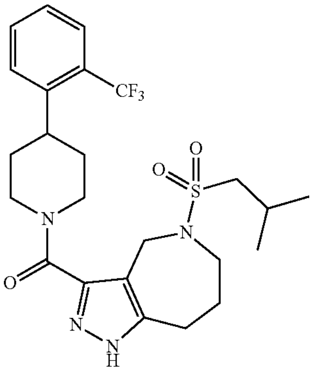
,
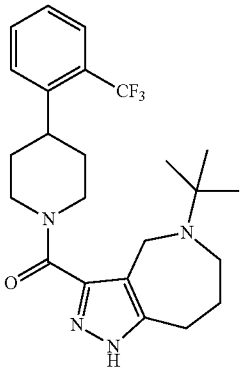
,
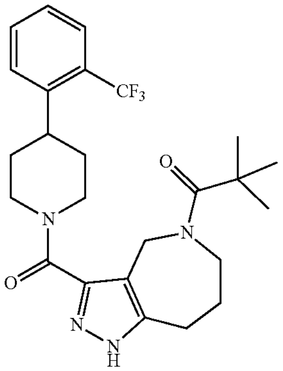
, -continued
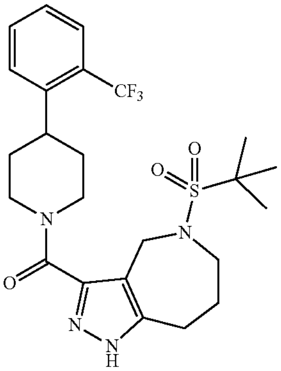
,
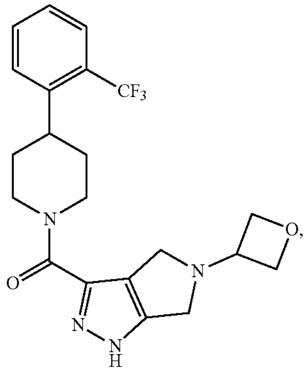
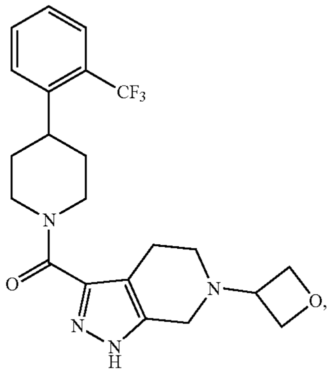
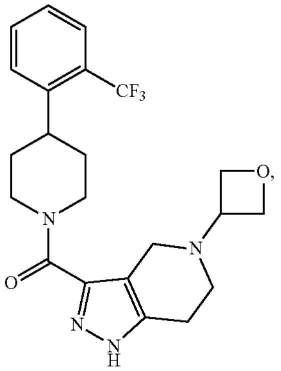
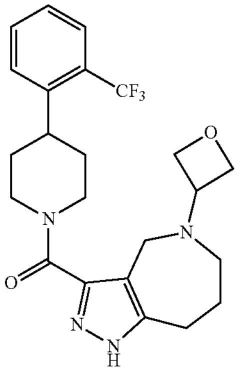
,
-continued
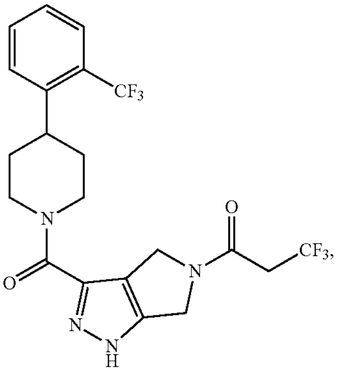
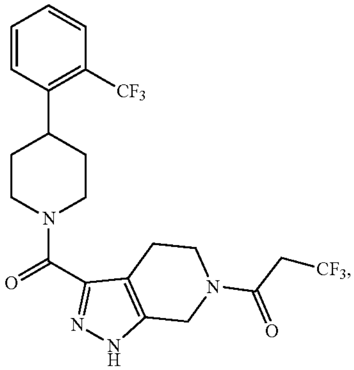
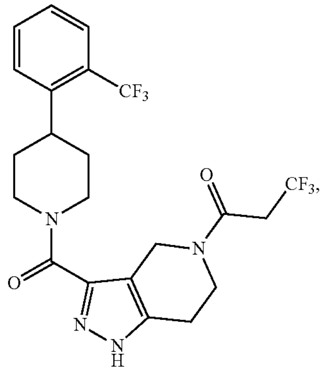
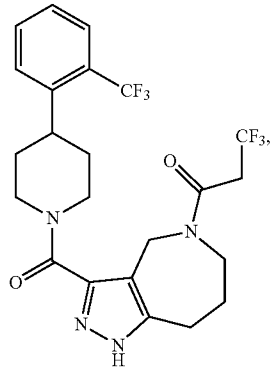

-continued
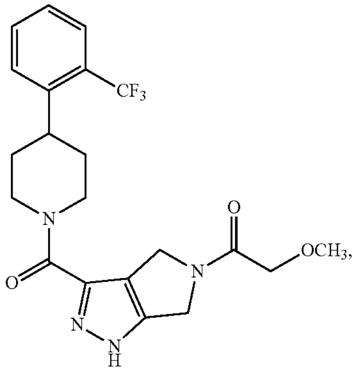
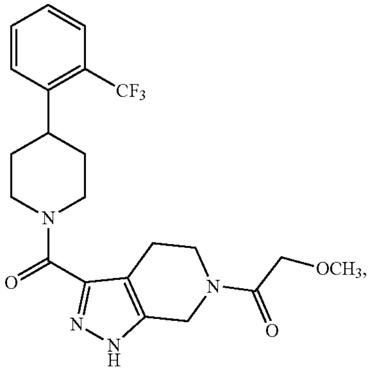
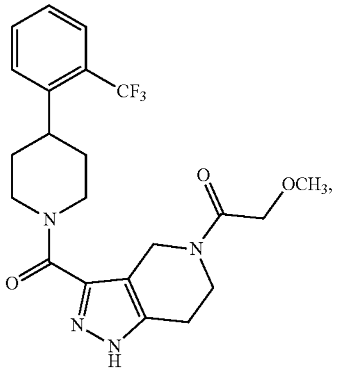
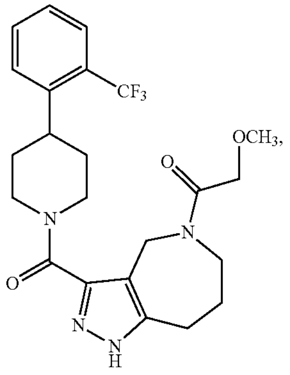
-continued
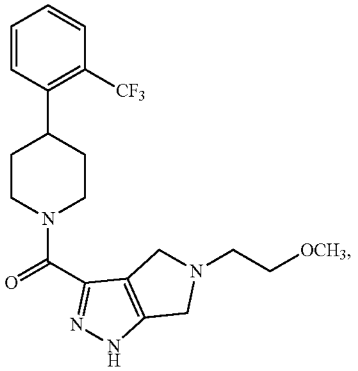
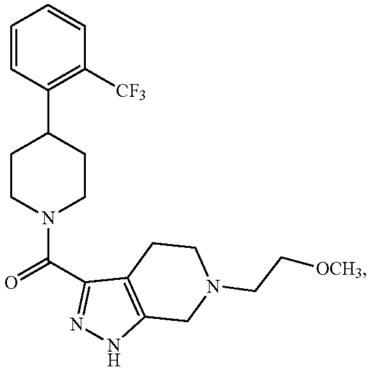
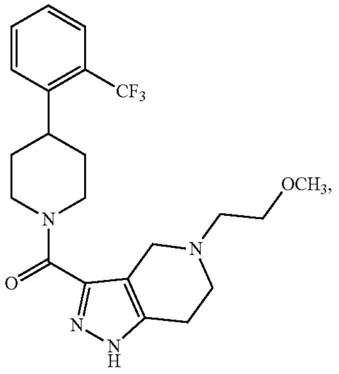
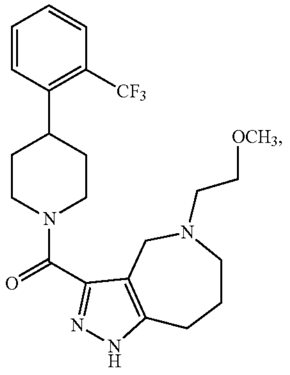

-continued
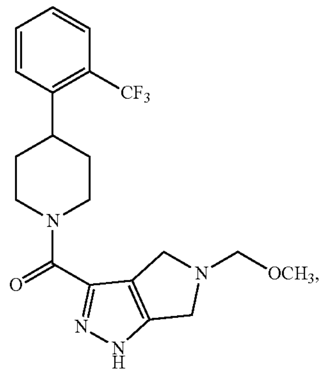
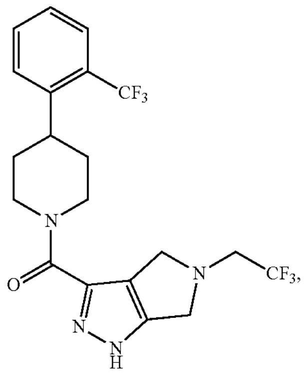
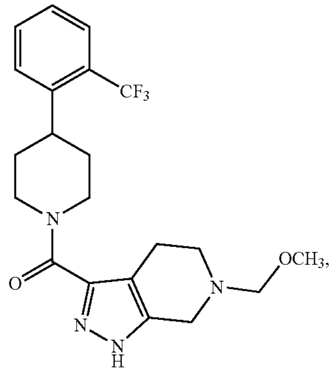
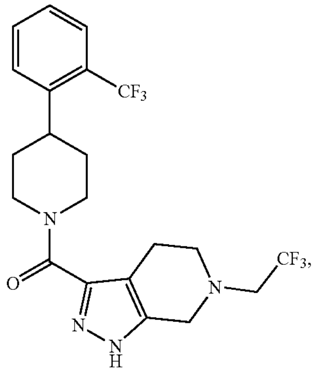
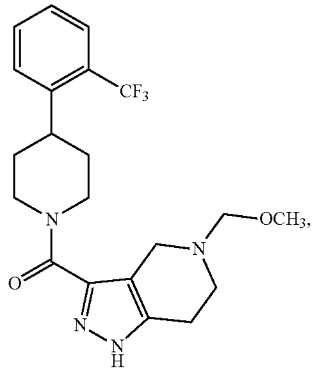
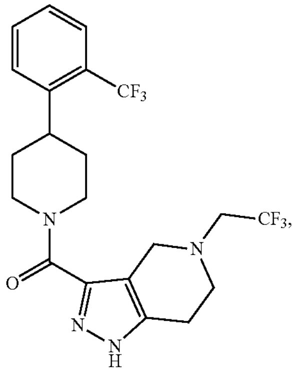
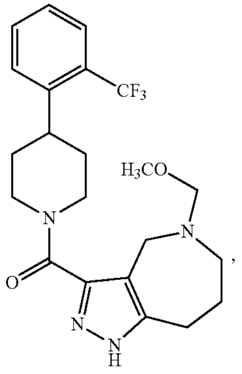
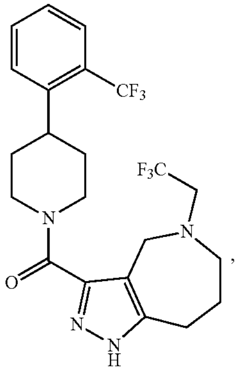

-continued
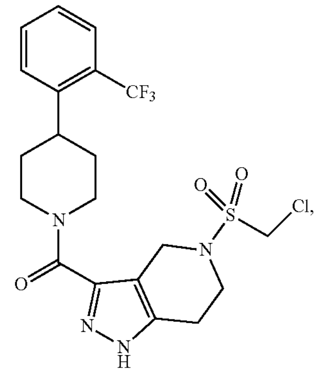
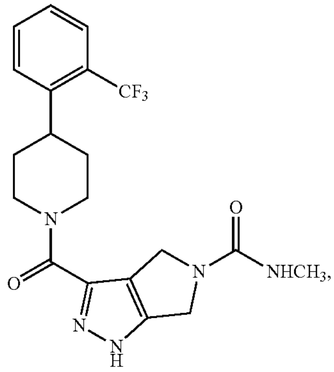
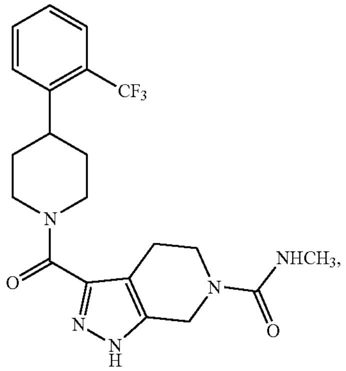
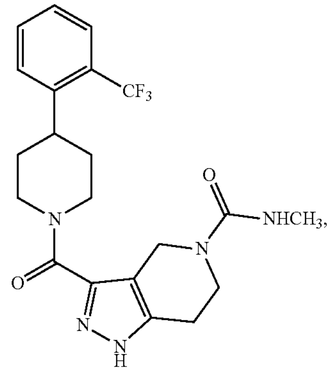
-continued
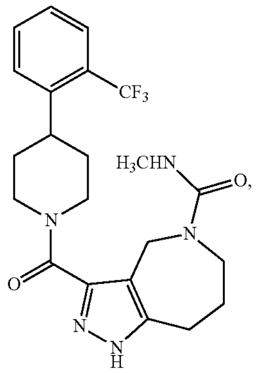
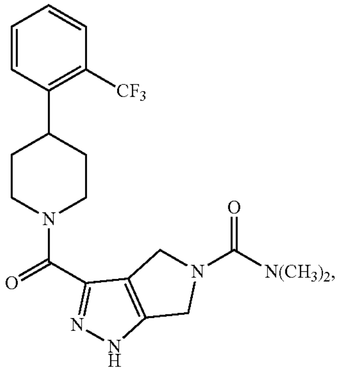
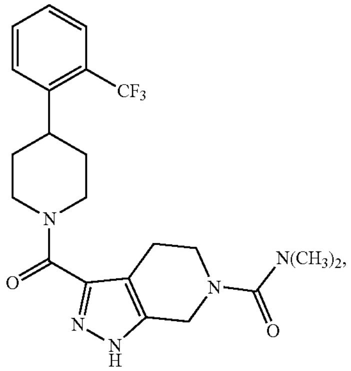
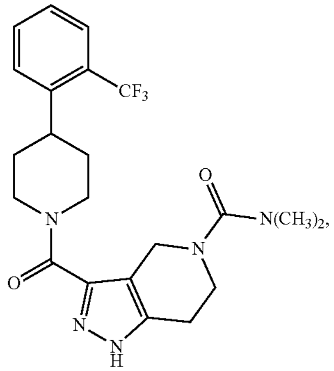

-continued
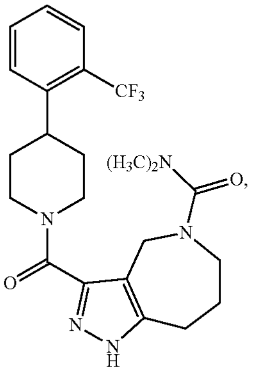
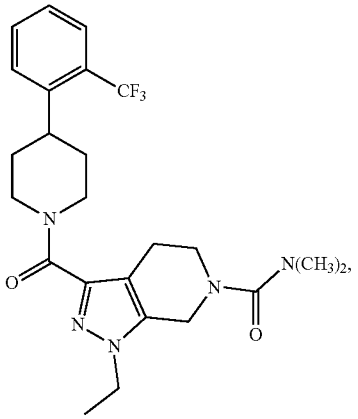
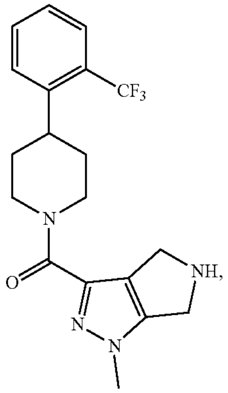
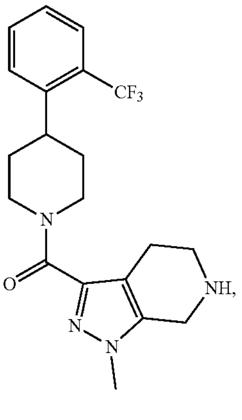
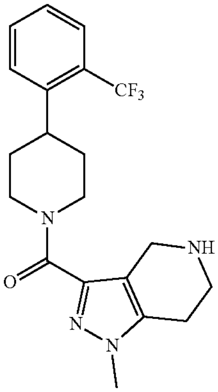
,
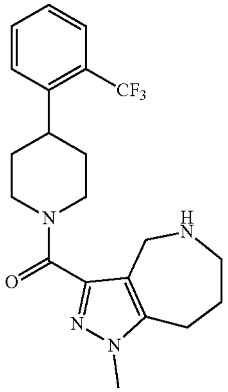
,
-continued
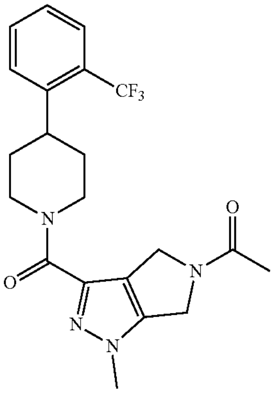
,
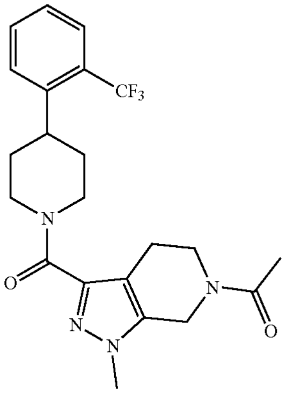
,
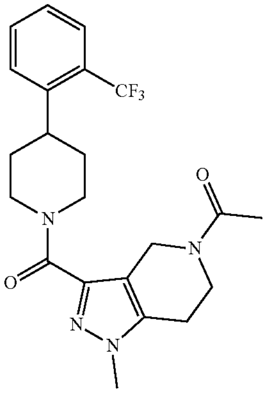
,
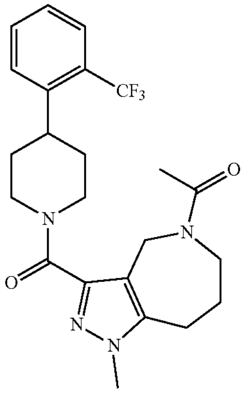
,
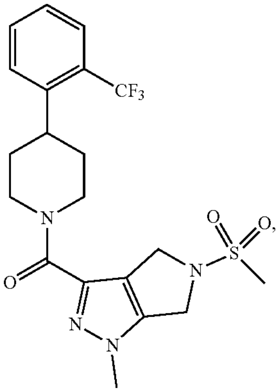

-continued
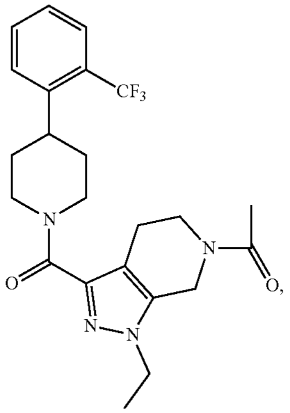
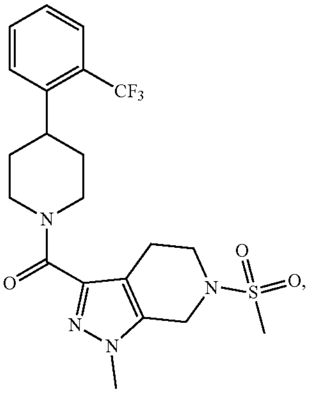
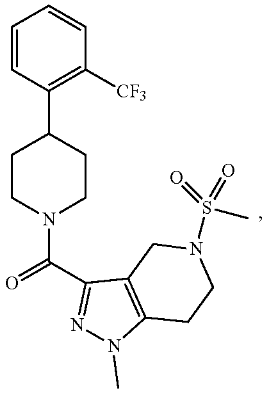
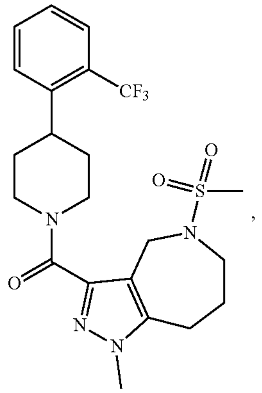
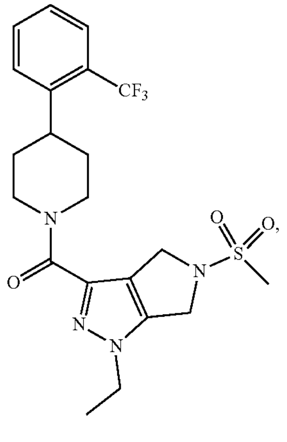
-continued
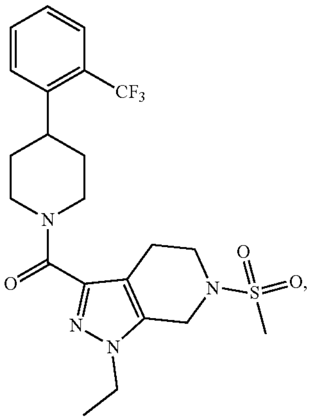
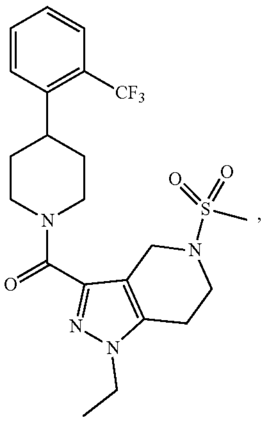
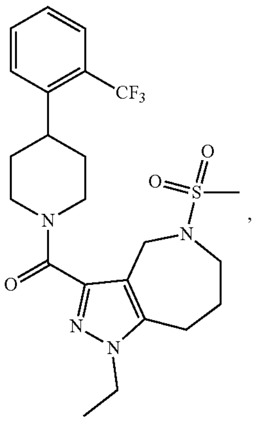
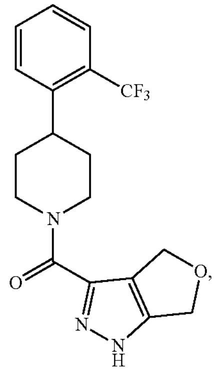
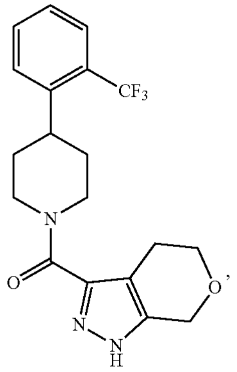
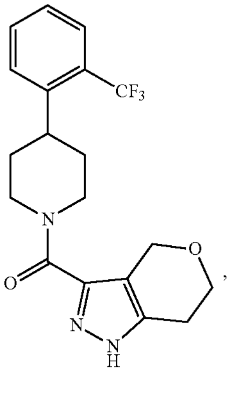
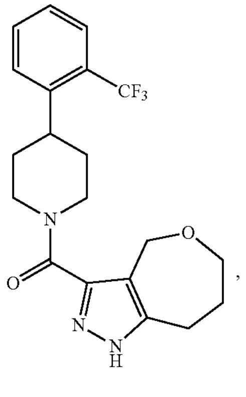

-continued
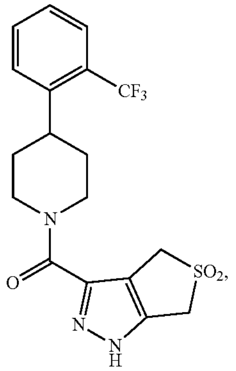
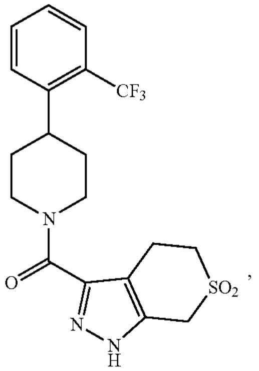
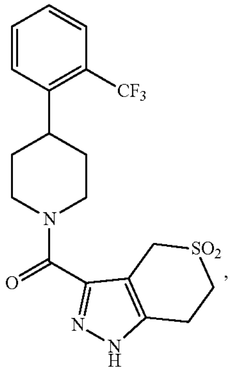
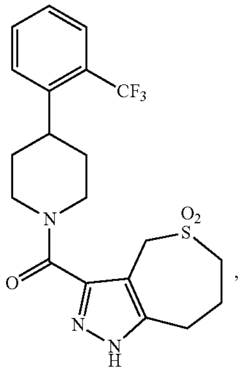
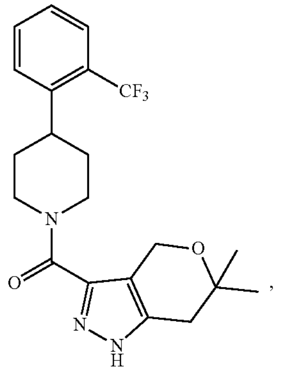
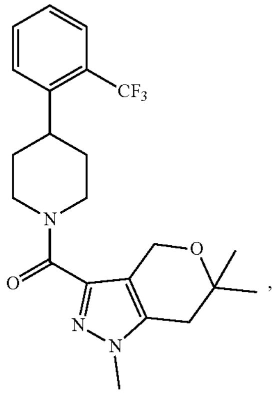
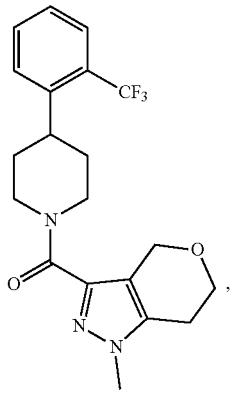
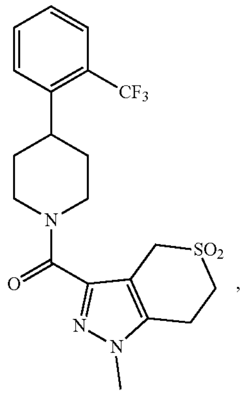
-continued
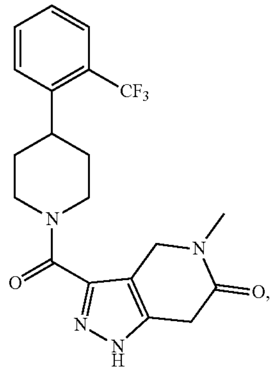
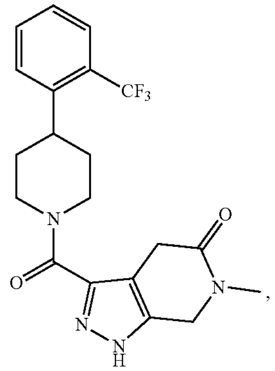
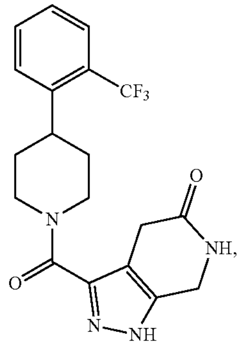
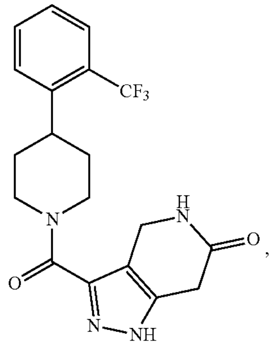
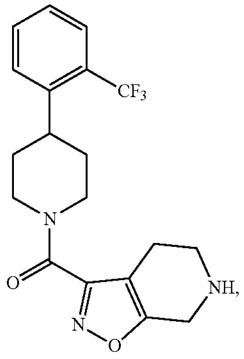
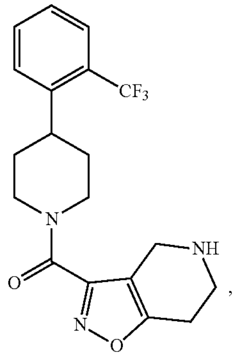
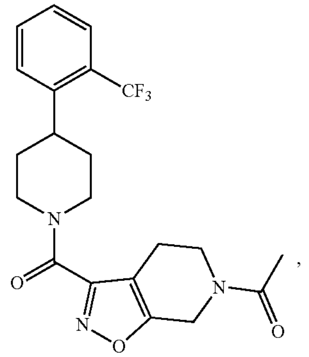

-continued
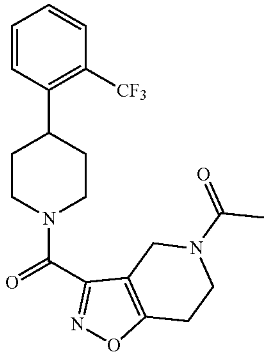
,
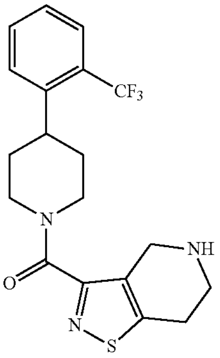
,
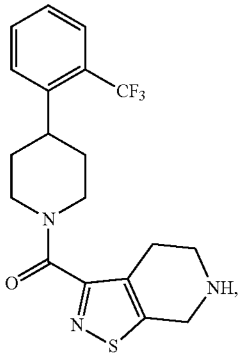
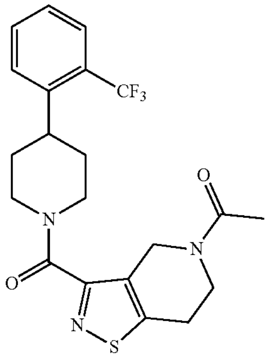
,
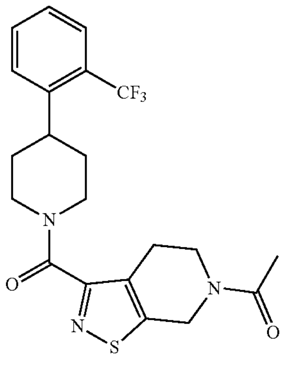
,
-continued
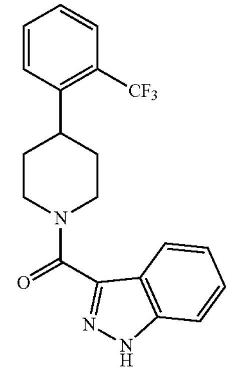
,
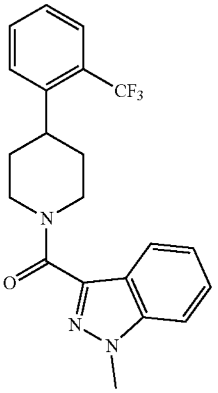
,
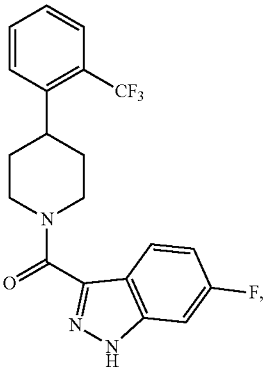
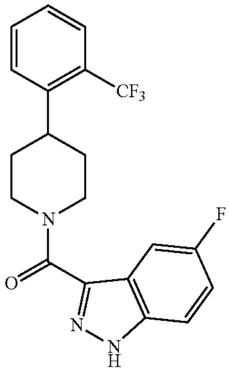
,
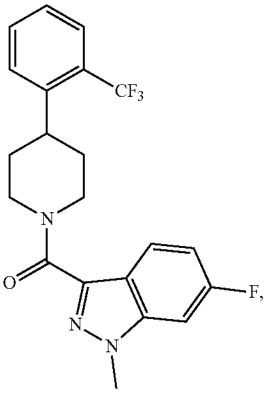
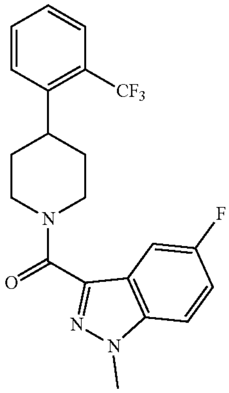
,
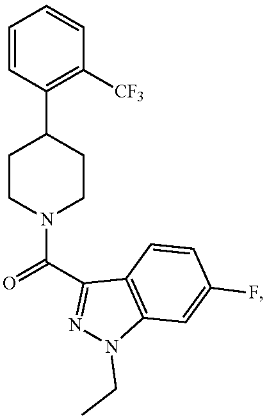
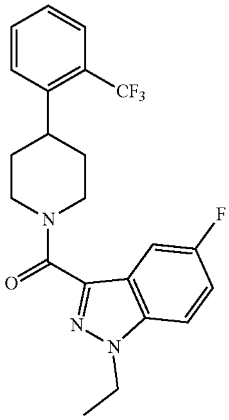
, -continued
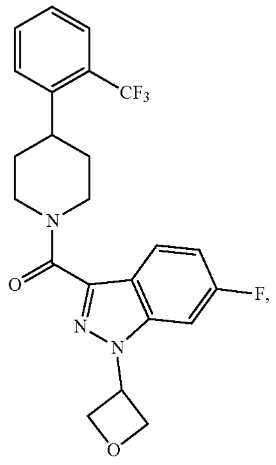
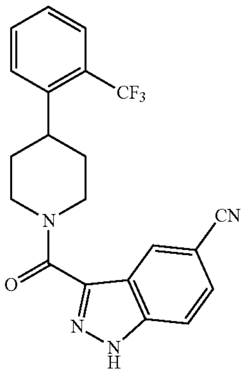
,
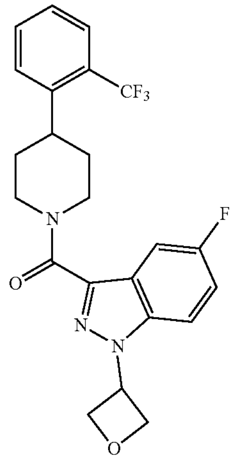
,
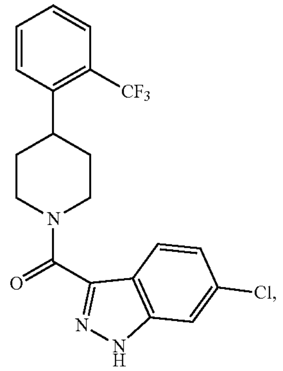
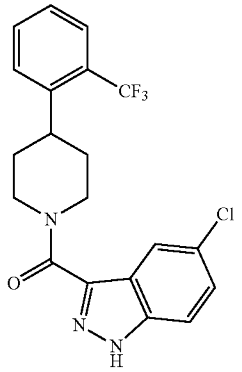
,
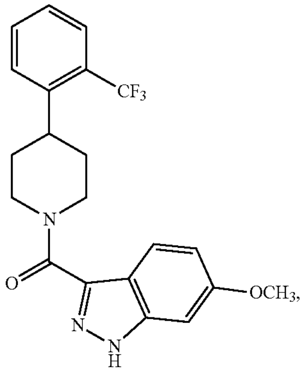
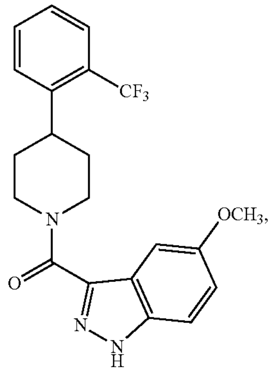
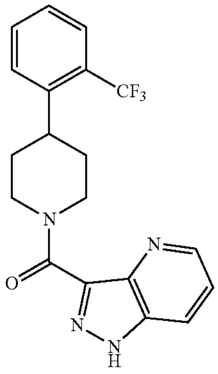
,
-continued
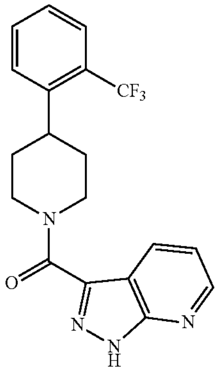
,
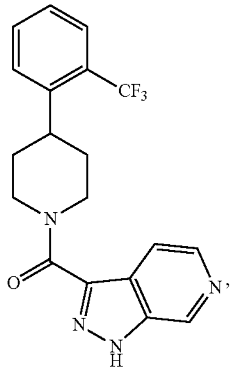
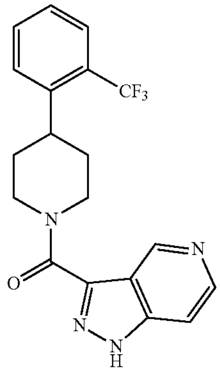
,
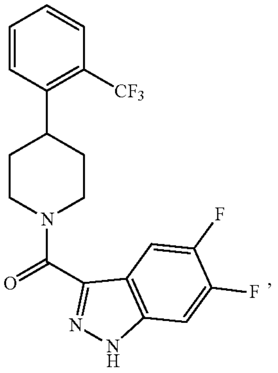
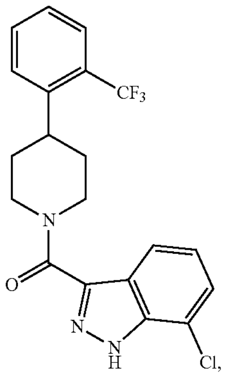
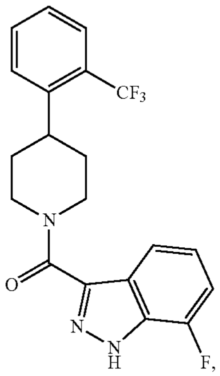
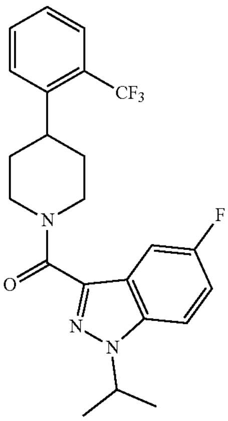
,
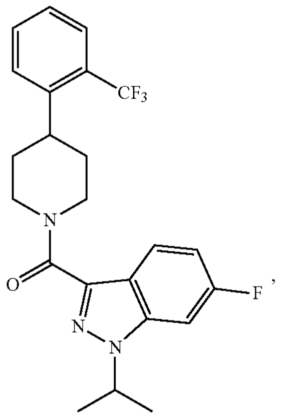

-continued
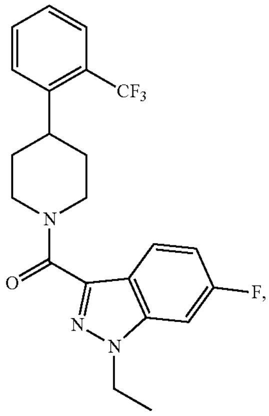
,
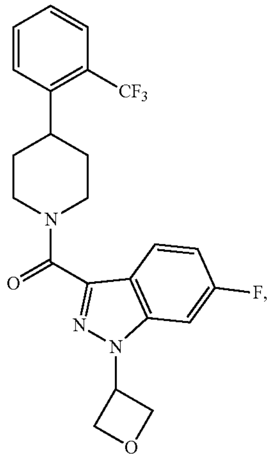
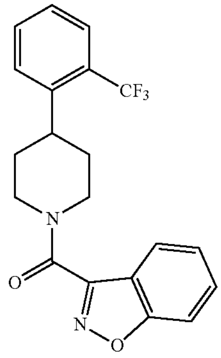
,
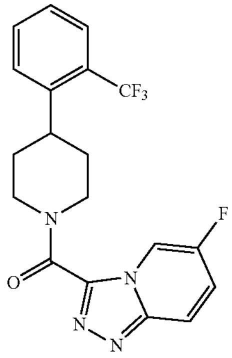
,
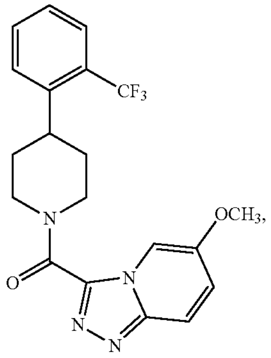
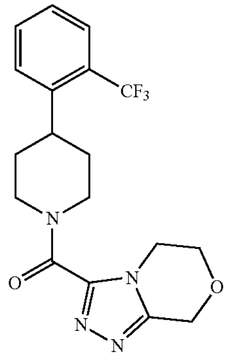
,
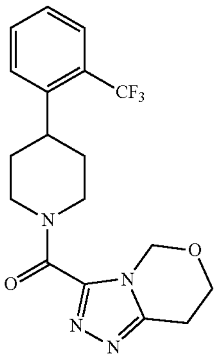
,
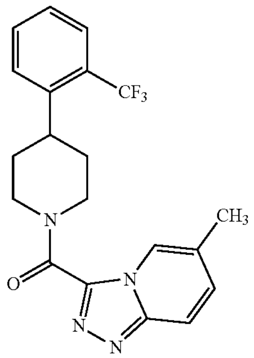
,
-continued
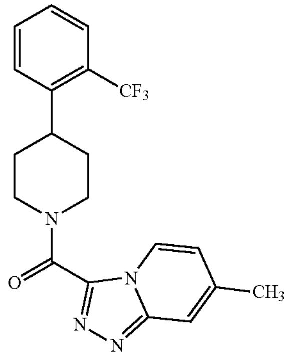
,
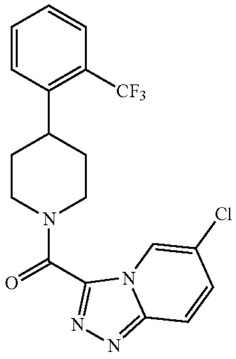
,
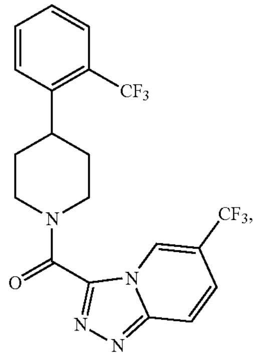
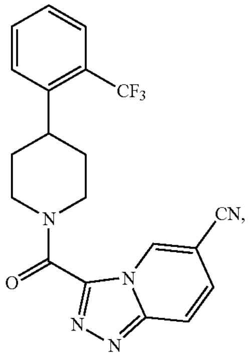
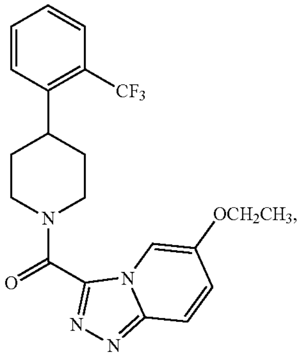
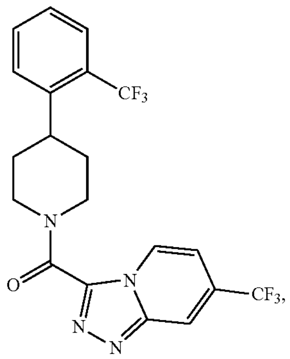

-continued
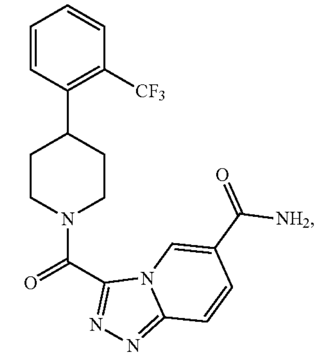
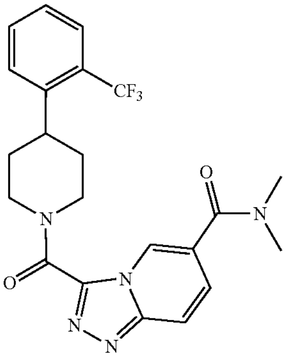
,
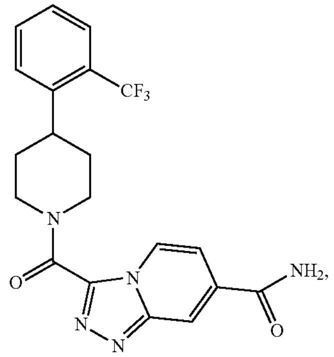
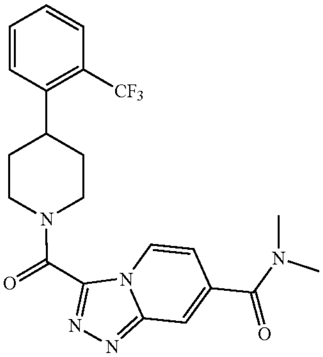
,
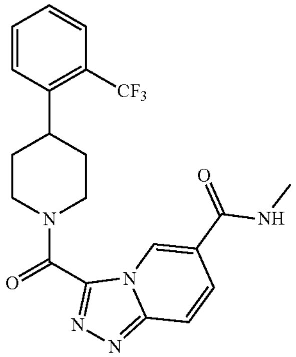
,
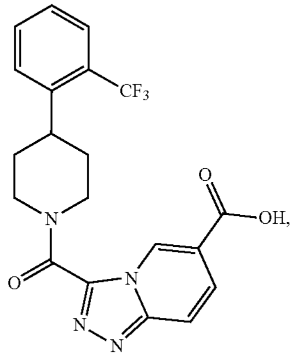
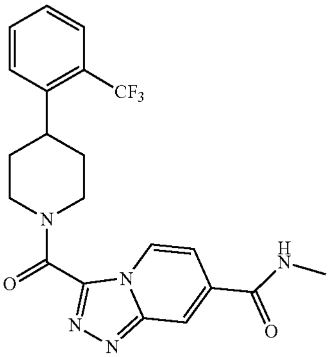
,
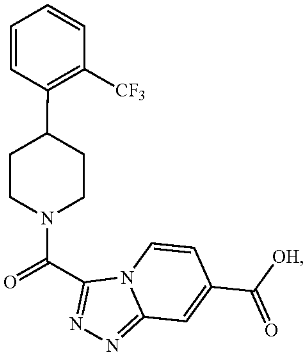

-continued
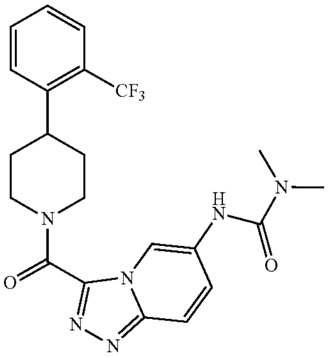
,
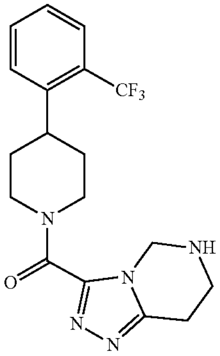
,
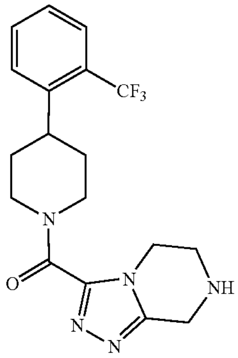
,
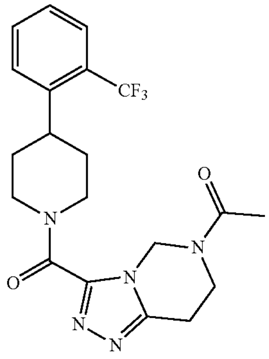
,
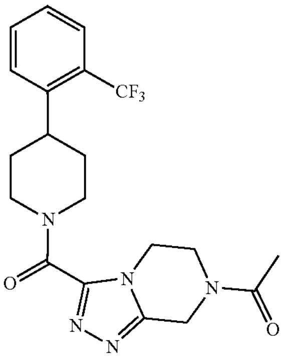
,
-continued
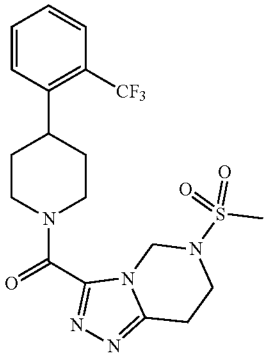
,
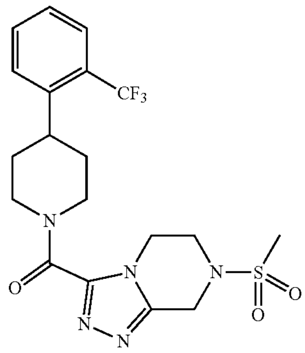
,
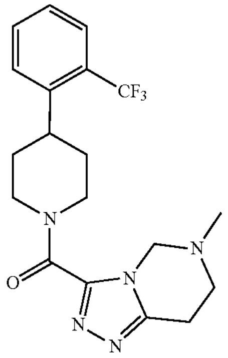
,
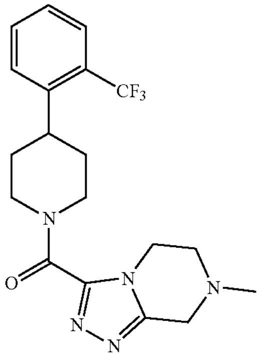
,
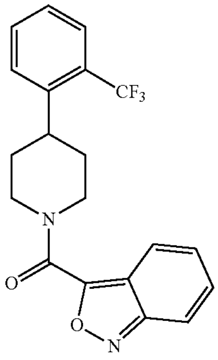
,
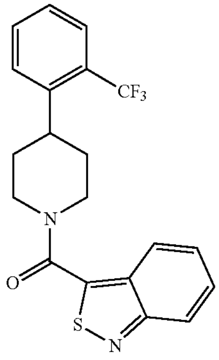
,
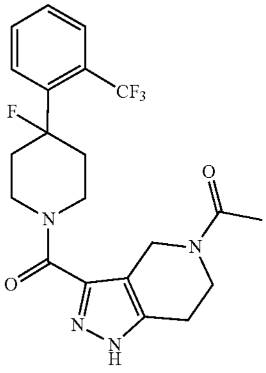
, -continued
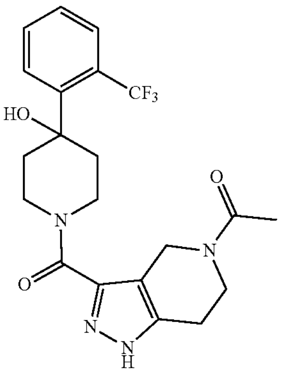
,
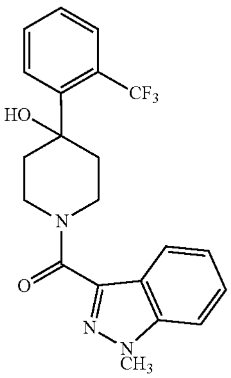
,
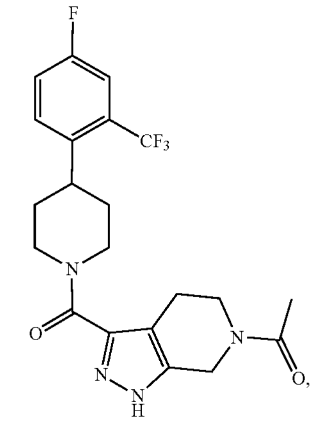
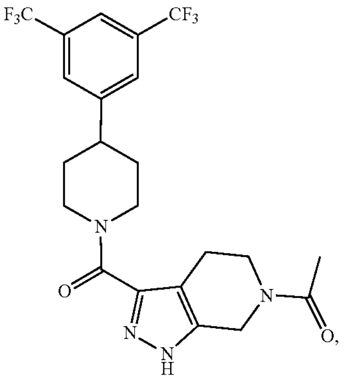
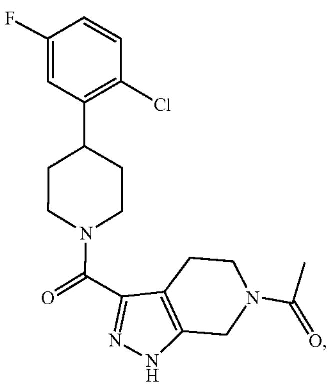
-continued
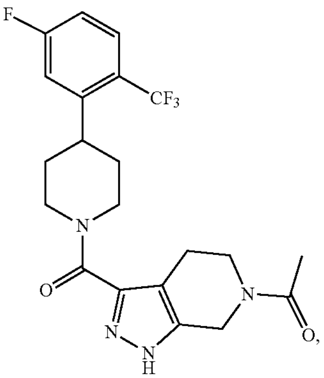
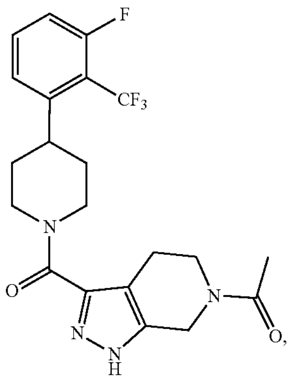
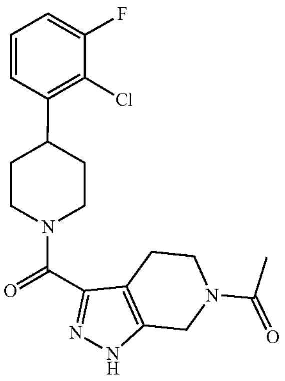
,
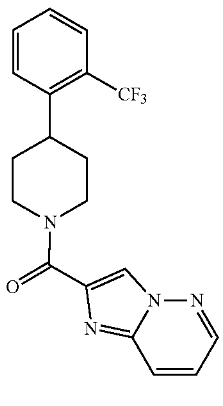
,
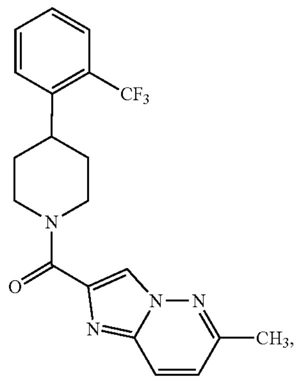

-continued
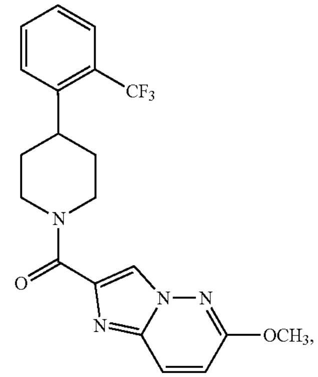
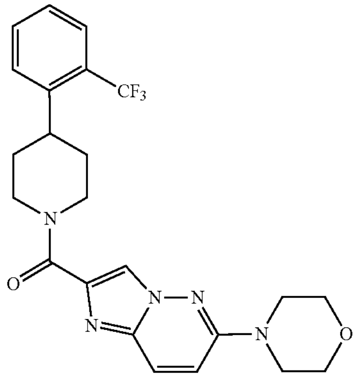
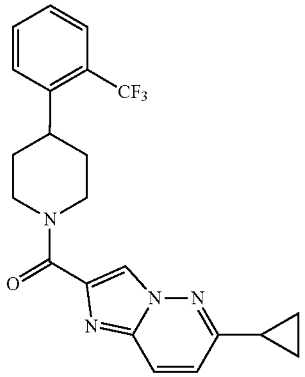
,
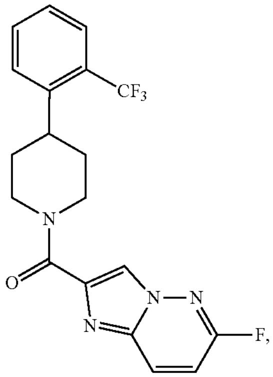
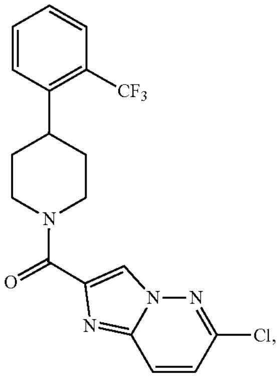
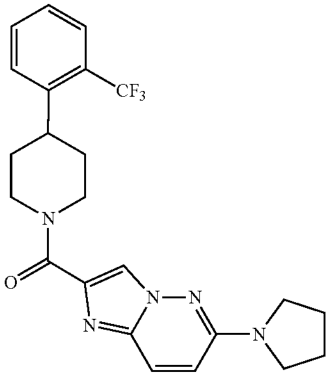
,
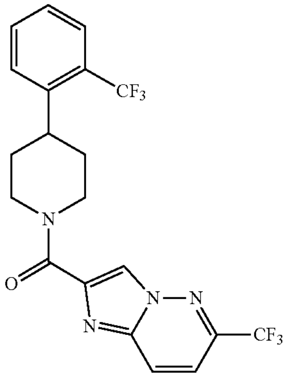
,
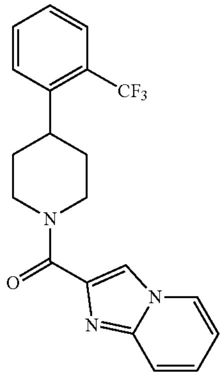
,
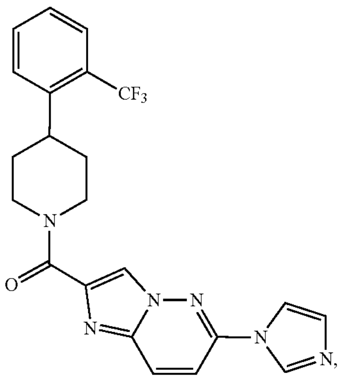
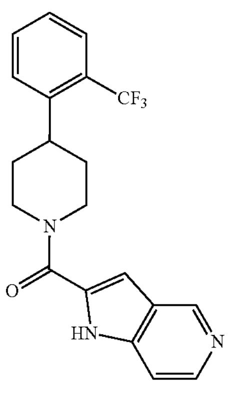
,
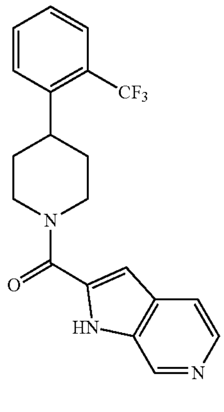
, -continued
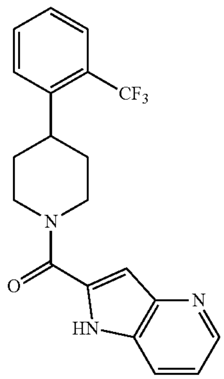
,
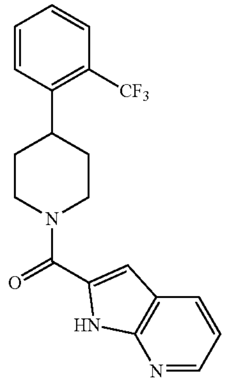
,
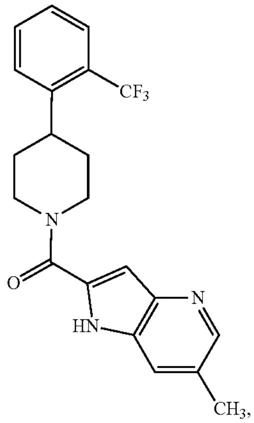
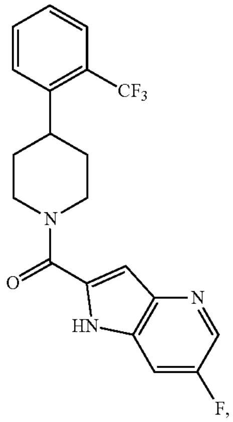
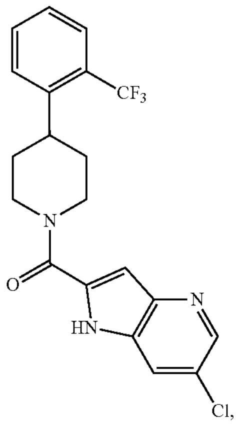
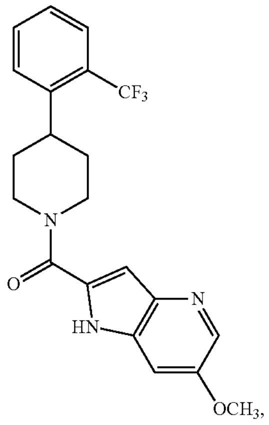
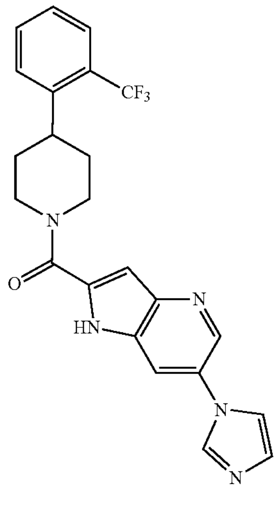
,
-continued
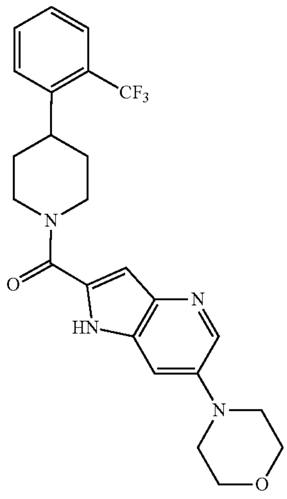
,
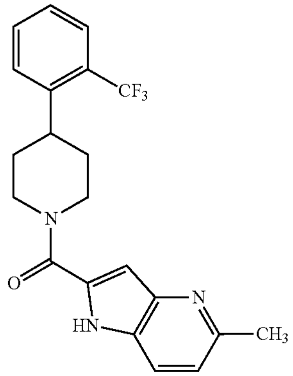
,
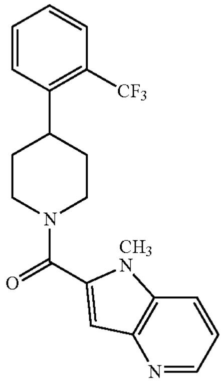
,
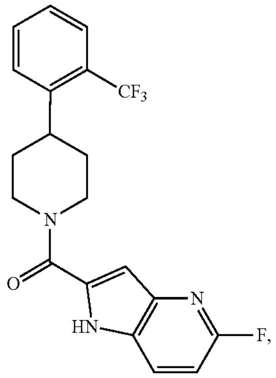
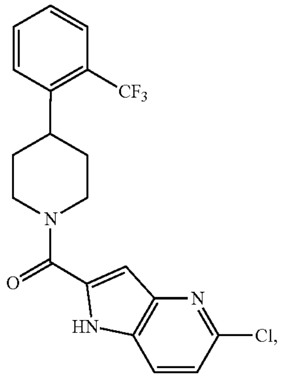
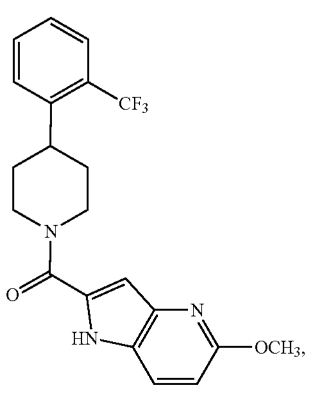

-continued
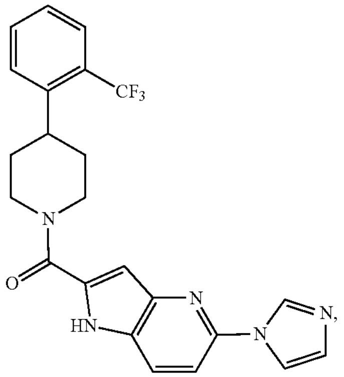
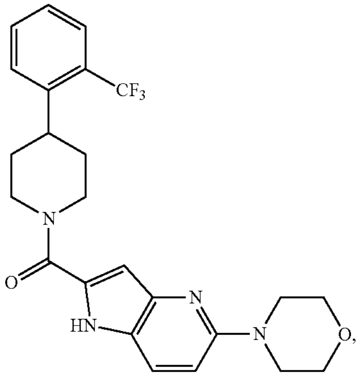
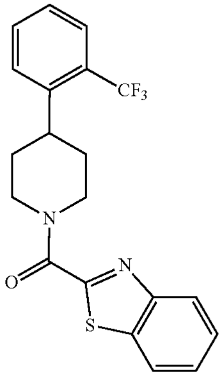
,
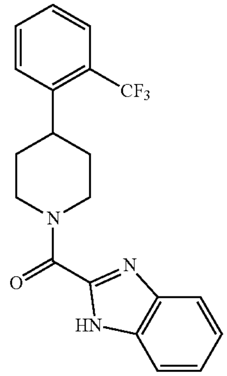
,
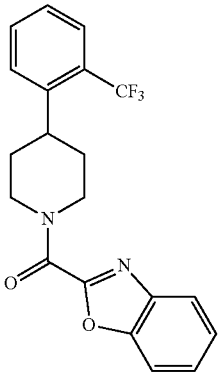
,
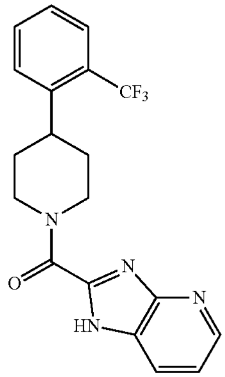
,
-continued
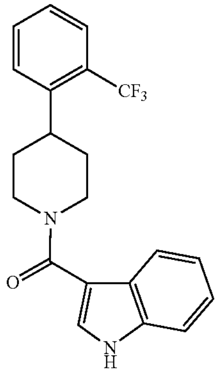
,
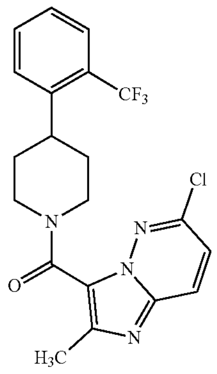
,
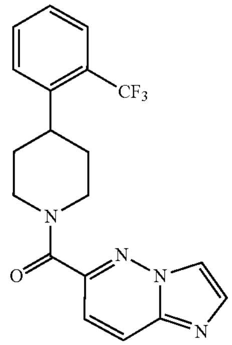
,
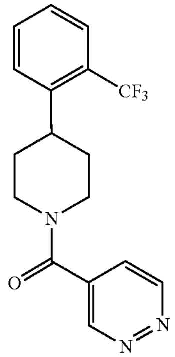
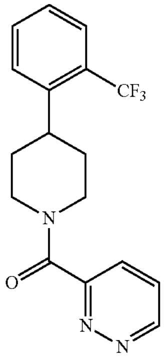
,
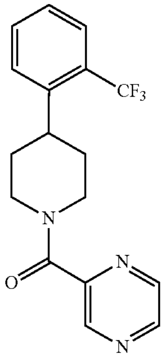
,
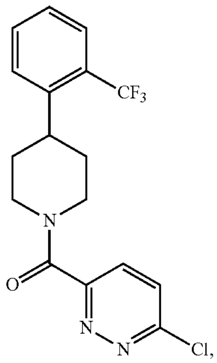
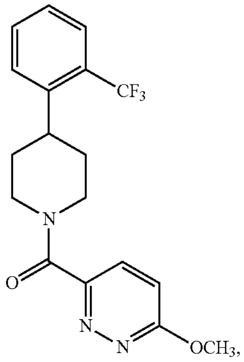

-continued
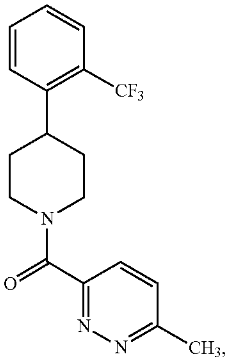
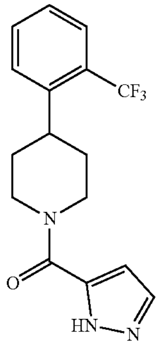
,
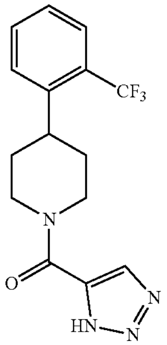
,
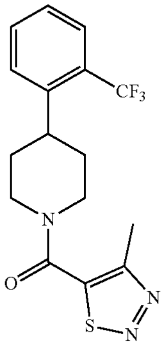
,
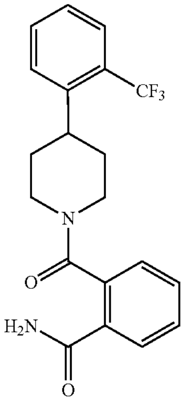
,
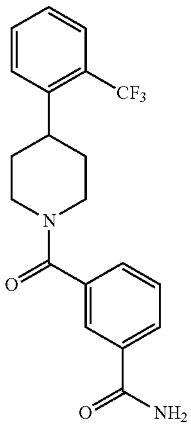
,
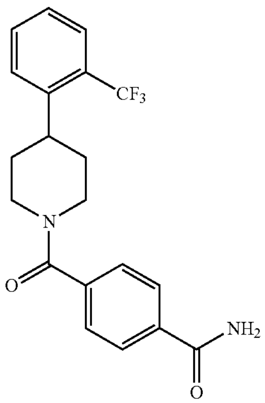
,
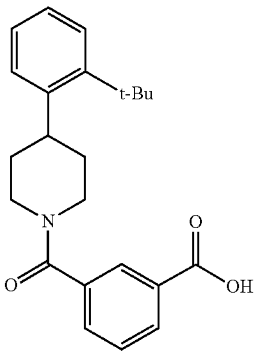
,
-continued
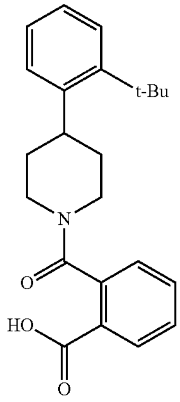
,
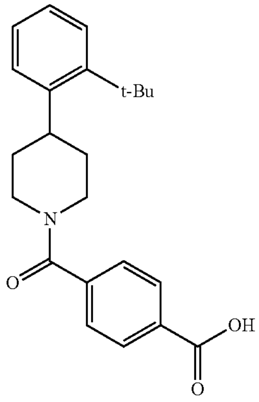
,
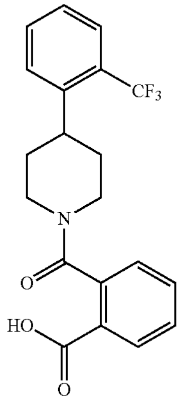
,
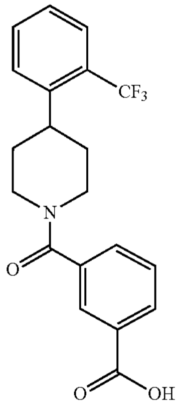
,
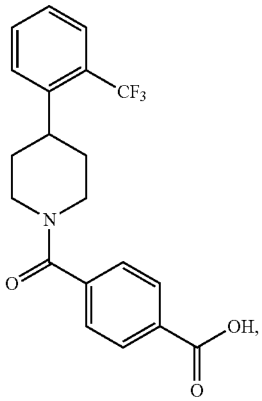
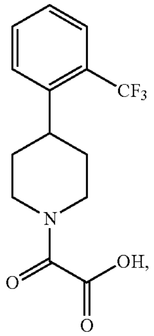
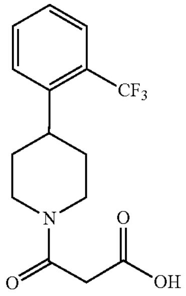
,
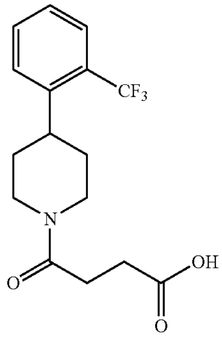
, -continued
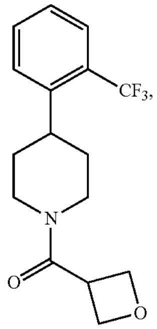
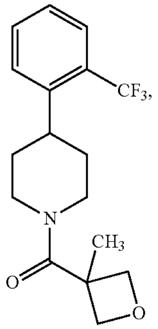
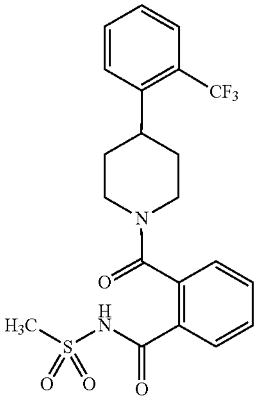
,
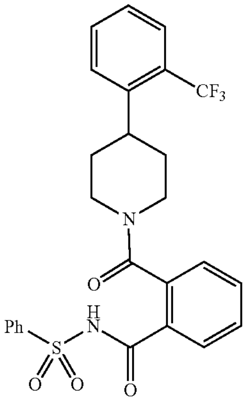
,
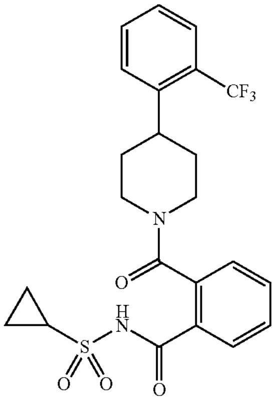
,
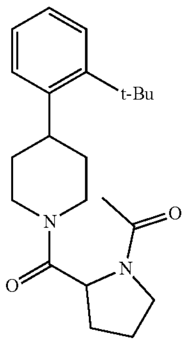
,
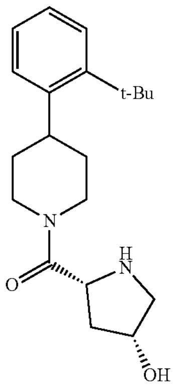
,
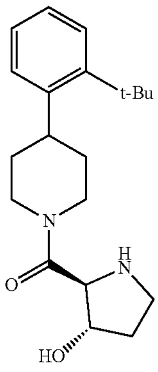
,
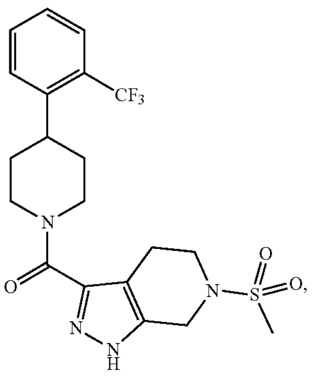
,
-continued
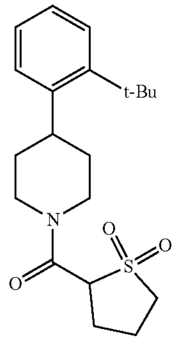
,
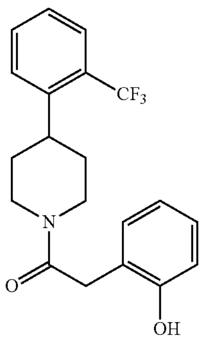
,
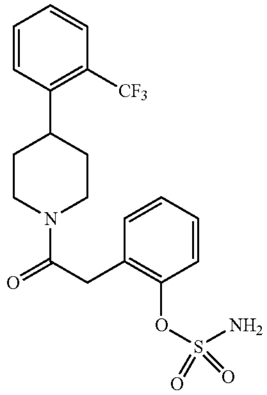
,
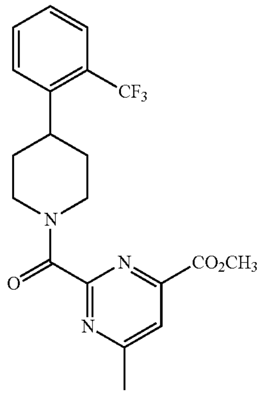
,
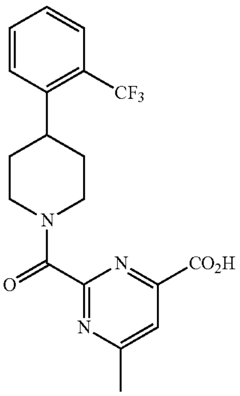

-continued
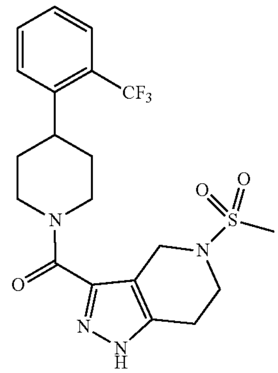
,
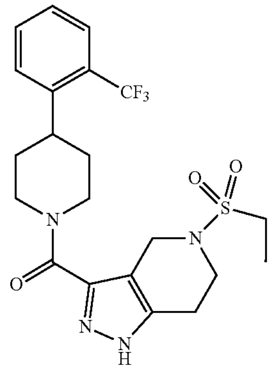
,
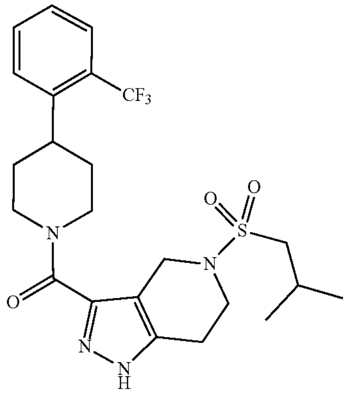
,
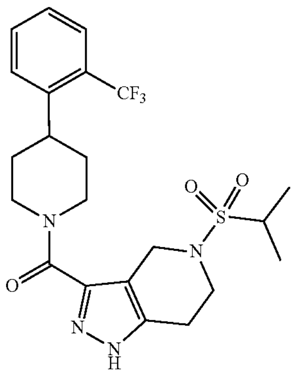
,
-continued
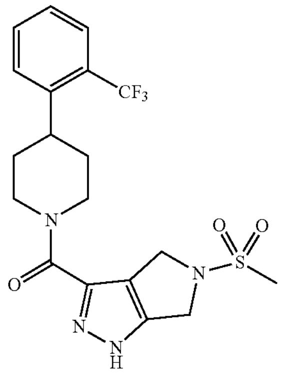
,
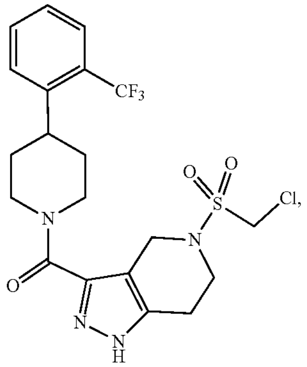
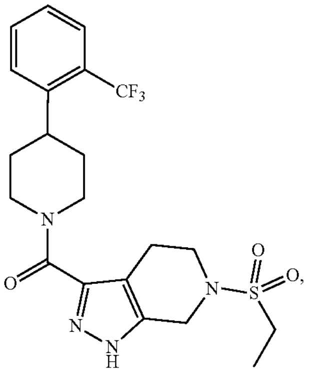
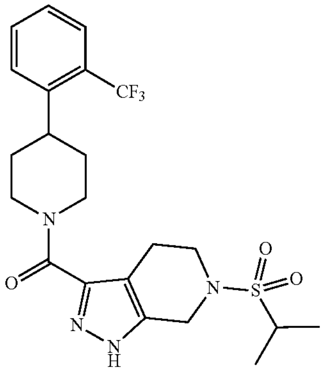
, -continued
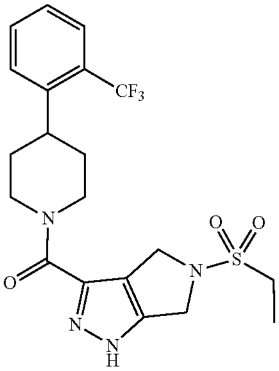
,
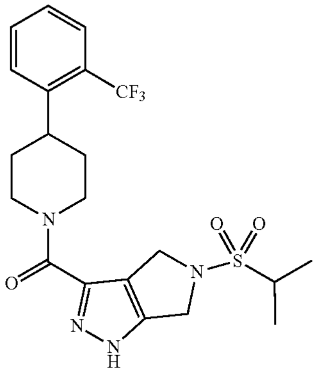
,
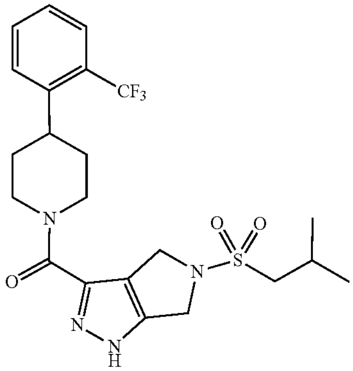
,
-continued
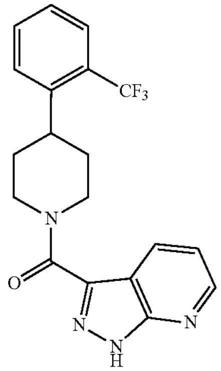
,
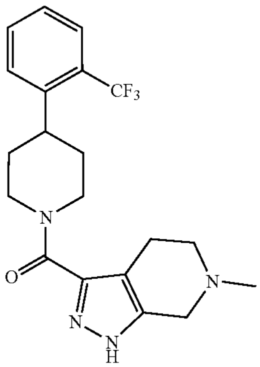
,
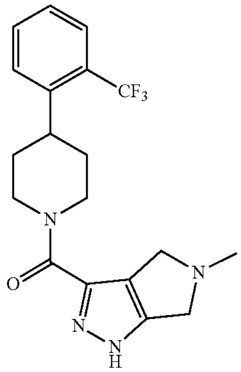
,
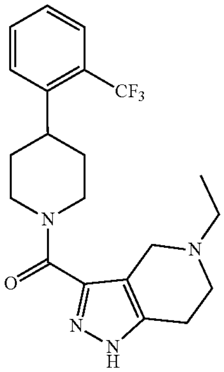
,
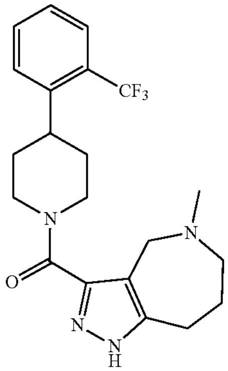
,
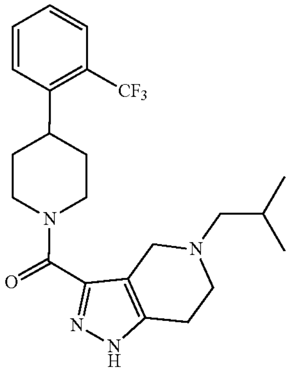
,
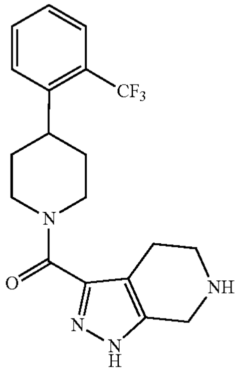
,
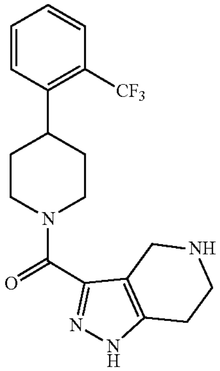
,
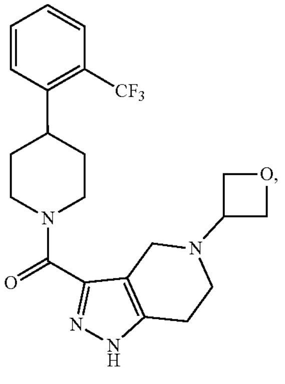

-continued
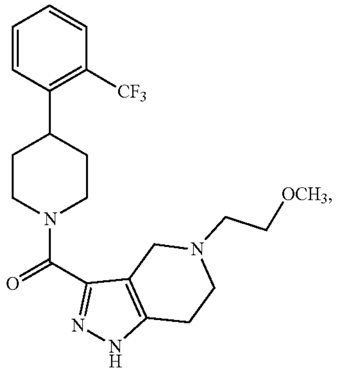
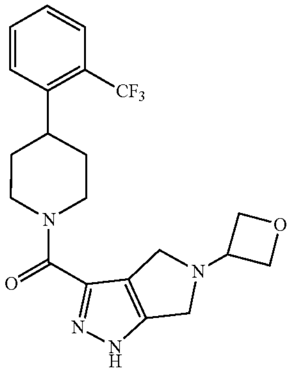
,
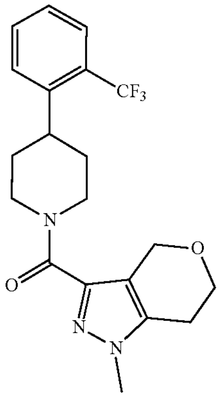
,
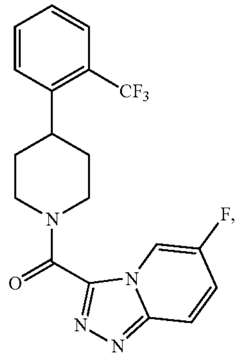
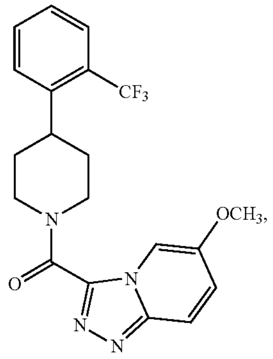
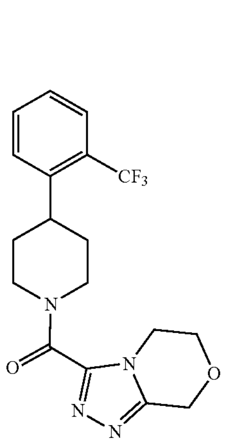
,
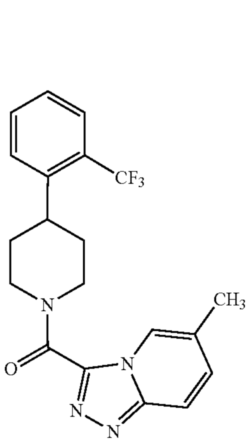
,
-continued
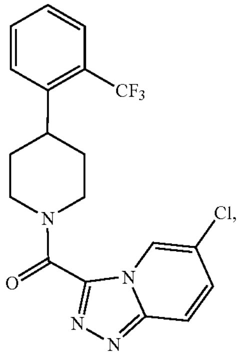
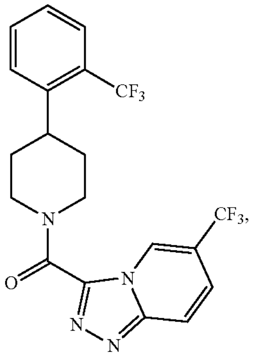
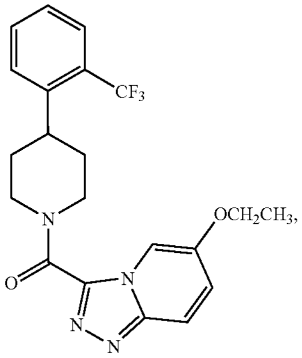
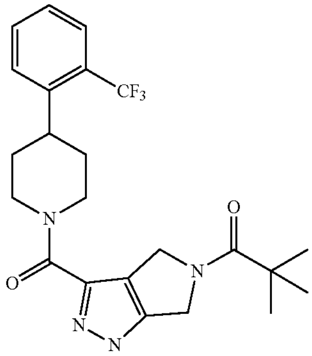
,
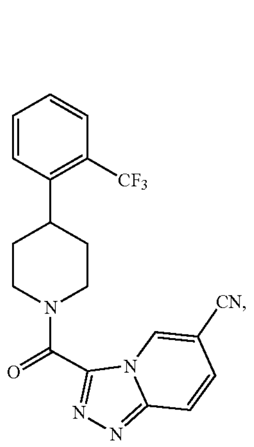

-continued
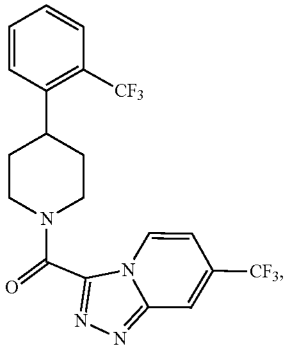
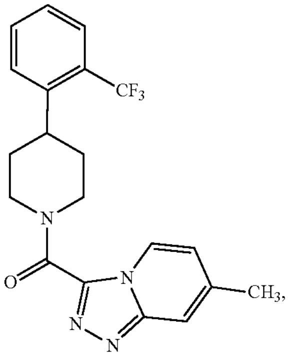
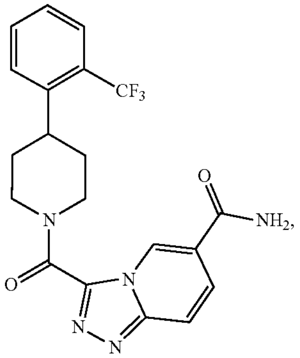
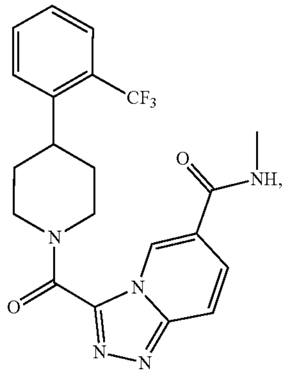
-continued
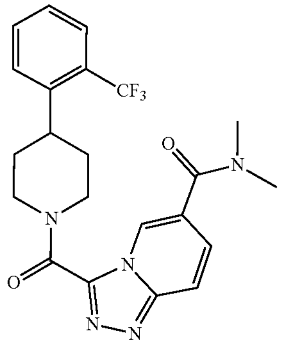
,
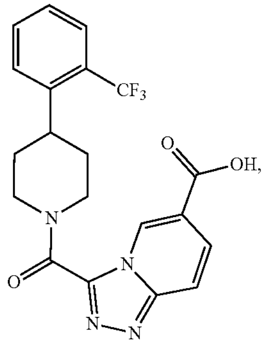
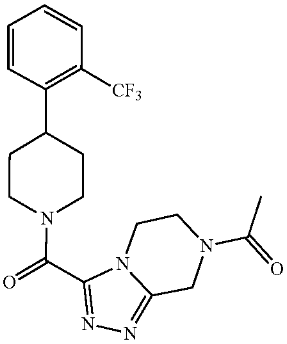
,
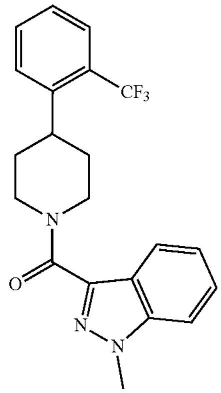
,
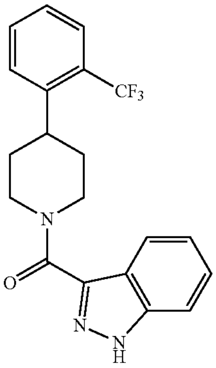
,
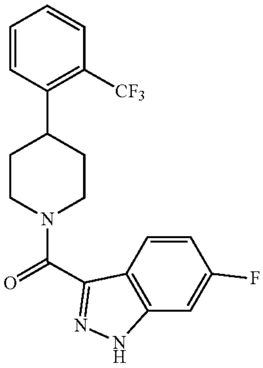
, -continued
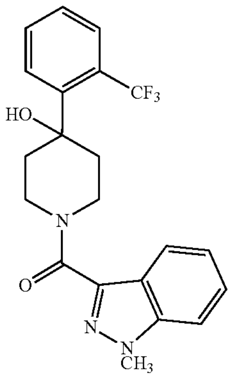
,
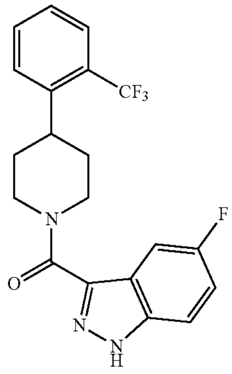
,
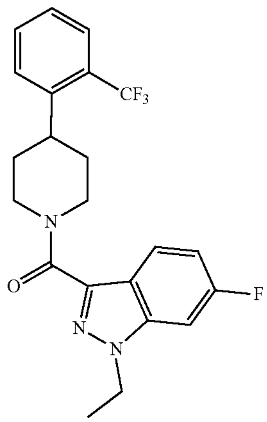
,
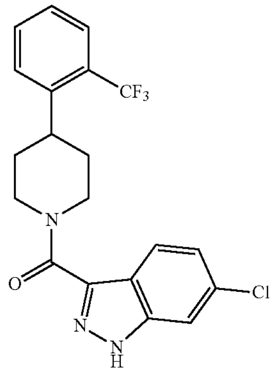
,
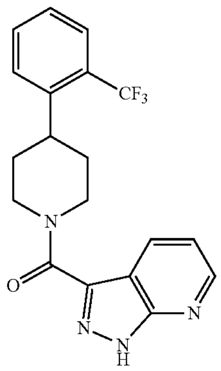
,
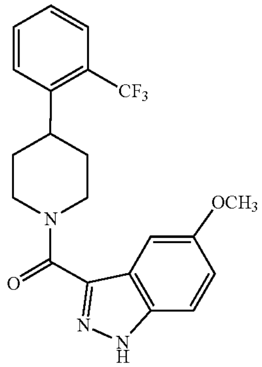
,
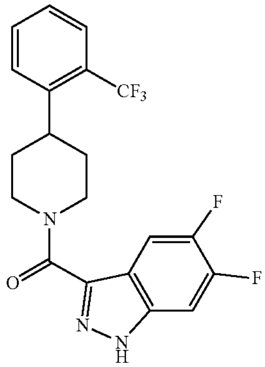
,
-continued
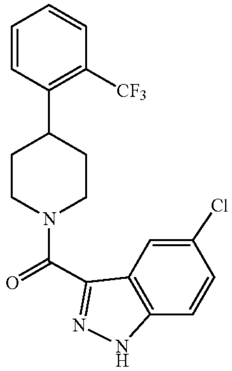
,
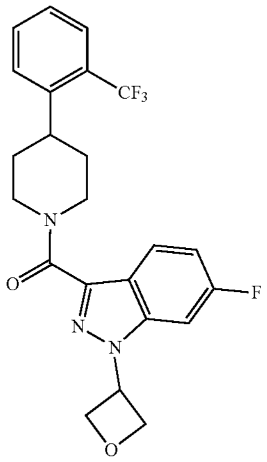
,
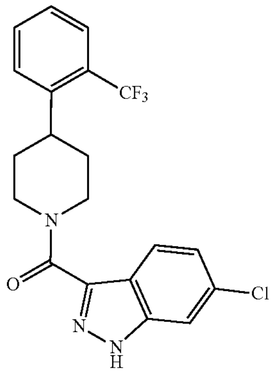
,
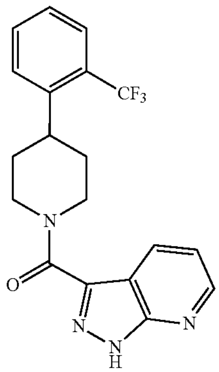
,
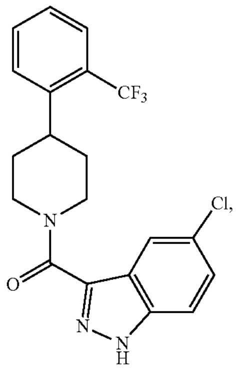
,
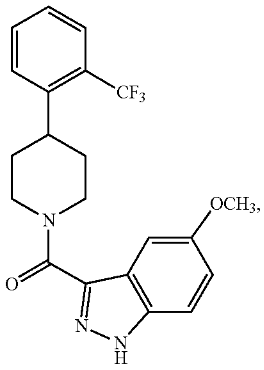
,
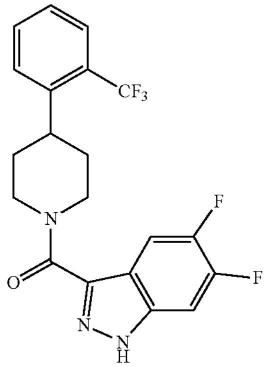
,
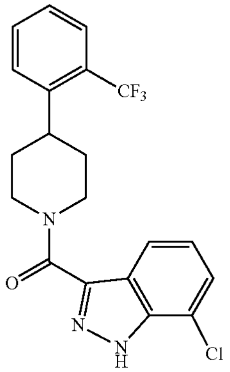
,

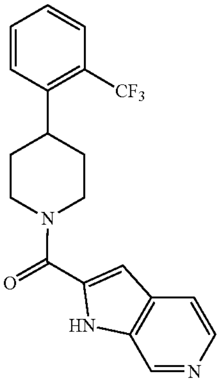
,
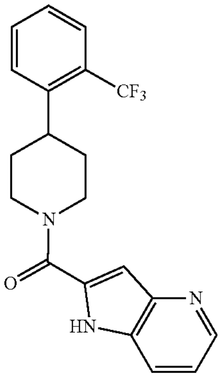
,
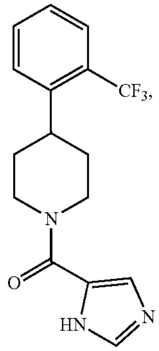
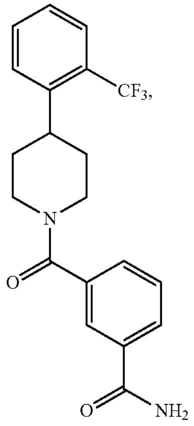
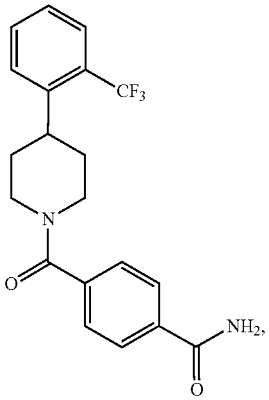
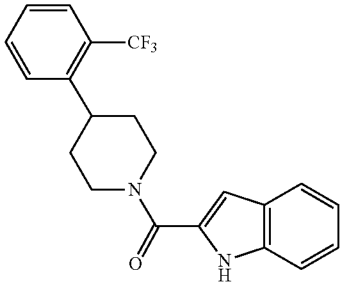
,
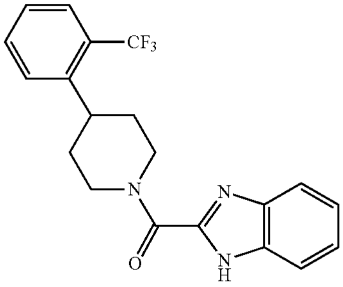
,
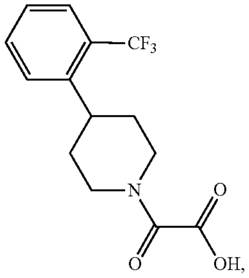
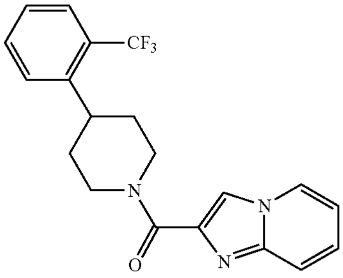
,
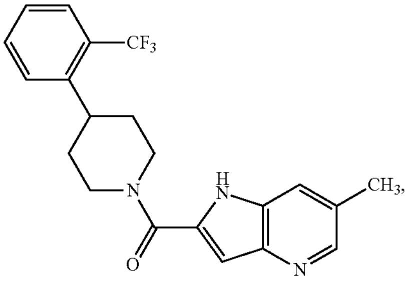
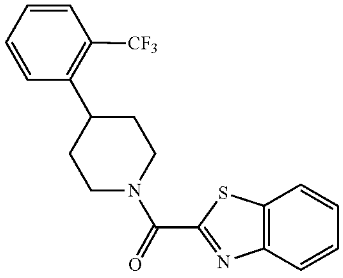
,
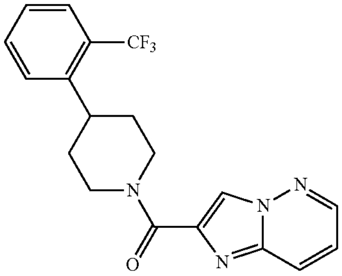
, -continued
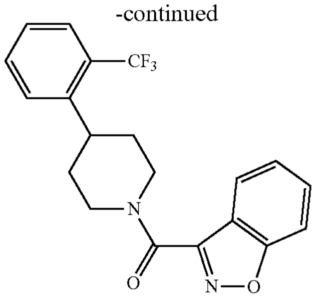
,
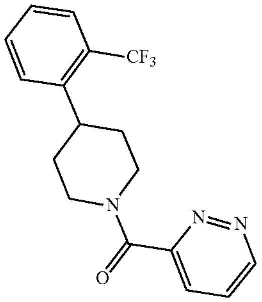
,
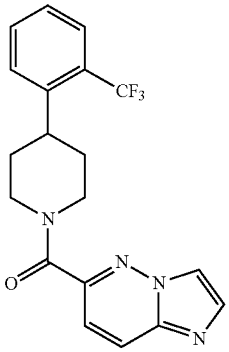
,
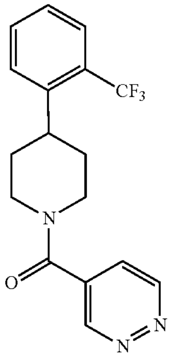
,
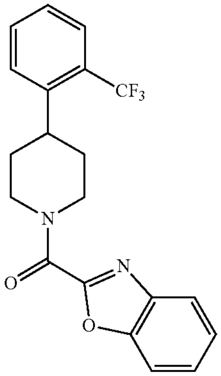
,
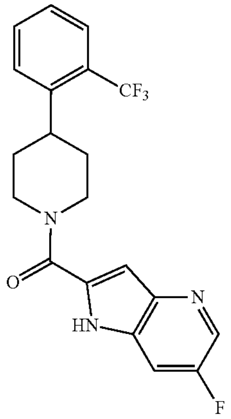
,
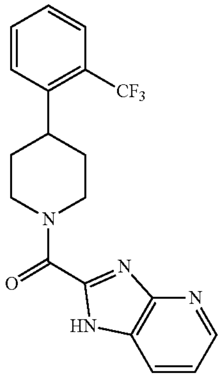
,
-continued
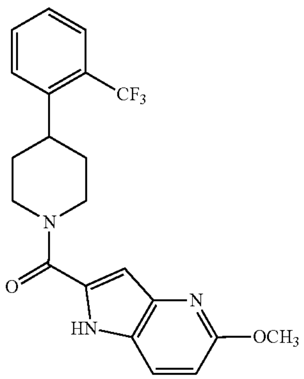
,
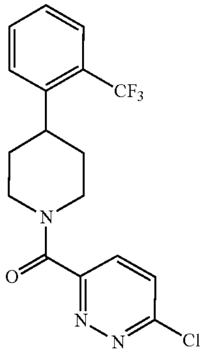
,
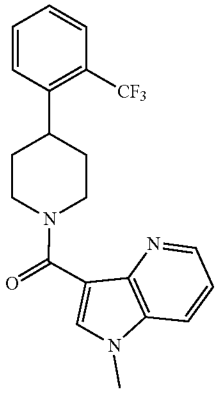
,
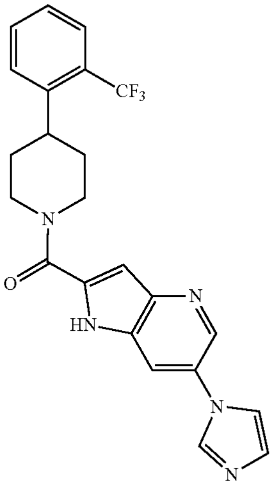
,
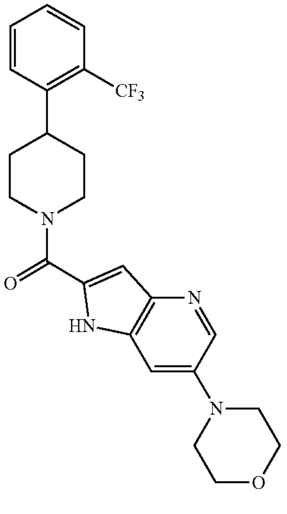
,
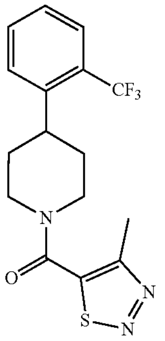
, -continued
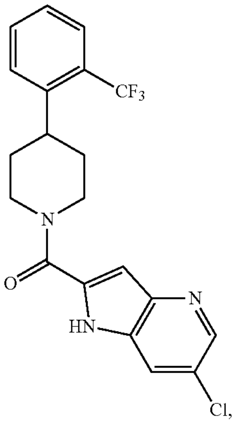
,
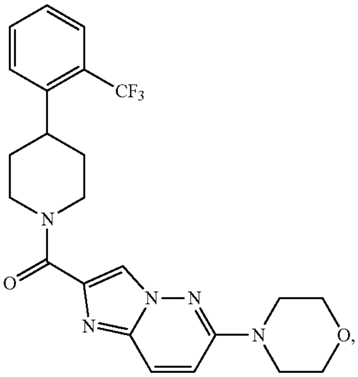
,
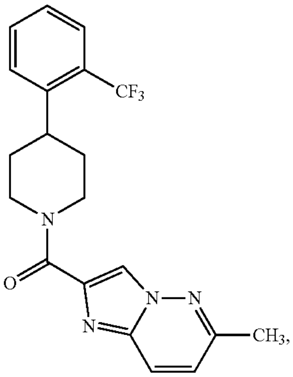
,
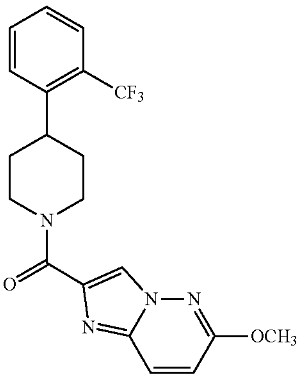
,
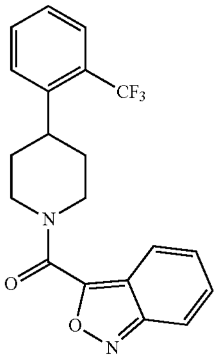
,
-continued
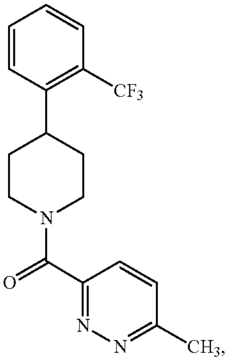
,
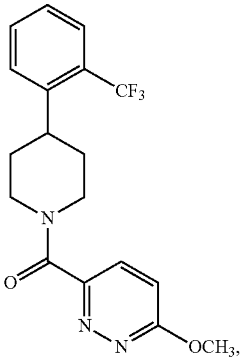
,
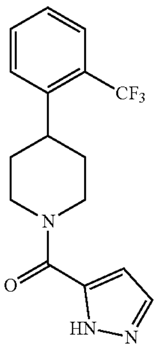
,
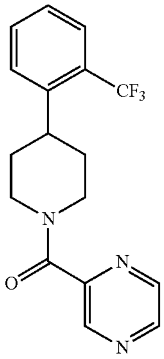
,
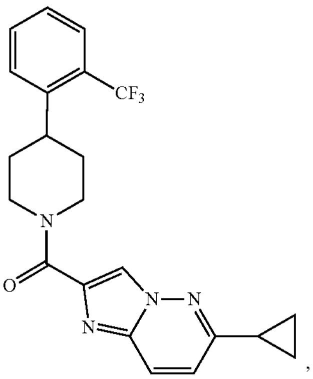
,
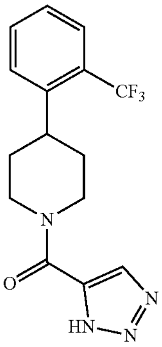
,
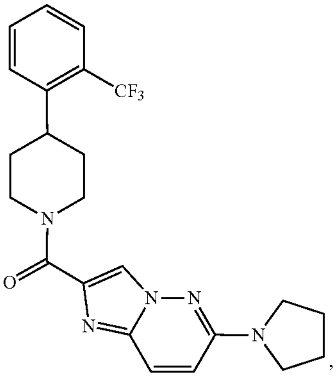
, -continued
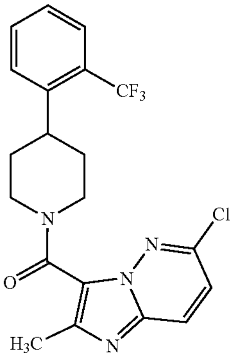
,
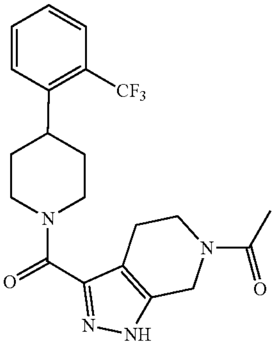
,
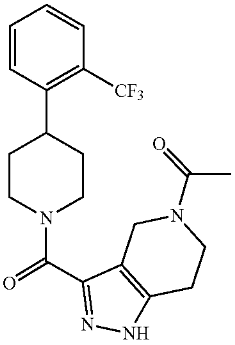
,
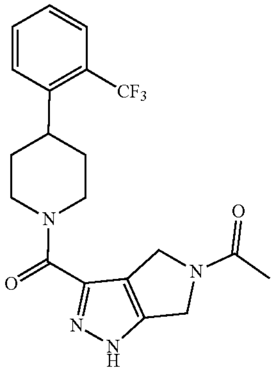
,
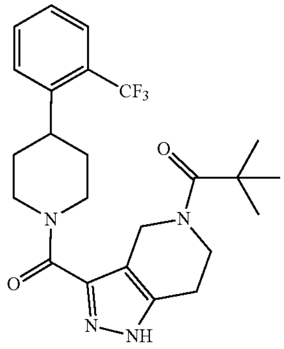
,
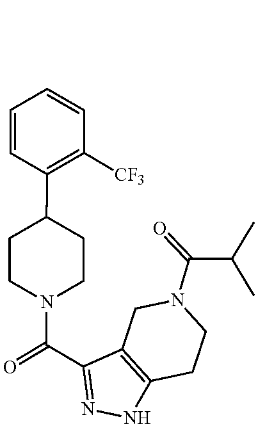
,
-continued
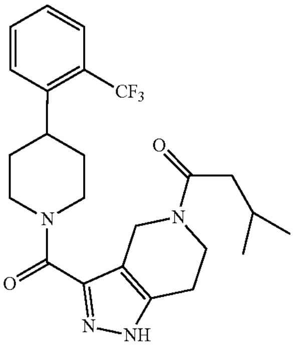
,
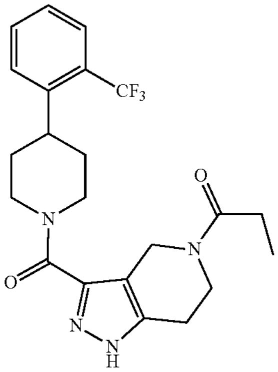
,
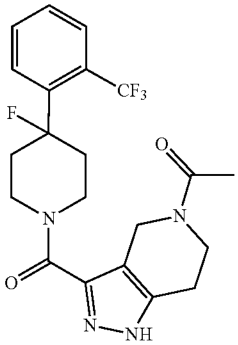
,
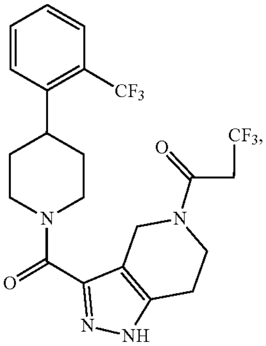
,
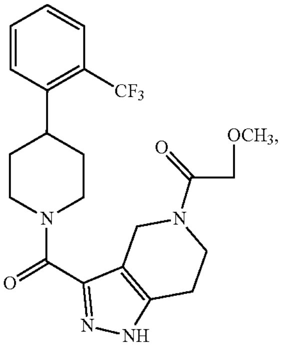
,
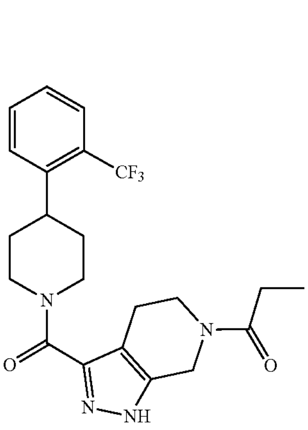
, -continued
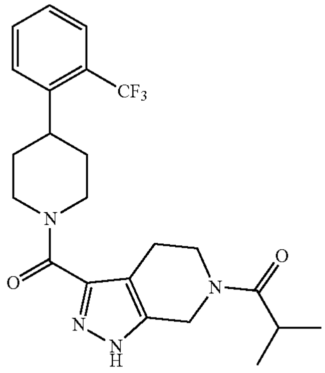
,
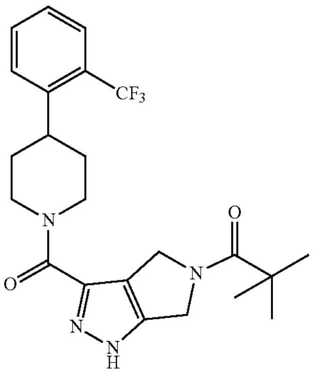
,
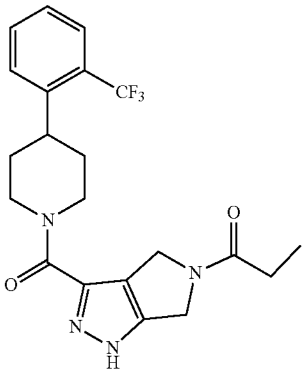
,
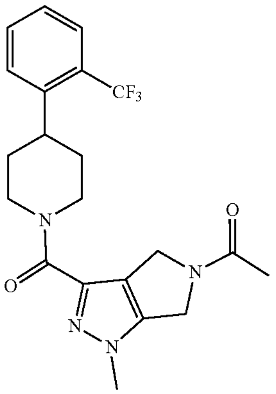
,
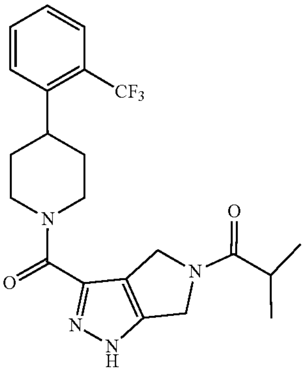
,
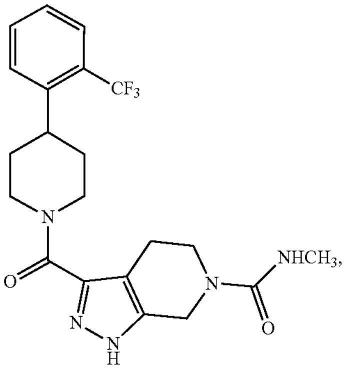
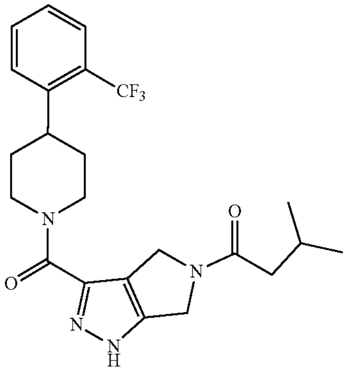
,
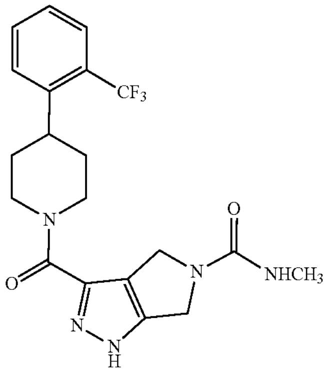
, or -continued
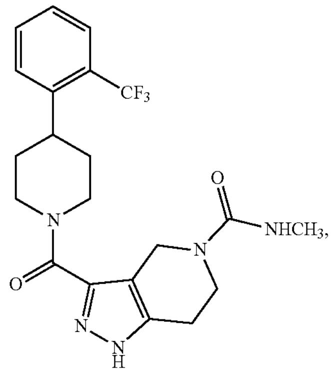
or pharmaceutically acceptable salt thereof.
In some embodiments, the compounds is
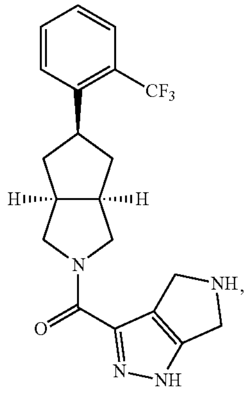
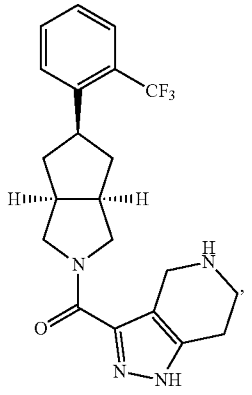
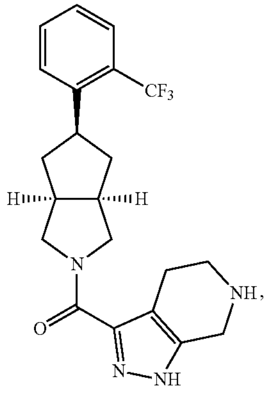
-continued
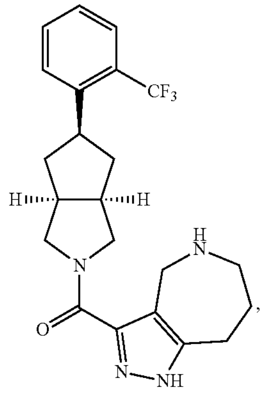
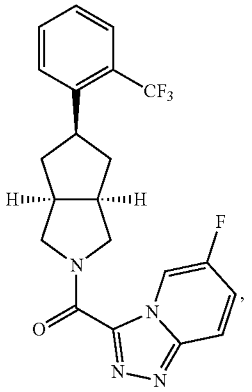
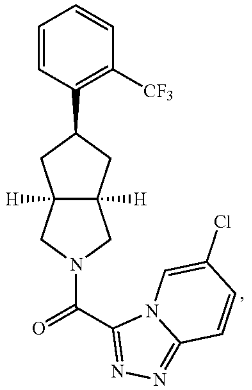
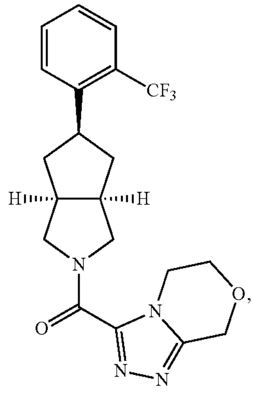

-continued
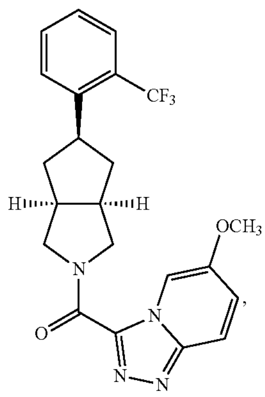
,
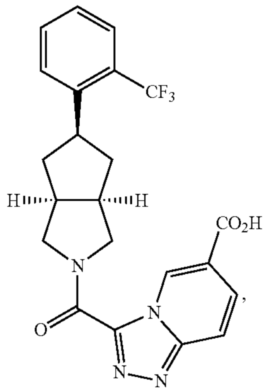
,
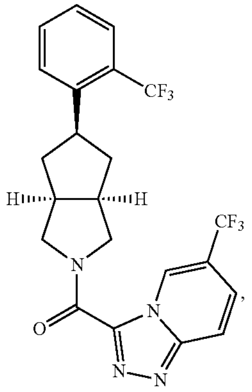
,
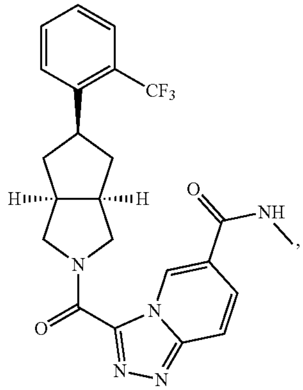
,
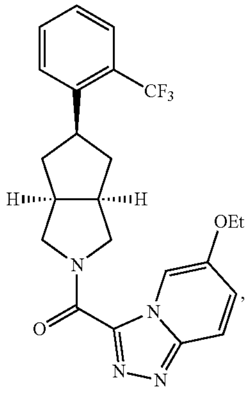
,
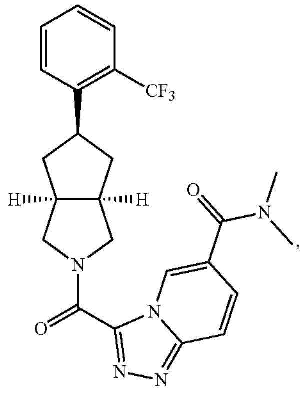
,
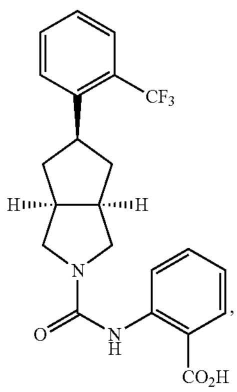
,
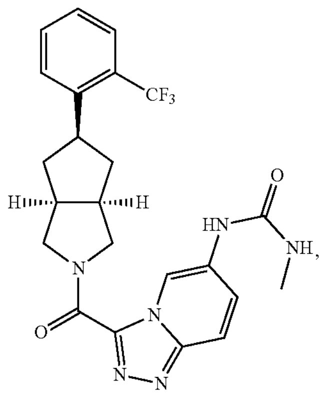
, -continued
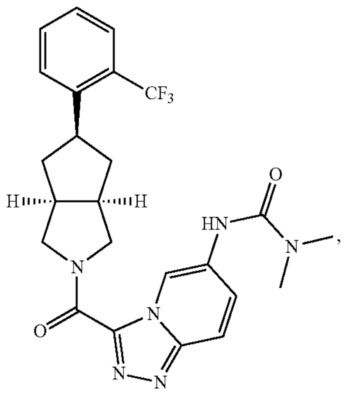
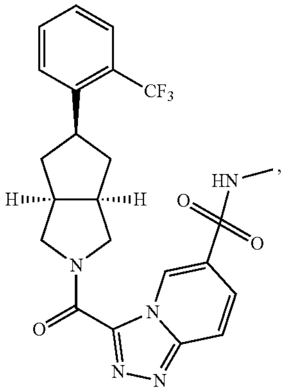
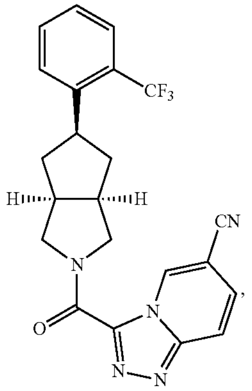
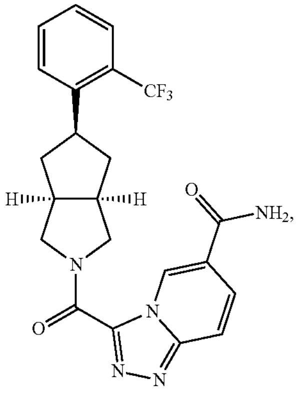
-continued
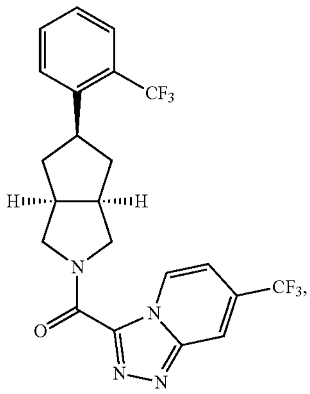
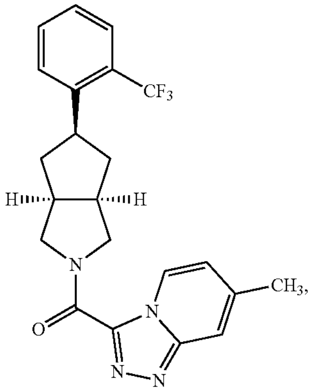
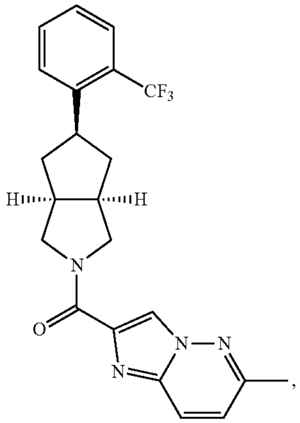
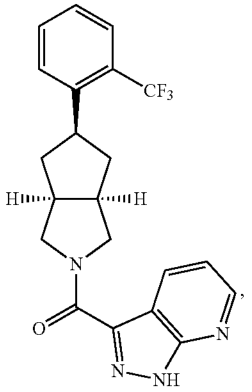

-continued
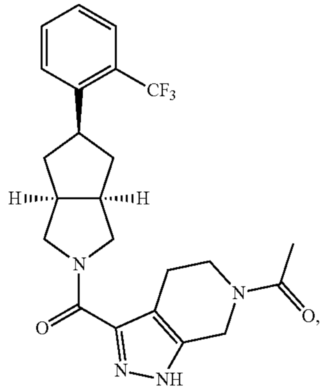
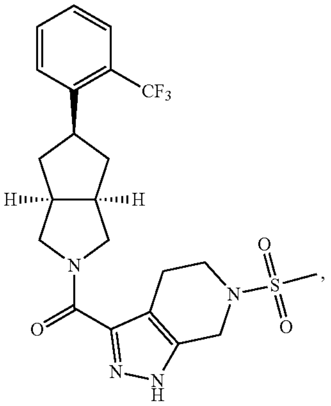
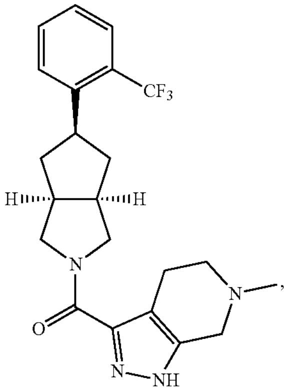
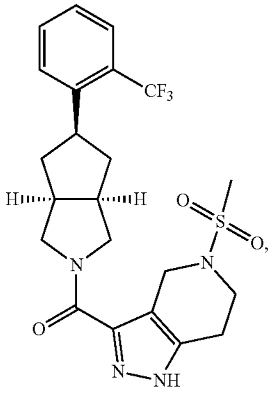
-continued
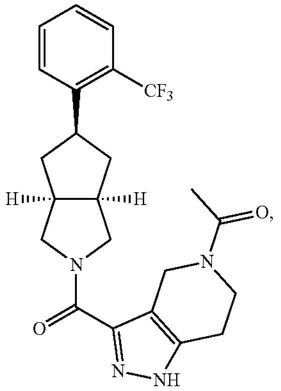
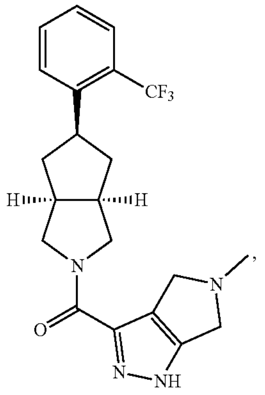
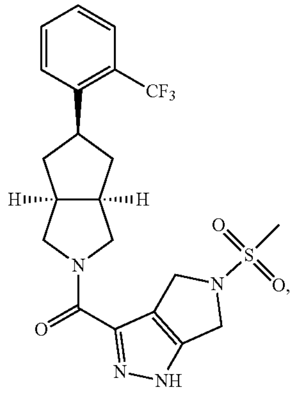
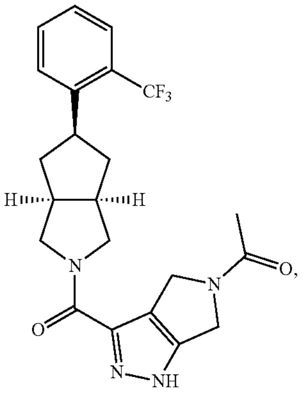

-continued
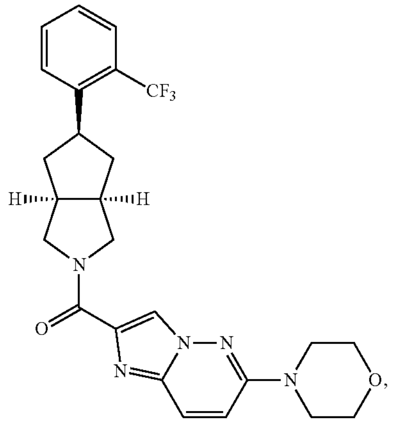
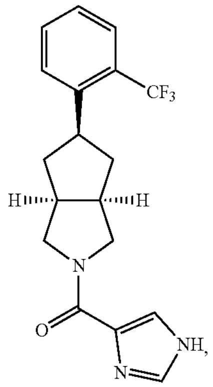
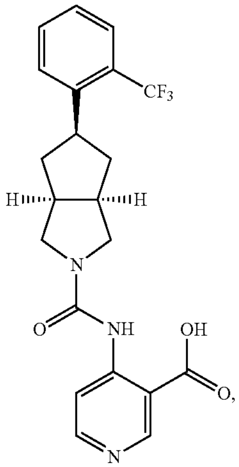
-continued
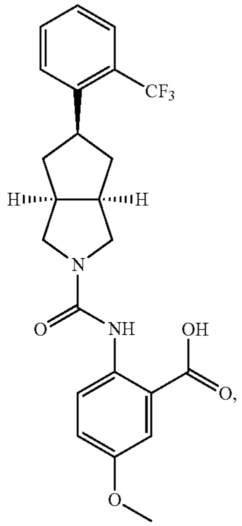
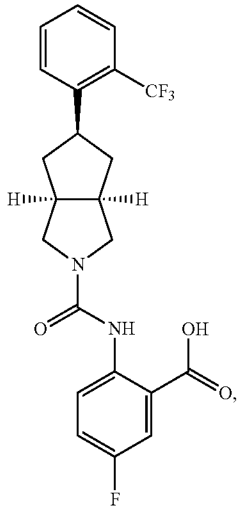
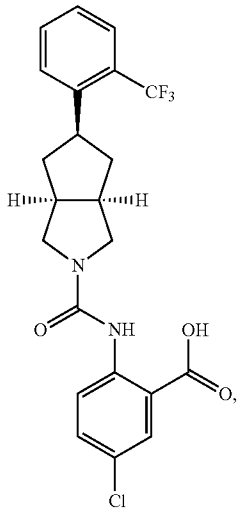

-continued
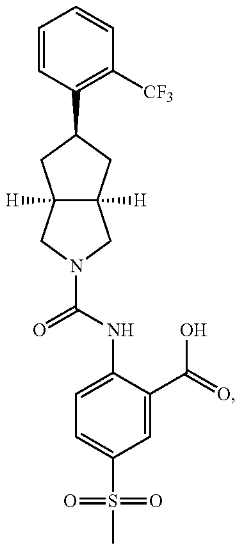
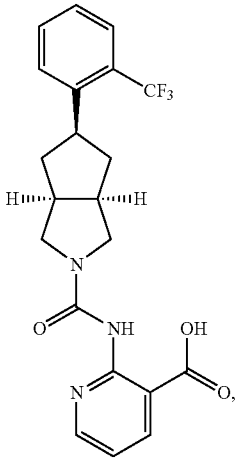
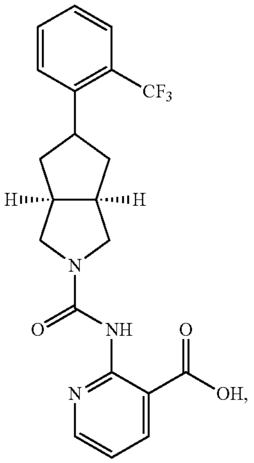
-continued
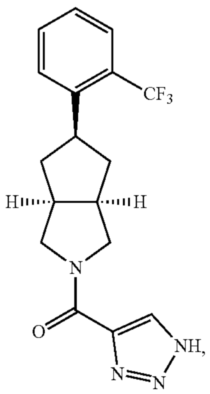
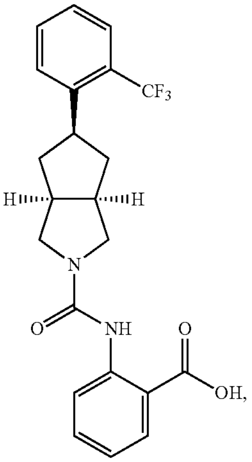
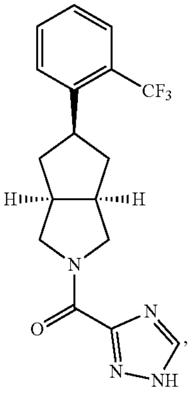
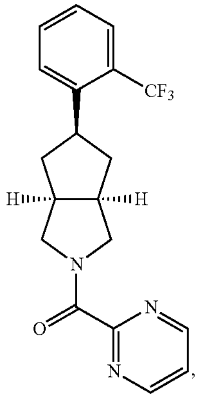

-continued
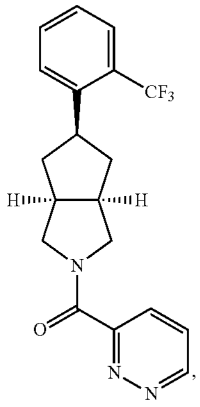
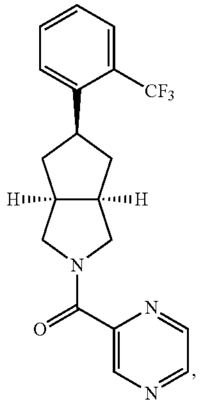
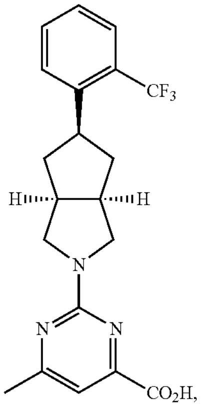
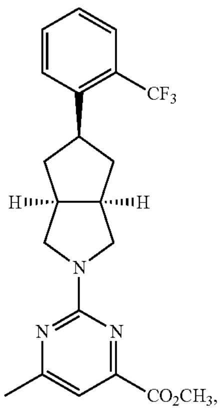
-continued
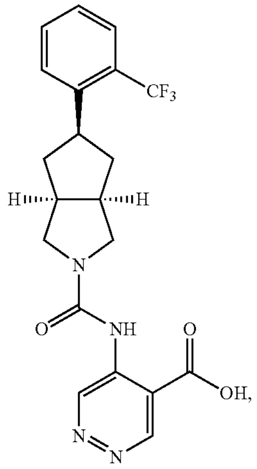
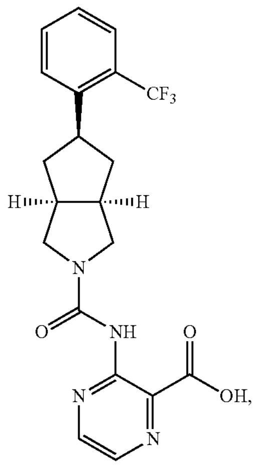
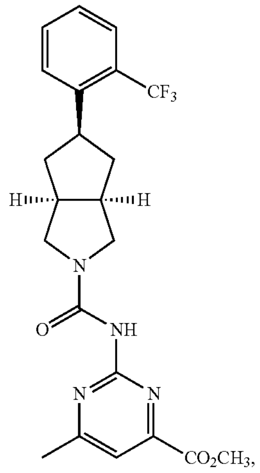

-continued
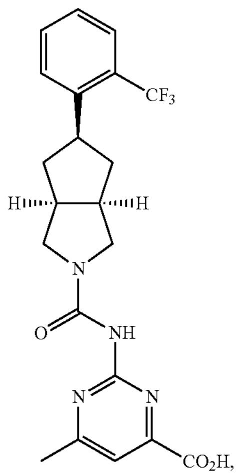
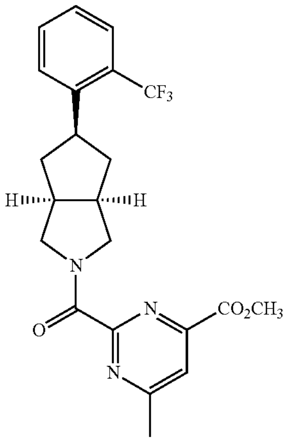
or
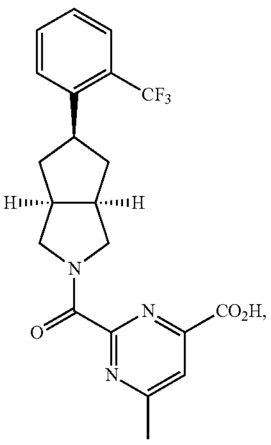
or a pharmaceutically acceptable salt thereof.
In some embodiments, the compound is
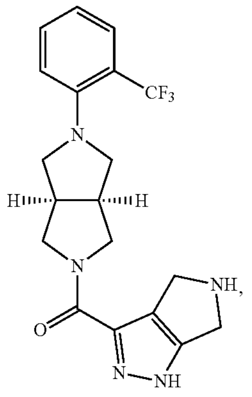
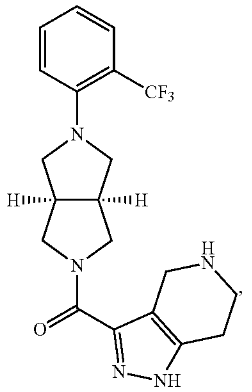
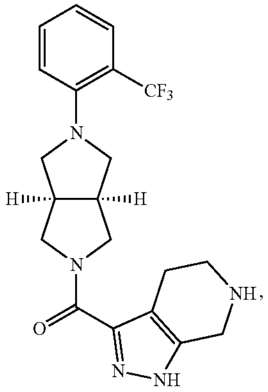
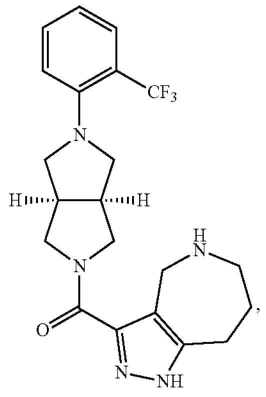

-continued
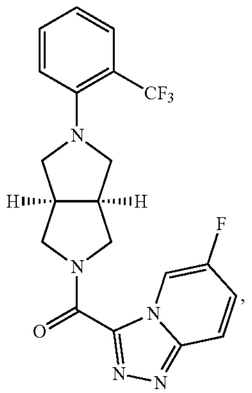
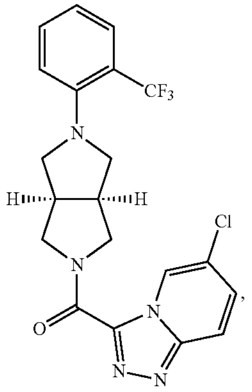
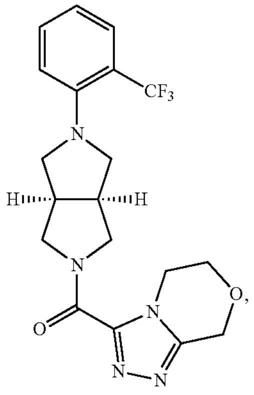
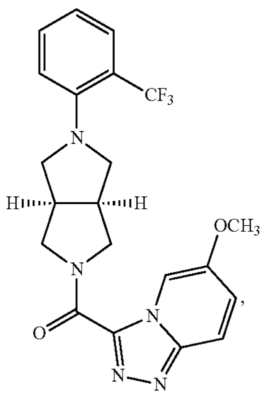
-continued
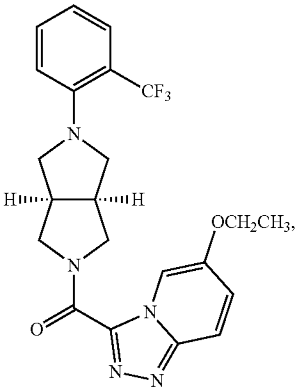
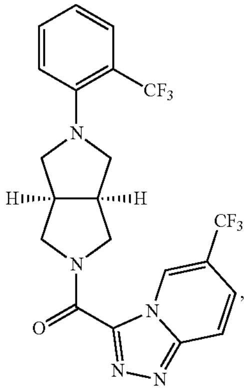
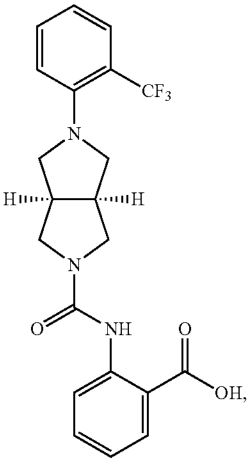
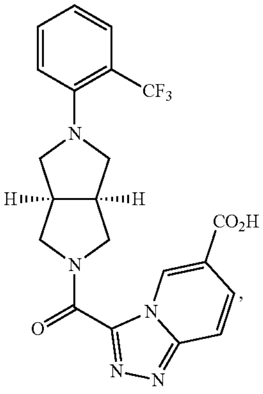

-continued
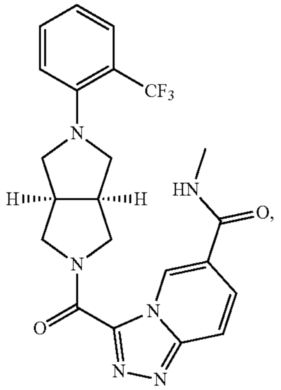
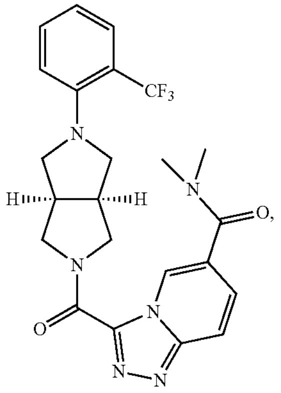
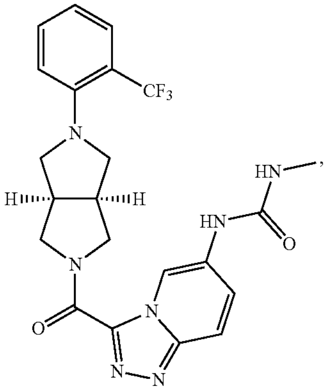
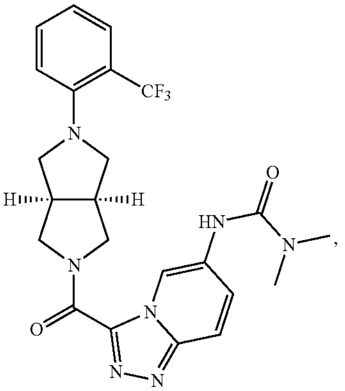
-continued
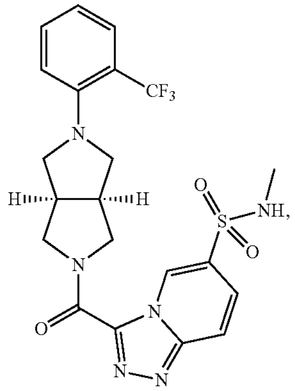
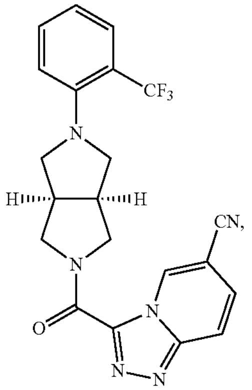
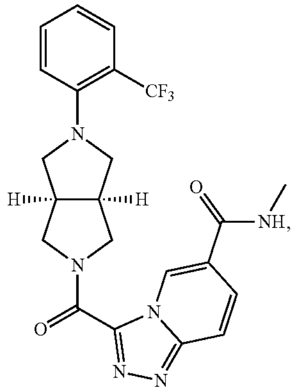
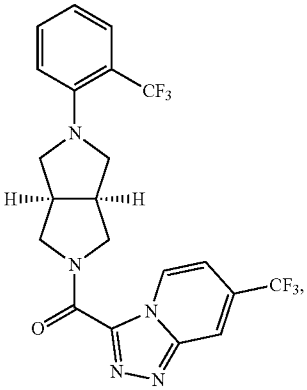

-continued
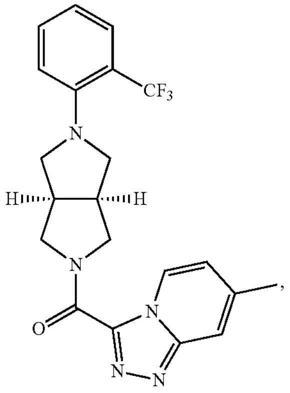
,
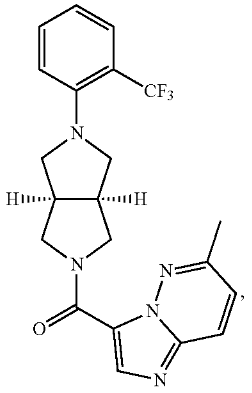
,
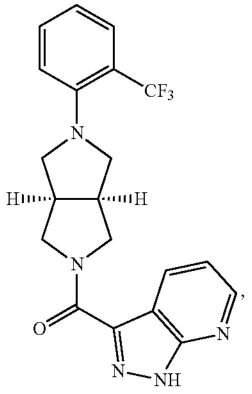
,
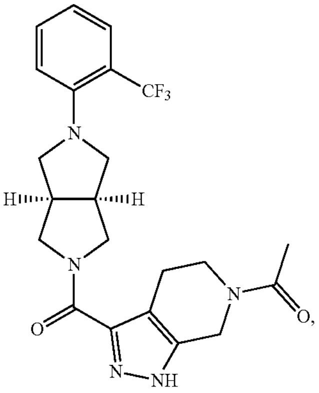
,
-continued
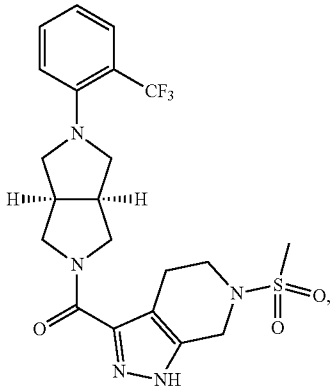
,
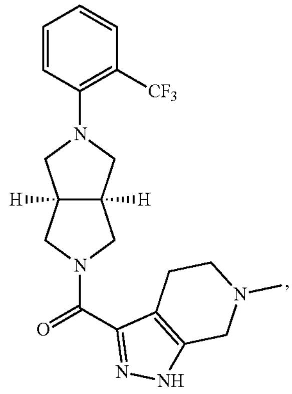
,
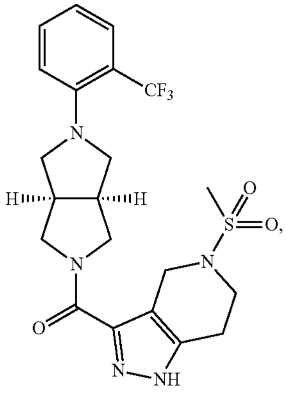
,
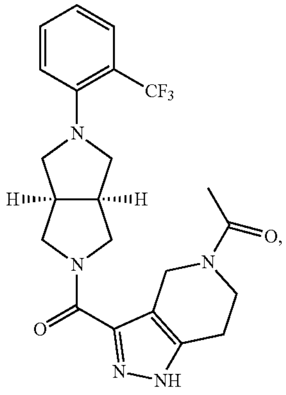
, -continued
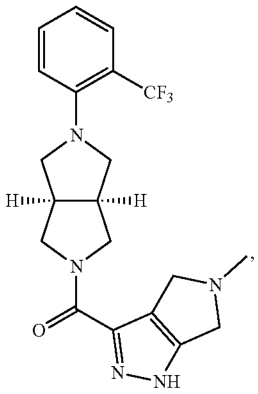
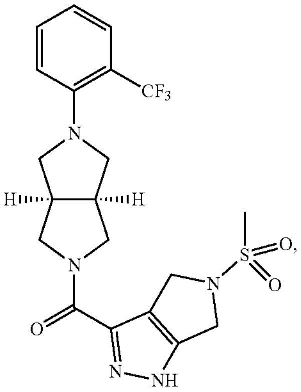
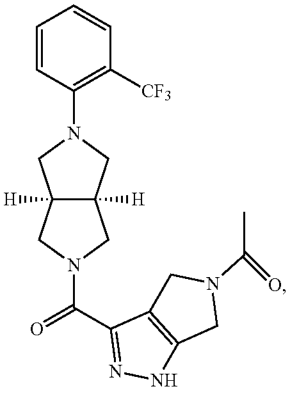
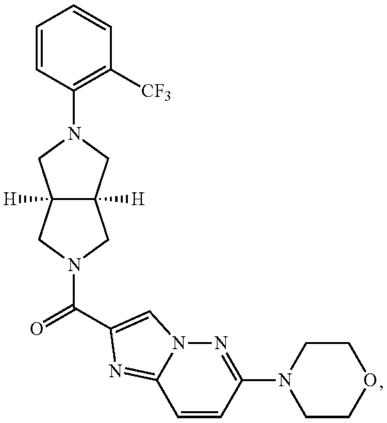
-continued
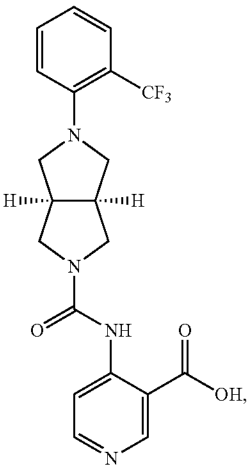
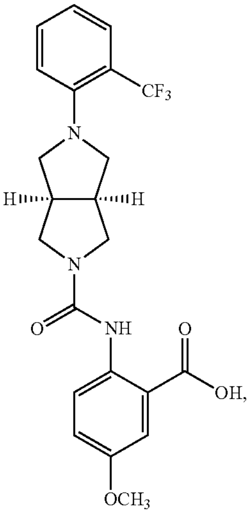
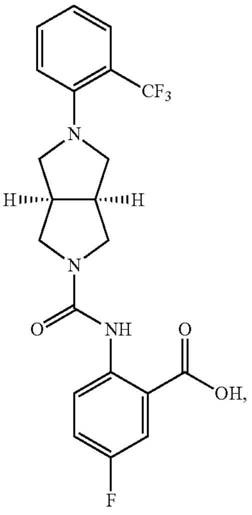

-continued
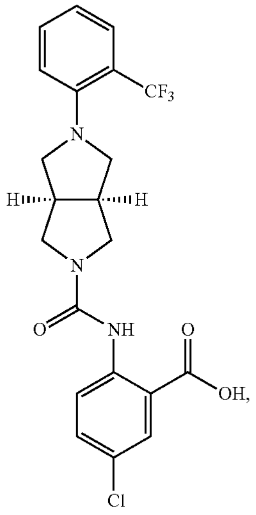
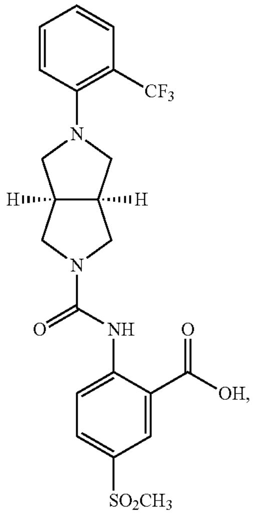
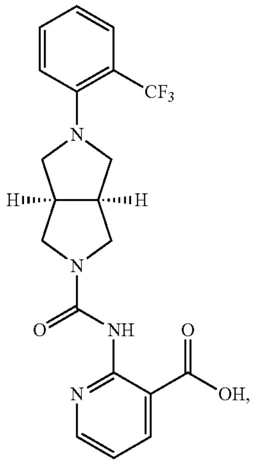
-continued
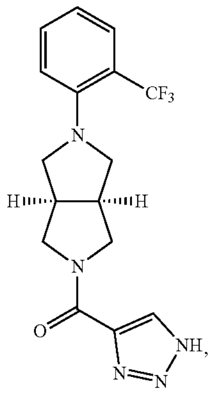
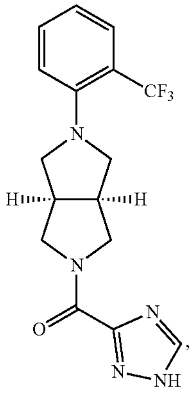
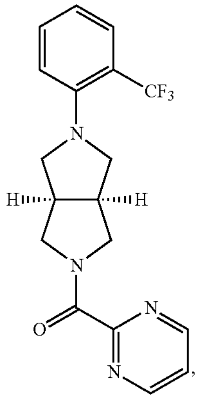
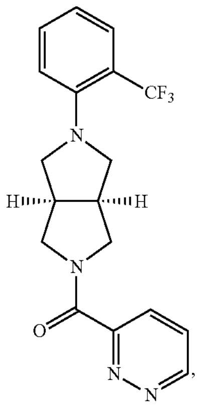

-continued
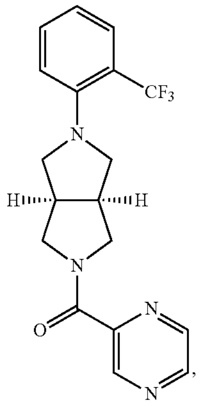
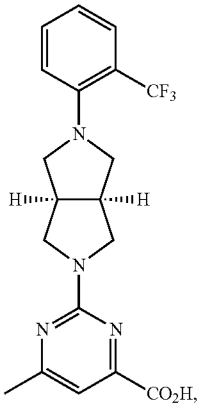
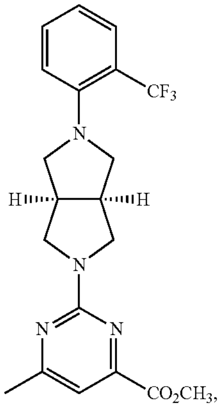
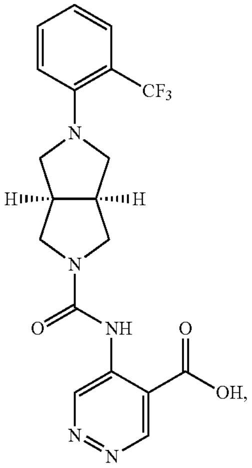
-continued
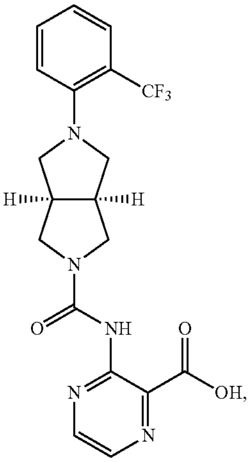
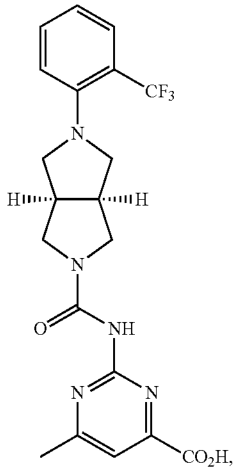
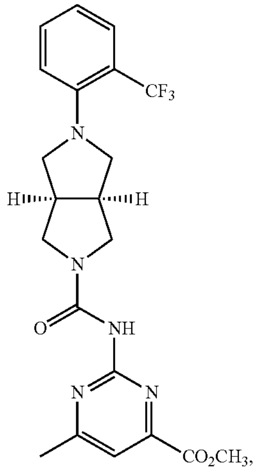

-continued
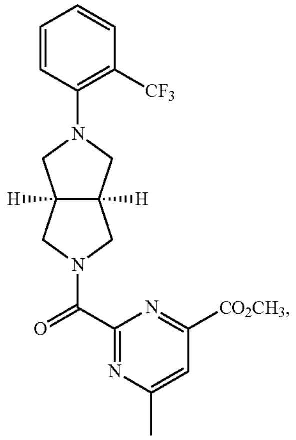
or
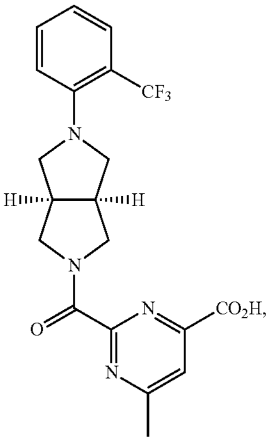
or a pharmaceutically acceptable salt thereof.
In some embodiments, the compound is
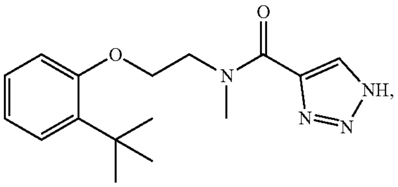
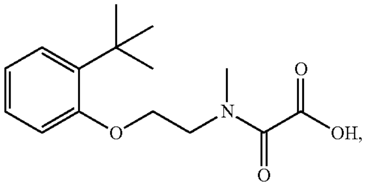
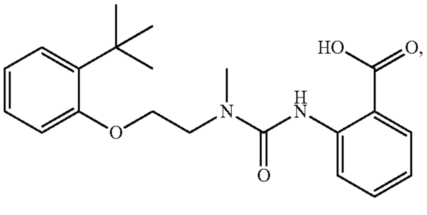
-continued
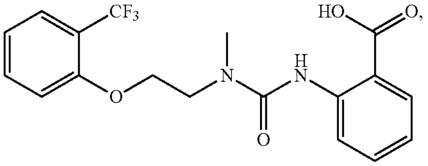
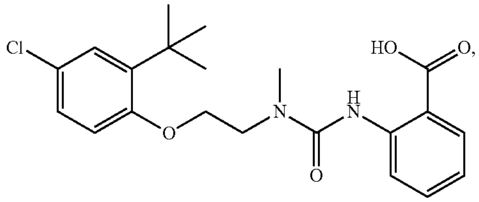
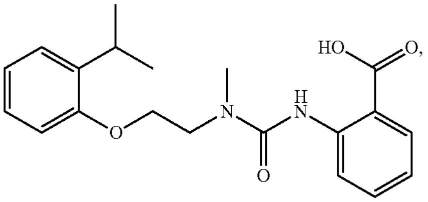
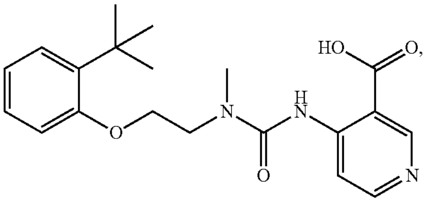
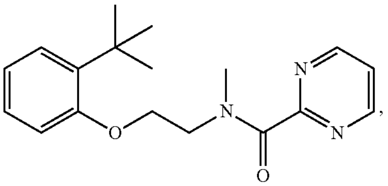
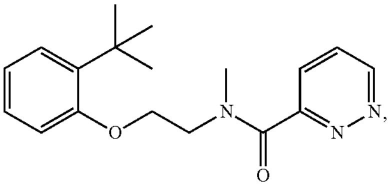
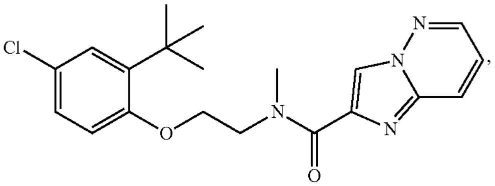
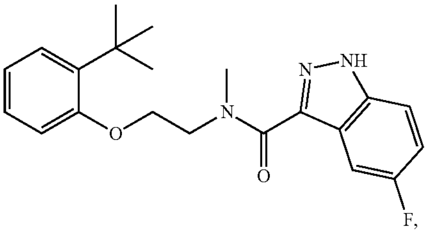

-continued
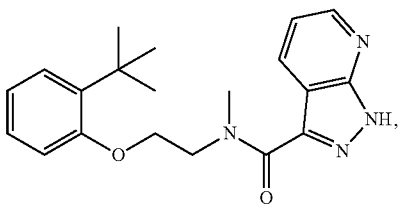
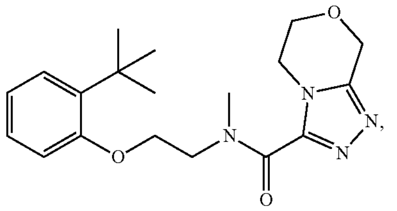
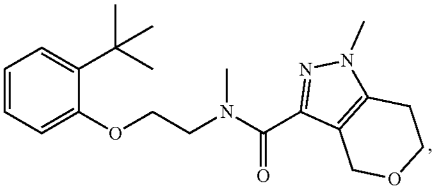
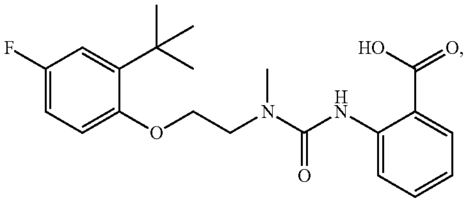
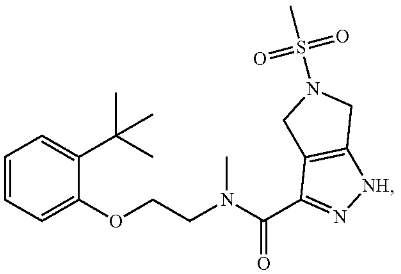
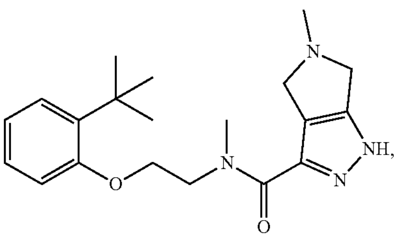
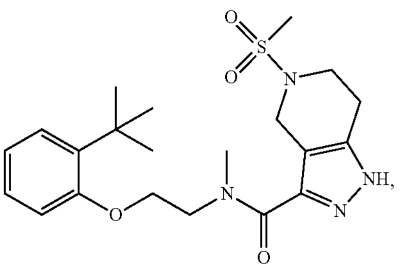
-continued
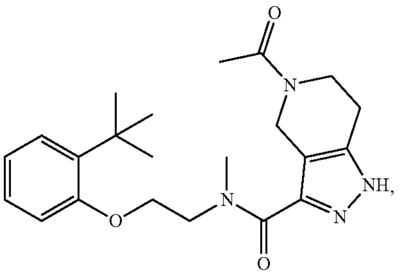
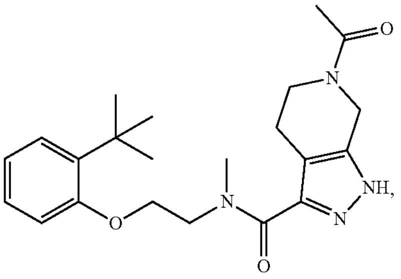
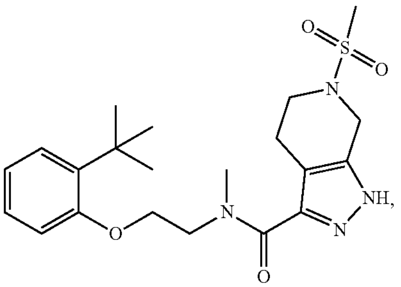
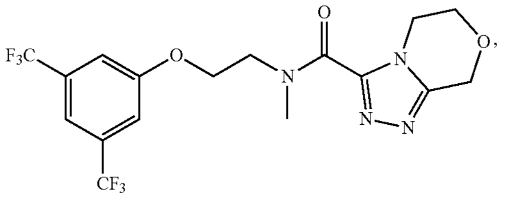
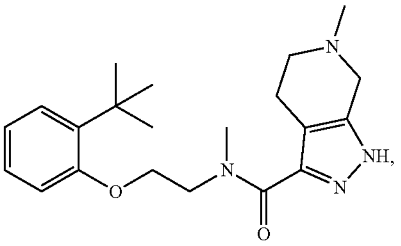
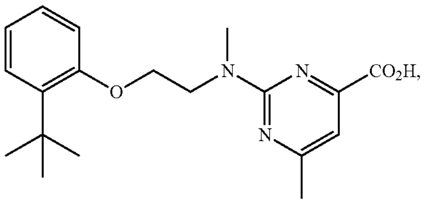
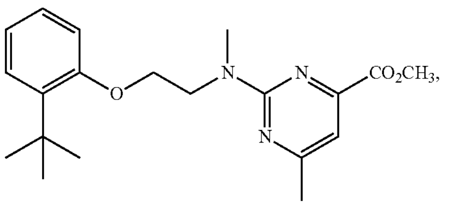

-continued
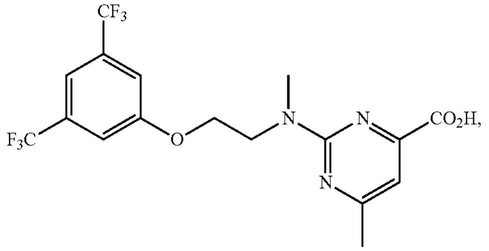
or
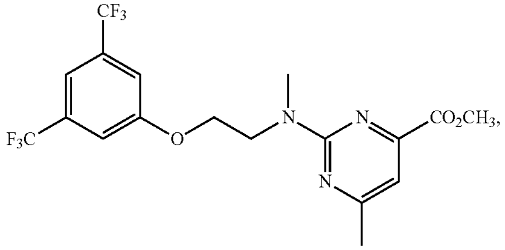
or a pharmaceutically acceptable salt thereof.
In some embodiments, the compound is
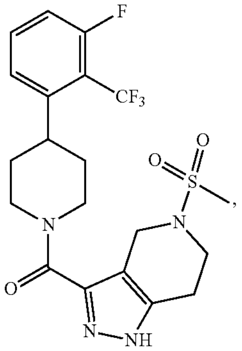
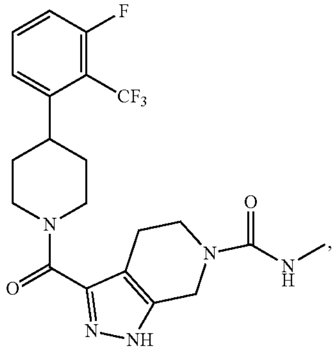
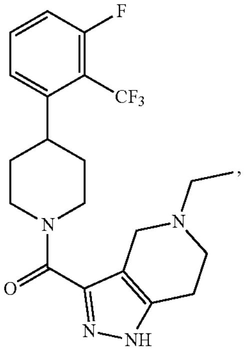
-continued
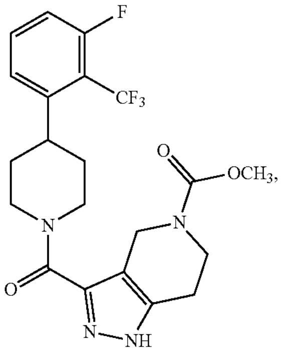
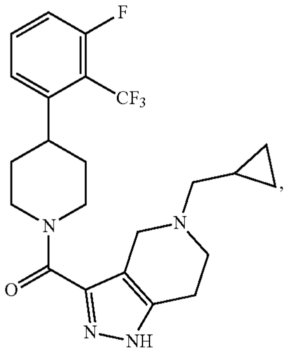
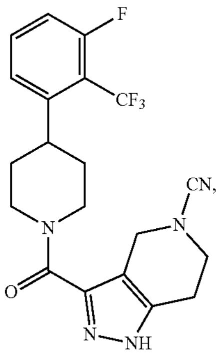
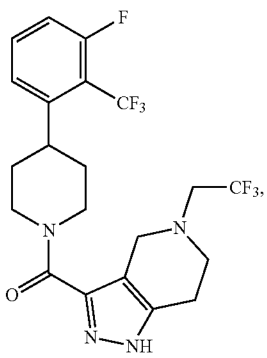

-continued
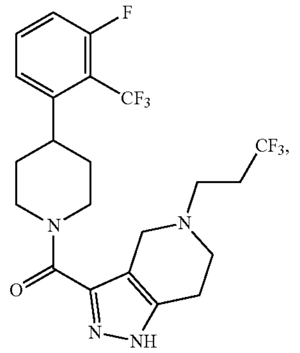
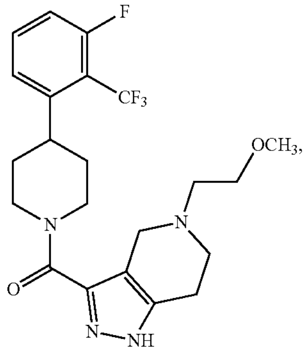
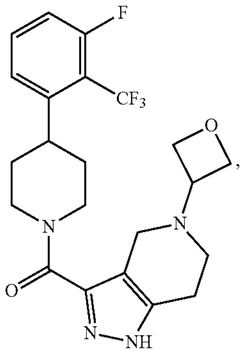
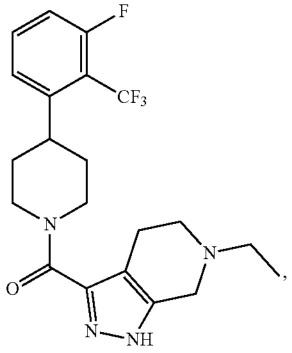
-continued
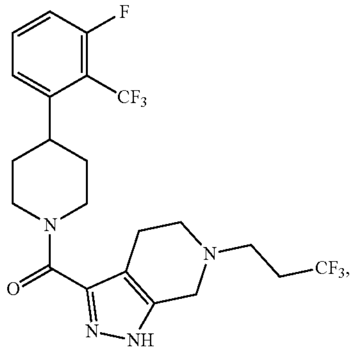
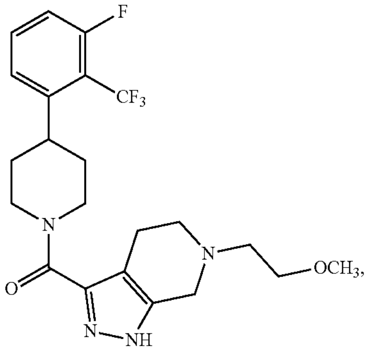
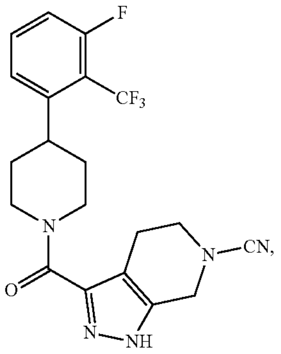
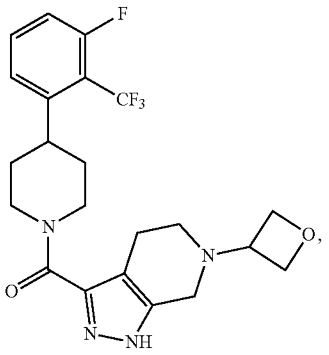

-continued
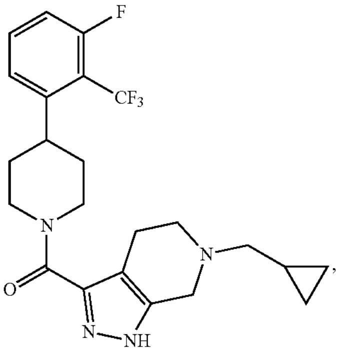
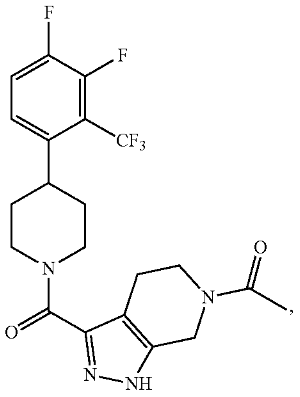
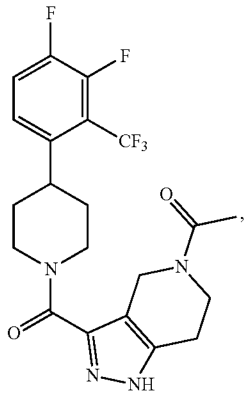
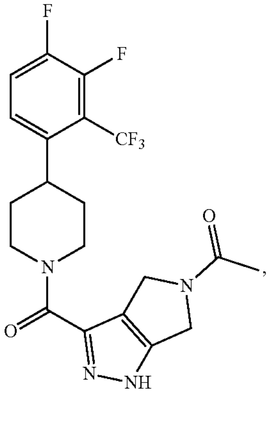
-continued
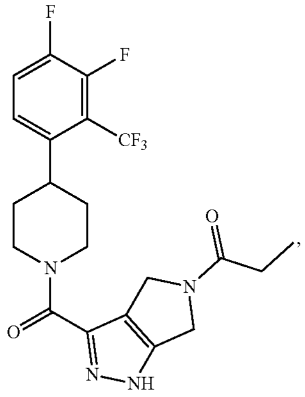
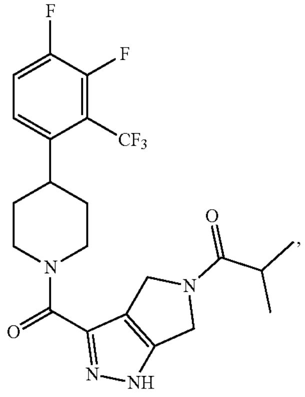
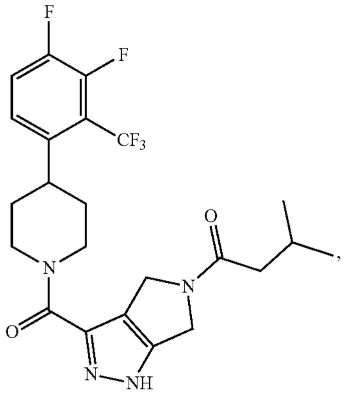
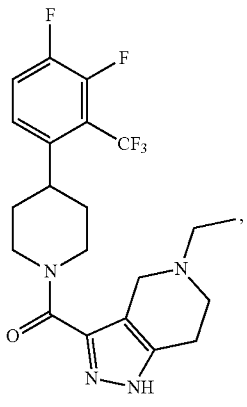

-continued
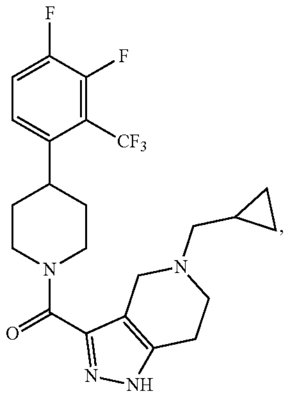
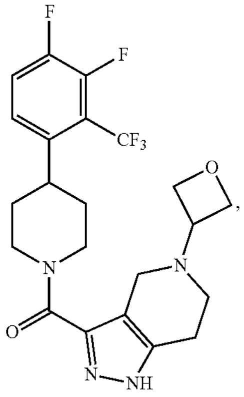
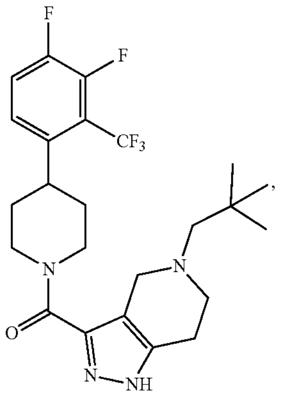
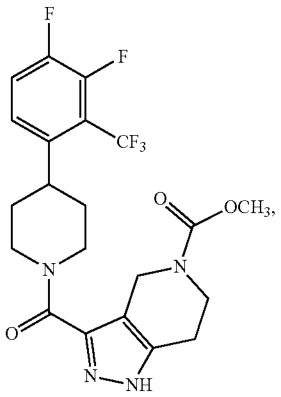
-continued
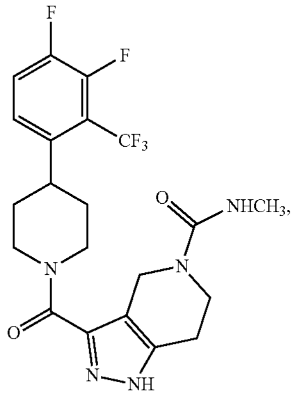
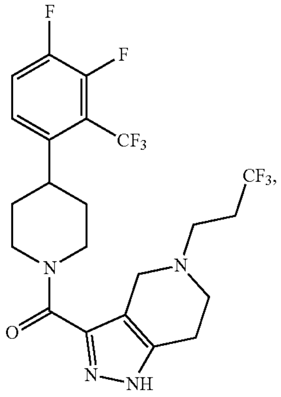
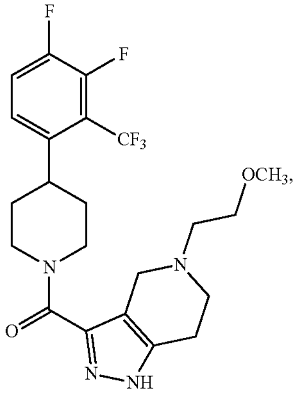
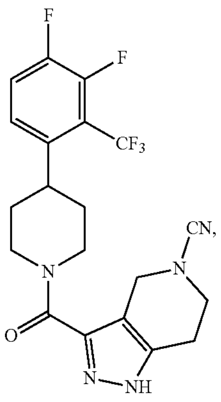

-continued
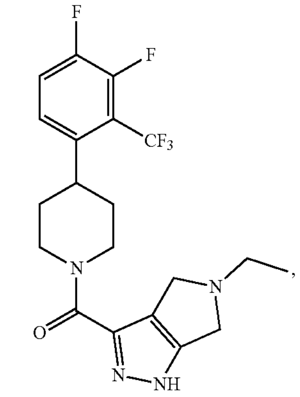
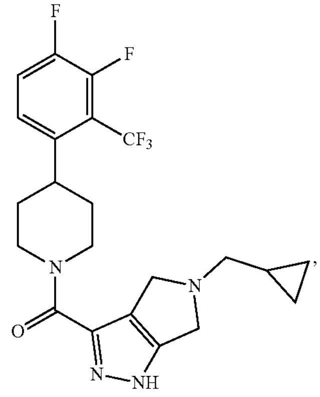
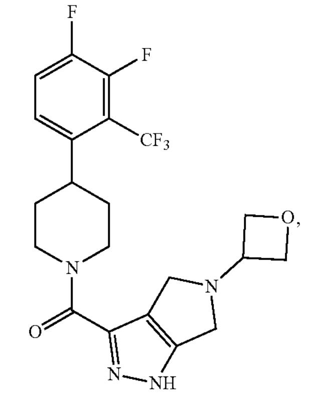
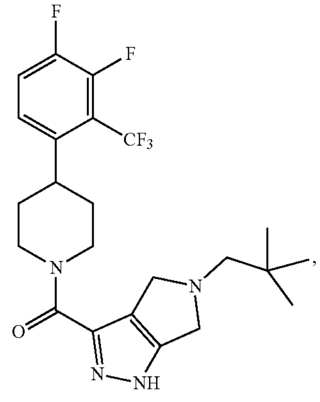
-continued
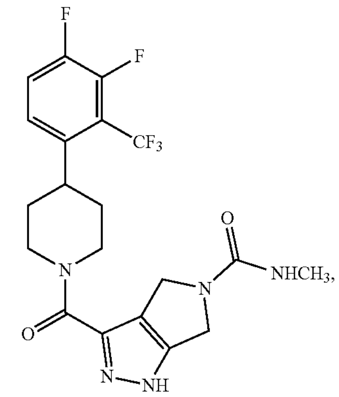
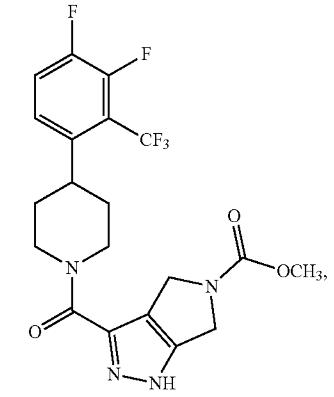
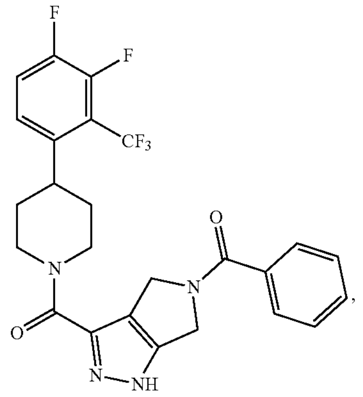
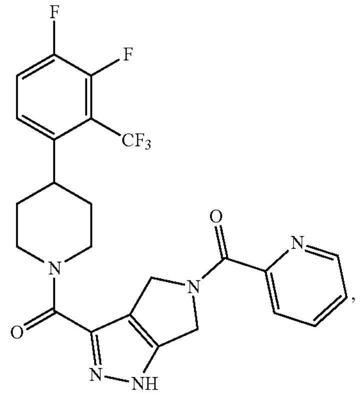

-continued
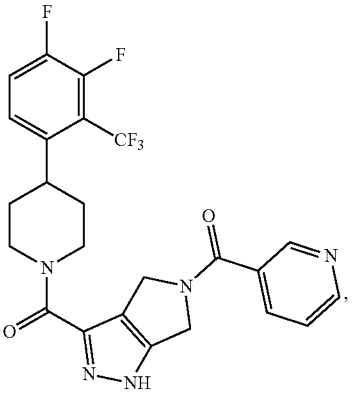
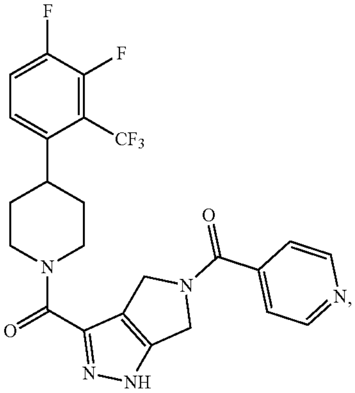
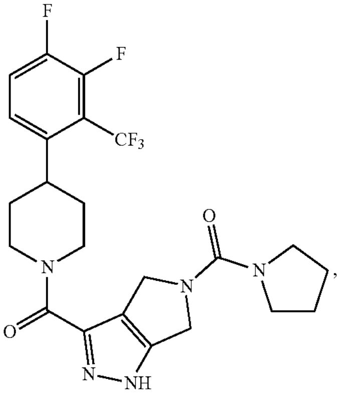
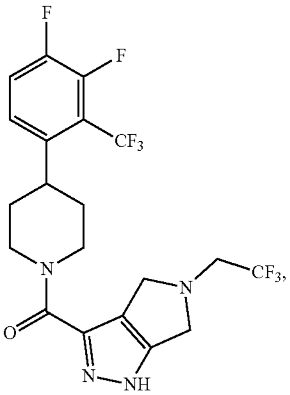
-continued
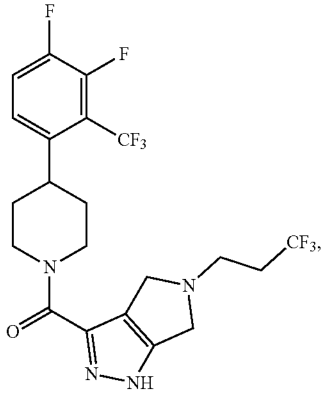
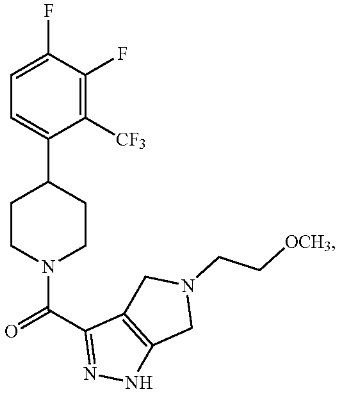
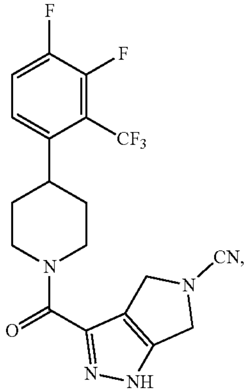
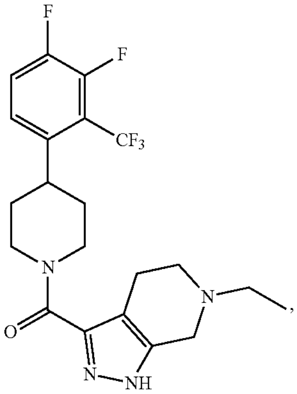

-continued
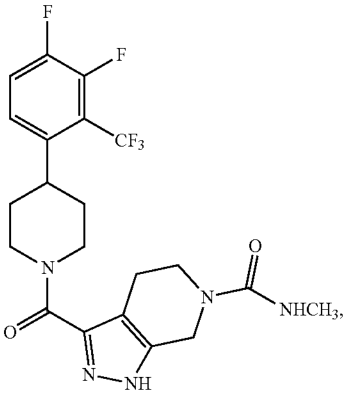
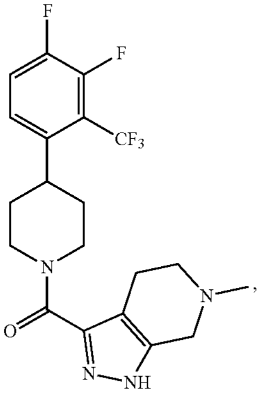
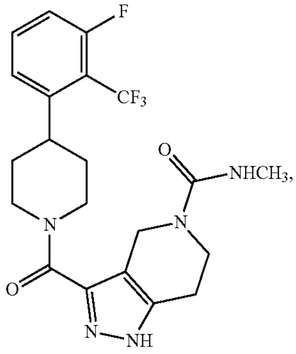
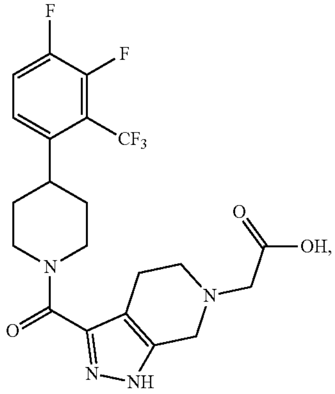
-continued
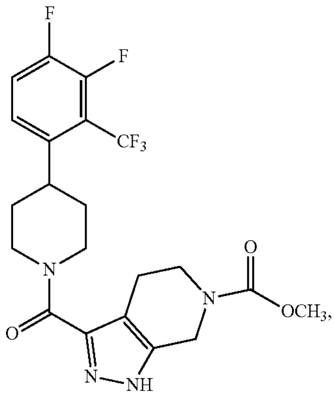
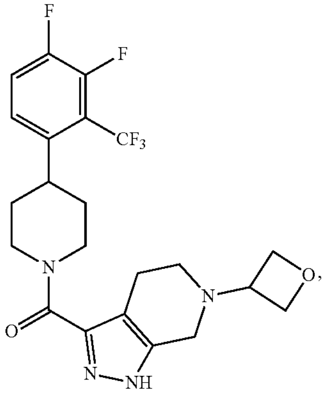
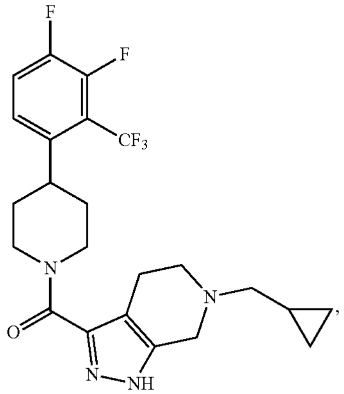
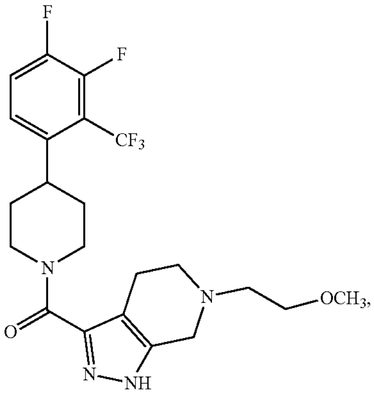

-continued
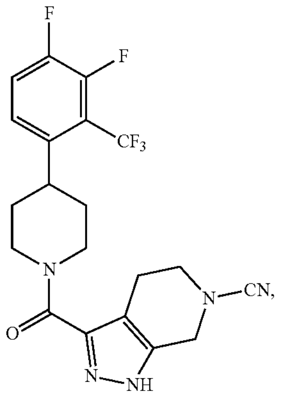
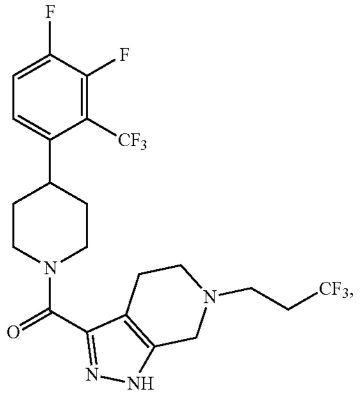
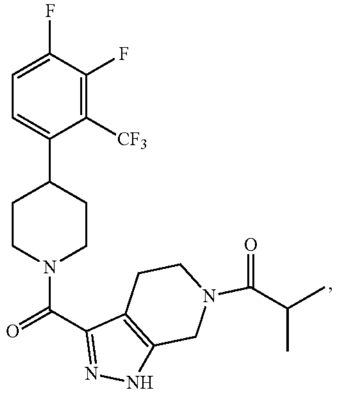
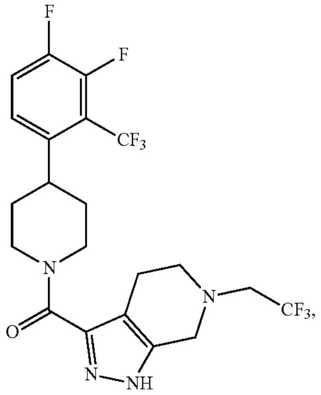
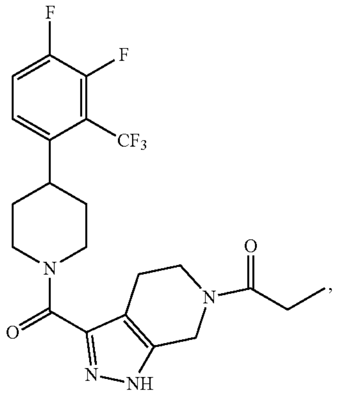
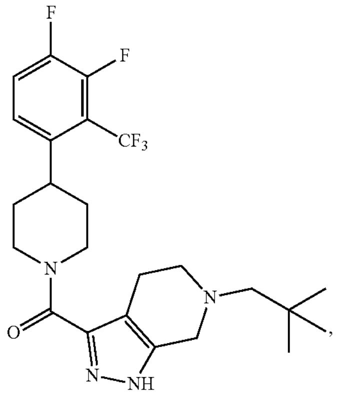
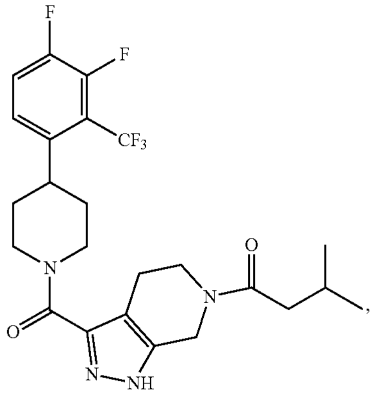
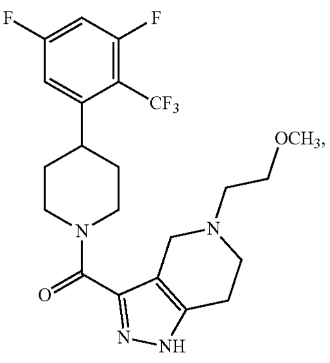
-continued -continued
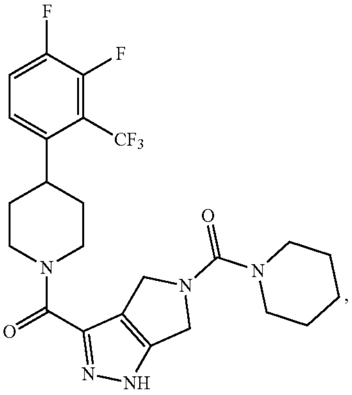
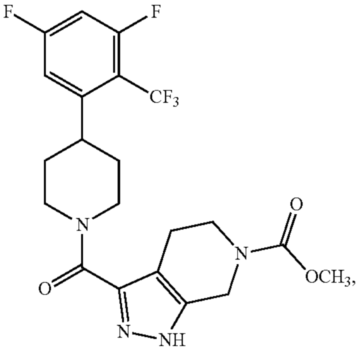
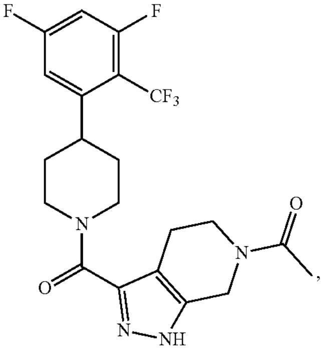
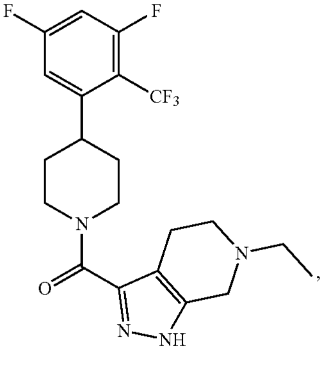
-continued
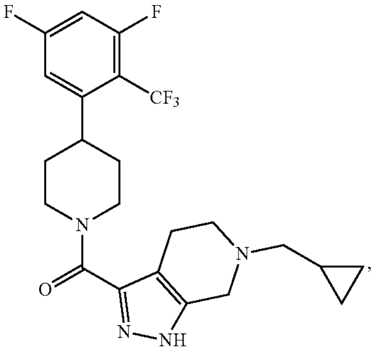
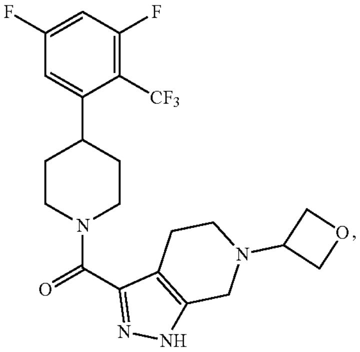
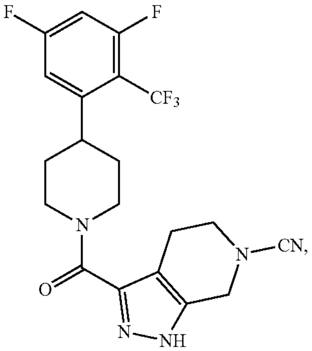
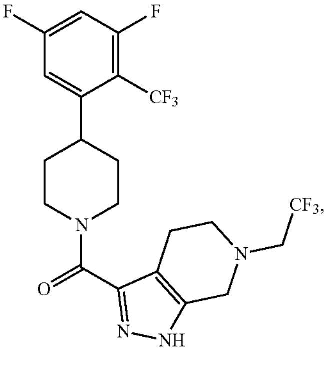

-continued
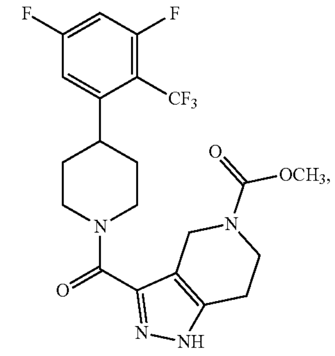
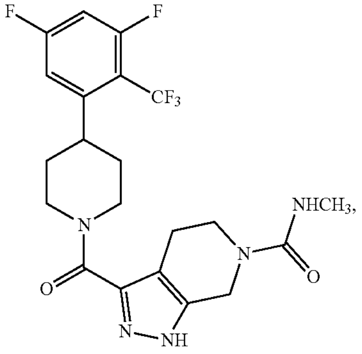
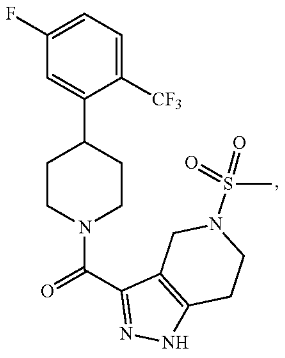
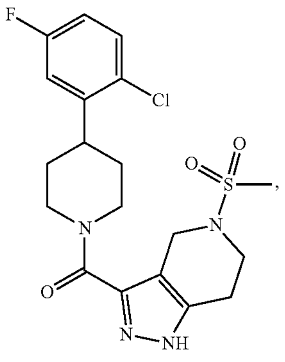
-continued
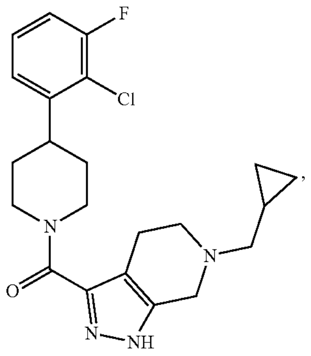
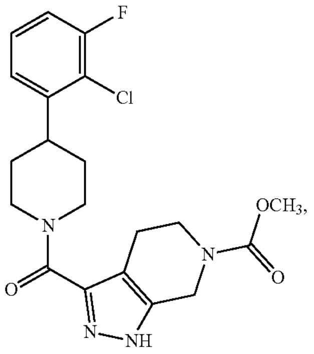
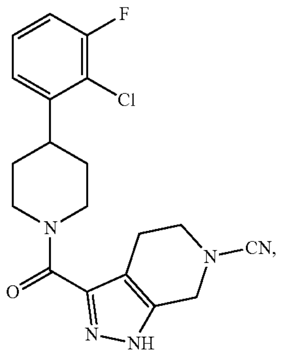
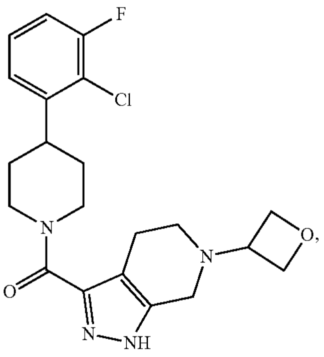

-continued
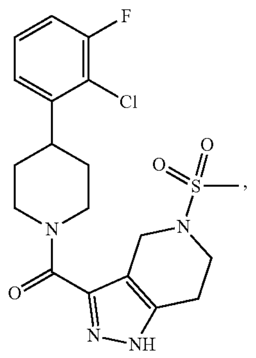
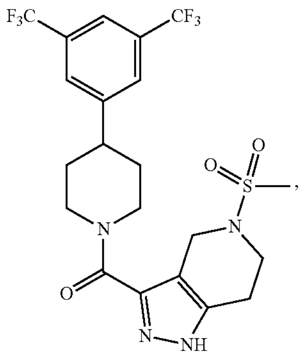
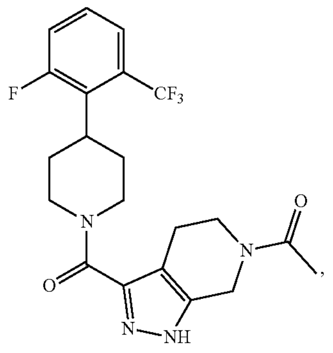
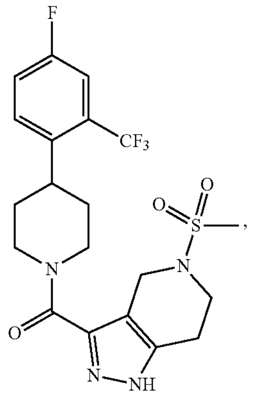
-continued
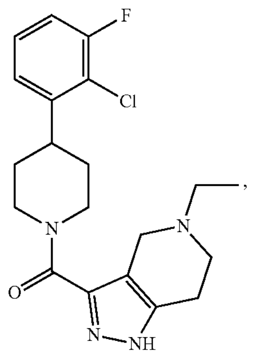
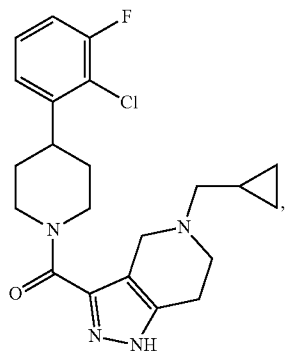
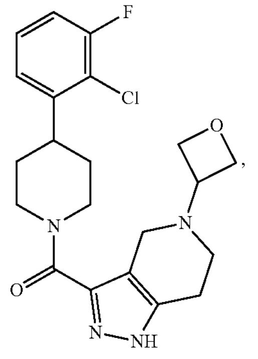
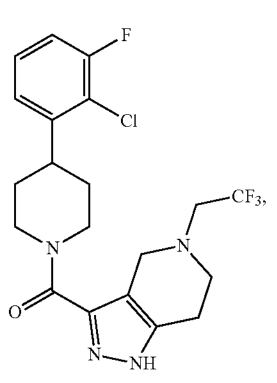

-continued
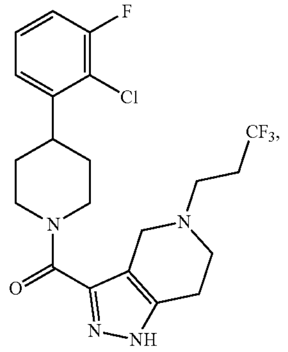
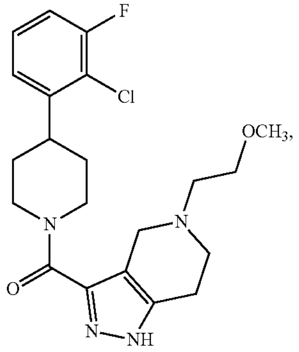
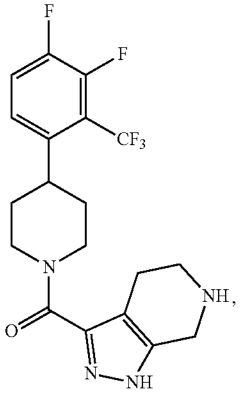
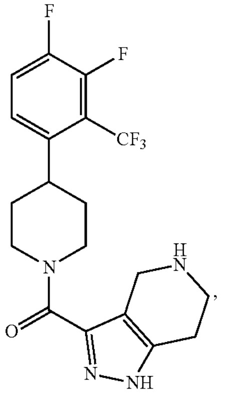
-continued
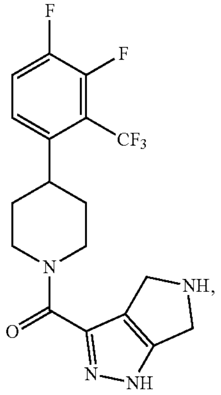
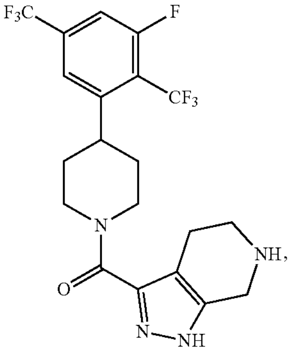
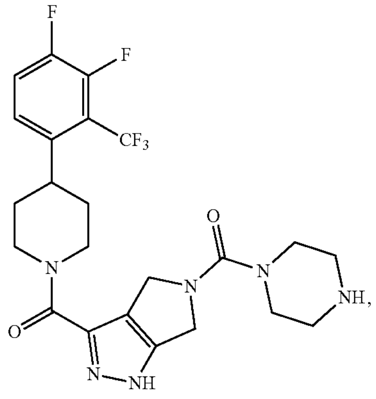
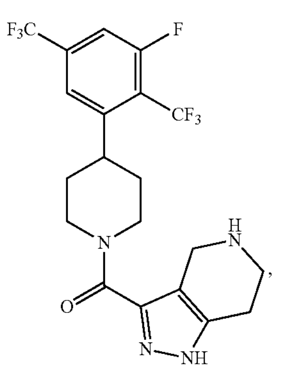

-continued
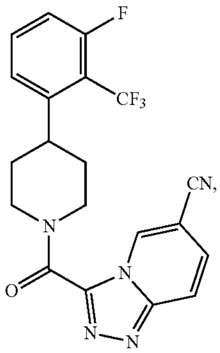
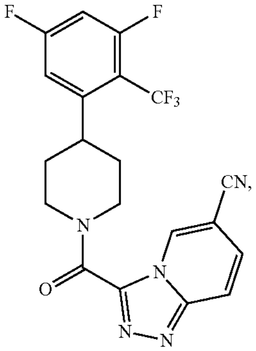
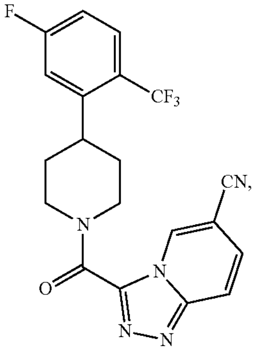
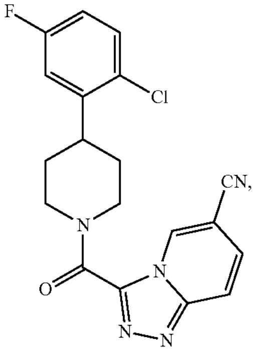
-continued
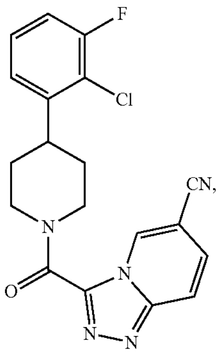
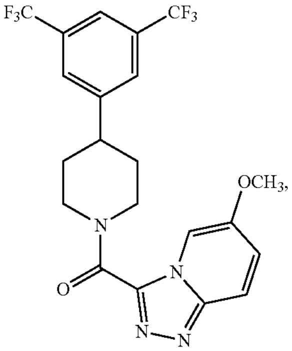
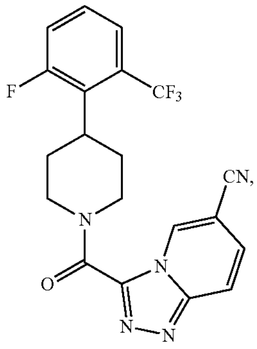
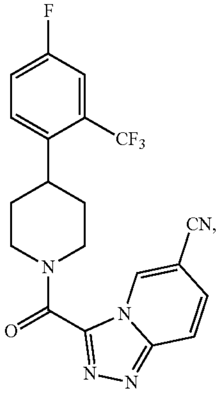

-continued
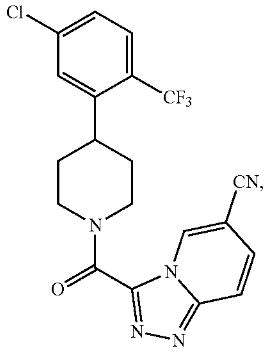
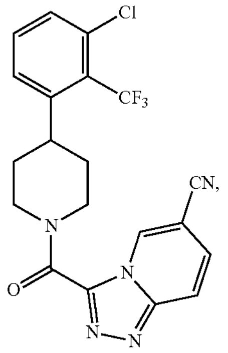
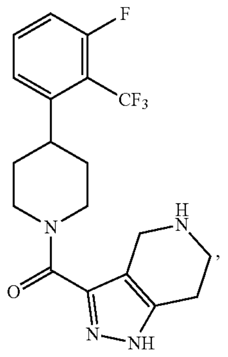
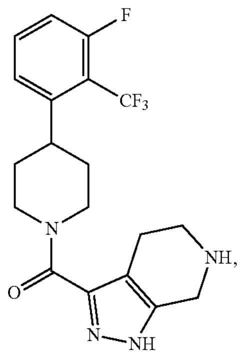
-continued
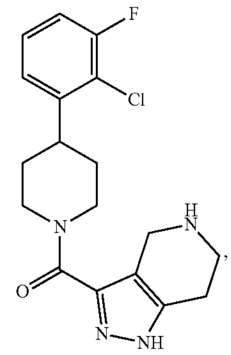
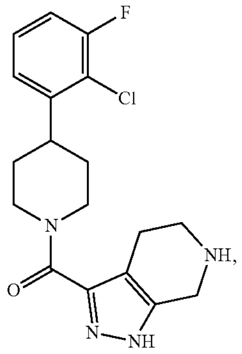
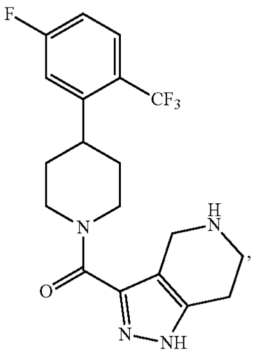
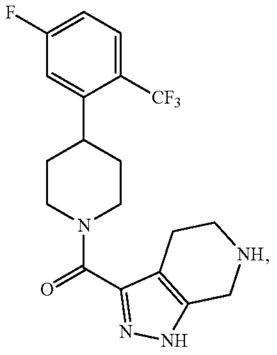

-continued
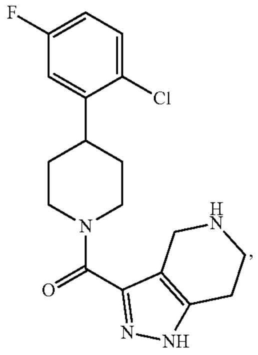
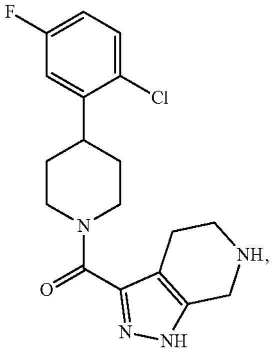
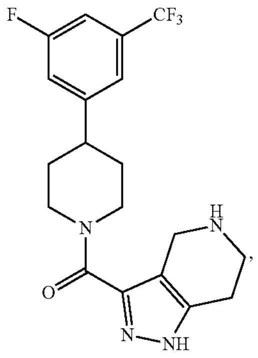
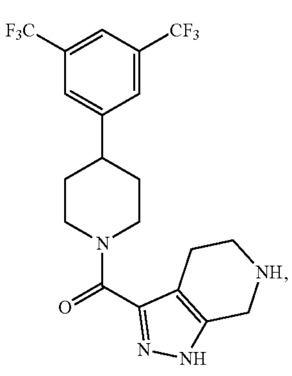
-continued
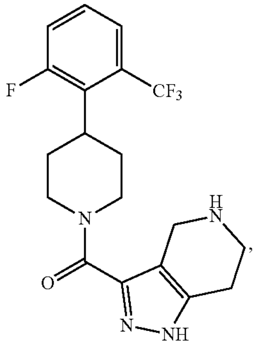
or
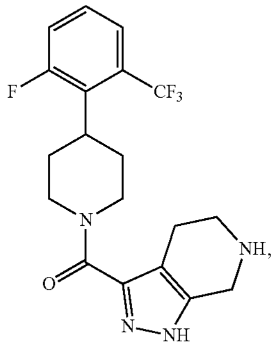
or a pharmaceutically acceptable salt thereof.
In some embodiments, the compound is
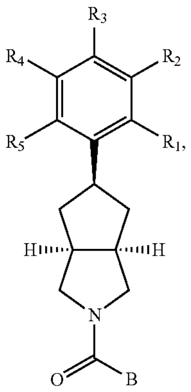
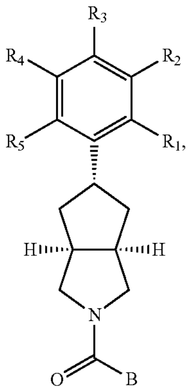

-continued
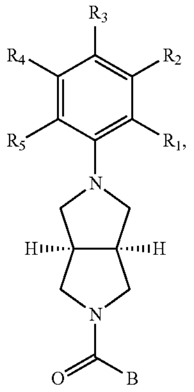
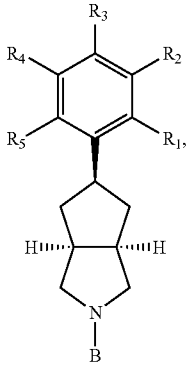
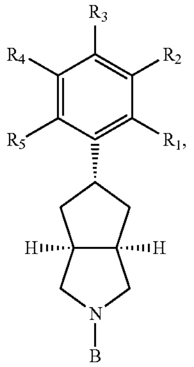
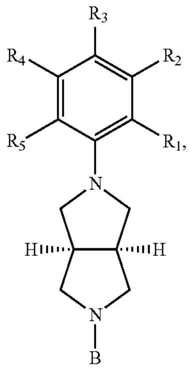
-continued
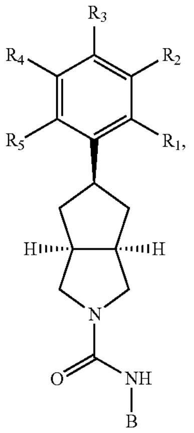
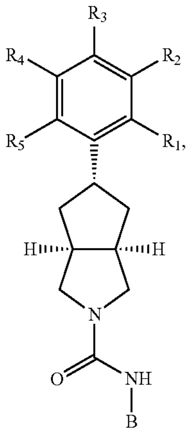
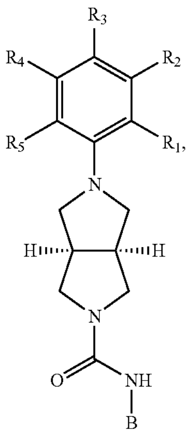
or a pharmaceutically acceptable salt thereof.

In some embodiments, the compound is
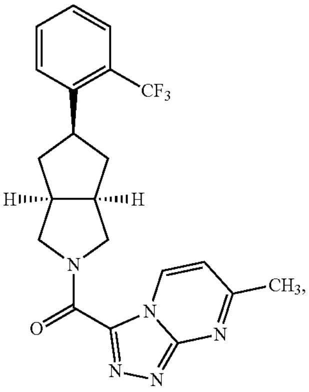
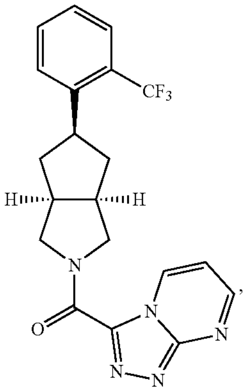
,
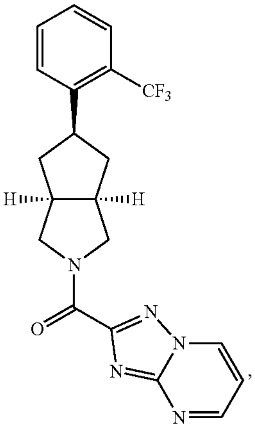
,
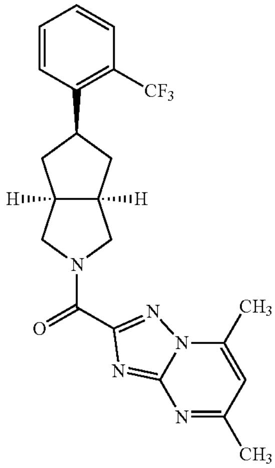
,
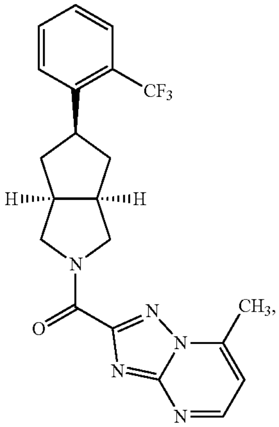
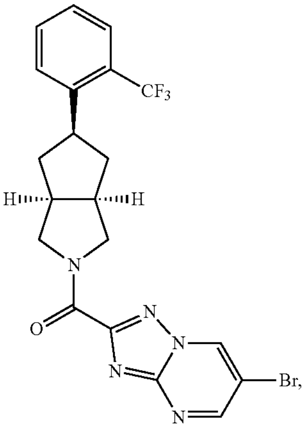
-continued
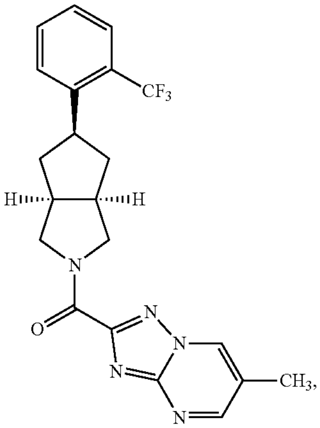
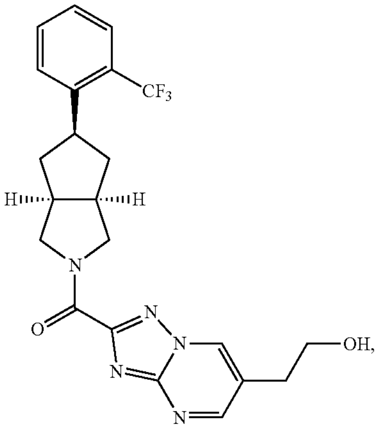
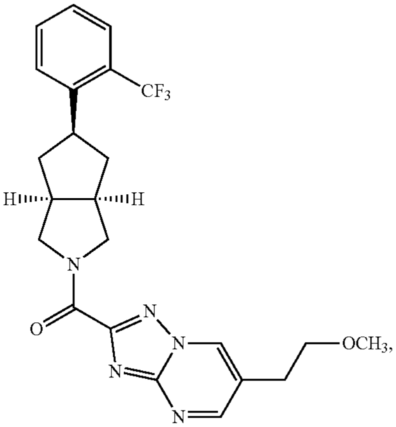
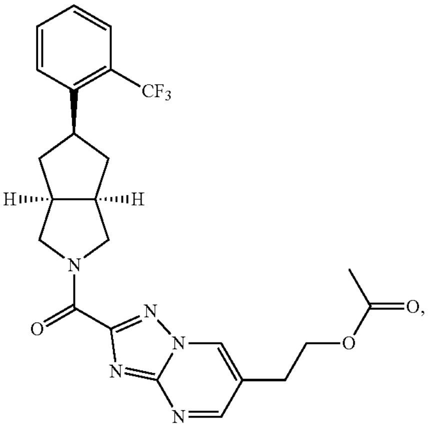

-continued
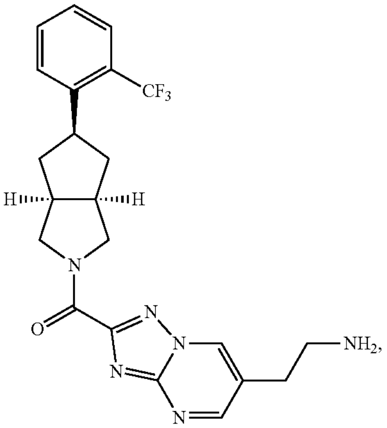
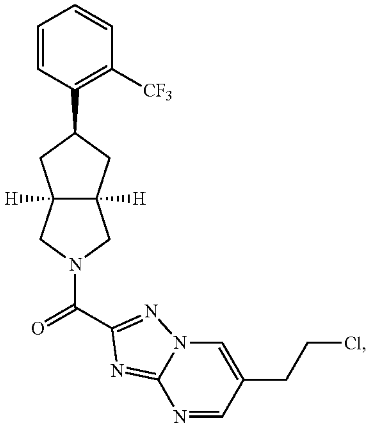
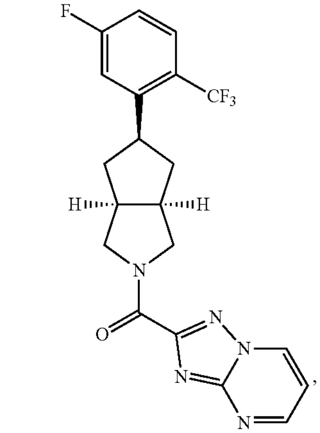
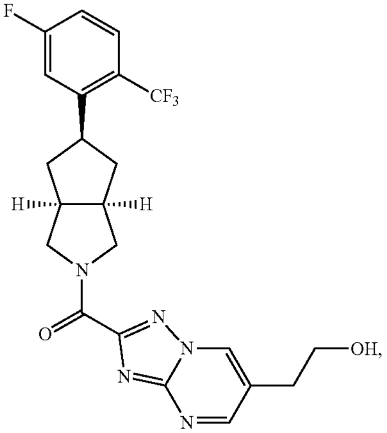
-continued
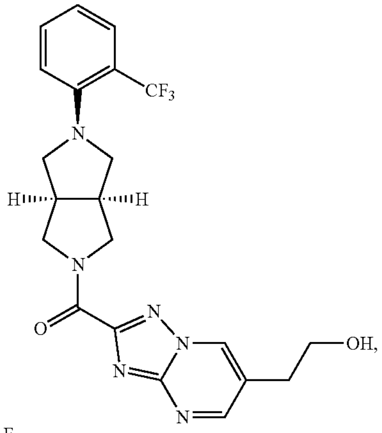
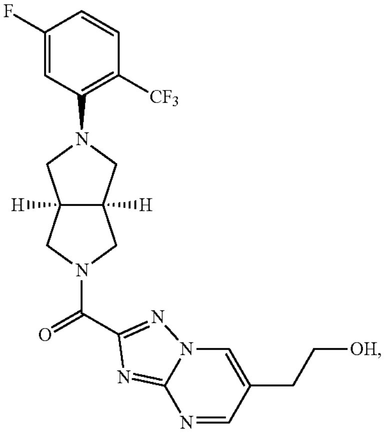
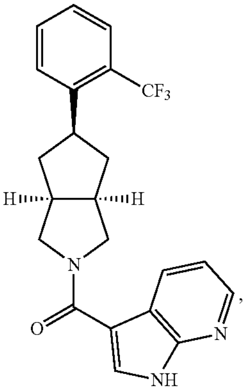
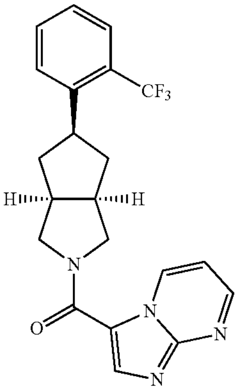
or
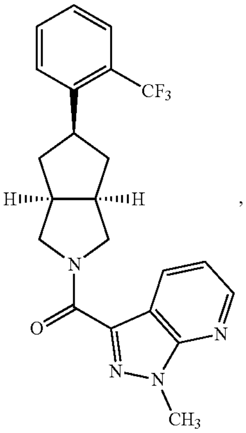
,
or a pharmaceutically acceptable salt thereof.

In some embodiments, the compound is

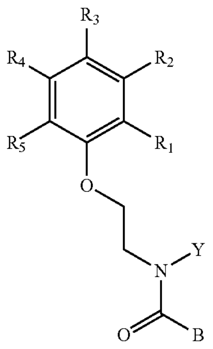

,

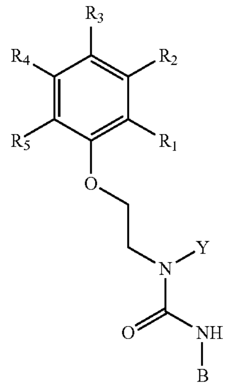

or

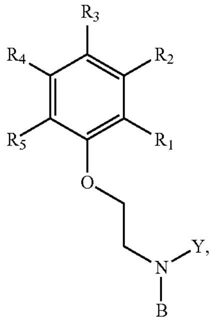

or a pharmaceutically acceptable salt thereof.

In some embodiments the compound is

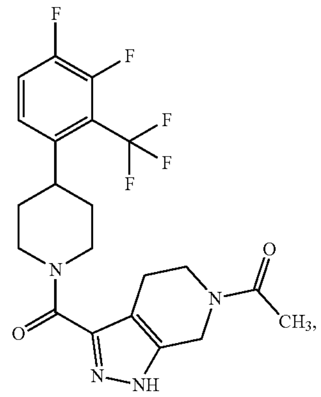

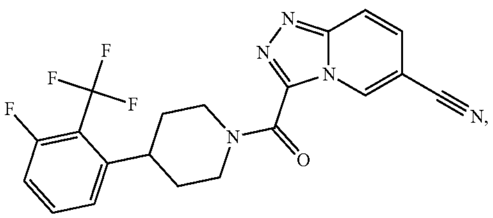

-continued

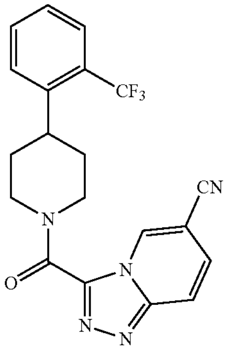

or

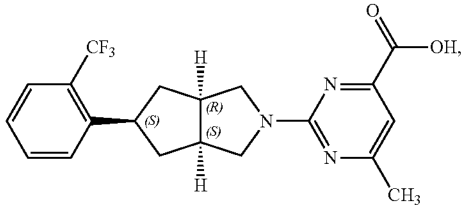

or a pharmaceutically acceptable salt thereof.

The method of the present invention includes a pharmaceutical composition wherein the compound has the structure:

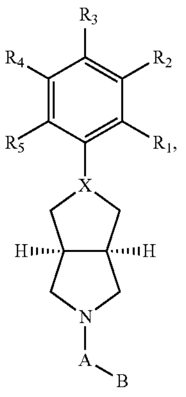

wherein $R_1$, $R_2$, $R_3$, $R_4$, and $R_5$ are each independently H, halogen, $CF_3$ or $C_1$-$C_4$ alkyl;

X is N or $CR_6$, wherein $R_6$ is H, OH, or halogen;

A is absent or present, and when present is

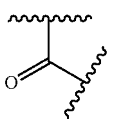

or

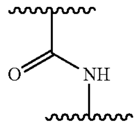

;

B has the structure:

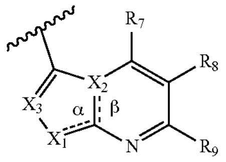

wherein

α and β are each a bond that is present or absent;

$X_1$ is N, NH or $NR_{10}$, wherein $R_{10}$ is alkyl, alkenyl or alkynyl;

$X_2$ is C or N;

$X_3$ is CH or N;

$R_7$, $R_8$ and $R_9$ are each, independently, H, halogen, alkyl, alkenyl, alkynyl, alkyl-OH, alkyl-$NH_2$, alkyl-OAc alkyl-O(CO)-alkyl, alkyl-O-alkyl, haloalkyl, cycloalkyl, O-alkyl, NH-alkyl, C(O)OH, C(O)—$NH_2$, C(O)—$N(CH_3)_2$, C(O)—$NHCH_3$, NHC(O)—$N(CH_3)_2$, CN or $CF_3$, wherein $X_1$, $X_2$ and $X_3$ are each N, α is present and β is absent; or $X_1$ is NH, $X_2$ is C, $X_3$ is CH, α is absent and β is present; or $X_1$ is N, $X_2$ is N, $X_3$ is CH, α is present and β is absent; or $X_1$ is NH or $NR_{10}$, $X_2$ is C, $X_3$ is N, α is absent and β is present, wherein when $X_1$ is NH, $X_2$ is C, $X_3$ is N, α is absent and β is present, then one of $R_7$, $R_8$ and $R_9$ is other than H, or B has the structure:

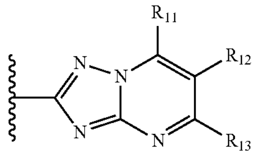

wherein $R_{11}$, $R_{12}$ and $R_{13}$ are each, independently, H, halogen, alkyl, alkenyl, alkynyl alkyl-OH, alkyl-$NH_2$, alkyl-OAc, alkyl-O(CO)-alkyl, alkyl-O-alkyl, haloalkyl, cycloalkyl, O-alkyl, NH-alkyl, C(O)OH, C(O)—$NH_2$, C(O)—$N(CH_3)_2$, C(O)—$NHCH_3$, NHC(O)—$N(CH_3)_2$, CN or $CF_3$, or a pharmaceutically acceptable salt thereof.

In some embodiments, the compound of the method has the structure:

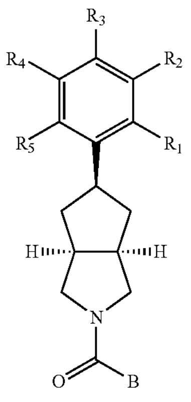

,

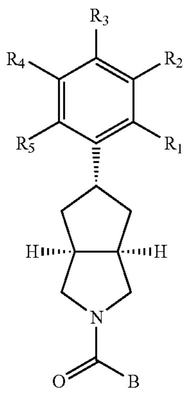

or

-continued

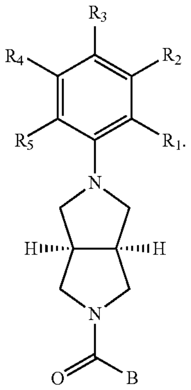

In some embodiments, the compound of the method has the structure:

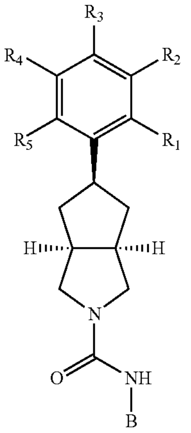

,

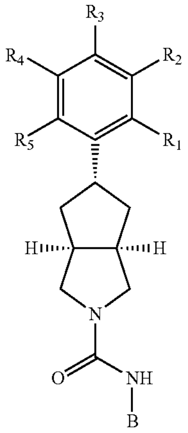

or

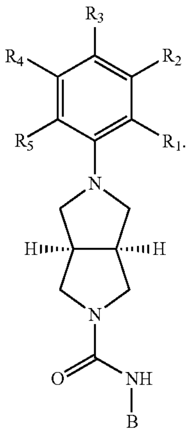

In some embodiments, the compound of the method has the structure:

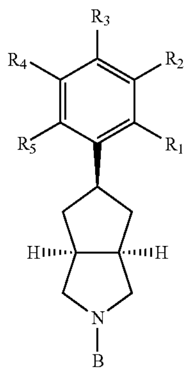

,

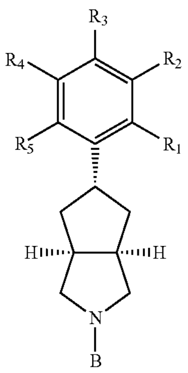

or

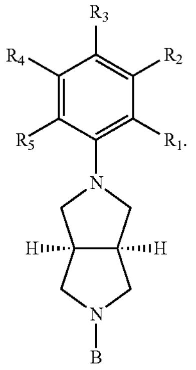

In some embodiments, the compound of the method has the structure:

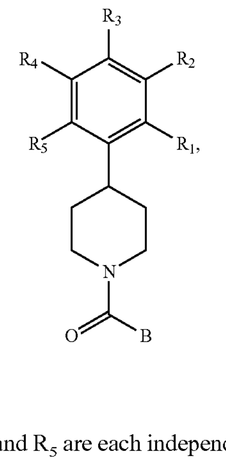

wherein $R_1$, $R_2$, $R_3$, $R_4$, and $R_5$ are each independently H, halogen, $CF_3$ or $C_1$-$C_4$ alkyl; and B has the structure:

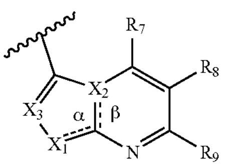

wherein

α and β are each a bond that is present or absent;

$X_1$ is N, NH or $NR_{10}$, wherein $R_{10}$ is alkyl, alkenyl or alkynyl;

$X_2$ is C or N;

$X_3$ is CH or N;

$R_7$, $R_8$ and $R_9$ are each, independently, H, halogen, alkyl, alkenyl, alkynyl, alkyl-OH, alkyl-$NH_2$, alkyl-OAc, alky-O-alkyl, haloalkyl, cycloalkyl, O-alkyl, NH-alkyl, C(O)OH, C(O)—$NH_2$, C(O)—$N(CH_3)_2$, C(O)—$NHCH_3$, NHC(O)—$N(CH_3)_2$, CN, or $CF_3$, wherein $X_1$, $X_2$ and $X_3$ are each N, α is present and β is absent; or $X_1$ is NH, $X_2$ is C, $X_3$ is CH, α is absent and β is present; or $X_1$ is N, $X_2$ is N, $X_3$ is CH, α is present and β is absent; or $X_1$ is NH or $NR_{10}$, $X_2$ is C, $X_3$ is N, α is absent and β is present, wherein when $X_1$ is NH, $X_2$ is C, $X_3$ is N, α is absent and β is present, then one of $R_7$, $R_8$ and $R_9$ is other than H, or B has the structure:

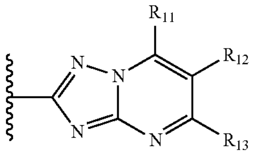

wherein $R_{11}$, $R_{12}$ and $R_{13}$ are each, independently, H, halogen, alkyl, alkyl-OH, alkyl-$NH_2$, alkyl-OAc, alky-O-alkyl, haloalkyl, cycloalkyl, O-alkyl, NH-alkyl, C(O)OH, C(O)—$NH_2$, C(O)—$N(CH_3)_2$, C(O)—$NHCH_3$, NHC (O)—$N(CH_3)_2$, CN, or $CF_3$, or a pharmaceutically acceptable salt thereof.

In some embodiments, the compound of the method has the structure:

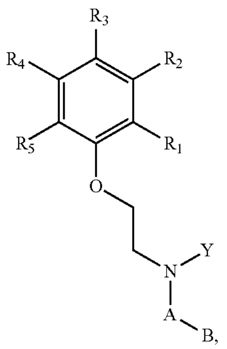

wherein $R_1$, $R_2$, $R_3$, $R_4$, and $R_5$ are each independently H, halogen, $CF_3$ or $C_1$-$C_4$ alkyl;

Y is alkyl;

A is absent or present, and when present is

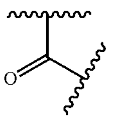

or

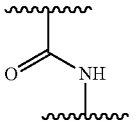

;

and

B has the structure:

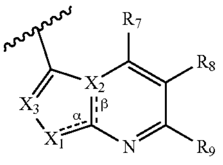

wherein

α and β are each a bond that is present or absent;

$X_1$ is N, NH or $NR_{10}$, wherein $R_{10}$ is alkyl, alkenyl or alkynyl;

$X_2$ is C or N;

$X_3$ is CH or N;

$R_7$, $R_8$ and $R_9$ are each, independently, H, halogen, alkyl, alkenyl, alkynyl, alkyl-OH, alkyl-$NH_2$, alkyl-OAc, alky-O-alkyl, haloalkyl, cycloalkyl, O-alkyl, NH-alkyl, C(O)OH, C(O)—$NH_2$, C(O)—$N(CH_3)_2$, C(O)—$NHCH_3$, NHC(O)—$N(CH_3)_2$, CN, or $CF_3$, wherein $X_1$, $X_2$ and $X_3$ are each N, α is present and β is absent; or $X_1$ is NH, $X_2$ is C, $X_3$ is CH, α is absent and β is present; or $X_1$ is N, $X_2$ is N, $X_3$ is CH, α is present and β is absent; or $X_1$ is NH or $NR_{10}$, $X_2$ is C, $X_3$ is N, α is absent and β is present, wherein when $X_1$ is NH, $X_2$ is C, $X_3$ is N, α is absent and β is present, then one of $R_7$, $R_8$ and $R_9$ is other than H, or B has the structure:

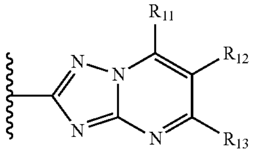

wherein $R_{11}$, $R_{12}$ and $R_{13}$ are each, independently, H, halogen, alkyl, alkyl-OH, alkyl-$NH_2$, alkyl-OAc, alky-O-alkyl, haloalkyl, cycloalkyl, O-alkyl, NH-alkyl, C(O)OH, C(O)—$NH_2$, C(O)—$N(CH_3)_2$, C(O)—$NHCH_3$, NHC(O)—$N(CH_3)_2$, CN, or $CF_3$, or a pharmaceutically acceptable salt thereof.

In some embodiments, the compound of the method has the structure:

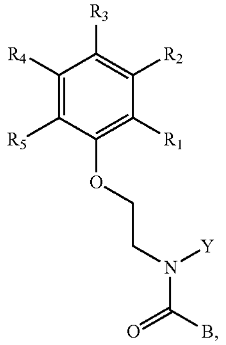

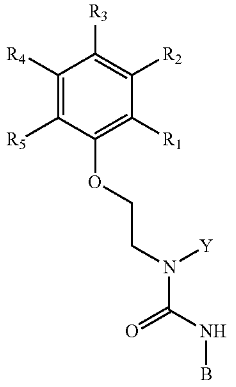

or

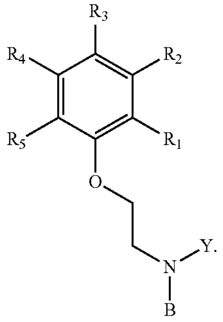

In some embodiments, the compound of the method has the structure:

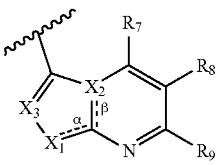

wherein

α and β are each a bond that is present or absent;

$X_1$ is N, NH or $NR_{10}$, wherein $R_{10}$ is alkyl, alkenyl or alkynyl;

$X_2$ is C or N;

$X_3$ is CH or N;

$R_7$, $R_8$ and $R_9$ are each, independently, H, halogen, alkyl, alkenyl, alkynyl, alkyl-OH, alkyl-$NH_2$, alkyl-OAc alkyl-O(CO)-alkyl, alkyl-O-alkyl, haloalkyl, cycloalkyl, O-alkyl, NH-alkyl, C(O)OH, C(O)—$NH_2$, C(O)—$N(CH_3)_2$, C(O)—$NHCH_3$, NHC(O)—$N(CH_3)_2$, CN or $CF_3$, wherein $X_1$, $X_2$ and $X_3$ are each N, α is present and β is absent; or $X_1$ is NH, $X_2$ is C, $X_3$ is CH, α is absent and β is present; or $X_1$ is N, $X_2$ is N, $X_3$ is CH, α is present and β is absent; or $X_1$ is NH or $NR_{10}$, $X_2$ is C, $X_3$ is N, α is absent and β is present, wherein when $X_1$ is NH, $X_2$ is C, $X_3$ is N, α is absent and β is present, then one of $R_7$, $R_8$ and $R_9$ is other than H.

In some embodiments, B or $B_2$ has the structure:

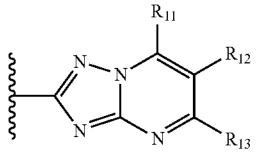

wherein $R_{11}$, $R_{12}$ and $R_{13}$ are each, independently, H, halogen, alkyl, alkenyl, alkynyl alkyl-OH, alkyl-$NH_2$, alkyl-OAc, alkyl-O(CO)-alkyl, alkyl-O-alkyl, haloalkyl, cycloalkyl, O-alkyl, NH-alkyl, C(O)OH, C(O)—$NH_2$, C(O)—$N(CH_3)_2$, C(O)—$NHCH_3$, NHC(O)—$N(CH_3)_2$, CN or $CF_3$.

In some embodiments, B or $B_2$ has the structure:

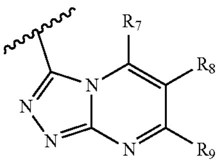

$R_7$, $R_8$ and $R_9$ are each, independently, H, halogen, alkyl, alkyl-OH, alkyl-$NH_2$, alkyl-OAc, alkyl-O-alkyl, haloalkyl, cycloalkyl, O-alkyl, NH-alkyl, C(O)OH, C(O)—$NH_2$, C(O)—$N(CH_3)_2$, C(O)—$NHCH_3$, NHC(O)—$N(CH_3)_2$, CN, or $CF_3$.

In some embodiments, B or $B_2$ has the structure:

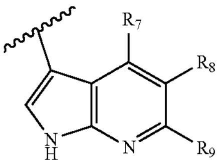

$R_7$, $R_8$ and $R_9$ are each, independently, H, halogen, alkyl, alkyl-OH, alkyl-$NH_2$, alkyl-OAc, alkyl-O-alkyl, haloalkyl, cycloalkyl, O-alkyl, NH-alkyl, C(O)OH, C(O)—$NH_2$, C(O)—$N(CH_3)_2$, C(O)—$NHCH_3$, NHC(O)—$N(CH_3)_2$, CN, or $CF_3$.

In some embodiments, B or $B_2$ has the structure:

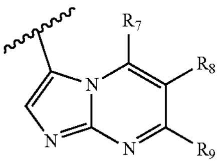

$R_7$, $R_8$ and $R_9$ are each, independently, H, halogen, alkyl, alkyl-OH, alkyl-$NH_2$, alkyl-OAc, alkyl-O-alkyl, haloalkyl, cycloalkyl, O-alkyl, NH-alkyl, C(O)OH, C(O)—$NH_2$, C(O)—$N(CH_3)_2$, C(O)—$NHCH_3$, NHC(O)—$N(CH_3)_2$, CN, or $CF_3$.

In some embodiments, B or $B_2$ has the structure:

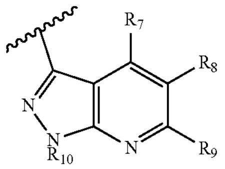

$R_7$, $R_8$ and $R_9$ are each, independently, H, halogen, alkyl, alkyl-OH, alkyl-$NH_2$, alkyl-OAc, alkyl-O-alkyl, haloalkyl, cycloalkyl, O-alkyl, NH-alkyl, C(O)OH, C(O)—$NH_2$, C(O)—$N(CH_3)_2$, C(O)—$NHCH_3$, NHC(O)—$N(CH_3)_2$, CN, or $CF_3$; and $R_{10}$ is alkyl, alkenyl or alkynyl.

In some embodiments, $R_7$, $R_8$ and $R_9$ are each, independently, H, Cl, Br, F, $OCH_3$, $OCH_2CH_3$, $CF_3$, CN, $CH_3$, $CH_3CH_3$, C(O)OH or C(O)—$NH_2$.

In some embodiments, $R_7$, $R_8$ and $R_9$ are each, independently, H, $CH_2CH_2OH$, $CH_2CH_2OCH_3$, $CH_2CH_2OAc$, $CH_2CH_2Cl$, $CH_2CH_2F$ or $CH_2CH_2Br$.

In some embodiments, $R_7$, $R_8$ and $R_9$ are each, independently, H, halogen or alkyl.

In some embodiments, two of $R_7$, $R_8$ and $R_9$ are each H and the remaining one of $R_7$, $R_8$ and $R_9$ is other than H.

In some embodiments, one of $R_7$, $R_8$ and $R_9$ is H and the remaining two of $R_7$, $R_8$ and $R_9$ are each other than H.

In some embodiments, B or $B_2$ has the structure:

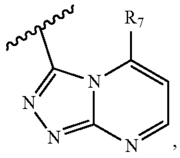 ,

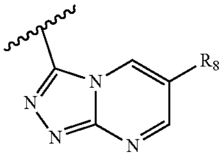 or

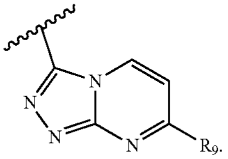

In some embodiments, $R_7$, $R_8$ and $R_9$ are each, independently, H, $CH_3$, Br, Cl, F, $CH_2CH_2OH$, $CH_2CH_2OCH_3$, $CH_2CH_2OAc$, $CH_2CH_2Cl$, $CH_2CH_2F$ or $CH_2CH_2Br$.

In some embodiments, B or $B_2$ has the structure:

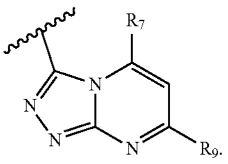

In some embodiments, $R_7$ and $R_9$ are each, independently, H, $CH_3$, Br, Cl, F, $CH_2CH_2OH$, $CH_2CH_2OCH_3$, $CH_2CH_2OAc$, $CH_2CH_2Cl$, $CH_2CH_2F$ or $CH_2CH_2Br$.

In some embodiments B or $B_2$ has the structure:

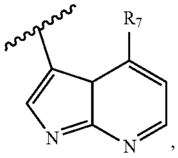
,
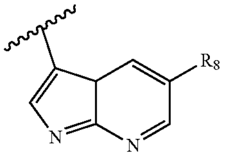
or
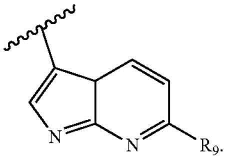

In some embodiments, $R_7$, $R_8$ and $R_9$ are each, independently, H, $CH_3$, Br, Cl, F, $CH_2CH_2OH$, $CH_2CH_2OCH_3$, $CH_2CH_2OAc$, $CH_2CH_2Cl$, $CH_2CH_2F$ or $CH_2CH_2Br$.

In some embodiments, B or $B_2$ has the structure:

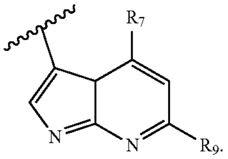

In some embodiments, $R_7$ and $R_8$ are each, independently, H, $CH_3$, Br, Cl, F, $CH_2CH_2OH$, $CH_2CH_2OCH_3$, $CH_2CH_2OAc$, $CH_2CH_2Cl$, $CH_2CH_2F$ or $CH_2CH_2Br$.

In some embodiments, the compound wherein B has the structure:

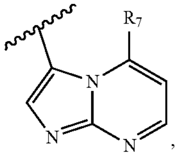
,
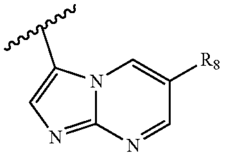
or
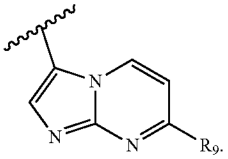

In some embodiments, $R_7$, $R_8$ and $R_9$ are each, independently, H, $CH_3$, Br, Cl, F, $CH_2CH_2OH$, $CH_2CH_2OCH_3$, $CH_2CH_2OAc$, $CH_2CH_2Cl$, $CH_2CH_2F$ or $CH_2CH_2Br$.

In some embodiments, B or $B_2$ has the structure:

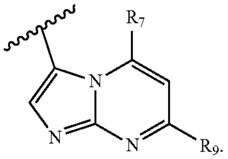

In some embodiments, $R_7$ and $R_9$ are each, independently, H, $CH_3$, Br, Cl, F, $CH_2CH_2OH$, $CH_2CH_2OCH_3$, $CH_2CH_2OAc$, $CH_2CH_2Cl$, $CH_2CH_2F$ or $CH_2CH_2Br$.

In some embodiments, B or $B_2$ has the structure:

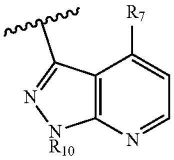
,
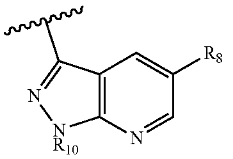
or
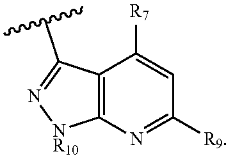

In some embodiments, the compound wherein $R_7$, $R_8$ and $R_9$ are each, independently, H, $CH_3$, Br, Cl, F, $CH_2CH_2OH$, $CH_2CH_2OCH_3$, $CH_2CH_2OAc$, $CH_2CH_2Cl$, $CH_2CH_2F$ or $CH_2CH_2Br$; and $R_{10}$ is alkyl.

In some embodiments, B or $B_2$ has the structure:

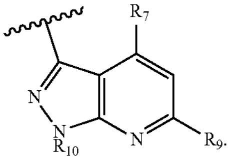

In some embodiments, $R_7$ and $R_9$ are each, independently, H, $CH_3$, Br, Cl, F, $CH_2CH_2OH$, $CH_2CH_2OCH_3$, $CH_2CH_2OAc$, $CH_2CH_2Cl$, $CH_2CH_2F$ or $CH_2CH_2Br$; and $R_{10}$ is alkyl.

In some embodiments, B or $B_2$ has the structure:

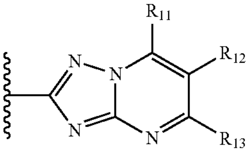

$R_{11}$, $R_{12}$ and $R_{13}$ are each, independently, H, halogen, alkyl, alkyl-OH, alkyl-$NH_2$, alkyl-OAc, alkyl-O-alkyl, haloalkyl, cycloalkyl, O-alkyl, NH-alkyl, C(O)OH, C(O)—$NH_2$, C(O)—$N(CH_3)_2$, C(O)—$NHCH_3$, NHC(O)—$N(CH_3)_2$, CN, or $CF_3$.

In some embodiments, $R_{11}$, $R_{12}$ and $R_{13}$ are each, independently, H, Cl, Br, F, $OCH_3$, $OCH_2CH_3$, $CF_3$, CN, $CH_3$, $CH_3CH_3$, C(O)OH or C(O)—$NH_2$.

In some embodiments, $R_{11}$, $R_{12}$ and $R_{13}$ are each, independently, H, $CH_2CH_2OH$, $CH_2CH_2OCH_3$, $CH_2CH_2OAc$, $CH_2CH_2Cl$, $CH_2CH_2F$ or $CH_2CH_2Br$.

In some embodiments, $R_{11}$, $R_{12}$ and $R_{13}$ are each, independently, H, halogen or alkyl.

In some embodiments, two of $R_{11}$, $R_{12}$ and $R_{13}$ are each H and the remaining one of $R_{11}$, $R_{12}$ and $R_{13}$ is other than H.

In some embodiments, one of $R_{11}$, $R_{12}$ and $R_{13}$ is H and the remaining two of $R_{11}$, $R_{12}$ and $R_{13}$ are each other than H.

In some embodiments, B or $B_2$ has the structure:

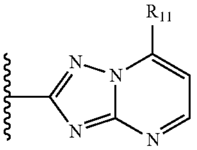,
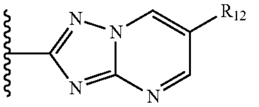 or
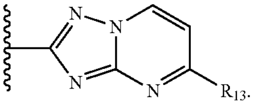

In some embodiments, $R_{11}$, $R_{12}$ and $R_{13}$ are each, independently, H, $CH_3$, Br, Cl, F, $CH_2CH_2OH$, $CH_2CH_2OCH_3$, $CH_2CH_2OAc$, $CH_2CH_2Cl$, $CH_2CH_2F$ or $CH_2CH_2Br$.

In some embodiments, B or $B_2$ has the structure:

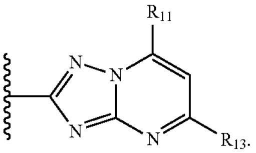

In some embodiments, $R_{11}$ and $R_{13}$ are each, independently, H, $CH_3$, Br, Cl, F, $CH_2CH_2OH$, $CH_2CH_2OCH_3$, $CH_2CH_2OAc$, $CH_2CH_2Cl$, $CH_2CH_2F$ or $CH_2CH_2Br$.

In some embodiments, X is N. In some embodiments, the compound wherein X is CH.

In some embodiments, $R_1$, $R_2$, $R_3$, $R_4$, and $R_5$ are each H, t-Bu, Cl, F, or $CF_3$.

In some embodiments, $R_1$, $R_2$, $R_3$, and $R_4$ are each H; and $R_5$ is $CF_3$ or t-Bu.

In some embodiments, $R_1$, $R_3$ and $R_4$ are each H;

$R_2$ is halogen;

$R_5$ is $CF_3$ or t-Bu.

In some embodiments, $R_1$, $R_2$, $R_3$, and $R_4$ are each H, $R_5$ is $CF_3$ or t-Bu.

In some embodiments, $R_1$, $R_2$, $R_3$, and $R_4$ are each H, $R_5$ is $CF_3$.

In some embodiments, one of $R_1$, $R_2$, $R_3$, $R_4$, and $R_5$ is other than H.

In some embodiments, two of $R_1$, $R_2$, $R_3$, $R_4$, and $R_5$ are other than H.

In some embodiments, two or more of $R_1$, $R_2$, $R_3$, $R_4$, and $R_5$ are other than H.

In some embodiments, three of $R_1$, $R_2$, $R_3$, $R_4$, and $R_5$ are other than H.

In some embodiments, three or more of $R_1$, $R_2$, $R_3$, $R_4$, and $R_5$ are other than H.

In some embodiments, the compound of the method has the structure:

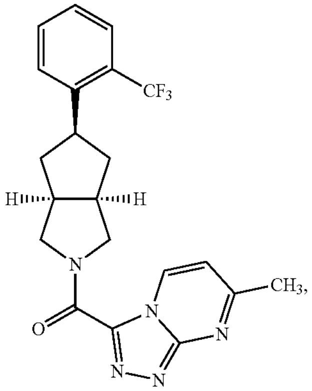
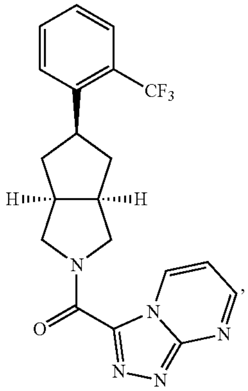,
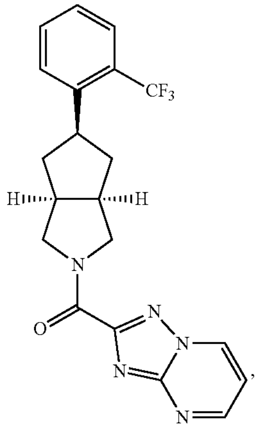,
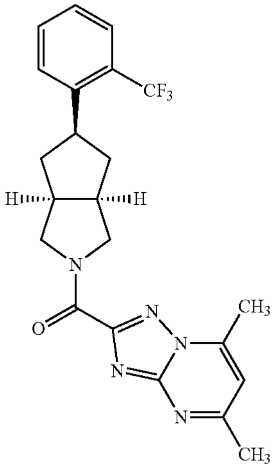,
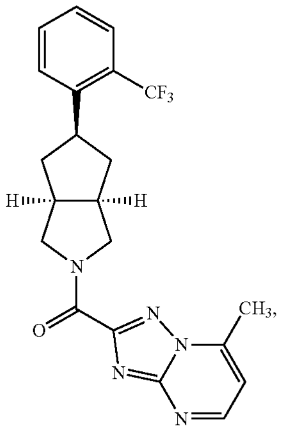

-continued
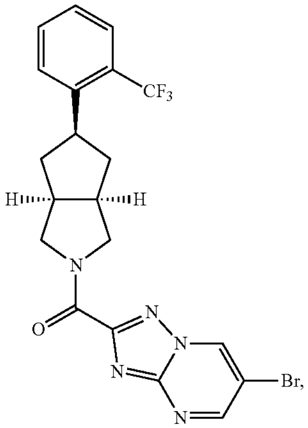
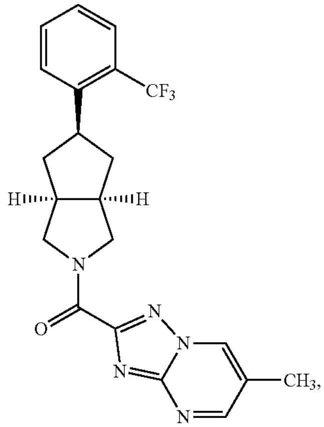
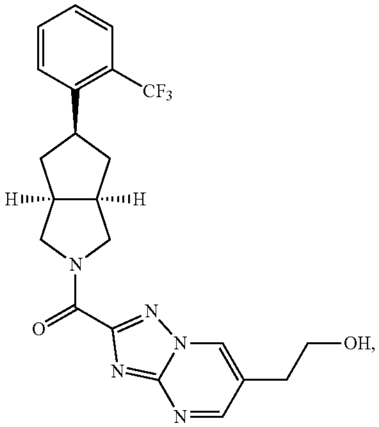
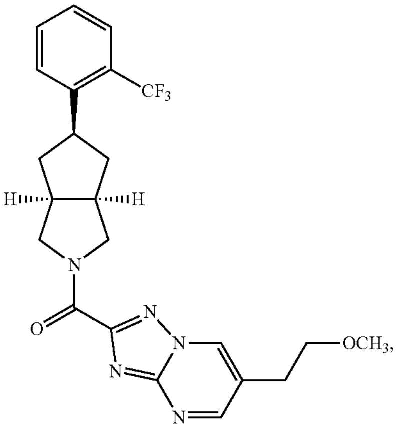
-continued
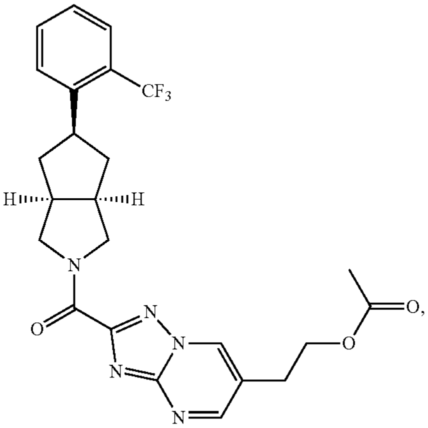
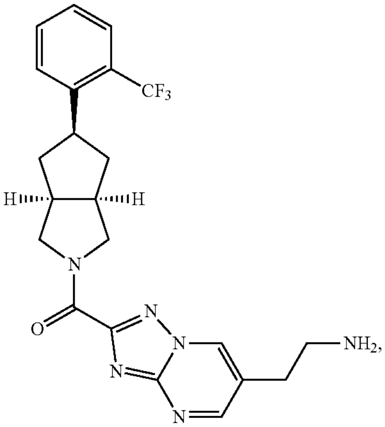
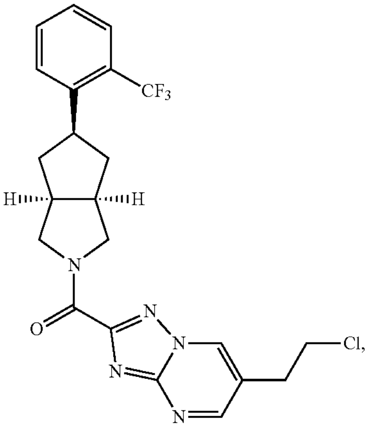
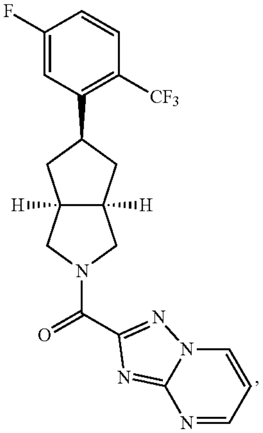

-continued

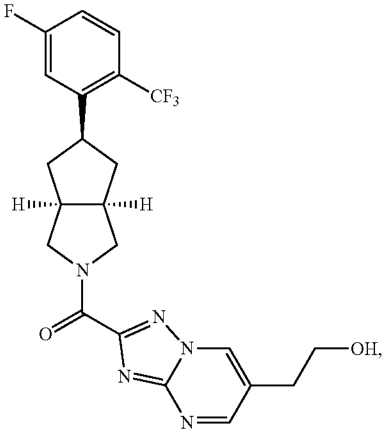

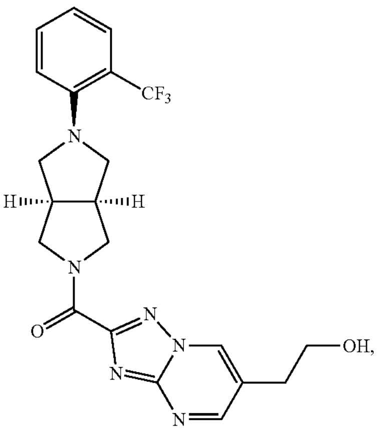

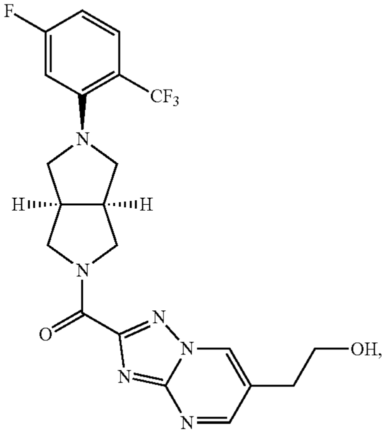

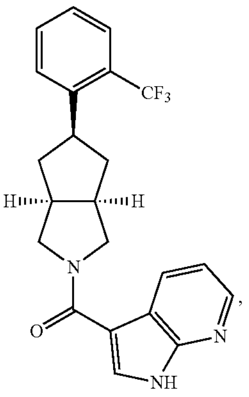

-continued

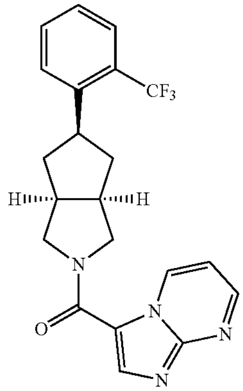

or

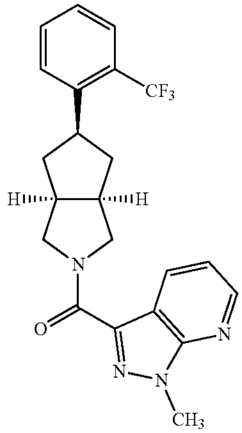

, or a pharmaceutically acceptable salt thereof.

In some embodiments, B or $B_2$ is other than

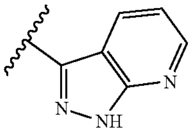

.

The present invention provides compound having the structure:

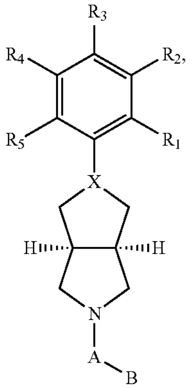

wherein $R_1$, $R_2$, $R_3$, $R_4$, and $R_5$ are each independently H, halogen, alkyl, haloalkyl, O-haloalkyl, aryl or heteroaryl;

X is N or $CR_6$, wherein $R_6$ is H, OH, or halogen;

A is absent or present, and when present is

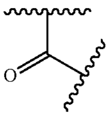

or

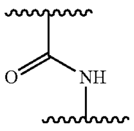

;

B has the structure:

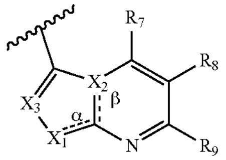

wherein

α and β are each a bond that is present or absent;

$X_1$ is N, NH or $NR_{10}$, wherein $R_{10}$ is alkyl, alkenyl or alkynyl;

$X_2$ is C or N;

$X_3$ is CH or N;

$R_7$, $R_8$ and $R_9$ are each, independently, H, halogen, alkyl, alkenyl, alkynyl, alkyl-OH, alkyl-$NH_2$, alkyl-OAc alkyl-O(CO)-alkyl, alkyl-O-alkyl, haloalkyl, cycloalkyl, O-alkyl, NH-alkyl, C(O)OH, C(O)—$NH_2$, C(O)—$N(CH_3)_2$, C(O)—$NHCH_3$, NHC(O)—$N(CH_3)_2$, CN or $CF_3$, wherein $X_1$, $X_2$ and $X_3$ are each N, α is present and β is absent; or $X_1$ is NH, $X_2$ is C, $X_3$ is CH, α is absent and β is present; or $X_1$ is N, $X_2$ is N, $X_3$ is CH, α is present and β is absent; or $X_1$ is NH or $NR_{10}$, $X_2$ is C, $X_3$ is N, α is absent and β is present, wherein when $X_1$ is NH, $X_2$ is C, $X_3$ is N, α is absent and β is present, then one of $R_7$, $R_8$ and $R_9$ is other than H, or B has the structure:

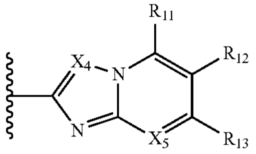

wherein $X_4$ and $X_5$ are each, independently, is N or CH; and $R_{11}$, $R_{12}$ and $R_{13}$ are each, independently, H, halogen, alkyl, alkenyl, alkynyl, alkyl-OH, alkyl-$NH_2$, alkyl-OAc, alkyl-O(CO)-alkyl, alkyl-O-alkyl, haloalkyl, cycloalkyl, O-alkyl, NH-alkyl, C(O)OH, C(O)—$NH_2$, C(O)—$N(CH_3)_2$, C(O)—$NHCH_3$, NHC(O)—$N(CH_3)_2$, CN or $CF_3$, or a pharmaceutically acceptable salt thereof.

54. A compound having the structure:

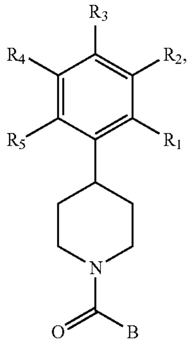

wherein $R_1$, $R_2$, $R_3$, $R_4$, and $R_5$ are each independently H, halogen, $CF_3$ or $C_1$-$C_4$ alkyl, aryl or heteroaryl; and B has the structure:

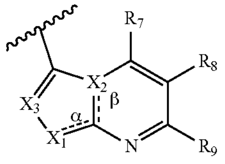

wherein

α and β are each a bond that is present or absent;

$X_1$ is N, NH or $NR_{10}$, wherein $R_{10}$ is alkyl, alkenyl or alkynyl;

$X_2$ is C or N;

$X_3$ is CH or N;

$R_7$, $R_8$ and $R_9$ are each, independently, H, halogen, alkyl, alkenyl, alkynyl, alkyl-OH, alkyl-$NH_2$, alkyl-OAc, alky-O-alkyl, haloalkyl, cycloalkyl, O-alkyl, NH-alkyl, C(O)OH, C(O)—$NH_2$, C(O)—$N(CH_3)_2$, C(O)—$NHCH_3$, NHC(O)—$N(CH_3)_2$, CN, or $CF_3$, wherein $X_1$, $X_2$ and $X_3$ are each N, α is present and β is absent; or $X_1$ is NH, $X_2$ is C, $X_3$ is CH, α is absent and β is present; or $X_1$ is N, $X_2$ is N, $X_3$ is CH, α is present and β is absent; or $X_1$ is NH or $NR_{10}$, $X_2$ is C, $X_3$ is N, α is absent and β is present, wherein when $X_1$ is NH, $X_2$ is C, $X_3$ is N, α is absent and β is present, then one of $R_7$, $R_8$ and $R_9$ is other than H, or B has the structure:

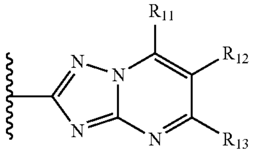

wherein $R_{11}$, $R_{12}$ and $R_{13}$ are each, independently, H, halogen, alkyl, alkyl-OH, alkyl-$NH_2$, alkyl-OAc, alky-O-alkyl, haloalkyl, cycloalkyl, O-alkyl, NH-alkyl, C(O)OH, C(O)—$NH_2$, C(O)—$N(CH_3)_2$, C(O)—$NHCH_3$, NHC(O)—$N(CH_3)_2$, CN, or $CF_3$, or a pharmaceutically acceptable salt thereof.

A compound having the structure:

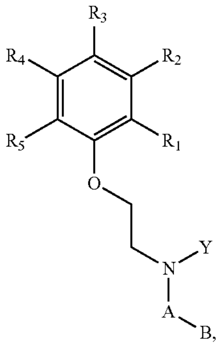

wherein $R_1$, $R_2$, $R_3$, $R_4$, and $R_5$ are each independently H, halogen, $CF_3$ or $C_1$-$C_4$ alkyl aryl or heteroaryl;

Y is alkyl;

A is absent or present, and when present is

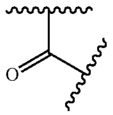

or

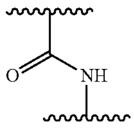

;

and

B has the structure:

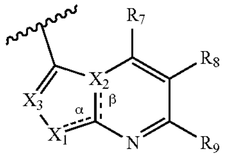

wherein

α and β are each a bond that is present or absent;

$X_1$ is N, NH or $NR_{10}$, wherein $R_{10}$ is alkyl, alkenyl or alkynyl;

$X_2$ is C or N;

$X_3$ is CH or N;

$R_7$, $R_8$ and $R_9$ are each, independently, H, halogen, alkyl, alkenyl, alkynyl, alkyl-OH, alkyl-$NH_2$, alkyl-OAc, alky-O-alkyl, haloalkyl, cycloalkyl, O-alkyl, NH-alkyl, C(O)OH, C(O)—$NH_2$, C(O)—$N(CH_3)_2$, C(O)—$NHCH_3$, NHC(O)—$N(CH_3)_2$, CN, or $CF_3$, wherein $X_1$, $X_2$ and $X_3$ are each N, α is present and β is absent; or $X_1$ is NH, $X_2$ is C, $X_3$ is CH, α is absent and β is present; or $X_1$ is N, $X_2$ is N, $X_3$ is CH, α is present and β is absent; or $X_1$ is NH or $NR_{10}$, $X_2$ is C, $X_3$ is N, α is absent and β is present, wherein when $X_1$ is NH, $X_2$ is C, $X_3$ is N, α is absent and β is present, then one of $R_7$, $R_8$ and $R_9$ is other than H, or B has the structure:

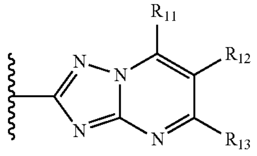

wherein $R_{11}$, $R_{12}$ and $R_{13}$ are each, independently, H, halogen, alkyl, alkyl-OH, alkyl-$NH_2$, alkyl-OAc, alky-O-alkyl, haloalkyl, cycloalkyl, O-alkyl, NH-alkyl, C(O)OH, C(O)—$NH_2$, C(O)—$N(CH_3)_2$, C(O)—$NHCH_3$, NHC(O)—$N(CH_3)_2$, CN, or $CF_3$, or a pharmaceutically acceptable salt thereof.

In some embodiments of the above compound, wherein one of $R_1$, $R_2$, $R_3$, $R_4$, and $R_5$ is other than H.

In some embodiments of the above compound, wherein two of $R_1$, $R_2$, $R_3$, $R_4$, and $R_5$ are other than H.

In some embodiments of the above compound, wherein $R_1$, $R_2$, $R_3$, $R_4$, and $R_5$ are each H, methyl, ethyl, phenyl, t-Bu, i-Pr, $OCF_3$, $CF_3$, $OCF_2CF_3$, $CF_2CF_3$, Cl, Br, or F.

In some embodiments of the above compound, wherein $R_1$, $R_2$, $R_3$, and $R_4$ are each H; and $R_5$ is —H, $OCF_3$, $CF_2CF_3$, methyl, ethyl, i-Pr or phenyl.

In some embodiments, the compound having the structure:

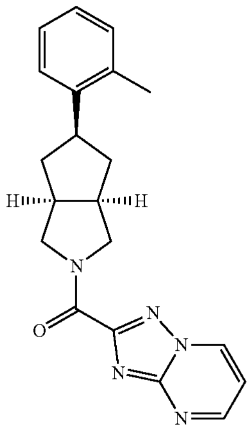

,

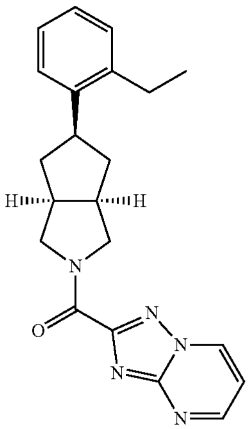

,

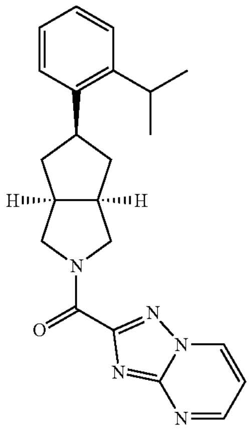

,

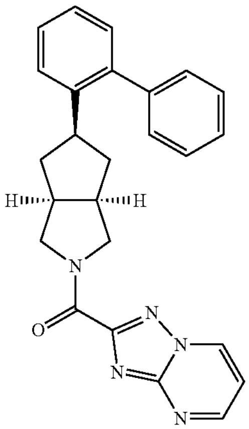

,

-continued
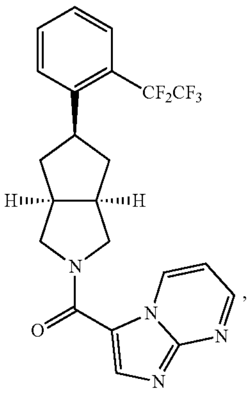
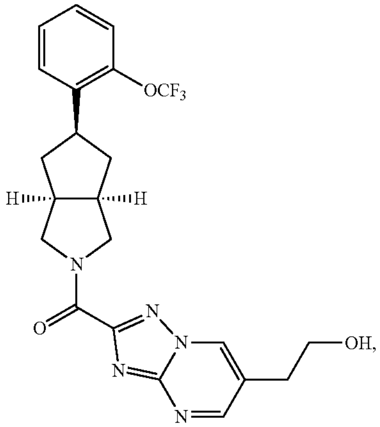
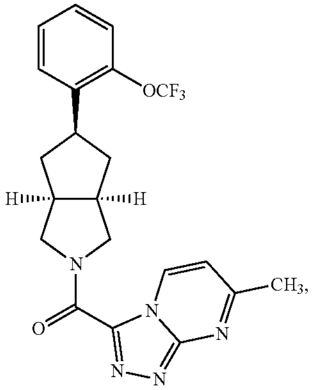
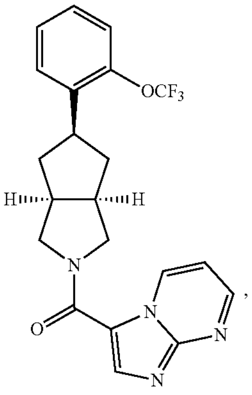
-continued
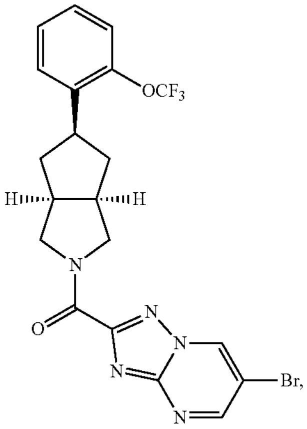
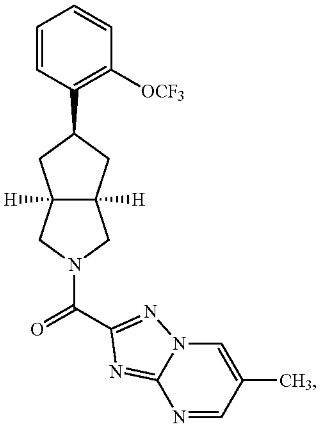
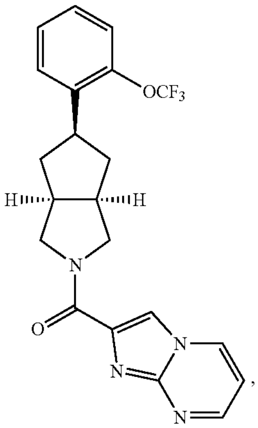

-continued

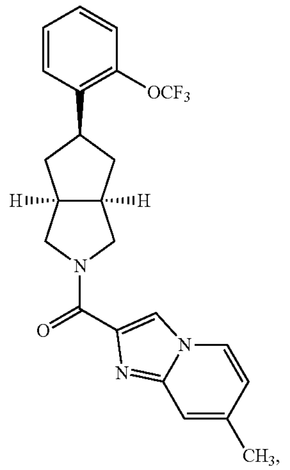

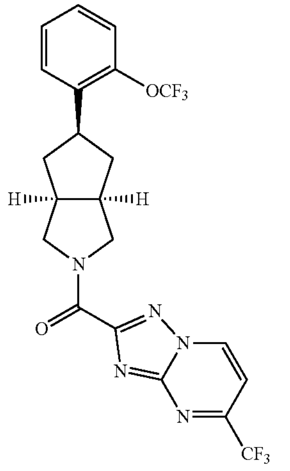

or

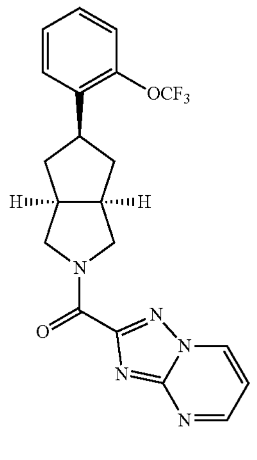

, or a pharmaceutically acceptable salt thereof.

The compounds and genera of compounds disclosed in PCT International Publication Nos. WO 2014/152013, WO 2015/168286, WO 2014/151959, WO 2014/152018, and WO 2014/151936 may be used in the methods of the present invention and thus the compounds and the genera of compounds disclosed in each of PCT International Publication Nos. WO 2014/152013, WO 2015/168286, WO 2014/151959, WO 2014/152018, and WO 2014/151936 are hereby incorporated by reference into the methods of this invention.

In embodiments, the compound is a RBP4 antagonist.

In an embodiment, the amount of the compound is 5-1000 mg, 5-800 mg, 5-200 mg, 45-200 mg, 45-1000 mg, 45-800 mg, 10-50 mg, 96 mg, 24 mg or 10 mg per day.

In some embodiments, the method further comprises administering an amount of a second agent which is (R)-(+)-(5,6-dichloro 2,3,9,9a-tetrahydro 3-oxo-9a-propyl-1H-fluoren-7-yl)oxy]acetic acid (DPOFA), a Nonsteroidal Anti-inflammatory Drug (NSAID) such as indomethacin, colchicine, lesinurad, corticosteroids (e.g., betamethasone, prednisone, dexamethasone, cortisone, cortisone, hydrocortisone, methylprednisone, prednisolone), biologic anti-IL-1alpha/beta agents (e.g., canakinumab, rilonacept, anakinra), allopurinol, benzbromarone, pegloticase and other forms of uricase enzymes, topiroxostat (FYX-051), ulodesine (BCX4208), KUX-1151, RLBN1001, RDEA3170, arhalofenate (MBX-102), levotofisopam, UR-1102, PF-06743649, BCX4208, SHR4640, Lumiracoxib, Tranilast, Topiroxostat, LC350189, Bucillamine, AC-201, HuZhen Capsules (include *Polygonum cuspidatum* and *Ligustrum lucidum*), MPC-004, FYU-981, Sodium Bicarbonate, SEL-212, SEL-037, Apremilast, TMX-67, SSS11, D-0120, febuxostat or probenecid, or esters or salts thereof effective to treat the subject, thereby treating the subject.

In one embodiment, the second agent is DPOFA.

In some embodiments, the subject is afflicted with gout.

In an embodiment, the amount of the second agent and/or the amount of the compound is effective in reducing uric acid levels in the blood of the subject. In another embodiment, the amount of the second agent and/or the amount of the compound is effective in decreasing uric acid reabsorption in the kidneys of the subject.

In one embodiment, the amount of the second agent is effective in increasing uric acid clearance in the subject.

In some embodiments, the amount of the second agent is effective in increasing uric acid levels in the urine of the subject.

In one embodiment, the amount of the second agent is effective in increasing renal clearance of uric acid in the subject. In additional embodiments, the amount of the second agent and/or the amount of the compound is effective in reducing one or more symptoms associated with gout in the subject.

In some embodiments, the one or more symptoms associated with gout are joint pain, joint inflammation, joint redness, decreased range of motion at the joint. In additional embodiments, the amount of second agent and/or the amount of the compound is effective in preventing gout in the subject.

In one embodiment, the preventing comprises increasing uric acid levels in the urine of the subject. In another embodiment, the preventing comprises reducing uric acid levels in the blood of the subject. In another embodiment, the preventing comprises increasing uric acid clearance in the subject. In another embodiment, the preventing comprises decreasing uric acid reabsorption in the kidneys of the subject.

In one embodiment, the preventing comprises increasing renal clearance of uric acid in the subject. In another embodiment, the preventing comprises reducing one or more symptoms associated with gout in the subject.

In some embodiments, the one or more symptoms associated with gout are joint pain, joint inflammation, joint redness, decreased range of motion at the joint.

In one embodiment, the gout is chronic gout. In a different embodiment, the gout is acute gout.

In some embodiments, the amount of the second agent and/or the amount of the compound prevents a recurrence of chronic gout.

The subject is a mammal in an embodiment of this invention.

In some embodiments, the subject is female and administration of the compound reduces the uric acid level 2.4-6.0 mg/dL. In another embodiment, the subject is male and administration of the compound reduces the uric acid level 3.4-7.0 mg/dL.

In another embodiment, the administration of the compound reduces uric acid levels in the subject to less than 7 mg/dL.

The invention also provides a pharmaceutical composition comprising an amount of a retinol-binding protein 4 (RBP4) antagonist or a compound defined above for treating a subject afflicted with a non-alcoholic fatty liver disease (NAFLD) disease or gout.

In some embodiments, the pharmaceutical composition further comprises an amount of second agent, for treating a subject afflicted with a non-alcoholic fatty liver disease (NAFLD) disease or gout.

In some embodiments, the RBP4 antagonist or the compound and a second agent are prepared to be administered simultaneously, contemporaneously or concomitantly.

The invention further provides a pharmaceutical composition comprising a retinol-binding protein 4 (RBP4) antagonist or a compound defined above for use in a combination therapy together with a pharmaceutical composition comprising a second agent, for the treatment of a non-alcoholic fatty liver disease (NAFLD) disease or gout.

The invention additionally provides a pharmaceutical composition comprising an amount of a retinol-binding protein 4 (RBP4) antagonist or a compound defined above for use in treating a subject afflicted with a non-alcoholic fatty liver disease (NAFLD) disease or gout as an add-on therapy to or in combination with a second agent.

The invention also provides for the use of a retinol-binding protein 4 (RBP4) antagonist or a compound defined above for the preparation of a medicament for treating a subject afflicted with a non-alcoholic fatty liver disease (NAFLD) disease or gout.

As used herein, "combination" means an assemblage of reagents for use in therapy either by simultaneous or contemporaneous administration. Simultaneous administration refers to administration of an admixture (whether a true mixture, a suspension, an emulsion or other physical combination) of the first compound and the second compound. In this case, the combination may be the admixture or separate containers of the first compound and the second compound that are combined just prior to administration. Contemporaneous administration refers to the separate administration of the first compound and the second compound at the same time, or at times sufficiently close together that an additive or preferably synergistic activity relative to the activity of either the first compound or the second compound alone is observed.

As used herein, "concomitant administration" or administering "concomitantly" means the administration of two agents given in close enough temporal proximately to allow the individual therapeutic effects of each agent to overlap.

As used herein, "add-on" or "add-on therapy" means an assemblage of reagents for use in therapy, wherein the subject receiving the therapy begins a first treatment regimen of one or more reagents prior to beginning a second treatment regimen of one or more different reagents in addition to the first treatment regimen, so that not all of the reagents used in the therapy are started at the same time. For example, adding Compound 1 therapy to a subject already receiving DPOFA therapy.

As used herein, a "non-retinoid RBP4 antagonist" is a RBP4 antagonist that is not a retinoid. A retinoid is a natural or synthetic analog of retinol which consists of four isoprenoid units joined in a head-to-tail manner. Retinoids are described in IUPAC-IUB Joint Commission on Biochemical Nomenclature 1982.

Except where otherwise specified, when the structure of a compound of this invention includes an asymmetric carbon atom, it is understood that the compound occurs as a racemate, racemic mixture, and isolated single enantiomer. All such isomeric forms of these compounds are expressly included in this invention. Except where otherwise specified, each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "Enantiomers, Racemates and Resolutions" by J. Jacques, A. Collet and S. Wilen, Pub. John Wiley & Sons, N Y, 1981. For example, the resolution may be carried out by preparative chromatography on a chiral column.

The subject invention is also intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include C-13 and C-14.

It will be noted that any notation of a carbon in structures throughout this application, when used without further notation, are intended to represent all isotopes of carbon, such as $^{12}C$, $^{13}C$, or $^{14}C$. Furthermore, any compounds containing $^{13}C$ or $^{14}C$ may specifically have the structure of any of the compounds disclosed herein.

It will also be noted that any notation of a hydrogen in structures throughout this application, when used without further notation, are intended to represent all isotopes of hydrogen, such as $^{1}H$, $^{2}H$, or $^{3}H$. Furthermore, any compounds containing $^{2}H$ or $^{3}H$ may specifically have the structure of any of the compounds disclosed herein.

Isotopically-labeled compounds can generally be prepared by conventional techniques known to those skilled in the art using appropriate isotopically-labeled reagents in place of the non-labeled reagents employed.

The term "substitution", "substituted" and "substituent" refers to a functional group as described above in which one or more bonds to a hydrogen atom contained therein are replaced by a bond to non-hydrogen or non-carbon atoms, provided that normal valencies are maintained and that the substitution results in a stable compound. Substituted groups also include groups in which one or more bonds to a carbon(s) or hydrogen(s) atom are replaced by one or more bonds, including double or triple bonds, to a heteroatom. Examples of substituent groups include the functional groups described above, and halogens (i.e., F, Cl, Br, and I); alkyl groups, such as methyl, ethyl, n-propyl, isoproprl, n-butyl, tert-butyl, and trifluoromethyl; hydroxyl; alkoxy groups, such as methoxy, ethoxy, n-propoxy, and isopropoxy; aryloxy groups, such as phenoxy; arylalkyloxy, such as benzyloxy (phenylmethoxy) and p-trifluoromethylbenzyloxy (4-trifluoromethylphenylmethoxy); heteroaryloxy groups; sulfonyl groups, such as trifluoromethanesulfonyl, methanesulfonyl, and p-toluenesulfonyl; nitro, nitrosyl; mercapto; sulfanyl groups, such as methylsulfanyl, ethylsulfanyl and propylsulfanyl; cyano; amino groups, such as amino, methylamino, dimethylamino, ethylamino, and diethylamino; and carboxyl. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

In the compounds used in the method of the present invention, the substituents may be substituted or unsubstituted, unless specifically defined otherwise.

In the compounds used in the method of the present invention, alkyl, heteroalkyl, monocycle, bicycle, aryl, heteroaryl and heterocycle groups can be further substituted by replacing one or more hydrogen atoms with alternative non-hydrogen groups. These include, but are not limited to, halo, hydroxy, mercapto, amino, carboxy, cyano and carbamoyl.

It is understood that substituents and substitution patterns on the compounds used in the method of the present invention can be selected by one of ordinary skill in the art to provide compounds that are chemically stable and that can be readily synthesized by techniques known in the art from readily available starting materials. If a substituent is itself substituted with more than one group, it is understood that these multiple groups may be on the same carbon or on different carbons, so long as a stable structure results.

In choosing the compounds used in the method of the present invention, one of ordinary skill in the art will recognize that the various substituents, i.e. $R_1$, $R_2$, etc. are to be chosen in conformity with well-known principles of chemical structure connectivity.

As used herein, "alkyl" is intended to include both branched and straight-chain saturated aliphatic hydrocarbon groups having the specified number of carbon atoms. Thus, $C_1$-$C_n$ as in "$C_1$-$C_n$ alkyl" is defined to include groups having 1, 2 . . . , n−1 or n carbons in a linear or branched arrangement, and specifically includes methyl, ethyl, propyl, butyl, pentyl, hexyl, heptyl, isopropyl, isobutyl, sec-butyl and so on. An embodiment can be $C_1$-$C_{12}$ alkyl, $C_2$-$C_{12}$ alkyl, $C_3$-$C_{12}$ alkyl, $C_4$-$C_{12}$ alkyl and so on. An embodiment can be $C_1$-$C_8$ alkyl, $C_2$-$C_8$ alkyl, $C_3$-$C_8$ alkyl, $C_4$-$C_8$ alkyl and so on. "Alkoxy" represents an alkyl group as described above attached through an oxygen bridge.

The term "alkenyl" refers to a non-aromatic hydrocarbon radical, straight or branched, containing at least 1 carbon to carbon double bond, and up to the maximum possible number of non-aromatic carbon-carbon double bonds may be present. Thus, $C_2$-$C_n$ alkenyl is defined to include groups having 1, 2 . . . , n−1 or n carbons. For example, "$C_2$-$C_6$ alkenyl" means an alkenyl radical having 2, 3, 4, 5, or 6 carbon atoms, and at least 1 carbon-carbon double bond, and up to, for example, 3 carbon-carbon double bonds in the case of a $C_6$ alkenyl, respectively. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated. An embodiment can be $C_2$-$C_{12}$ alkenyl or $C_2$-$C_8$ alkenyl.

The term "alkynyl" refers to a hydrocarbon radical straight or branched, containing at least 1 carbon to carbon triple bond, and up to the maximum possible number of non-aromatic carbon-carbon triple bonds may be present. Thus, $C_2$-$C_n$ alkynyl is defined to include groups having 1, 2 . . . , n−1 or n carbons. For example, "$C_2$-$C_6$ alkynyl" means an alkynyl radical having 2 or 3 carbon atoms, and 1 carbon-carbon triple bond, or having 4 or 5 carbon atoms, and up to 2 carbon-carbon triple bonds, or having 6 carbon atoms, and up to 3 carbon-carbon triple bonds. Alkynyl groups include ethynyl, propynyl and butynyl. As described above with respect to alkyl, the straight or branched portion of the alkynyl group may contain triple bonds and may be substituted if a substituted alkynyl group is indicated. An embodiment can be a $C_2$-$C_n$ alkynyl. An embodiment can be $C_2$-$C_{12}$ alkynyl or $C_3$-$C_8$ alkynyl.

Alkyl groups can be unsubstituted or substituted with one or more substituents, including but not limited to halogen, alkoxy, alkylthio, trifluoromethyl, difluoromethyl, methoxy, and hydroxyl.

As used herein, "$C_1$-$C_4$ alkyl" includes both branched and straight-chain $C_1$-$C_4$ alkyl.

As used herein, "heteroalkyl" includes both branched and straight-chain saturated aliphatic hydrocarbon groups having at least 1 heteroatom within the chain or branch.

As used herein, "cycloalkyl" includes cyclic rings of alkanes of three to eight total carbon atoms, or any number within this range (i.e., cyclopropyl, cyclobutyl, cyclopentyl, cyclohexyl, cycloheptyl or cyclooctyl).

As used herein, "heterocycloalkyl" is intended to mean a 5- to 10-membered nonaromatic ring containing from 1 to 4 heteroatoms selected from the group consisting of O, N and S, and includes bicyclic groups. "Heterocyclyl" therefore includes, but is not limited to the following: imidazolyl, piperazinyl, piperidinyl, pyrrolidinyl, morpholinyl, thiomorpholinyl, tetrahydropyranyl, dihydropiperidinyl, tetrahydrothiophenyl and the like. If the heterocycle contains nitrogen, it is understood that the corresponding N-oxides thereof are also encompassed by this definition.

As used herein, "aryl" is intended to mean any stable monocyclic, bicyclic or polycyclic carbon ring of up to 10 atoms in each ring, wherein at least one ring is aromatic, and may be unsubstituted or substituted. Examples of such aryl elements include but are not limited to: phenyl, p-toluenyl (4-methylphenyl), naphthyl, tetrahydro-naphthyl, indanyl, phenanthryl, anthryl or acenaphthyl. In cases where the aryl substituent is bicyclic and one ring is non-aromatic, it is understood that attachment is via the aromatic ring.

The term "alkylaryl" refers to alkyl groups as described above wherein one or more bonds to hydrogen contained therein are replaced by a bond to an aryl group as described above. It is understood that an "alkylaryl" group is connected to a core molecule through a bond from the alkyl group and that the aryl group acts as a substituent on the alkyl group. Examples of arylalkyl moieties include, but are not limited to, benzyl (phenylmethyl), p-trifluoromethylbenzyl (4-trifluoromethylphenylmethyl), 1-phenylethyl, 2-phenylethyl, 3-phenylpropyl, 2-phenylpropyl and the like.

The term "heteroaryl" as used herein, represents a stable monocyclic, bicyclic or polycyclic ring of up to 10 atoms in each ring, wherein at least one ring is aromatic and contains from 1 to 4 heteroatoms selected from the group consisting of O, N and S. Bicyclic aromatic heteroaryl groups include but are not limited to phenyl, pyridine, pyrimidine or pyridizine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

As used herein, "monocycle" includes any stable polycyclic carbon ring of up to 10 atoms and may be unsubstituted or substituted. Examples of such non-aromatic monocycle elements include but are not limited to: cyclobutyl, cyclopentyl, cyclohexyl, and cycloheptyl. Examples of such aromatic monocycle elements include but are not limited to: phenyl. As used herein, "heteromonocycle" includes any monocycle containing at least one heteroatom.

As used herein, "bicycle" includes any stable polycyclic carbon ring of up to 10 atoms that is fused to a polycyclic carbon ring of up to 10 atoms with each ring being independently unsubstituted or substituted. Examples of such non-aromatic bicycle elements include but are not limited to: decahydronaphthalene. Examples of such aromatic bicycle elements include but are not limited to: naphthalene. As used herein, "heterobicycle" includes any bicycle containing at least one heteroatom.

The term "phenyl" is intended to mean an aromatic six membered ring containing six carbons, and any substituted derivative thereof.

The term "benzyl" is intended to mean a methylene attached directly to a benzene ring. A benzyl group is a methyl group wherein a hydrogen is replaced with a phenyl group, and any substituted derivative thereof.

The term "pyridine" is intended to mean a heteroaryl having a six-membered ring containing 5 carbon atoms and 1 nitrogen atom, and any substituted derivative thereof.

The term "pyrazole" is intended to mean a heteroaryl having a five-membered ring containing three carbon atoms and two nitrogen atoms wherein the nitrogen atoms are adjacent to each other, and any substituted derivative thereof.

The term "indole" is intended to mean a heteroaryl having a five-membered ring fused to a phenyl ring with the five-membered ring containing 1 nitrogen atom directly attached to the phenyl ring.

The term "oxatane" is intended to mean a non-aromatic four-membered ring containing three carbon atoms and one oxygen atom, and any substituted derivative thereof.

The compounds used in the method of the present invention may be prepared by techniques well know in organic synthesis and familiar to a practitioner ordinarily skilled in the art. However, these may not be the only means by which to synthesize or obtain the desired compounds.

The compounds of present invention may be prepared by techniques described in Vogel's Textbook of Practical Organic Chemistry, A. I. Vogel, A. R. Tatchell, B. S. Furnis, A. J. Hannaford, P. W. G. Smith, (Prentice Hall) $5^{th}$ Edition (1996), March's Advanced Organic Chemistry: Reactions, Mechanisms, and Structure, Michael B. Smith, Jerry March, (Wiley-Interscience) $5^{th}$ Edition (2007), and references therein, which are incorporated by reference herein. However, these may not be the only means by which to synthesize or obtain the desired compounds.

The compounds of present invention may be prepared by techniques described herein or in PCT International Publication Nos. WO/2014/152013, WO/2015/168286, WO/2014/151959, WO/2014/152018, and WO/2014/151936, the contents of each of which are hereby incorporated by reference.

The various R groups attached to the aromatic rings of the compounds disclosed herein may be added to the rings by standard procedures, for example those set forth in Advanced Organic Chemistry: Part B: Reaction and Synthesis, Francis Carey and Richard Sundberg, (Springer) 5th ed. Edition. (2007), the content of which is hereby incorporated by reference.

Another aspect of the invention comprises a compound of the present invention as a pharmaceutical composition.

As used herein, the term "pharmaceutically active agent" means any substance or compound suitable for administration to a subject and furnishes biological activity or other direct effect in the treatment, cure, mitigation, diagnosis, or prevention of disease, or affects the structure or any function of the subject. Pharmaceutically active agents include, but are not limited to, substances and compounds described in the Physicians' Desk Reference (PDR Network, LLC; 64th edition; Nov. 15, 2009) and "Approved Drug Products with Therapeutic Equivalence Evaluations" (U.S. Department Of Health And Human Services, $30^{th}$ edition, 2010), which are hereby incorporated by reference. Pharmaceutically active agents which have pendant carboxylic acid groups may be modified in accordance with the present invention using standard esterification reactions and methods readily available and known to those having ordinary skill in the art of chemical synthesis. Where a pharmaceutically active agent does not possess a carboxylic acid group, the ordinarily skilled artisan will be able to design and incorporate a carboxylic acid group into the pharmaceutically active agent where esterification may subsequently be carried out so long as the modification does not interfere with the pharmaceutically active agent's biological activity or effect.

The compounds of the present invention may be in a salt form. As used herein, a "salt" is a salt of the instant compounds which has been modified by making acid or base salts of the compounds. In the case of compounds used to treat a disease, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1-19).

A salt or pharmaceutically acceptable salt is contemplated for all compounds disclosed herein. In some embodiments, a pharmaceutically acceptable salt or salt of any of the above compounds of the present invention.

As used herein, "treating" means preventing, slowing, halting, or reversing the progression of a disease or infection. Treating may also mean improving one or more symptoms of a disease or infection. An embodiment of "treating gout" is delaying or preventing the onset, progression, or mitigating severity of the gout.

As used here, "normalize", as to normalize a concentration in a subject afflicted with a disease, means increasing or reducing the concentration such that the concentration is closer to what the concentration would be in a subject without the disease.

As used here, "elevated", as in the RBP4 concentration is elevated in a subject afflicted with a disease, means that the RBP4 concentration is elevated in comparison to what the concentration would be in a subject without the disease.

The compounds of the present invention may be administered in various forms, including those detailed herein. The treatment with the compound may be a component of a combination therapy or an adjunct therapy, i.e. the subject or patient in need of the drug is treated or given another drug for the disease in conjunction with one or more of the instant compounds. This combination therapy can be sequential therapy where the patient is treated first with one drug and then the other or the two drugs are given simultaneously. These can be administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compounds to the animal or human. The carrier may be liquid or solid and is selected with the planned manner of administration in mind. Liposomes are also a pharmaceutically acceptable carrier.

The dosage of the compounds administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds used in the method of the present invention may comprise a single compound or mixtures thereof with additional agents. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection, topical application, or other methods, into or onto a site of infection, all using dosage forms well known to those of ordinary skill in the pharmaceutical arts.

The compounds used in the method of the present invention can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral, rectal, topical, intravenous or direct injection or parenteral administration. The compounds can be administered alone or mixed with a pharmaceutically acceptable carrier. This carrier can be a solid or liquid, and the type of carrier is generally chosen based on the type of administration being used. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds used in the method of the present invention may also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines. The compounds may be administered as components of tissue-targeted emulsions.

The compounds used in the method of the present invention may also be coupled to soluble polymers as targetable drug carriers or as a prodrug. Such polymers include polyvinylpyrrolidone, pyran copolymer, polyhydroxylpropylmethacrylamide-phenol, polyhydroxyethylasparta-midephenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient compounds and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

For oral administration in liquid dosage form, the oral drug components are combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

The compounds used in the method of the present invention may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials to make them compatible with the type of injection or delivery system chosen.

Each embodiment disclosed herein is contemplated as being applicable to each of the other disclosed embodiments. Thus, all combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Example 1

Figure 1:
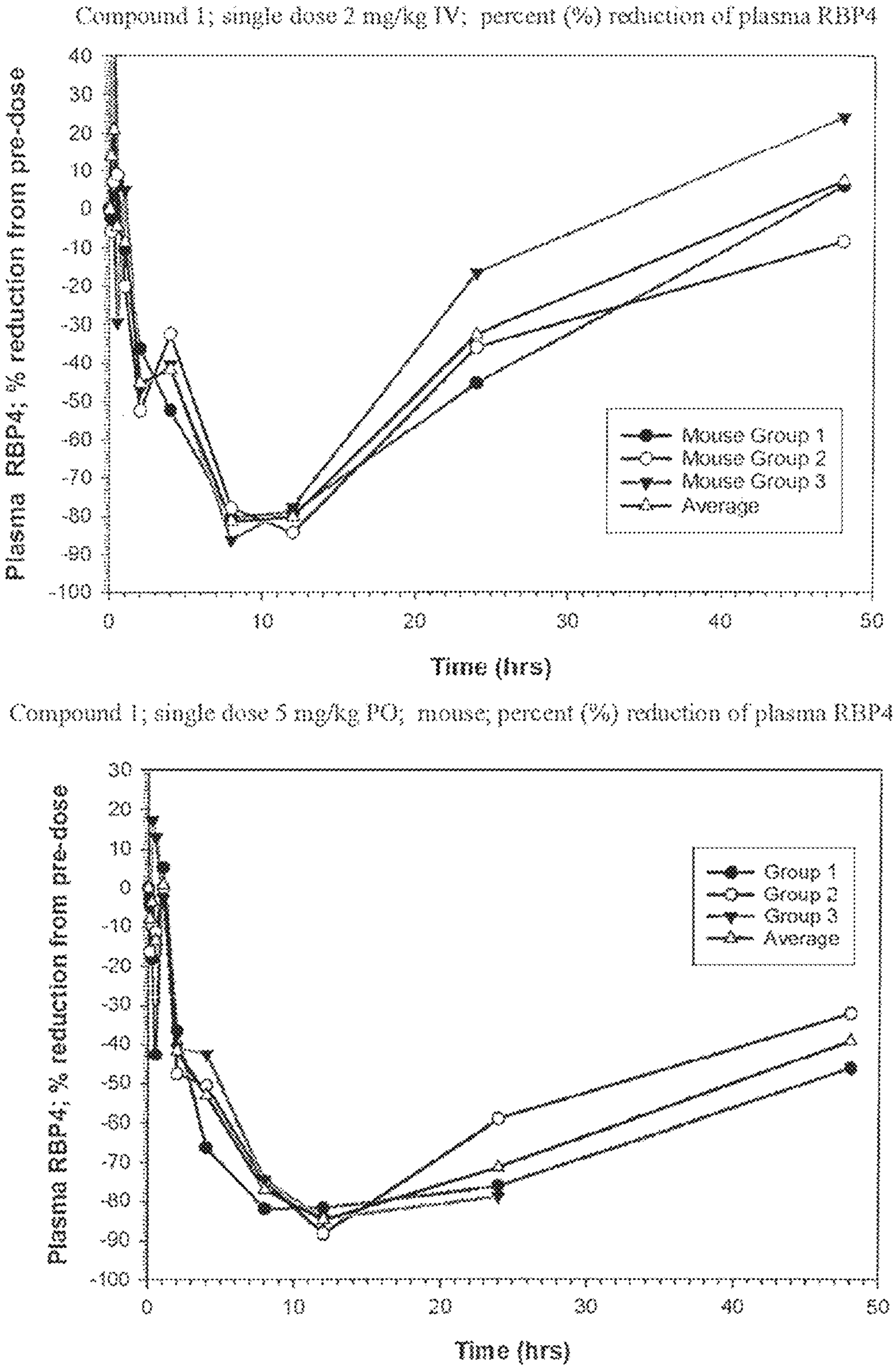
FIG. 1: Single oral administration (PO) or intravenous administration (IV) of a dose of Compound 1 induces robust reduction in circulating levels of serum RBP4 in wild-type mice. The top figure shows data from intravenous administration of 2 mg of Compound 1 per kilogram of the mouse's bodyweight. The bottom figure shows data from oral administration of 5 mg of Compound 1 per kilogram of the mouse's bodyweight.

Single oral and intravenous dose of Compound 1 can induce robust reduction in circulating levels of serum RBP4 in wild-type mice as shown by FIG. 1.

The main objective of this study was to determine the in vivo target engagement of Compound 1 in mice and to determine whether Compound 1 has in vivo activity in mice. In order to make this determination, the effect of oral and intravenous Compound 1 administration in male CD-1 mice on dynamics of plasma RBP4 levels was studied. Aliquots of plasma samples collected were used to analyze plasma RBP4 concentrations using the standard ELISA protocol as described by the manufacturer of the ELISA kit (Adipogen RBP4 (mouse/rat) Dual ELISA Kit). Plasma RBP4 concentration was determined at 10 time points following the IV or PO compound administration. Due to the low blood volume in mice, blood samples can be collected from a single animal a maximum of 3 times. Samples from different animals were used to analyze RBP4 concentration at different time points. Pre-dose plasma samples were collected from all animals enrolled in the study, and the average pre-dose concentration of RBP4 was used as a baseline. Experimental design of the study is outlined in Table 1.

TABLE 1

Experimental design and mouse group assignments

| Group | Test Article | Dose Level | Dose Conc. (mg/ml) | Dosing Volume (ml/kg) | Dose Route | Sub-Group | No. of Animals [a] | Plasma Collection Time Point (hr) |
|---|---|---|---|---|---|---|---|---|
| 1 | Compound 1 | 2 | 1.0 | 2 | iv [b] | A | 3 | Pre-dose −1, 0.083, 1 |
| | | | | | | B | 3 | Pre-dose −1, 0.25, 4 |
| | | | | | | C | 3 | Pre-dose −1, 0.5, 8 |
| | | | | | | D | 3 | Pre-close −1, 2, 12 |
| | | | | | | E | 3 | Pre-dose −1, 24, 48 |
| 2 | Compound 1 | 5 | 1.0 | 5 | po | A | 3 | Pre-dose −1, 0.083, 1 |
| | | | | | | B | 3 | Pre-dose −1, 0.25, 4 |
| | | | | | | C | 3 | Pre-dose −1, 0.5, 8 |
| | | | | | | D | 3 | Pre-close −1, 2, 12 |
| | | | | | | E | 3 | Pre-dose −1, 24, 48 |

[a] Blood was collected from 3 untreated mice for baseline control plasma samples.
[b] iv route was via tail vein.

For IV administration the compound was prepared as a solution in 3% DMA/45% PEG300/12% ethanol/40% sterile water. For PO administration the compound was prepared as a suspension in 2% Tween® 80 in 0.9% saline. In summary, in male CD-1 mice, oral (5 mg/kg) and intravenous (2 mg/kg) administration of Compound 1 induced a significant reduction in concentration of plasma RPB4. Maximal average plasma RBP4 reduction was 84.9% after oral (PO) dosing at 12 hours post dosing and 81.4% after intravenous (IV) dosing at 8 hours post dosing. The results of the study provided proof of in viva activity for the test compound in mice.

Example 2

Emerging evidence suggests that in addition to its retinol-trafficking function RBP4 may play a pathogenic role in several common diseases such as insulin resistance, type 2 diabetes (T2D), metabolic syndrome, and low-grade vascular inflammation. There is substantial evidence supporting association of elevated circulating levels of RBP4 with NAFLD development.

A transgenic mouse model ("adi-hRBP4 mice") where human RBP4 is specifically expressed in adipocytes has been recently reported in Lee 2016. The transgenic mice have mildly elevated circulating levels of RBP4 due to increase in production of human RBP4 in mouse adipose tissue. The transgenic mice display an increase in body weight and develop hepatic steatosis. In fact, when fed a conventional chow diet, these mice develop NAFLD by 3-4 months of age and when fed a high fat diet (HFD), the metabolic phenotype worsens more quickly than that of littermate controls. Accordingly, adi-hRBP4 mice are a transgenic model of hepatic steatosis.

An evaluation of Compound 1, an advanced RBP4 antagonist, was conducted in adi-hRBP4 mice. In this experiment, male adi-hRBP4 mice were separated into three age-matched treatment groups. The first group was fed normal chow (hereafter referred to as "the normal chow group"), the second group was fed a high fat diet (HFD) (hereafter referred to as "the HFD only group") and the third group was fed a HFD and Compound 1 (hereafter referred to as "the treatment group"). Compound 1 was formulated into chow to provide a daily oral dose to the treatment group of 20 mg Compound 1 per kg of bodyweight of the mouse. The treatment duration is four (4) weeks. The following variables were measured: body weight, food consumption, liver lipids, blood chemistry, urinalysis, liver histology, kidney histology, retina-histology, and ERG.

The experimental design is summarized in FIG. 2 and the experimental data for this experiment is show in FIGS. 3-14.

Both human and mouse RBP4 are present in mouse circulation (serum) as shown by FIG. 4. Human RBP4 is expressed and secreted from adipose tissue while mouse RBP4 is produced predominantly in the liver. However, the circulating concentration of human RBP4 produced in adipose tissue in untreated animals is ~5% of the mouse RBP4 produced predominantly in the liver. As shown by FIG. 4, administration of Compound 1 significantly reduced circulating levels of both human and mouse serum RBP4 levels in HFD fed adi-hRBP4 mice.

Compound 1 was also found to significantly reduce HFD induced body weight gain as shown by FIGS. 6 and 7 despite no difference in food intake between the HFD only group and the treatment group (FIG. 8). Compound 1 was further found to significantly reduce liver triglycerides and hepatic free fatty acid concentration compared to the HFD only group (FIGS. 9 and 10).

FIG. 14 shows that fatty acids can serve as ligands for RBP4 which indicates that RBP4 may be involved in trafficking of fatty acids from adipose tissue to the liver. Compound 1, as well as other RBP4 antagonists, can inhibit this trafficking as they compete for binding to the same ligand-binding pocket in RBP4.

Therefore, lowering the level of human and mouse RBP4 was associated with significant efficacy of Compound 1 in reducing the body weight gain and normalizing the concentration of triglycerides and free fatty acids in the liver.

This data indicates that Compound 1 and similar compounds can be used as a treatment for the diseases of the NAFLD spectrum in humans. Compound 1 and similar compounds are especially useful for treatment of diseases of the NAFLD spectrum in patients with elevated levels of serum RBP4.

Example 3: Treatment of Gout

Hepatic steatosis in NAFLD induces upregulation of xanthine oxidase in the liver leading to increased production of uric acid. In humans with NAFLD, increased concentration of uric acid in circulation leads to symptoms of gout. NAFLD is strongly associated with development of hyperuricemia.

Administration of Compound 1 to transgenic mice described in Example 2 significantly reduced circulating levels of uric acid. Accordingly, Compound 1 and similar compounds may be used for treatment of gout and gouty arthritis in NAFLD patients. Compound 1 and similar compounds may also be used for treatment of gout and gouty arthritis in patients without NAFLD.

Example 4: Combination Treatment of Gout

Since Compound 1 inhibits the production of uric acid in the liver, Compound 1, and similar compounds, can be used in combination with drugs that induce excretion of uric acid in the kidney. An example of such drug is DPOFA, which is exemplified in PCT International Publication No. WO/2017/083652, which is hereby incorporated by reference. In view of the disclosure herein, these two compounds have complimentary mechanisms of action. Specifically, DPOFA increases excretion of uric acid through the urine while Compound 1 inhibits NAFLD-induced upregulation of xanthine oxidase (XO) in the liver. XO is an enzyme responsible for uric acid synthesis in the liver which is a major site of urate production. Thus, in combination, Compound 1 decreases the production of uric acid while DPOFA increases the excretion of uric acid from the body thereby treating the subject.

Example 5: Efficacy in a Mammalian Model

The effectiveness of the compounds listed herein are tested in adi-hRBP4 mice. The adi-hRBP4 mouse model manifests moderately increased expression of human RBP4 in mouse adipose tissue and is considered a model for hepatic steatosis. Compounds are orally dosed for 4 weeks at 20 mg/kg. There is a reduction in the serum level of human and mouse RBP4 in treated animals. The levels of RBP4 and free fatty acids (FFA) in the liver are reduced in treated mice. The levels of (1) free fatty acids in the serum (2) triglycerides in the liver, (3) serum uric acid levels are also reduced.

Example 6. Administration to a Subject

An amount of Compound 1 is administered to a subject afflicted with a NAFLD. The amount of the compound is effective to treat the subject.

An amount of Compound 1 is administered to a subject afflicted with a NAFLD and elevated circulating levels of serum RBP4. The amount of the compound is effective to treat the subject.

An amount of Compound 1 is administered to a subject afflicted with hepatic steatosis. The amount of the compound is effective to treat the subject.

An amount of Compound 1 is administered to a subject afflicted with nonalcoholic steatohepatitis (NASH). The amount of the compound is effective to treat the subject.

An amount of Compound 1 is administered to a subject afflicted with cirrhosis. The amount of the compound is effective to treat the subject.

An amount of Compound 1 is administered to a subject afflicted with hepatocellular carcinoma. The amount of the compound is effective to treat the subject.

An amount of Compound 1 is administered to a subject afflicted with gout. The amount of the compound is effective to treat the subject.

The structure of compounds 2-4 are shown below.

Compound 2

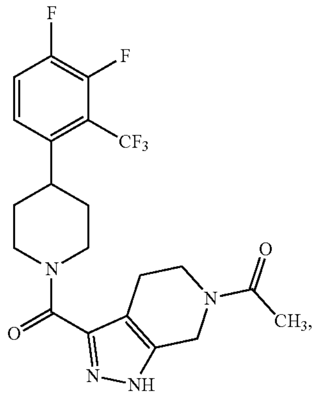

Compound 3

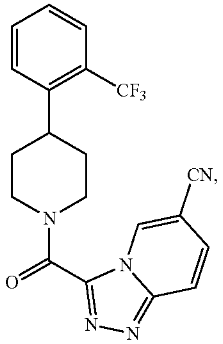

Compound 4

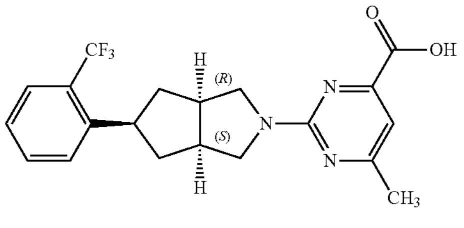

An amount of Compound 2 is administered to a subject afflicted with a NAFLD. The amount of the compound is effective to treat the subject.

An amount of a Compound 2 is administered to a subject afflicted with hepatic steatosis. The amount of the compound is effective to treat the subject.

An amount of Compound 2 is administered to a subject afflicted with nonalcoholic steatohepatitis (NASH). The amount of the compound is effective to treat the subject.

An amount of Compound 2 is administered to a subject afflicted with cirrhosis. The amount of the compound is effective to treat the subject.

An amount of Compound 2 is administered to a subject afflicted with hepatocellular carcinoma. The amount of the compound is effective to treat the subject.

An amount of Compound 2 is administered to a subject afflicted with gout. The amount of the compound is effective to treat the subject.

An amount of Compound 3 is administered to a subject afflicted with a NAFLD. The amount of the compound is effective to treat the subject.

An amount of Compound 3 is administered to a subject afflicted with hepatic steatosis. The amount of the compound is effective to treat the subject.

An amount of Compound 3 is administered to a subject afflicted with nonalcoholic steatohepatitis (NASH). The amount of the compound is effective to treat the subject.

An amount of Compound 3 is administered to a subject afflicted with cirrhosis. The amount of the compound is effective to treat the subject.

An amount of Compound 3 is administered to a subject afflicted with hepatocellular carcinoma. The amount of the compound is effective to treat the subject.

An amount of Compound 3 is administered to a subject afflicted with gout. The amount of the compound is effective to treat the subject.

An amount of Compound 4 is administered to a subject afflicted with a NAFLD. The amount of the compound is effective to treat the subject.

An amount of Compound 4 is administered to a subject afflicted with hepatic steatosis. The amount of the compound is effective to treat the subject.

An amount of Compound 4 is administered to a subject afflicted with nonalcoholic steatohepatitis (NASH). The amount of the compound is effective to treat the subject.

An amount of Compound 4 is administered to a subject afflicted with cirrhosis. The amount of the compound is effective to treat the subject.

An amount of Compound 4 is administered to a subject afflicted with hepatocellular carcinoma. The amount of the compound is effective to treat the subject.

An amount of Compound 4 is administered to a subject afflicted with gout. The amount of the compound is effective to treat the subject.

Example 7. DPOFA in Combination with Compound 1

An amount of compound DPOFA in combination with Compound 1 is administered to a subject afflicted with gout. The amount of the DPOFA and Compound 1 is effective to treat the subject afflicted with gout. The combination is more effective in treating the gout than each compound administered alone.

Example 8. DPOFA in Combination with Compound 1

An amount of compound DPOFA in combination with Compound 1 is administered to a subject afflicted with gout and a NAFLD. The amount of the DPOFA and Compound 1 is effective to treat the subject afflicted with gout and NAFLD. The combination is more effective in treating the gout and NAFLD than each compound administered alone.

Example 9. DPOFA in Combination with Compound 1 Prevents Gout in Subjects

An amount of compound DPOFA in combination with Compound 1 is administered to a subject with history of gout flares or who is at risk for a gout flare. The amount of the DPODA and Compound 1 is effective to prevent gout flares in the subject. The combination is more effective in preventing the gout than each compound administered alone.

Example 10: In Vivo Activity: PK Characteristics of 1 and Compound 3 in Rodents Both Compound 1 and Compound 3 possessed favorable PK profiles in naive male CD-1 mice and adult Sprague-Dawley male rats (FIG. 15). The compounds exhibited moderate to low clearance and good half-lives ($t_{1/2}$) in both species. Adequate exposures ($AUC_{last}$) and good oral bioavailability (% F) were also achieved. The good oral bioavailability, moderate half-lives, and decent exposures achieved in mice coupled with favorable ADME profiles fully justified the use of Compound 1 and Compound 3 to establish PK/PD and ultimately proof-of-concept in murine animal models.

Example 11: In Vivo Activity: PK/PD Correlations of Compound 1 in Mouse

Before testing Compound 1 in the murine transgenic model of hepatic steatosis, acute dosing studies were conducted with Compound 1 in mouse to measure the compound's effect on circulating plasma RBP4 levels and to establish PK/PD correlations (FIG. 16). After a single oral dose of Compound 1 (5 mg/kg), 85% maximal reduction in plasma RBP4 was observed (FIG. 16A), whereas plasma RBP4 was decreased by 81% following a 2 mg/kg intravenous dose (FIG. 16B). In vivo serum RBP4 lowering after both oral and intravenous dosing of Compound 1 (FIG. 16A, B) showed a good correlation with the compound concentration in plasma (FIG. 16C, D). The long exposure and moderate to low clearance of Compound 1 achieved after a single oral dose correlated well with the extent of the RBP4 reduction (85% reduction at the 12 h time point) and the duration of the RBP4 lowering effect (71% reduction at the 24 h time point).

Furthermore, the magnitude of RBP4 lowering correlated very well with the projected free drug concentration of Compound 1 in the plasma, which exceeded that required for disrupting the RBP4-TTR interaction measured in the in vitro HTRF assay. This data confirms in vivo target engagement for Compound 1 and reveals an excellent PK/PD relationship between compound exposure and biological response in mice, additionally justifying characterization of Compound 1 in the mouse transgenic model of hepatic steatosis.

Example 12: Compound 1 Reduces Circulating Levels of Adipose-Derived RBP4 in the Mouse Transgenic Model of Hepatic Steatosis As reported previously by Blaner and co-workers, (Lee, S.-A. et al. 2016) the mouse genetic model of hepatic steatosis was generated by targeting the human RBP4 (hRBP) cDNA construct with a loxP-neor-stop cassette to the mouse Rosa26 locus. To specifically express hRBP4 in mouse adipocytes, knock-in mice were bred with adiponectin-Cre mice.22 Specific expression of human RBP4 in mouse adipocytes yielded no significant elevation in the circulating levels of RBP4 and no changes in retinoid levels in plasma, liver, and adipose tissue while inducing obesity, impaired glucose tolerance, and pronounced increase in hepatic triglyceride (TG) levels (Lee, S.-A. et al. 2016).

Figure 17:
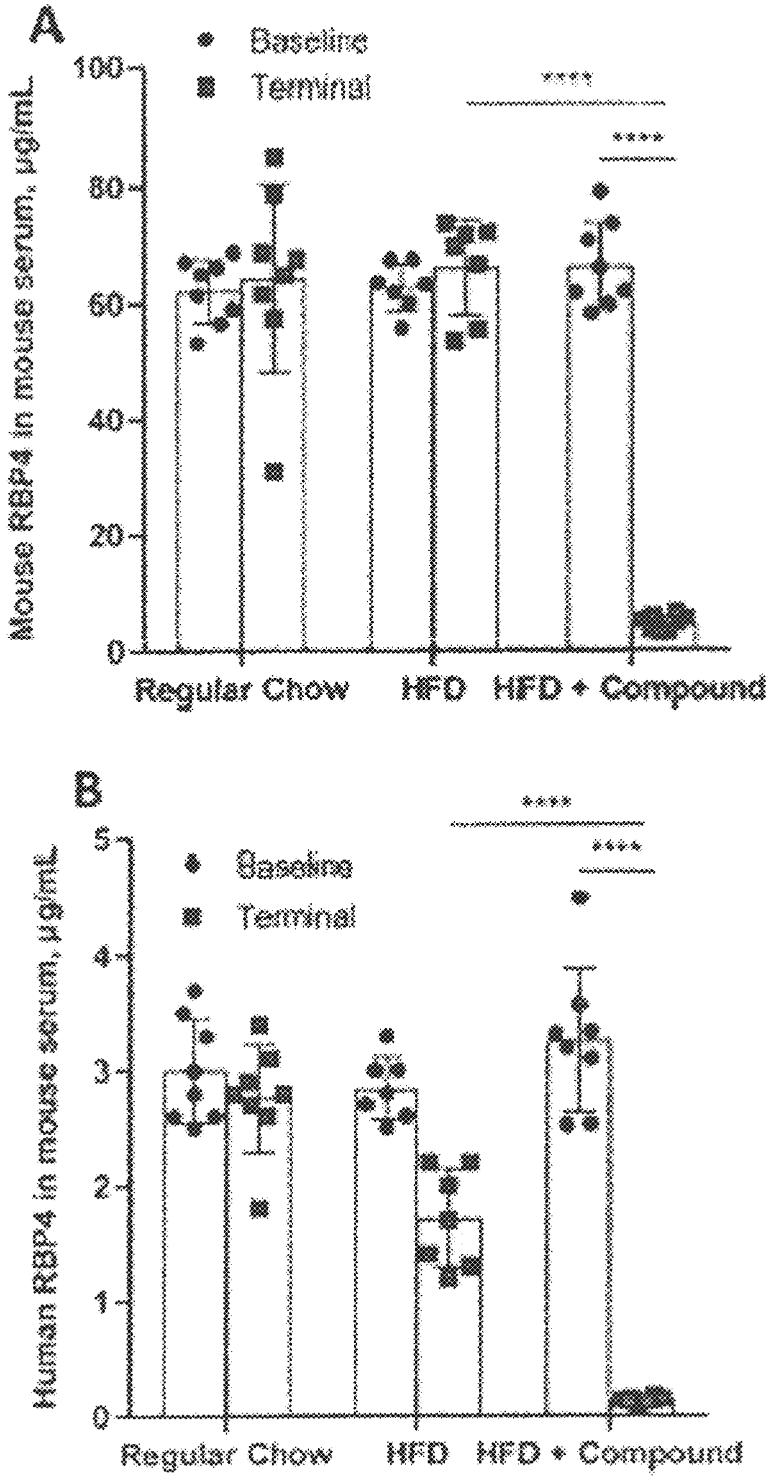

To examine the effect of Compound 1 on metabolic parameters in male adi-hRBP4 mice, the compound was administered as a formulation into the HFD chow at a dose of 20 mg/kg per day for 29 days. Compound administration started at 20 weeks of age when the animals were switched from a standard chow to a high-fat diet (60% of calories from fat). Chronic oral administration of Compound 1 induced a 90% decrease in circulating levels of both mouse and human (adipose tissue-secreted) serum RBP4 (FIG. 17). In untreated adi-hRBP4 mice, circulating levels of adipose-derived human RBP4 (2-3 μg/mL) represented a small 3-5% fraction of mouse-specific serum RBP4 produced predominantly in the liver (FIG. 17). Remarkably, this modest increase in circulating levels of RBP4 conferred by adipocyte secretion was sufficient to trigger the induction of the strong metabolic phenotype.

Example 13: Compound 1 Reduces Body Weight Gain in Obese adi-hWMP4 Mice

Over the 29 day study period, the adihRBP4 mice on high-fat diet gained significantly more weight than transgenic animals kept on a standard chow (FIG. 18A). A statistically significant difference between the chow-fed and HFD adi-hRBP mice in percent weight gain was evident 5 days after initiation of the high-fat feeding (FIG. 18A). Body weight gain in HFD animals was significantly reduced by administration of Compound 1. A statistically significant difference in body weight gains between Compound 1-treated and untreated HFD mice was evident after 19 days of high fat diet feeding (FIG. 18A). At the end of the 29 day treatment (2.2±1.7 g) was 53% less than in the untreated animals on HFD (4.7±1.6 g). Reduction in the body weight gain in Compound 1-treated adi-RBP4 mice was not associated with decreased food intake as Compound 1 did not alter consumption of the HFD chow (FIG. 10B).

Example 14: Reduction of Hepatic Lipid Levels by Compound 1 in Obese adi-hRBP4 Mice In accordance with the previous report, (Lee, S.-A. et al. 2016) hepatic free fatty acid (FFA) and triglyceride (TG) levels in adi-hRBP4 mice maintained on the high-fat diet were significantly higher than in transgenic animals kept on a standard chow (FIG. 19; P<0.0001 for both FFA and TG). Administration of Compound 1 lowered the FFA levels by 30% (FIG. 11A; P=0.0107) and TG levels by 29% (FIG. 11B; P=0.0104).

Consistent with the dynamics of hepatic TG accumulation, histological examination of oil red O-stained frozen liver sections (FIG. 20A) and hepatic steatosis grading (FIG. 20A) confirmed significantly more steatosis in adi-hRBP4 mice maintained on HFD in comparison to the chow-fed transgenic mice, which showed no evidence of hepatic steatosis.

Significant improvement in hepatic steatosis was seen in the Compound 1-treated adi-hRBP4 obese mice, which exhibited fewer and smaller lipid droplets in comparison with the untreated adihRBP4 mice maintained on HFD (FIG. 18B). Hepatic steatosis grading (FIG. 12B) revealed a significant 43% reduction in the degree of steatosis in Compound 1-treated HFD-fed adihRBP4 mice (P<0.001), which further confirmed the ability of Compound 1 to alleviate hepatic steatosis in adi-hRBP4 mice.

Example 15: Binding of Fatty Acid Ligands to RBP4

It remains unclear how the modestly increased expression of RBP4 in adipose tissue contributes to the development of hepatic steatosis. One can surmise that this ability of RBP4 may relate to binding and trafficking of endogenous non-retinoid ligands, the nature and abundance of which is unknown at this point. Consistent with the ability of RBP4 to interact with nonretinoid ligands, previous crystallographic studies of heterologously expressed RBP4 revealed fortuitous fatty acid ligands from the expression host (oleic acid and linoleic acid) bound within the ligand binding pocket of RBP4 (Huang, H.-J. et al. 2009; Nanao, M. S. et al. 2009).

Recent X-ray crystallographic and mass spectrometry findings reported by Monaco and coworkers confirmed that RBP4 is capable of binding fatty acids (Perduca, M. et al. 2018) The capacity of retinol-binding proteins to bind hydrophobic nonretinoid ligands may be general, as illustrated by recently described interactions of cellular retinol-binding protein 1 with certain cannabinoids (Silvaroli, J. A. et al. 2019)

The affinity of palmitic acid, oleic acid, linoleic acid, and docosahexaenoic acid for RBP4 was tested using a SPA assay that measures displacement of radioactive retinol from purified human RBP4 (FIG. 21A). These competition binding experiments confirmed the ability of the tested fatty acids to function as weak RBP4 ligands. Our docking model is also consistent with the ability of RBP4 to bind fatty acid ligands. FIG. 13B presents overlays of Compound 3 and the fatty acids palmitic acid, oleic acid, linoleic acid, and docosahexaenoic acid docked within our 3FMZ model and of all-trans-retinol docked within our 5NU7 (holo-RBP4) model. The figure shows a good overlay between all-trans-retinol and Compound 3 as both present similar geometric poses and project their polar fragments toward the opening of the binding cavity where they engage in H-bond interactions with Gln98 and Arg121, respectively. Similar to all-trans-retinol and Compound 3, the fatty acids also extend their hydrophobic tails through the narrow β-barrel and into the β-ionone pocket and their polar carboxylic acids bind to residues residing closer to the opening of the binding cavity, namely, Leu36 and Phe36.

Discussion

In one aspect, the present invention relates to small molecules for treatment of NAFLD diseases. Disclosed herein is the specific use of the small molecules as non-retinoid RBP4 antagonists to treat a non-alcoholic fatty liver disease (NAFLD) disease. Compounds listed herein have been shown to bind RBP4 in vitro and/or to antagonize RBP4-TTR interaction in vitro at biologically significant concentrations. Additional compounds described herein, which are analogs of compound listed herein analogously bind RBP4 in vitro and antagonize RBP4-TTR interaction in vitro at biologically significant concentrations.

Fenretinide [N-(4-hydroxy-phenyl)retinamide, 4HRP] is a retinoid drug previously developed for the treatment of cancer. Similar to other retinoid drugs, fenretinide is nonspecific and thus capable of engaging multiple drug targets. Its anti-cancer activity is ascribed to the ability to generate reactive oxygen species and induce apoptosis in malignant cells. Some other activities of this compound are mediated by its action as a ligand for nuclear receptor RAR. In the spectrum of different activities of fenretinide, its ability to act as an RBP4 ligand is well characterized. For example, fenretinide was found to bind to RBP4, displace all-trans retinol from RBP4 (Berni 1992), disrupt the RBP4-TTR interaction (Berni 1992, Schaffer 1993), reduce serum RBP4 and retinol (Adams 1995), and inhibit ocular all-trans retinol uptake and slow down the visual cycle (Radu 2005). However, it is known from the literature that beneficial effects of fenretinide in diabetes and obesity models are not mediated by its activity as an RBP4 antagonist. Koh 2012 reported that fenretinide is capable of improving insulin sensitivity and reduce hepatic lipid levels in obese mice. This observation is consistent with an earlier report that demonstrated that long-term administration of fenretinide prevented high-fat diet-induced obesity, insulin resistance and hepatic steatosis (Preitner 2009). However, it was convincingly shown in Preitner that beneficial effects of fenretinide on reduction of HFD-induced adiposity is not mediated by its activity as an RBP4 antagonist given that fenretinide was equally efficacious in reducing adiposity in the RBP4 knock-out animals. Motani 2009 also proved that fenretinide's ability to improve insulin sensitivity in HFD-fed mice is unrelated to its activity as an RBP4 antagonist. Overall, while Koh (along with earlier work of Preitner and Motani) showed the beneficial effect of fenretinide in relevant HFD-induced obesity models, the earlier work of Preitner and Motani convincingly ascribed these beneficial effects to activities of fenretinide which are unrelated to the engagement of RBP4. For these reasons, a person of ordinary skill in the art would not have reasonably expected administration of a RBP4 antagonist to treat a NAFLD disease in view of Koh 2012 and Preitner 2009.

Fenretinide is also toxic and teratogenic. As such, fenretinide's safety profile may be incompatible with long-term dosing in individuals with non-life threatening conditions.

As briefly discussed above, Koh 2012 discloses the use of fenretinide ("FEN") in genetically obese (ob/ob) mice. In Koh, ob/ob mice were separated into two groups and both were fed a high fat diet (HFD) but FEN was only administered to one group. Koh 2012 reported that FEN decreases weight gain, insulin resistance and fatty liver in ob/ob mice fed a high-fat diet. Koh also reported that FEN decreased circulating RBP4 and TTR levels (page 371). Additionally, Koh reported a reduction in RBP4 level in adipose tissue in FEN treated obese mice (page 374 right column). Koh stated that "[i]t is possible that lower levels of circulating lipids are transported to tissues, including the liver, following fenretinide treatment" (page 374 right column). Contrary to Koh 2012, Lee 2016 showed that, in mice not administered a high fat diet, free fatty acids were redistributed from adipose tissue to the liver, and not to all tissues as implied by Koh.

Koh 2012 further indicated that plasma adiponectin levels differed between vehicle treated and FEN-treated mice and that this might be linked to reduced triglycerides (TG) synthesis and enhanced free fatty acid (FFA) oxidation in FEN treated mice. However, because of increases in the level of adiponectin-stimulated transcription factor PPARα, Koh later indicated that their results suggest that FEN may universally affect fatty acid oxidizing enzymes in obese mice (pages 374 to 375). Koh further concludes that lower hepatic fat accumulation originates from increased fatty acid oxidation and not from reduced lipogenesis (page 375). In contrast, Lee 2016 found that increased TNF and leptin expression cause RBP4 induced inflammation in adipose tissue which causes increased lipolysis. Lee 2016 further stated that free fatty acids, which is a product of lipolysis, are uptaken by the liver and that this causes elevated TG levels and the hepatic steatosis.

Therefore, not only has it been shown that the positive attributes of fenretinide in HFD induced obesity models are unrelated its activity as a RBP4 antagonist, but Koh 2012 suggests incorrect mechanisms for its proposed treatment with fenretinide.

Additionally, Koh 2012 does not disclose using any RBP4 antagonist to treat non-alcoholic fatty liver disease (NAFLD) and the mice used in Koh's study were not specific models for NAFLDs. In comparison, the data in this application is from a transgenic model of hepatic steatosis, a NAFLD disease.

Thus, Koh 2012 does not provide any reasonable expectation that RBP4 antagonists would be able to successfully treat a NAFLD.

Although Lee 2016 disclosed that there is substantial evidence associating elevated circulating levels of RBP4 with NAFLD development (page 1534), Lee 2016 also points to studies reporting evidence showing a lack of association between RBP4 and NAFLD (page 1543). Thus, the complete role of elevated circulating levels of RBP4 in NAFLD development was unknown.

Lee 2016 further states that the development of obesity leads to increased expression of RBP4 by adipocytes (page 1534). However, Lee is clear that "it remains to be established whether RBP4 can actually stimulate hepatic steatosis in a liver autonomous manner". Similar to Koh 2012, Lee 2016 found that there was no increase in the rate of de novo lipogenesis in the livers of adi-hRBP4 mice (page 1540). However, unlike Koh, Lee did not find any statistically significant genotype-dependent difference in free fatty acids (FFA) oxidation. Rather, Lee indicates that its data supports the conclusion that increased hepatic uptake of circulating free fatty acids (FFA) accounts "substantially" for the fatty liver phenotype observed in adi-hRBP4 mice.

However, Lee 2016 has not shown what affects a RBP4 antagonist would have on the adi-hRBP4 mice or what effect a RBP4 antagonist would have on any subject. For example, none of the experiments disclosed in Lee 2016 administer any RBP4 antagonists to a subject. In fact, Lee 2016 does not suggest that RBP4 antagonists can be used to treat a NAFLD.

Herein, applicants have shown, inter alia, that the RBP4 antagonists can normalize the concentration of triglycerides and free fatty acids in the liver thereby treating NAFLD diseases.

Currently, there is no FDA-approved pharmacotherapy for any form of NAFLD. The present invention identified non-retinoid RBP4 antagonists that are useful for the treatment of NAFLD and other conditions characterized by excessive accumulation of RBP4 in adipocytes. Without wishing to be bound by any scientific theory, as accumulation of RBP4 in adipocytes seems to be a direct cause of fatty liver in NAFLD, the compounds described herein are disease-modifying agents since they directly address a cause of NAFLD. The present invention provides novel methods of treatment that will treat the liver in NAFLD patients, and patients' suffering from conditions characterized by excessive RBP4 in adipocytes.

REFERENCES

Adams W R, Smith J E, Green M H. Effects of N-(4-hydroxyphenyl)retinamide on vitamin A metabolism in rats. Proc Soc Exp Biol Med. 1995 February; 208(2):178-85.

Berni R, Formelli F. In vitro interaction of fenretinide with plasma retinol-binding protein and its functional consequences. FEBS Lett. 1992 Aug. 10; 308(1):43-5.

Bonanni B, Lazzeroni M, Veronesi U. Synthetic retinoid fenretinide in breast cancer chemoprevention. Expert Rev Anticancer Ther. 2007 April; 7 (4):423-32.

Clifford J L, Menter D G, Wang M, Lotan R, Lippman S M. Retinoid receptor-dependent and -independent effects of N-(4-hydroxyphenyl)retinamide in F9 embryonal carcinoma cells. Cancer Res. 1999 Jan. 1; 59(1):14-8.

Fontana J A, Rishi A K. Classical and novel retinoids: their targets in cancer therapy. Leukemia. 2002 April; 16(4):463-72.

Holmes W F, Soprano D R, Soprano K J. Synthetic retinoids as inducers of apoptosis in ovarian carcinoma cell lines. J Cell Physiol. 2004 June; 199 (3):317-29.

Huang, H.-J.; Nanao, M.; Stout, T.; Rosen, J. 2WR6: Structure of the Complex of RBP4 with Linoleic Acid; Protein Data Bank, 2009.

IUPAC-IUB Joint Commission on Biochemical Nomenclature (JCBN). Nomenclature of Retinoids. Eur. J. Biochem. 129, 1-5 (1982).

Koh I U, Jun H S, Choi J S, Lim J H, Kim W H, Yoon J B, et al. Fenretinide ameliorates insulin resistance and fatty liver in obese mice. *Biol Pharm Bull* 2012; 35:369-375.

Lee, Seung-Ah et al. "Adipocyte-Specific Over-Expression of Retinol Binding Protein 4 (RBP4) Causes Hepatic Steatosis in Mice." Hepatology (Baltimore, Md.) 64.5 (2016): 1534-1546. PMC.

Lee, S. A., Yuen, J. J., Jiang, H., Kahn, B. B. & Blaner, W. S. Adipocyte-specific overexpression of retinol-binding protein 4 causes hepatic steatosis in mice. Hepatology 64, 1534-1546 (2016).

Motani A. et al., (2009) Identification and characterization of a non-retinoid ligand for retinol-binding protein 4, which lowers serum retinol-binding protein 4 levels in vivo. J. Biol. Chem. 284, 7673-7680.

Nanao, M. S.; Mercer, D.; Nguyen, L.; Buckley, D.; Stout, T. J. 2WQ9: Crystal Structure of RBP4 bound to Oleic Acid; Protein Data Bank, 2009.

Perduca, M.; Nicolis, S.; Mannucci, B.; Galliano, M.; Monaco, H. L. Human plasma retinol-binding protein (RBP4) is also a fatty acid-binding protein. Biochim. Biophys. Acta, Mol. Cell Biol. Lipids 2018, 1863, 458-466.

Preitner et al, Long-term Fenretinide treatment prevents high-fat diet-induced obesity, insulin resistance, and hepatic steatosis. Am J Physiol Endocrinol Metab 297: E1420-E1429, 2009.

Puduvalli V K, Saito Y, Xu R, Kouraklis G P, Levin V A, Kyritsis A P. Fenretinide activates caspases and induces apoptosis in gliomas. Clin Cancer Res. 1999 August; 5(8):2230-5.

Radu R A, Han Y, Bui T V, Nusinowitz S, Bok D, Lichter J, Widder K, Travis G H, Mata N L. Reductions in serum vitamin A arrest accumulation of toxic retinal fluorophores: a potential therapy for treatment of lipofuscin-based retinal diseases. Invest Ophthalmol Vis Sci. 2005 December; 46(12):4393-401.

Sabichi A L, Xu H, Fischer S, Zou C, Yang X, Steele V E, Kelloff G J, Lotan R, Clifford J L. Retinoid receptor-dependent and independent biological activities of novel fenretinide analogues and metabolites. Clin Cancer Res. 2003 Oct. 1; 9(12):4606-13.

Samuel W, Kutty R K, Nagineni S, Vijayasarathy C, Chandraratna R A, Wiggert B. N-(4-hydroxyphenyl)retinamide induces apoptosis in human retinal pigment epithelial cells: retinoic acid receptors regulate apoptosis, reactive oxygen species generation, and the expression of heme oxygenase-1 and Gadd153. J Cell Physiol. 2006 December; 209(3):854-65.

Schaffer E M, Ritter S J, Smith J E. N-(4-hydroxyphenyl) retinamide (fenretinide) induces retinol-binding protein secretion from liver and accumulation in the kidneys in rats. J Nutr. 1993 September; 123(9):1497-503.

Silvaroli, J. A.; Widjaja-Adhi, M. A. K.; Trischman, T.; Chelstowska, S.; Horwitz, S.; Banerjee, S.; Kiser, P. D.; Blaner, W. S.; Golczak, M. Abnormal cannabidiol modulates vitamin A metabolism by acting as a competitive inhibitor of CRBP1. ACS Chem. Biol. 2019, 434.

Simeone A M, Ekmekcioglu S, Broemeling L D, Grimm E A, Tari A M. A novel mechanism by which N-(4-hydroxyphenyl)retinamide inhibits breast cancer cell growth: the production of nitric oxide. Mol Cancer Ther. 2002 October; 1(12):1009-17.

What is claimed is:

1. A method for treating gout in a subject afflicted therewith comprising administering to the subject a pharmaceutical composition comprising an amount of a compound effective to treat the subject, thereby treating the subject, wherein compound has the structure

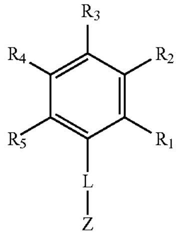

wherein L is a linking group having the structure:

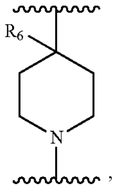 ,

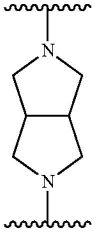 ,

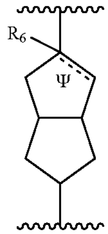 ,

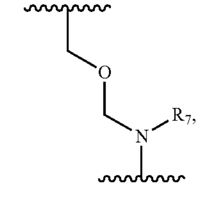 or

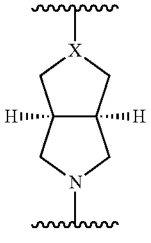

and Z is a group having the structure:

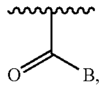 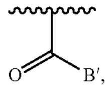 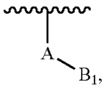 or 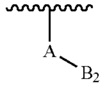

wherein $R_1$, $R_2$, $R_3$, $R_4$, and $R_5$ are each independently H, halogen, $CF_3$ or $C_1$-$C_4$ alkyl, aryl or heteroaryl;

$R_6$ is H, OH, or halogen or absent;

ψ is absent or present, and when present is a bond;

B is a substituted or unsubstituted heterobicycle, pyridazine, pyrazole, pyrazine, thiadiazole, or triazole, wherein the heterobicycle is other than chloro substituted indole; and the pyrazole, when substituted, is substituted with other than trifluoromethyl;

B' is a substituted or unsubstituted phenyl, pyridine, pyrimidine, benzyl, pyrrolidine, sulfolane, oxetane, $CO_2H$ or ($C_1$-$C_4$ alkyl)-$CO_2H$, wherein the substituted phenyl is substituted with other than trifluoromethyl or 3-(methyl carboxylate), the substituted pyridine is substituted with other than trifluoromethyl and the substituted pyrrolidine is substituted with other than hydroxamic acid, and the substituted or unsubstituted pyrrolidine is bound to the carbonyl through a carbon-carbon bond;

A is absent or present, and when present is

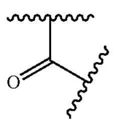 or 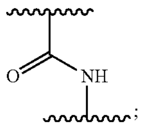;

$B_1$ is substituted or unsubstituted monocycle, bicycle, heteromonocycle, heterobicycle, benzyl, $CO_2H$ or ($C_1$-$C_4$ alkyl)-$CO_2H$, wherein when $B_1$ is $CO_2H$, then A is present and is

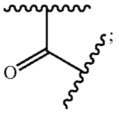;

$R_7$ is alkyl;

X is N or $CR_8$, wherein $R_8$ is H, OH, or halogen;

$B_2$ has the structure:

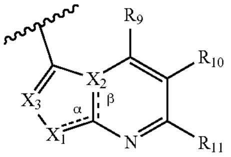

wherein

α and β are each a bond that is present or absent;

$X_1$ is N, NH or $NR_{99}$, wherein $R_{99}$ is alkyl, alkenyl or alkynyl;

$X_2$ is C or N;

$X_3$ is CH or N;

$R_9$, $R_{10}$ and $R_{11}$ are each, independently, H, halogen, alkyl, alkenyl, alkynyl, alkyl-OH, alkyl-$NH_2$, alkyl-OAc alkyl-O(CO)-alkyl, alkyl-O-alkyl, haloalkyl, cycloalkyl, O-alkyl, NH-alkyl, C(O)OH, C(O)—$NH_2$, C(O)—$N(CH_3)_2$, C(O)—$NHCH_3$, NHC(O)—$N(CH_3)_2$, CN or $CF_3$, wherein $X_1$, $X_2$ and $X_3$ are each N, α is present and β is absent; or $X_1$, $X_2$ and $X_3$ are each N, α is present and β is absent; or $X_1$, $X_2$ and $X_3$ are each N, α is present and β is absent; or $X_1$ is NH or $NR_{99}$, $X_2$ is C, $X_3$ is N, α is absent and β is present, wherein when $X_1$ is NH, $X_2$ is C, $X_3$ is N, α is absent and β is present, then one of $R_9$, $R_{10}$ and $R_{11}$ is other than H, or $B_2$ has the structure:

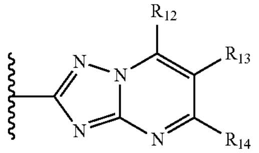

wherein $R_{12}$, $R_{13}$ and $R_{14}$ are each, independently, H, halogen, alkyl, alkenyl, alkynyl alkyl-OH, alkyl-$NH_2$, alkyl-OAc, alkyl-O(CO)-alkyl, alkyl-O-alkyl, haloalkyl, cycloalkyl, O-alkyl, NH-alkyl, C(O)OH, C(O)—$NH_2$, C(O)—$N(CH_3)_2$, C(O)—$NHCH_3$, NHC(O)—$N(CH_3)_2$, CN or $CF_3$, or a pharmaceutically acceptable salt thereof.

2. The method of claim 1, wherein in the compound, $R_1$, $R_2$, $R_3$, $R_4$, and $R_5$ are each independently H, halogen, $CF_3$ or $C_1$-$C_4$ alkyl.

3. The method of claim 1, wherein the method further comprises a step of determining, or having determined, the level of RBP4 in adipose tissue or in serum in the subject and administering the pharmaceutical composition if the level of RBP4 in adipose tissue or in serum is elevated.

4. The method of claim 1, wherein the amount of the compound is effective in reducing RBP4 levels in serum in the subject by about 90% or reducing uric acid levels in the serum of the subject to less than 7 mg/dL.

5. The method of claim 1, wherein the amount of the compound is effective to normalize the concentration of triglycerides in the liver of the subject, or normalize the concentration of free fatty acids in the serum of the subject, or normalize the concentration of free fatty acids in the liver of the subject, wherein normalize comprises increasing or reducing the concentration of triglycerides or free fatty acids such that the concentration of triglycerides or free fatty acids is closer to the concentration of triglycerides or free fatty acids in a subject without gout; or wherein the amount of the compound is effective to prevent trafficking of a fatty acid by RBP4, or to prevent trafficking of a fatty acid to the liver by RBP4, or inhibit binding between RBP4 and a fatty acid.

6. The method of claim 5, wherein the amount of the compound is effective to normalize the concentration of fatty acid in the liver.

7. The method of claim 1, wherein the subject has elevated serum RBP4 levels; or wherein the subject has serum RBP4 levels elevated by more than 3 microgram per ml.

8. The method of claim 1, wherein in the compound,

L is

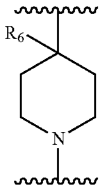

and Z is

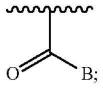

or wherein

L is

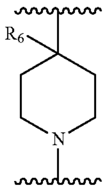

and Z is

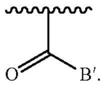

9. The method of claim 1, wherein in the compound,

L is

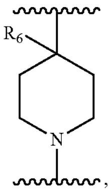,

Z is

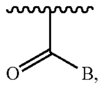

two or more of $R_1$, $R_2$, $R_3$, $R_4$, or $R_5$ are other than H, and when $R_1$ is $CF_3$, $R_2$ is H, $R_3$ is F, $R_4$ is H, and $R_5$ is H, or $R_1$ is H, $R_2$ is $CF_3$, $R_3$ is H, $R_4$ is $CF_3$, and $R_5$ is H, or $R_1$ is Cl, $R_2$ is H, $R_3$ is H, $R_4$ is F, and $R_5$ is H, or $R_1$ is $CF_3$, $R_2$ is H, $R_3$ is F, $R_4$ is H, and $R_5$ is H, or $R_1$ is $CF_3$, $R_2$ is F, $R_3$ is H, $R_4$ is H, and $R_5$ is H, or $R_1$ is Cl, $R_2$ is F, $R_3$ is H, $R_4$ is H, and $R_5$ is H, then B is other than

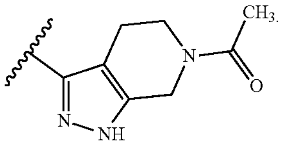 [SMILES: *c1n[nH]c2c1CCN(C(C)=O)C2]

10. The method of claim 1, wherein in the compound,

L is

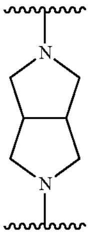 [SMILES: *N1CC2CN(*)CC2C1]

and Z is

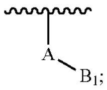

or wherein

L is

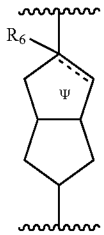

Z is
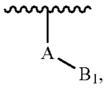
and
$R_6$ is absent or present, and when present is H, OH, or halogen
and when $\psi$ is present, then $R_6$ is absent and when $\psi$ is absent, then $R_6$ is present; or
wherein
L is
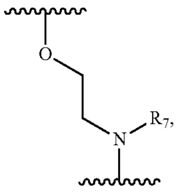
and Z is
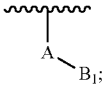
or
wherein
L is
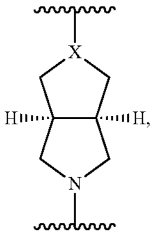
and Z is
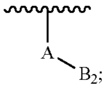
or
wherein
L is
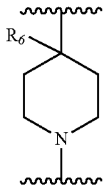
,
Z is
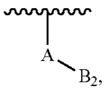
$R_6$ is H, and A is
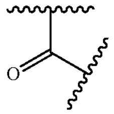
;
or
wherein
L is
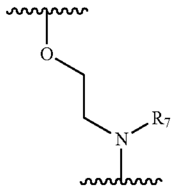
and Z is
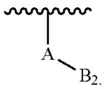
11. The method of claim 1, wherein the compound is
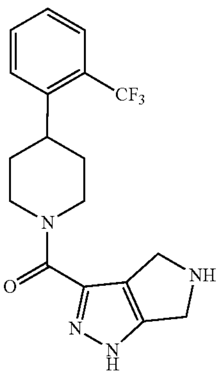
,
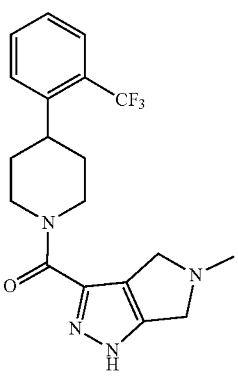
, -continued
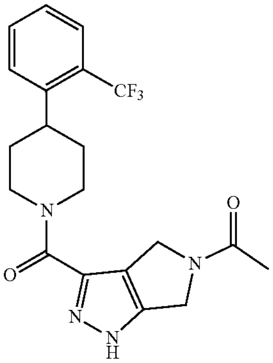
,
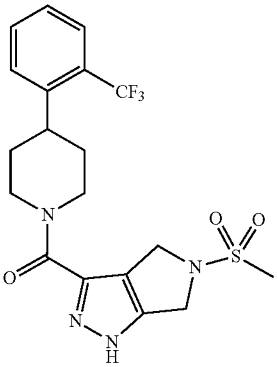
,
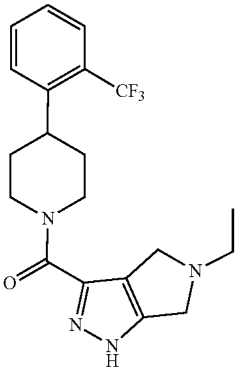
,
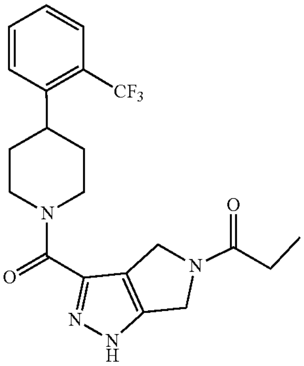
,
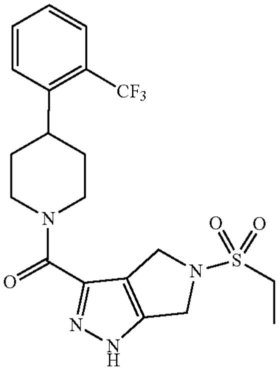
,
-continued
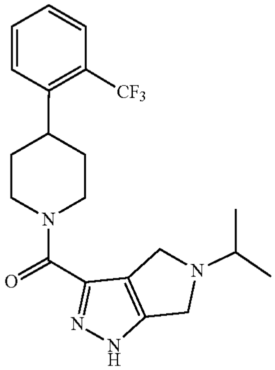
,
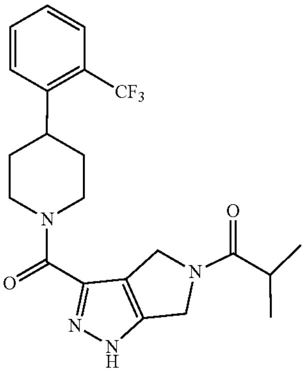
,
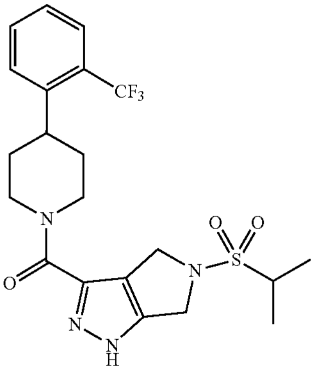
,
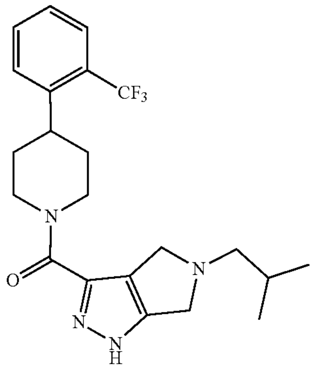
, -continued
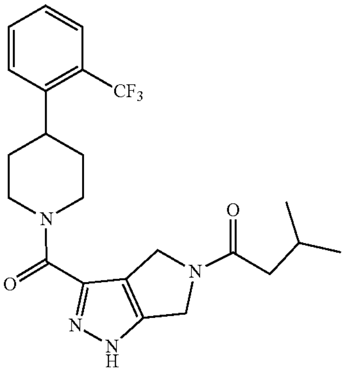
,
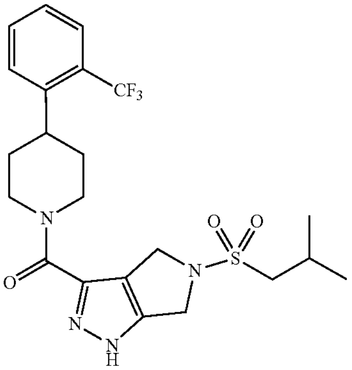
,
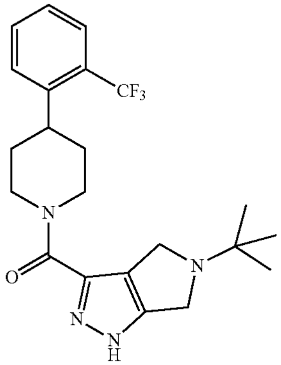
,
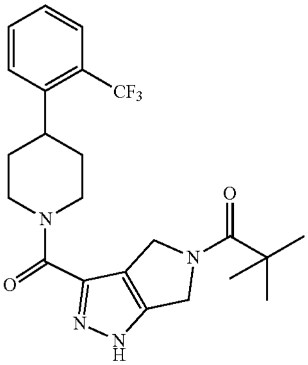
,
-continued
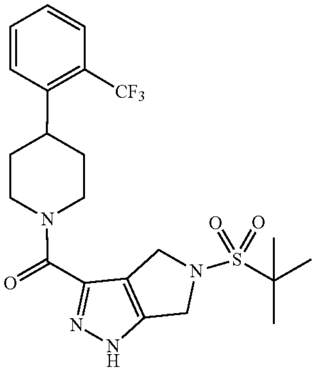
,
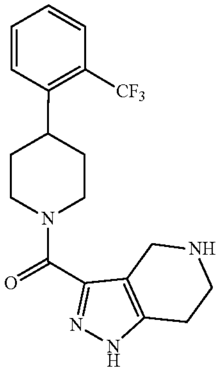
,
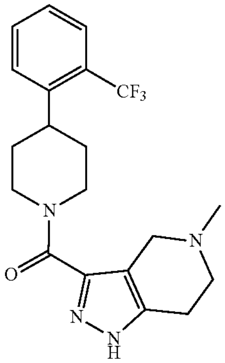
,
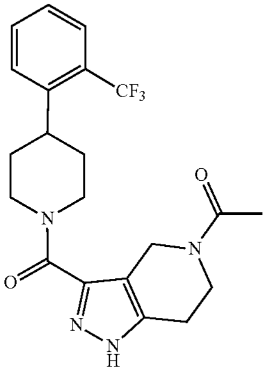
,
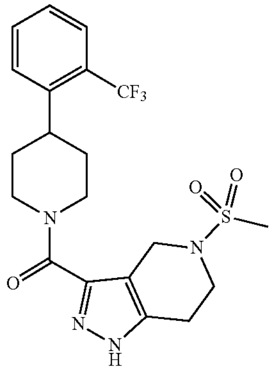
,
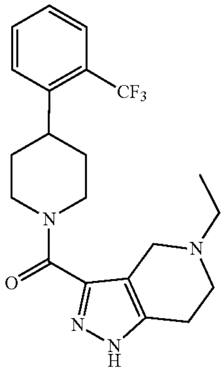
,
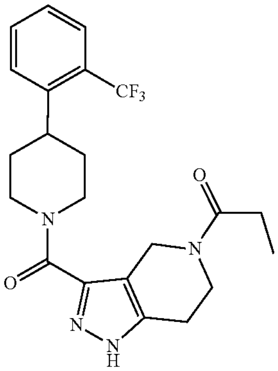
, -continued
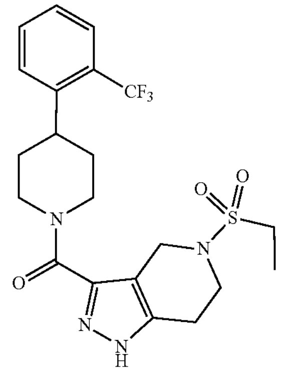
,
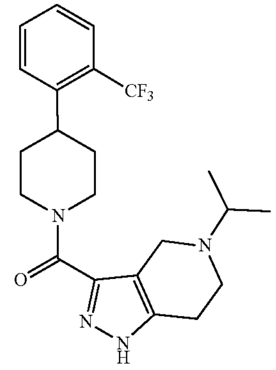
,
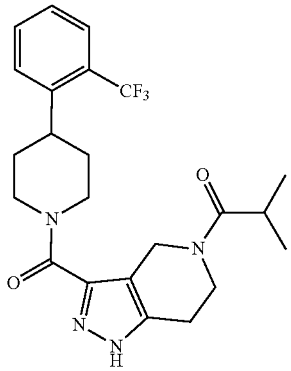
,
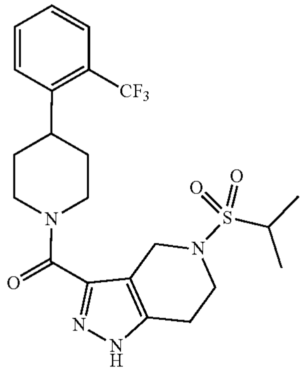
,
-continued
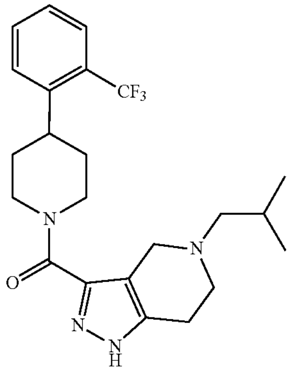
,
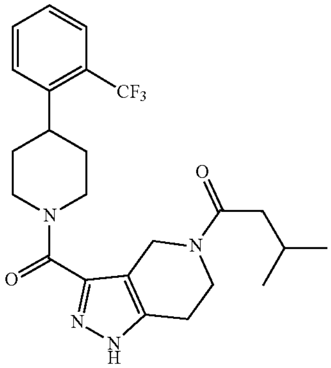
,
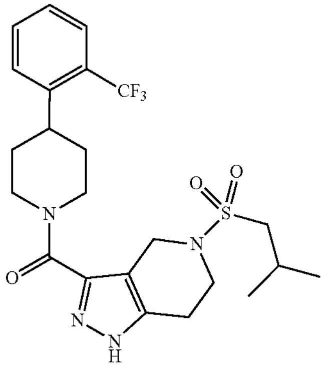
,
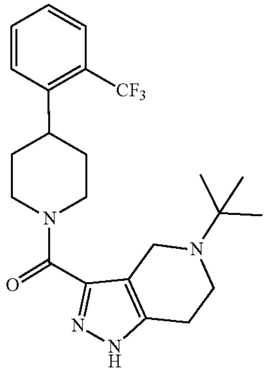
, -continued
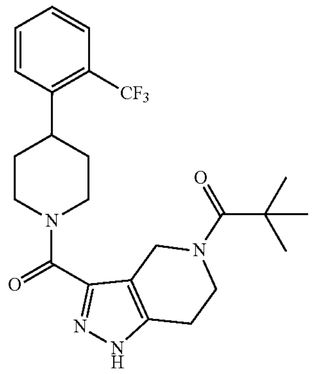
,
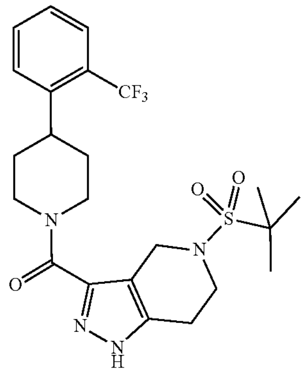
,
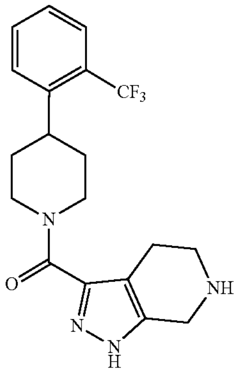
,
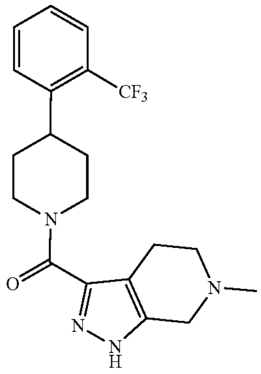
,
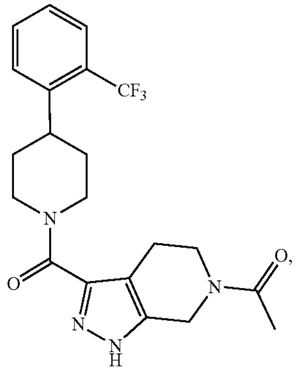
-continued
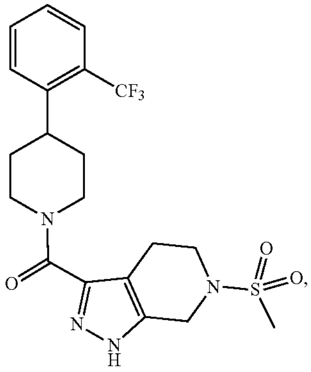
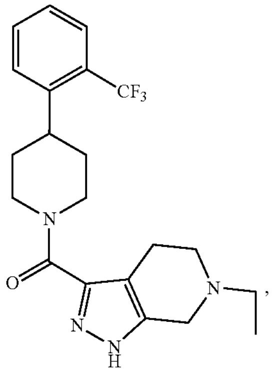
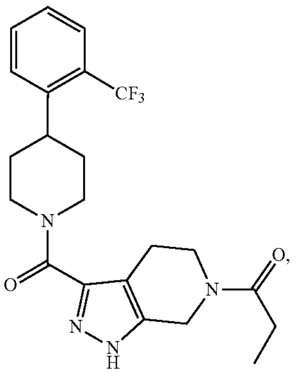
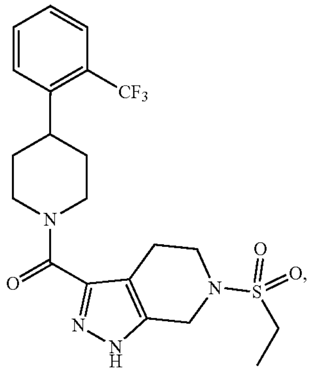

-continued
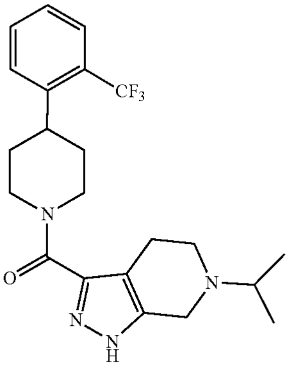
,
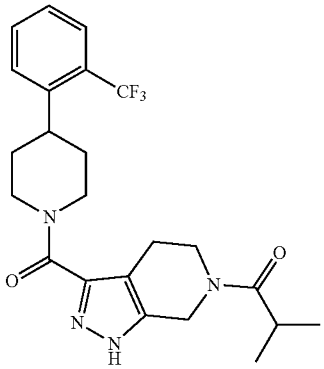
,
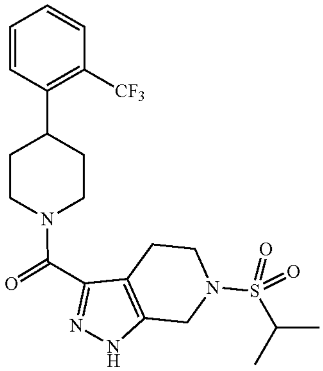
,
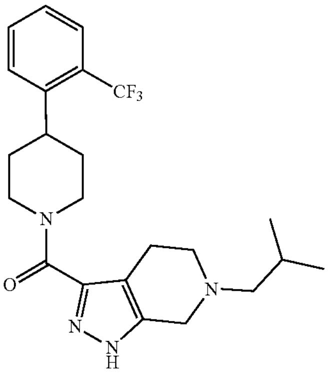
,
-continued
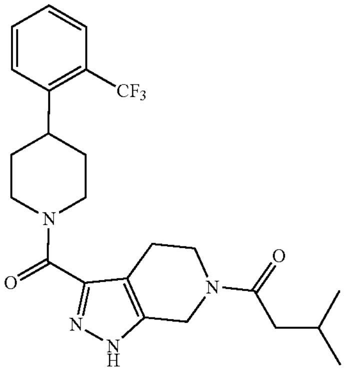
,
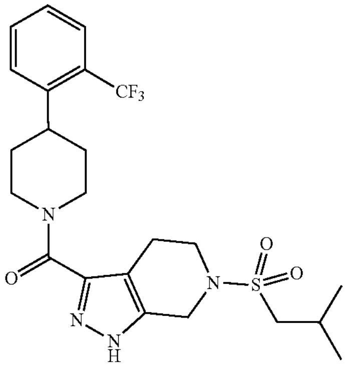
,
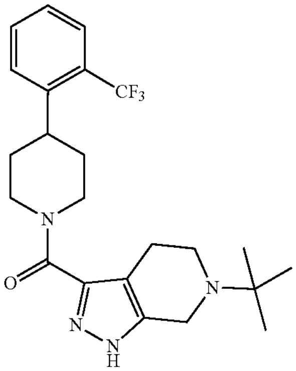
,
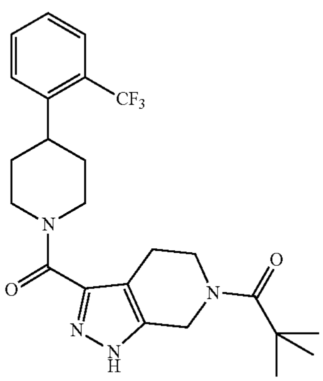
, -continued
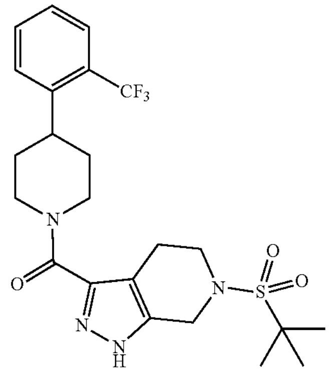
,
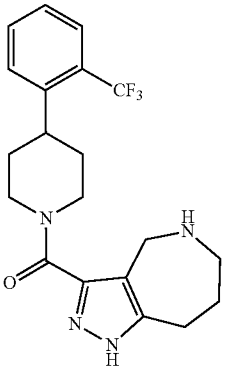
,
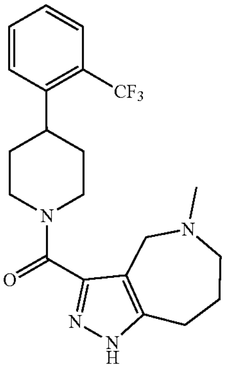
,
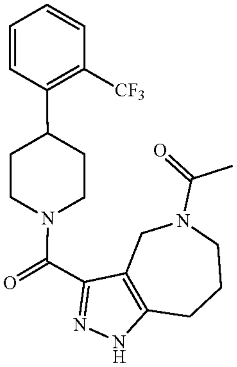
,
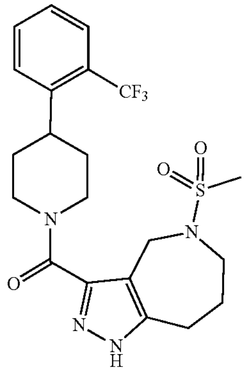
,
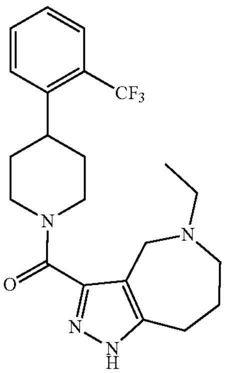
,
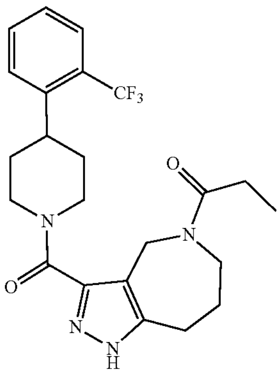
,
-continued
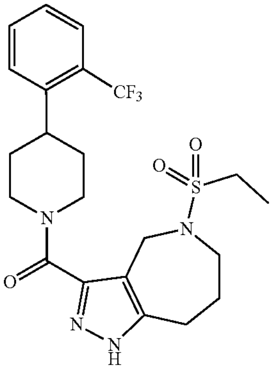
,
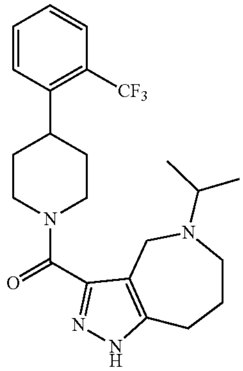
,
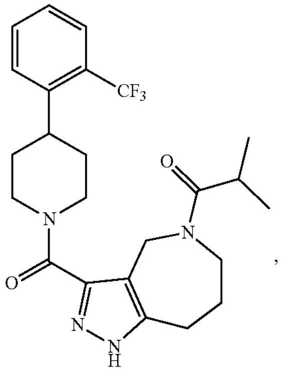
,
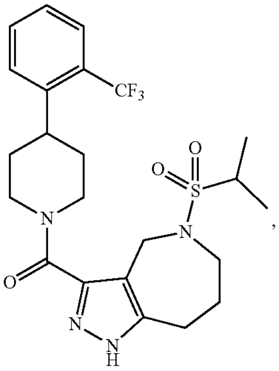
,
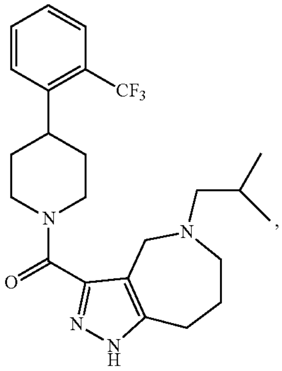
,
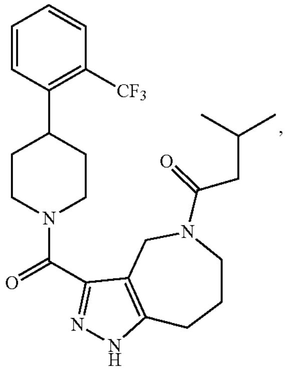
, -continued
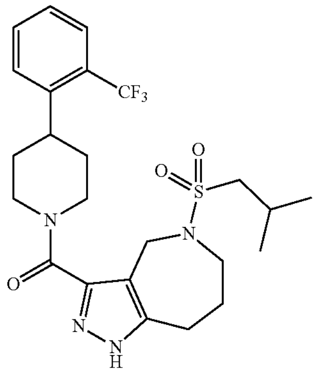
,
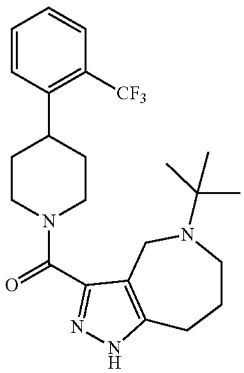
,
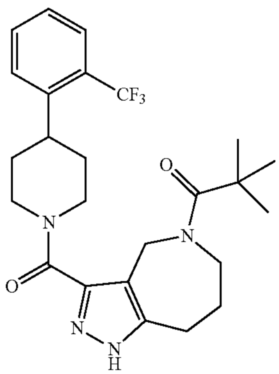
,
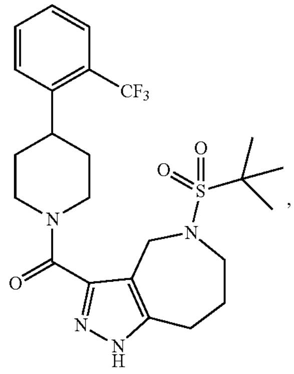
,
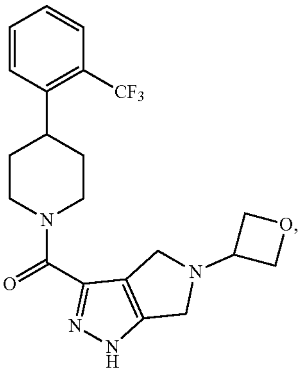
-continued
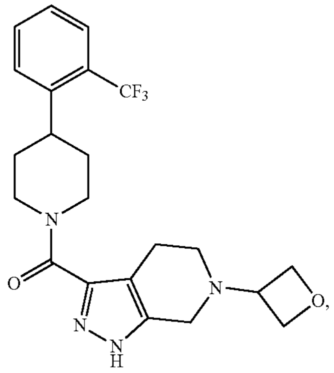
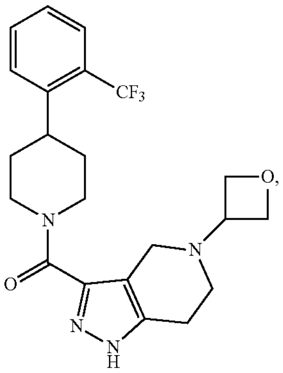
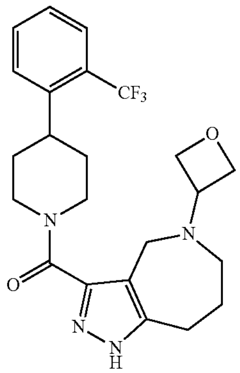
,
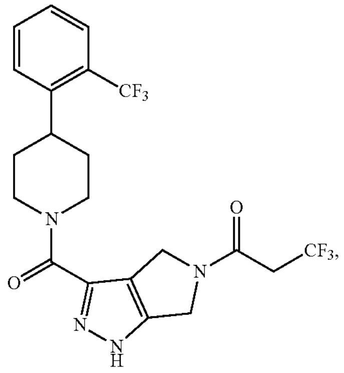
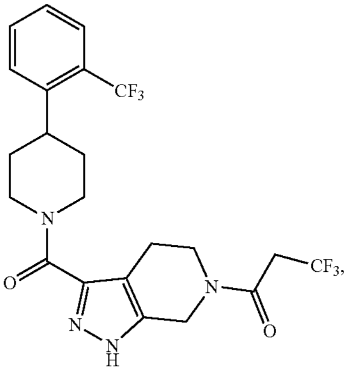

-continued
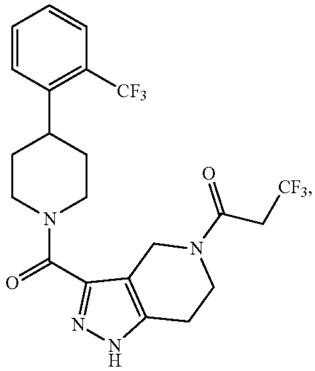
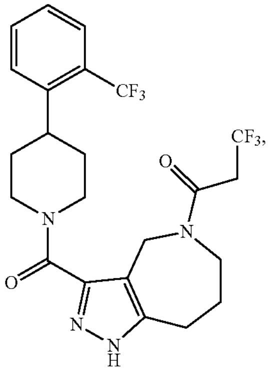
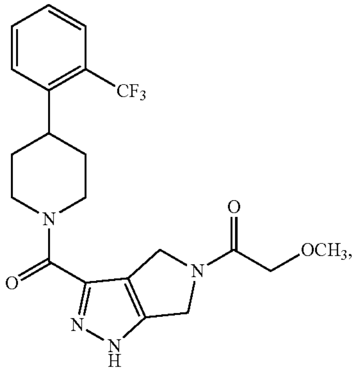
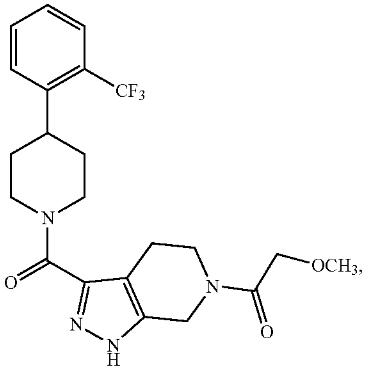
-continued
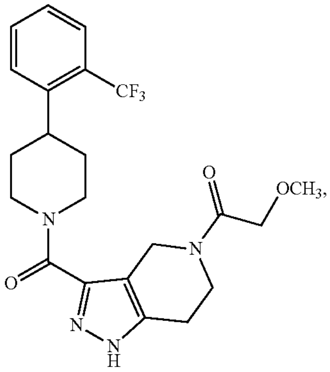
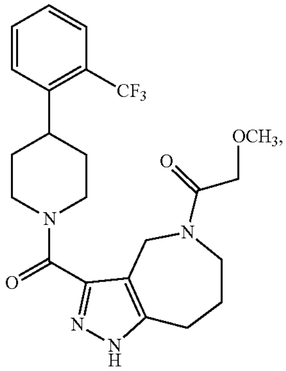
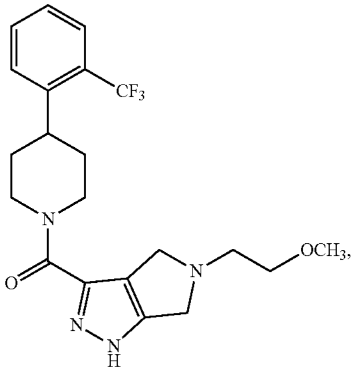
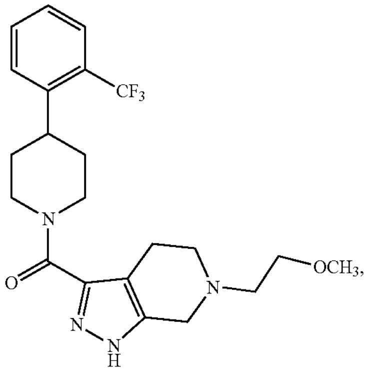

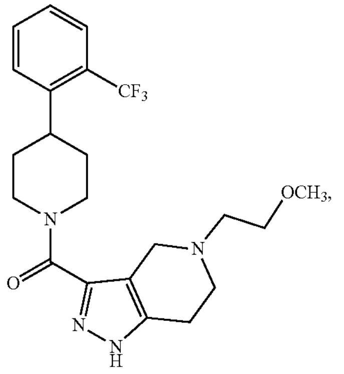
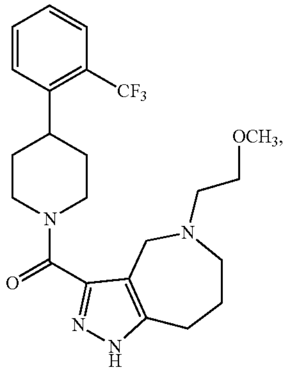
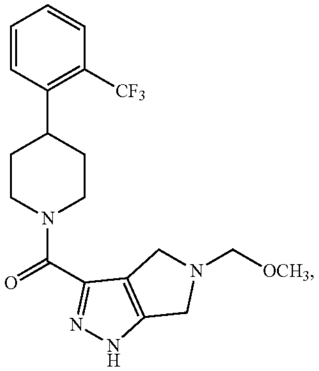
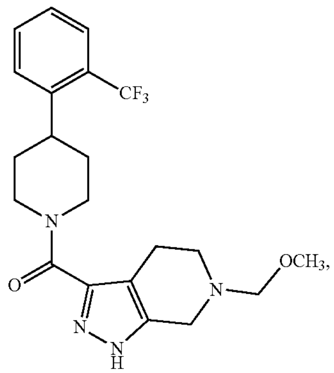
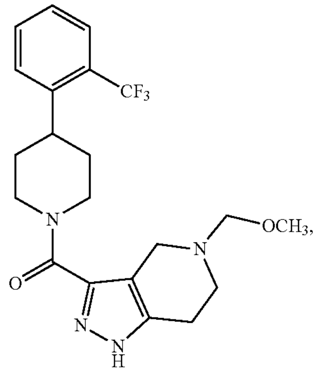
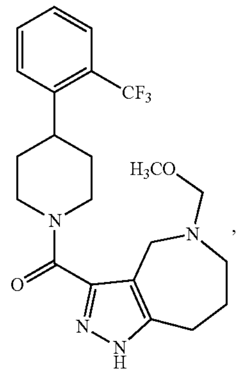
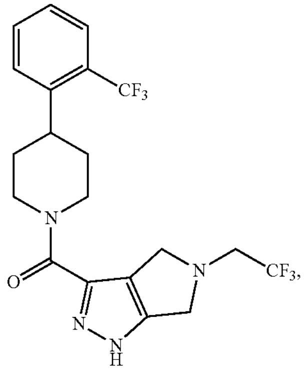
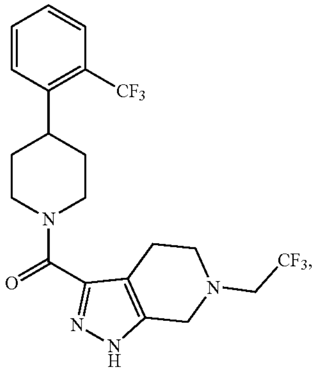
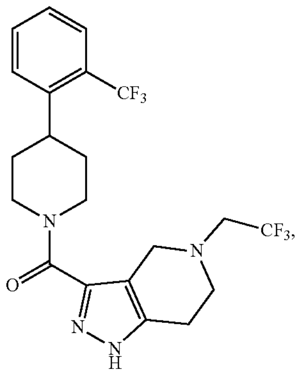
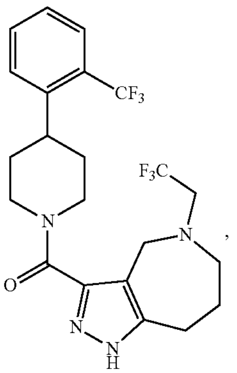

-continued
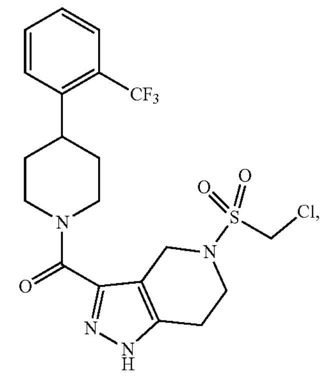
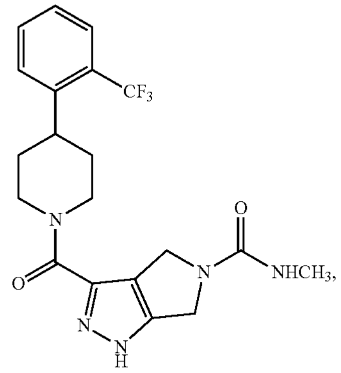 [SMILES: CNC(=O)N1Cc2[nH]nc(C(=O)N3CCC(c4ccccc4C(F)(F)F)CC3)c2C1]
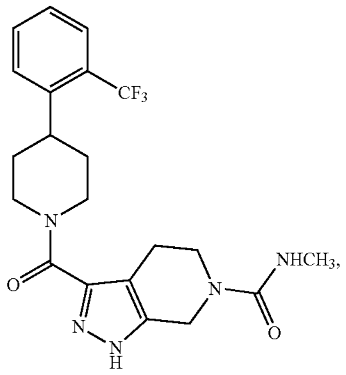
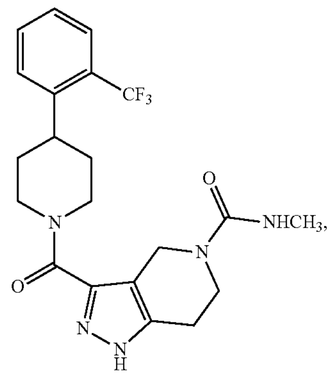
-continued
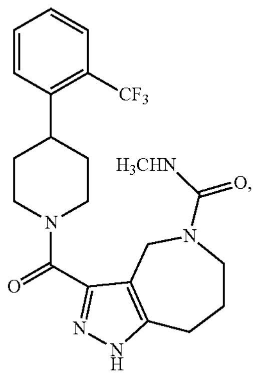
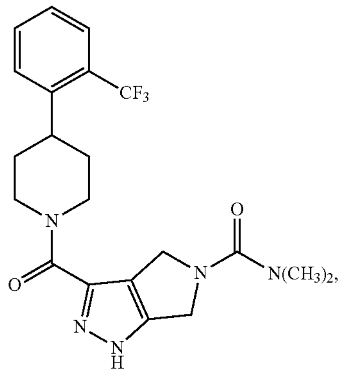
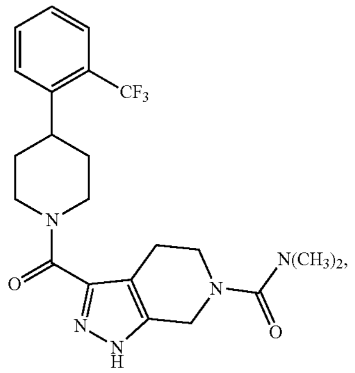
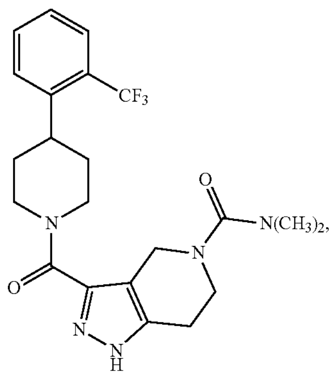

-continued
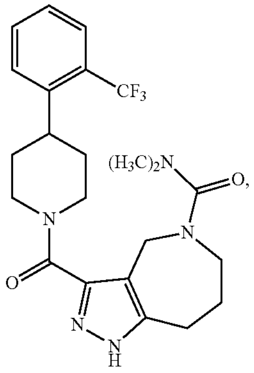
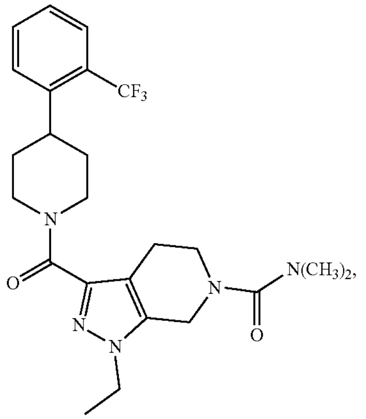
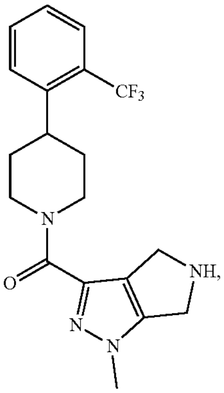
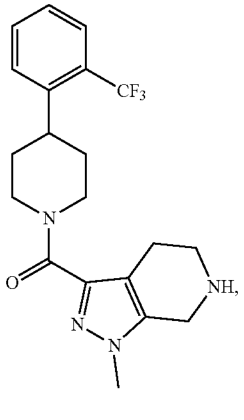
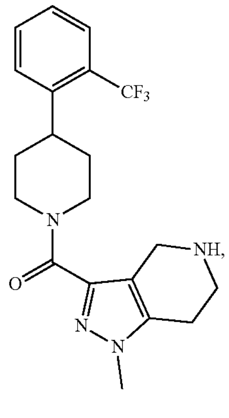
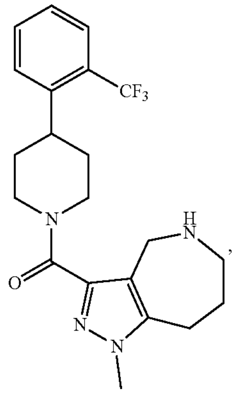
-continued
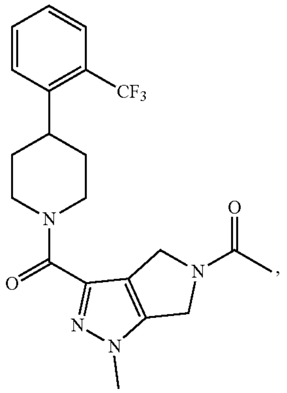
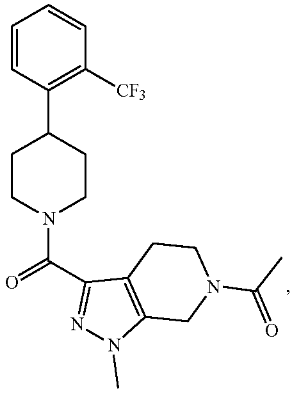
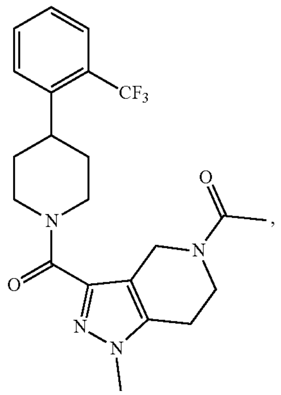
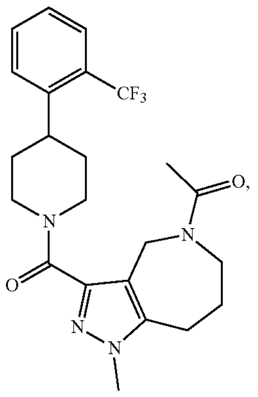
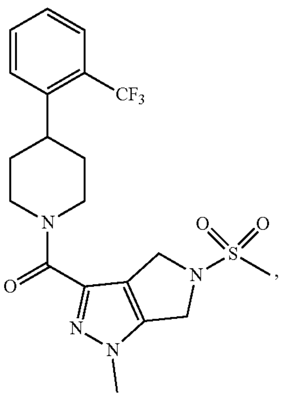

-continued
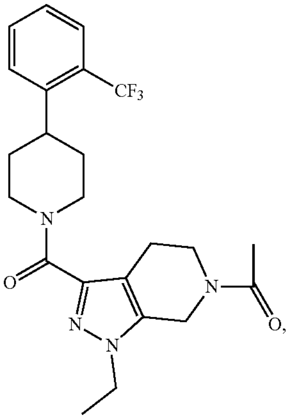
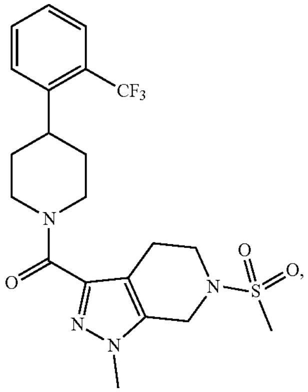
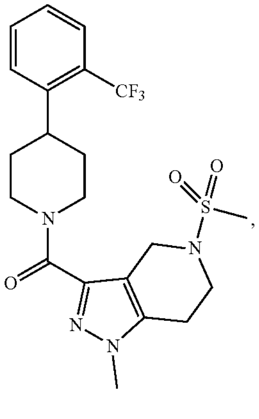
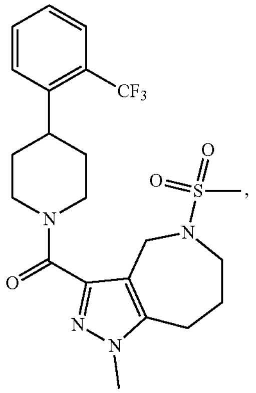
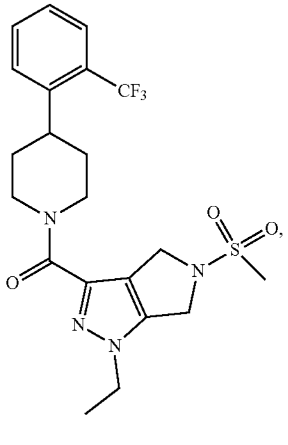
-continued
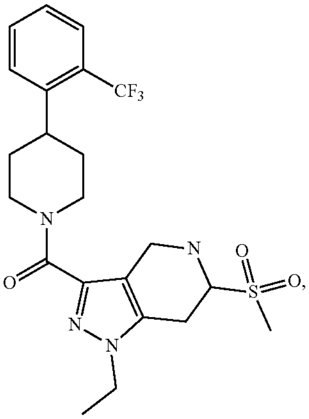
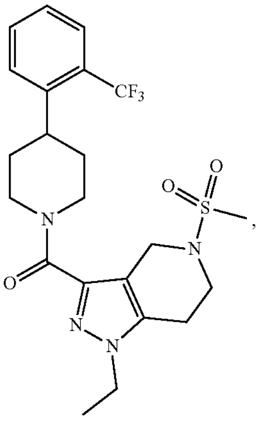
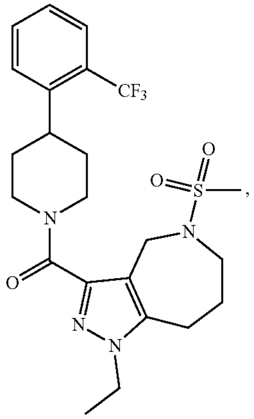
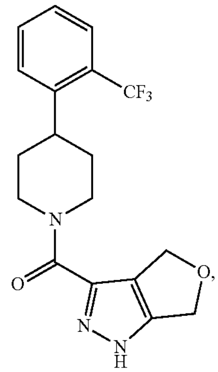
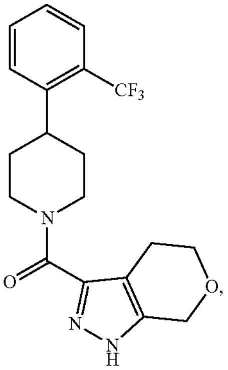
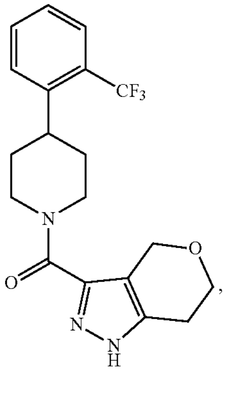
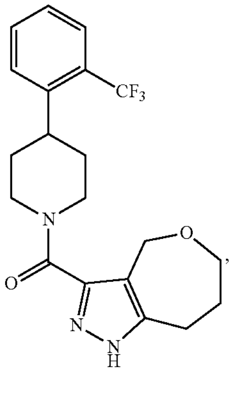

-continued
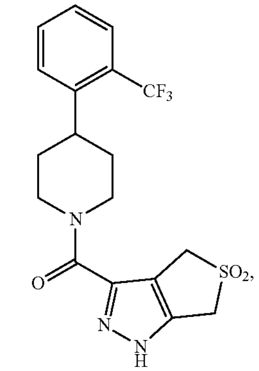
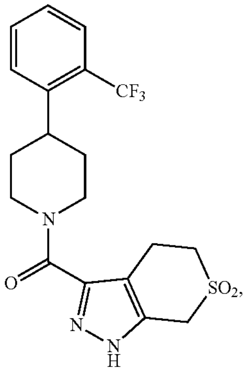
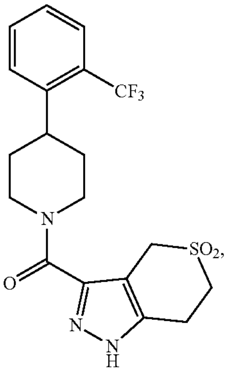
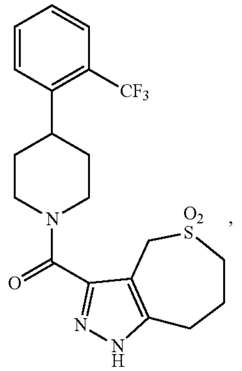
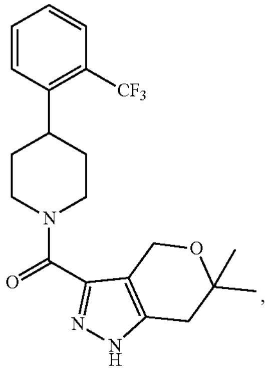
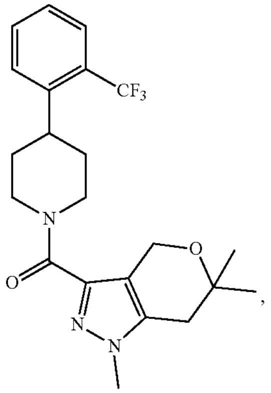
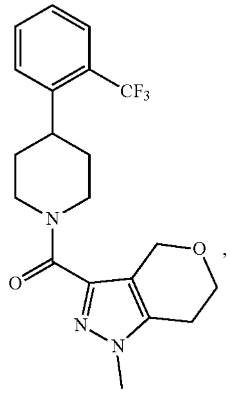
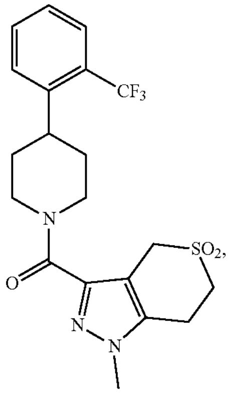
-continued
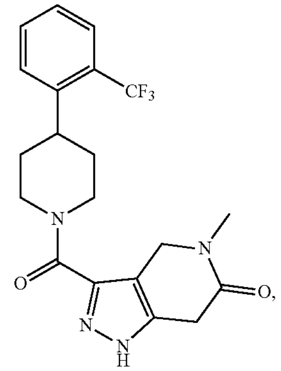
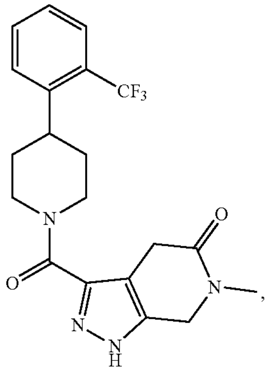
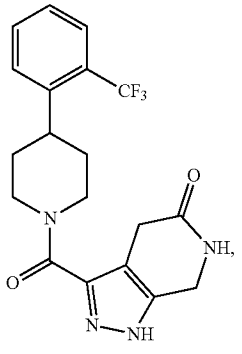
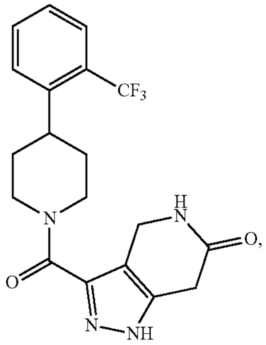
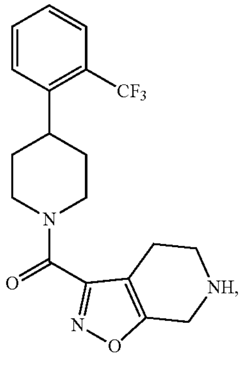
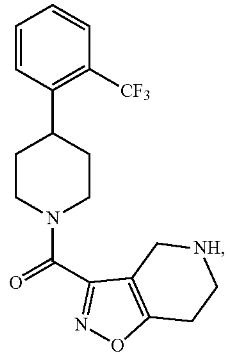
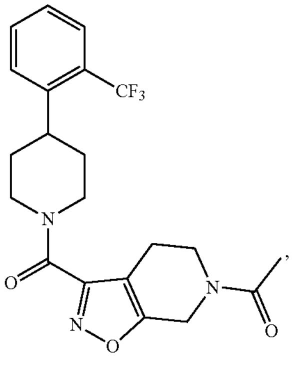
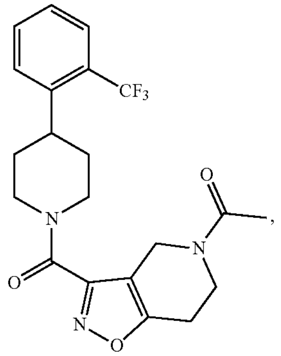

-continued
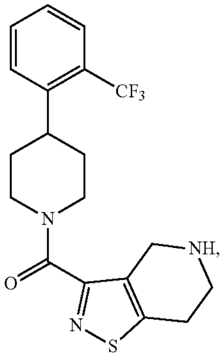
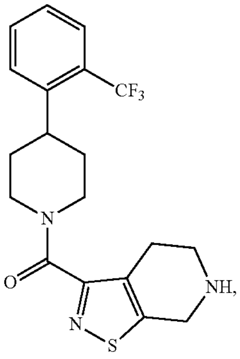
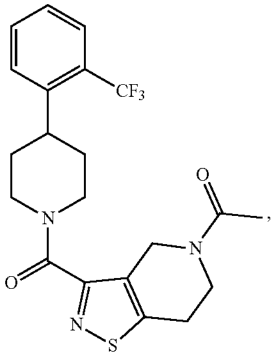
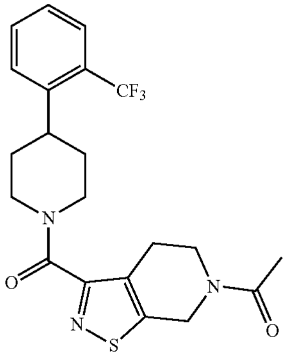
,
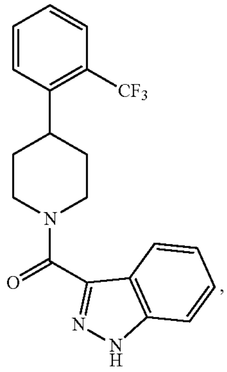
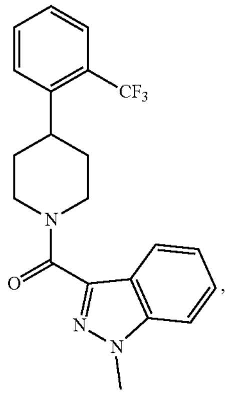
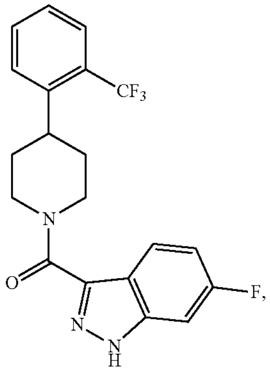
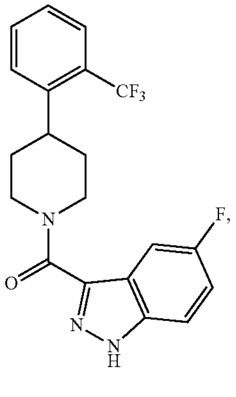
-continued
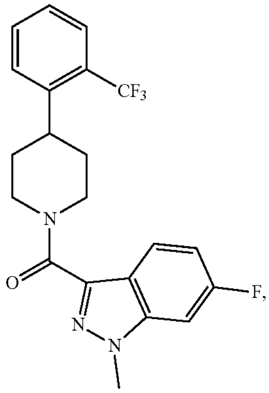
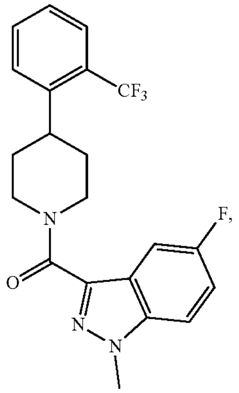
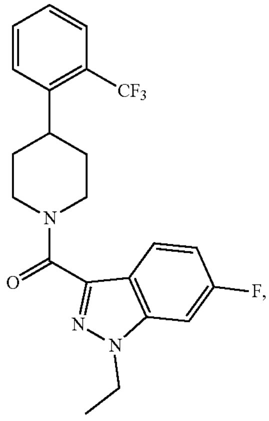
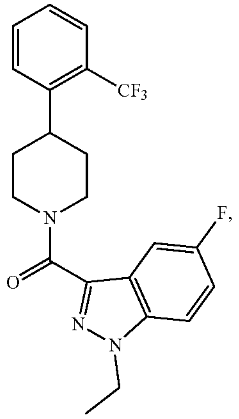
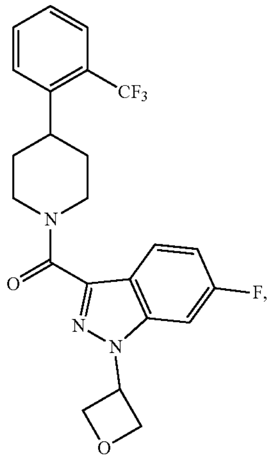
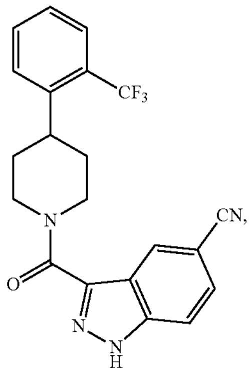

-continued
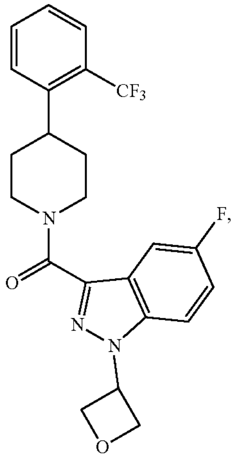
,
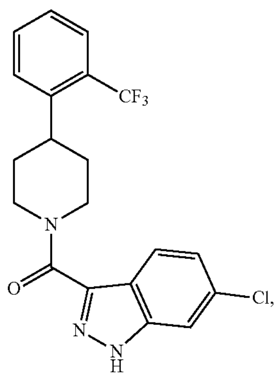
,
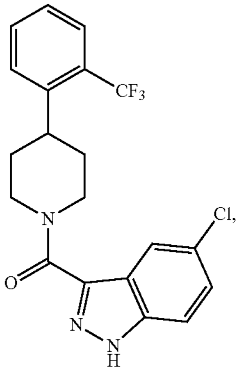
,
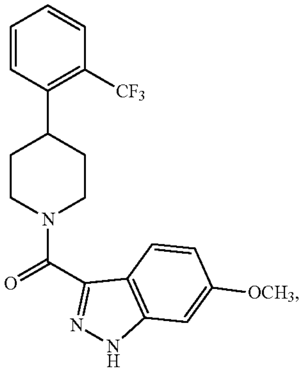
,
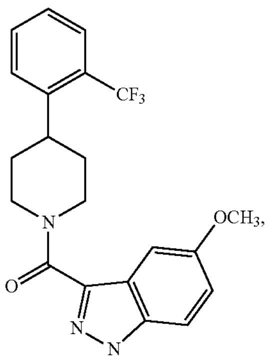
,
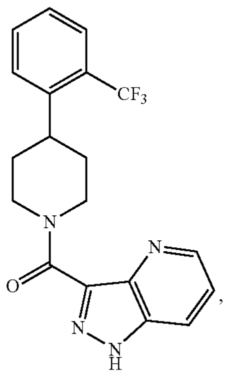
,
-continued
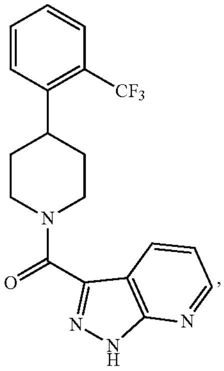
,
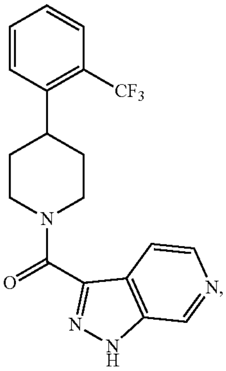
,
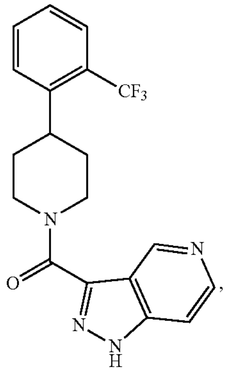
,
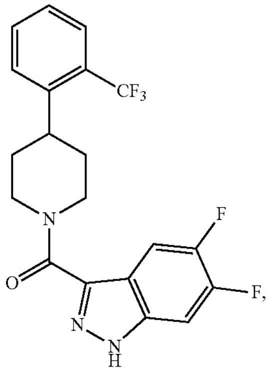
,
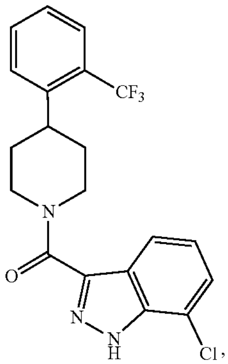
,
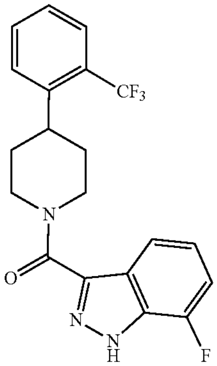
,
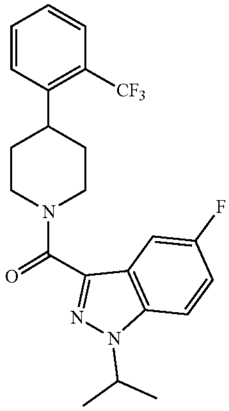
,
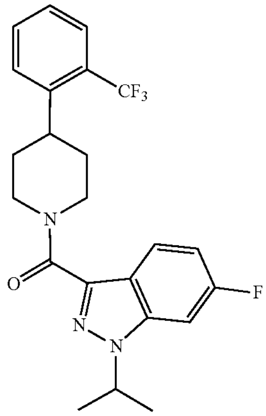
, -continued
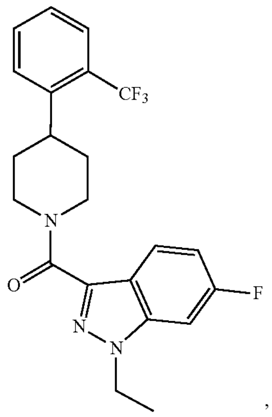
,
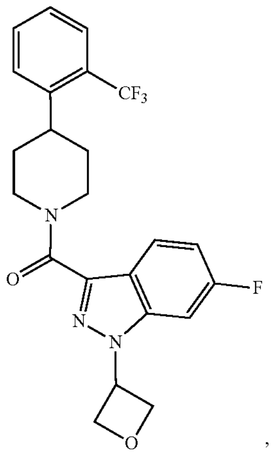
,
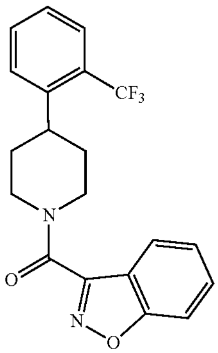
,
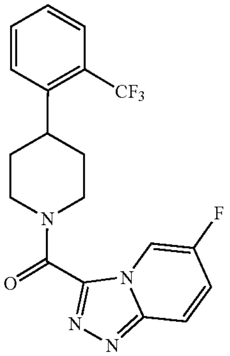
,
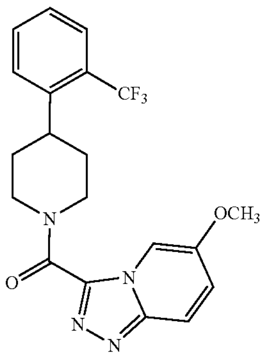
,
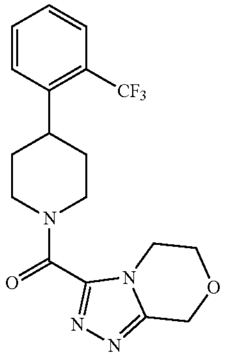
,
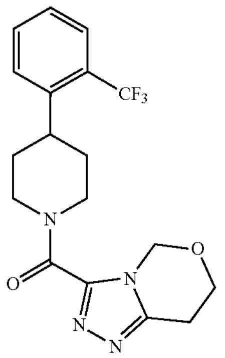
,
-continued
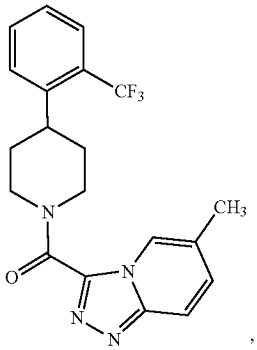
,
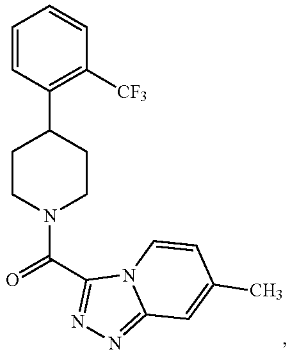
,
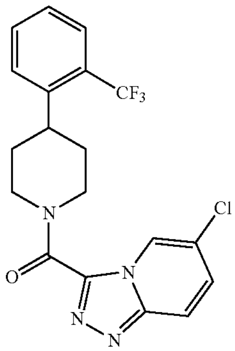
,
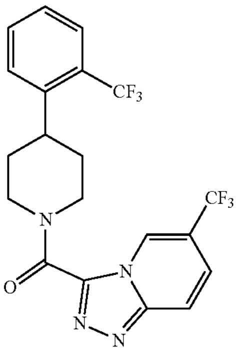
,
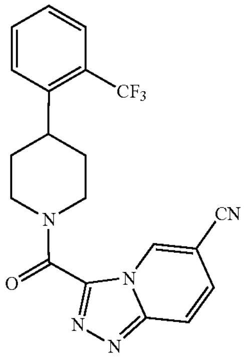
,
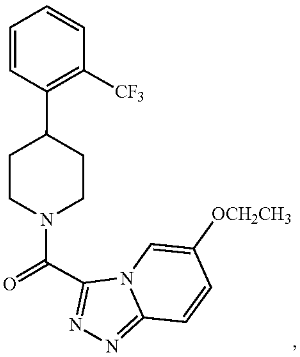
,
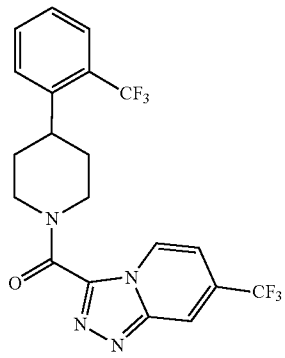
, -continued
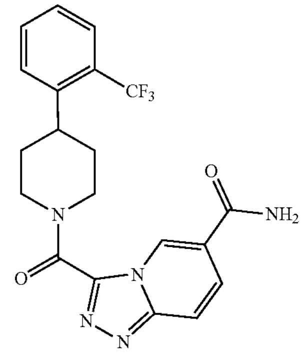
,
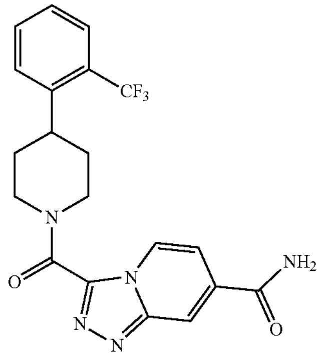
,
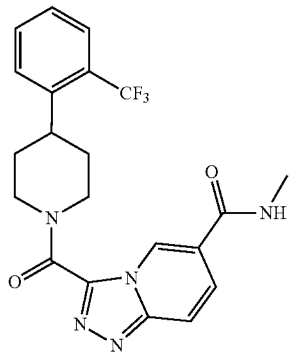
,
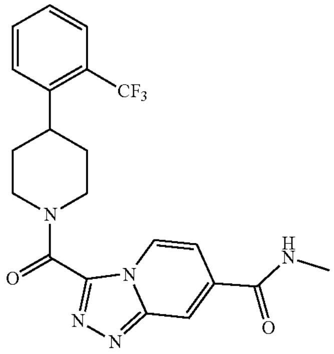
,
-continued
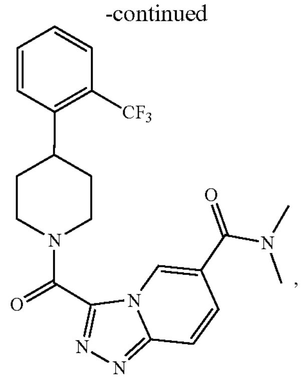
,
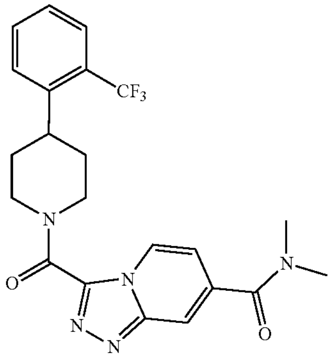
,
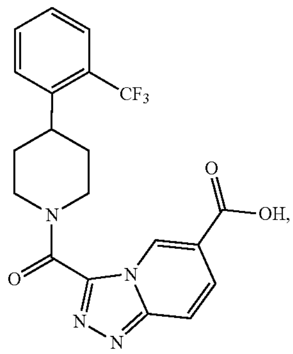
,
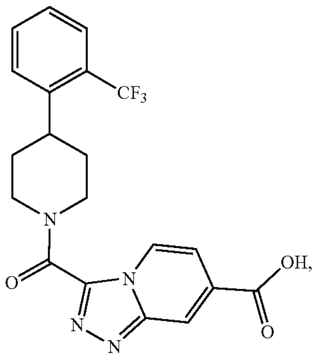
,

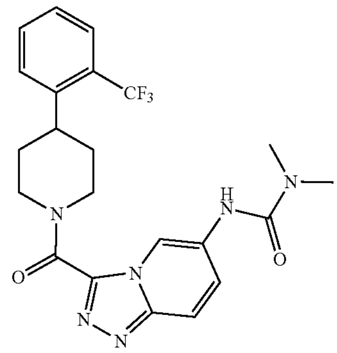
,
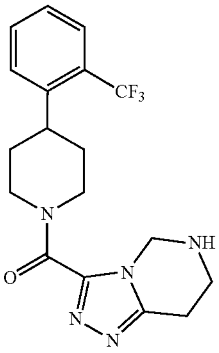
,
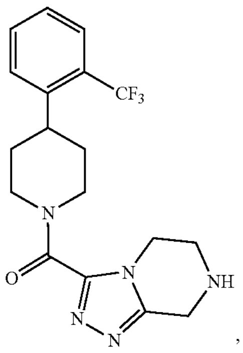
,
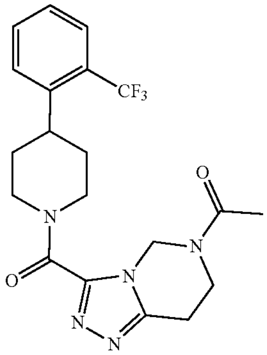
,
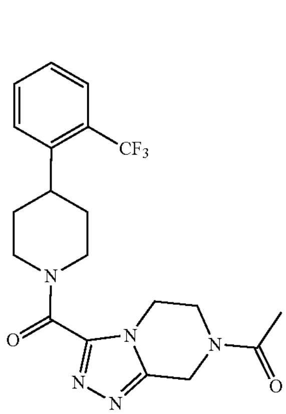
,
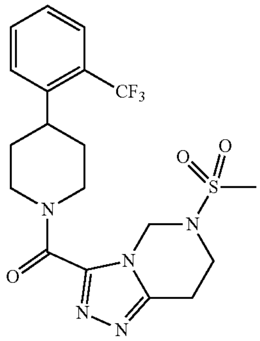
,
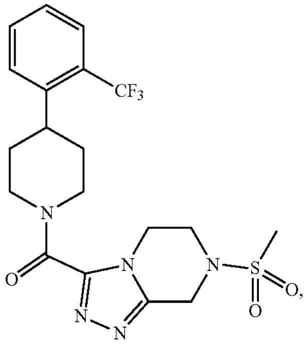
,
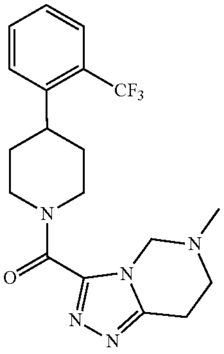
,
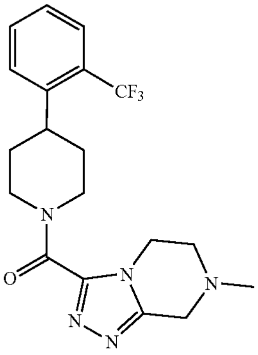
,
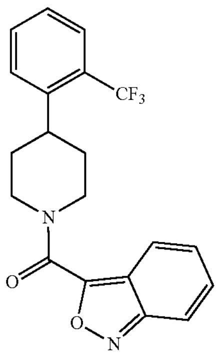
,
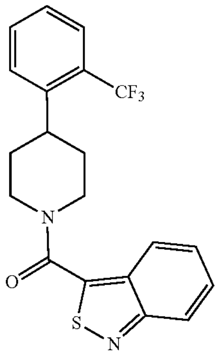
, -continued
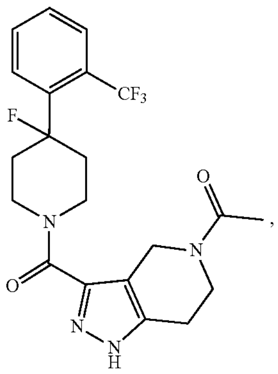
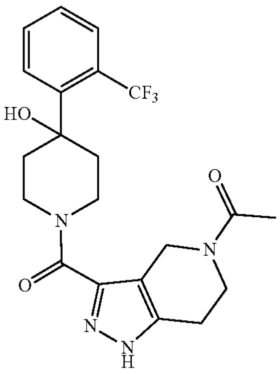
,
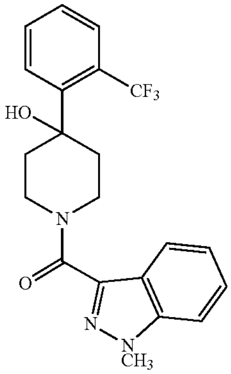
,
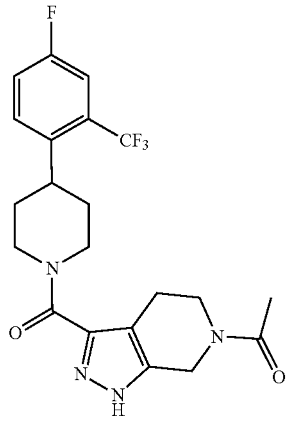
,
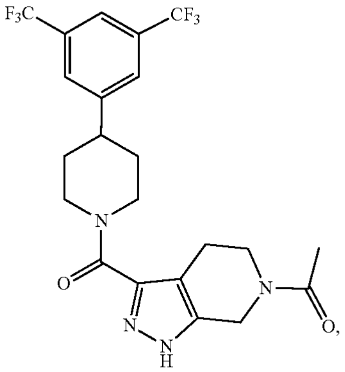
-continued
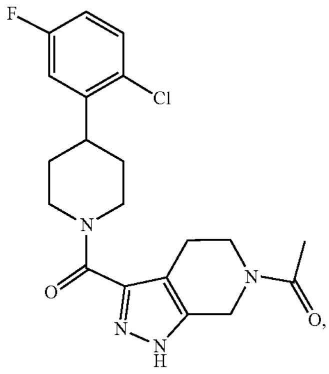
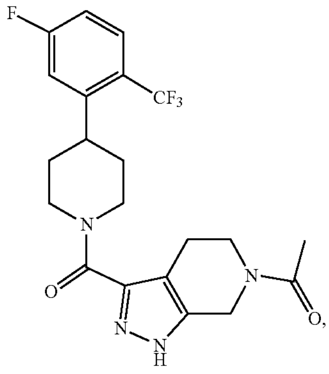
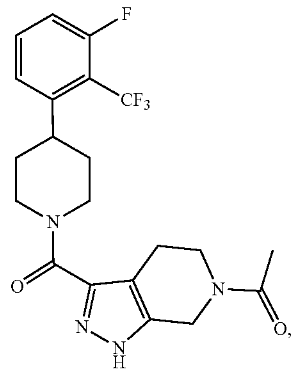
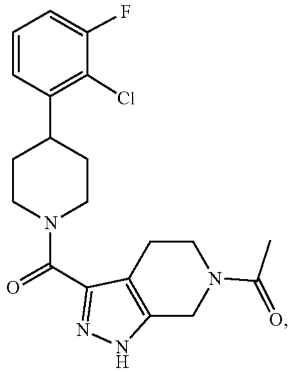

-continued
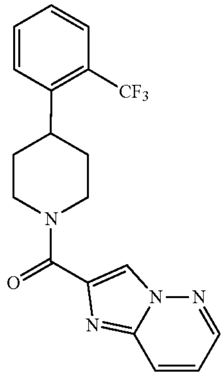
,
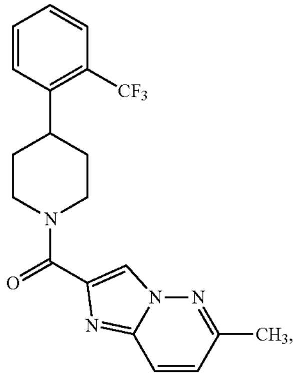
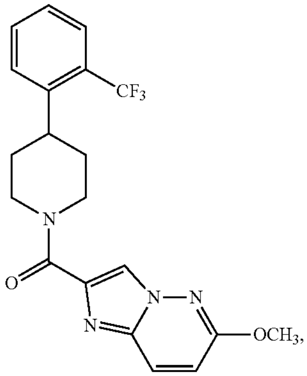
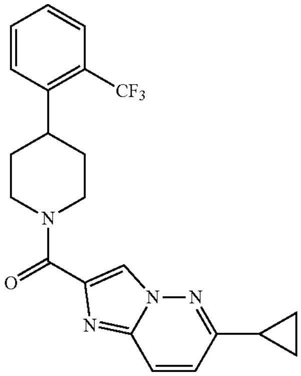
,
-continued
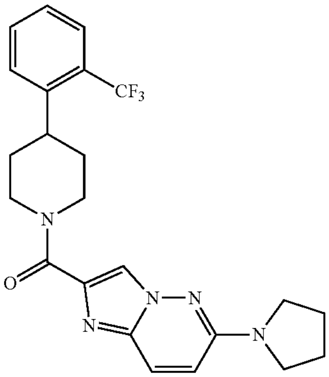
,
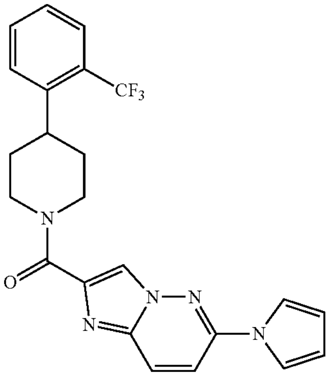
,
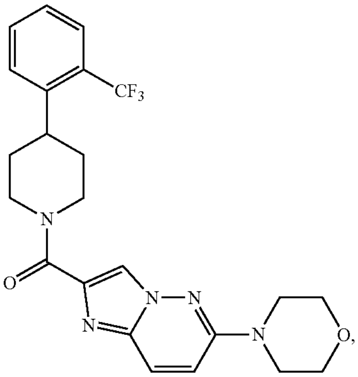
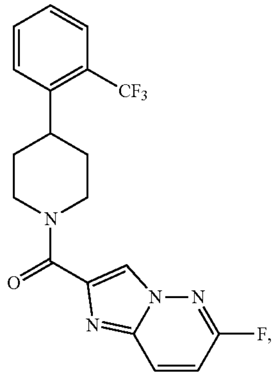

-continued
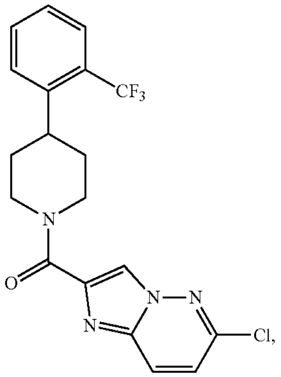
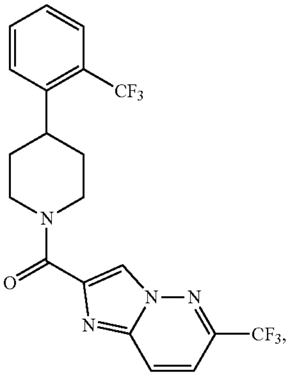
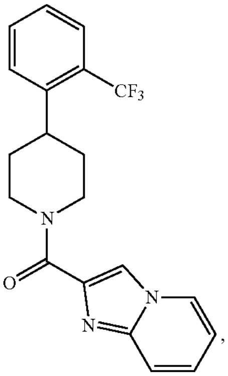
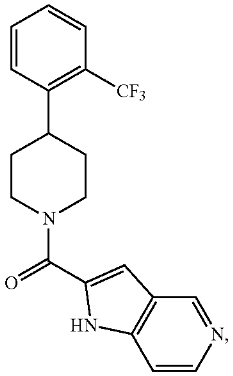
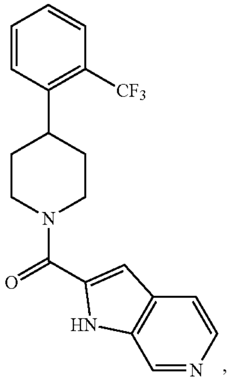
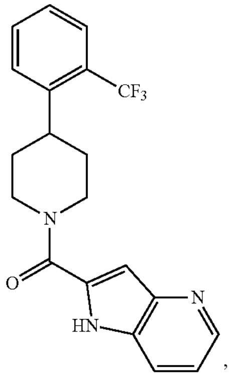
-continued
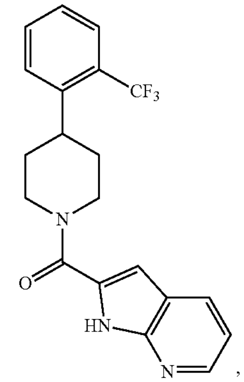
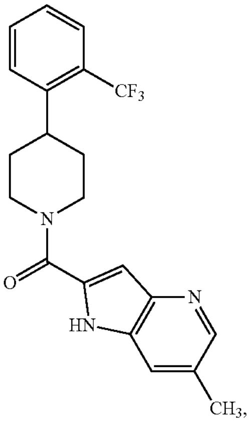
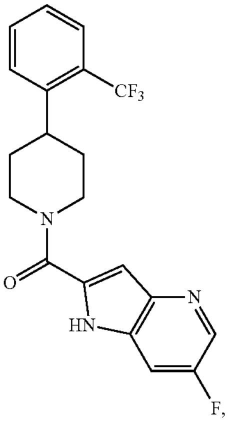
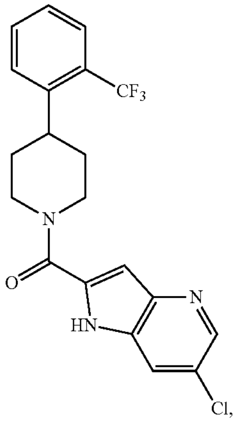
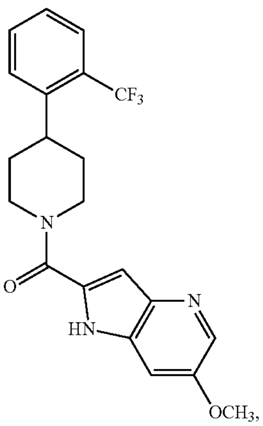
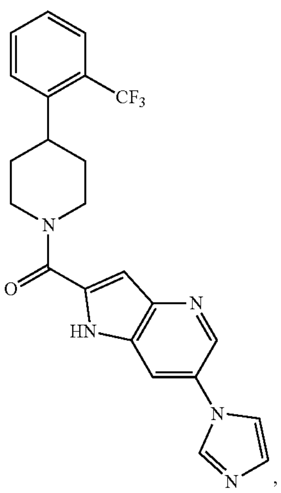

-continued
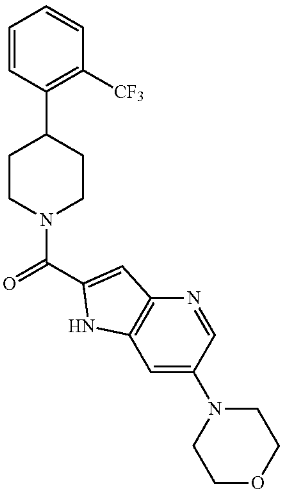
,
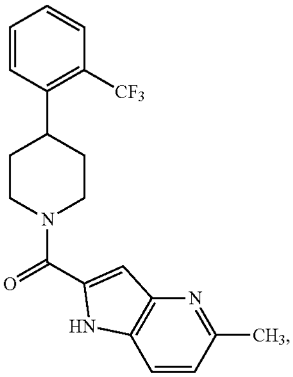
,
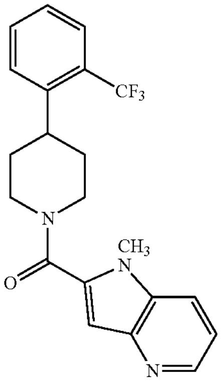
,
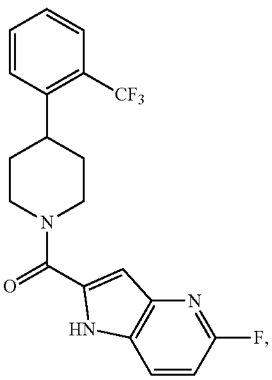
,
-continued
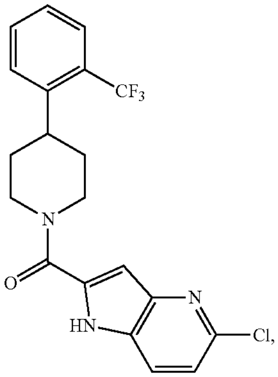
,
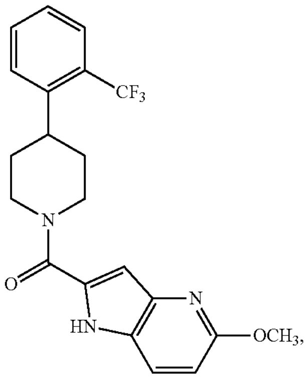
,
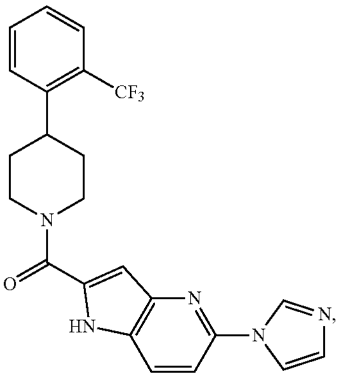
,
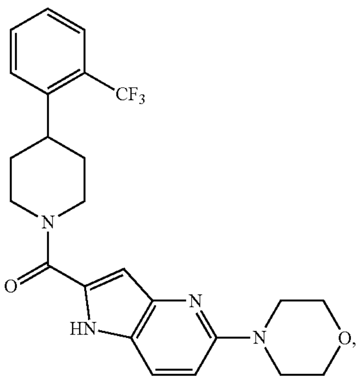
, -continued
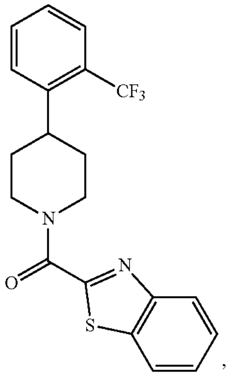
,
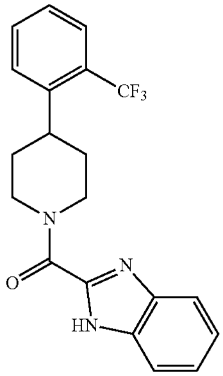
,
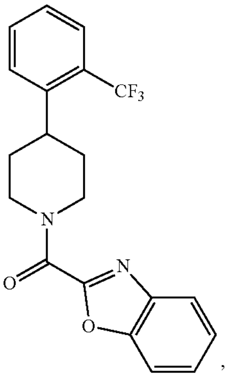
,
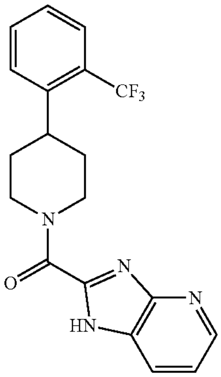
,
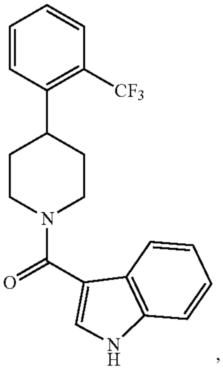
,
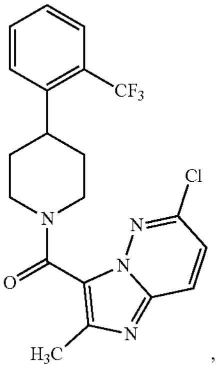
,
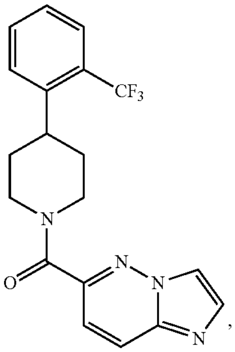
,
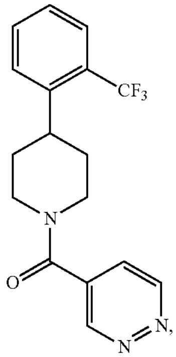
-continued
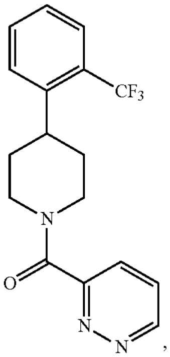
,
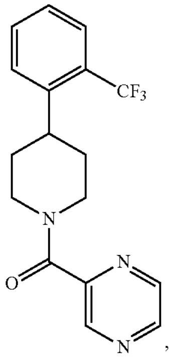
,
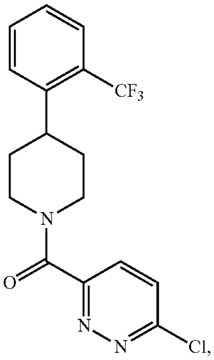
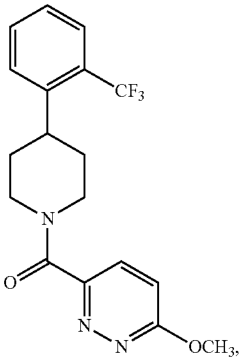
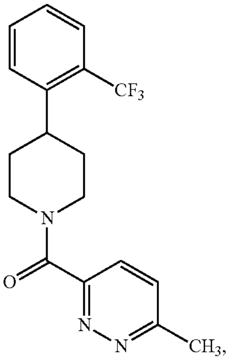
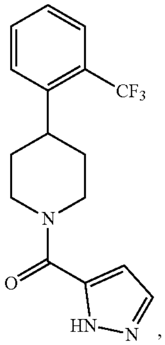
,
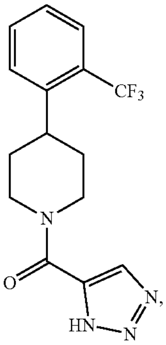
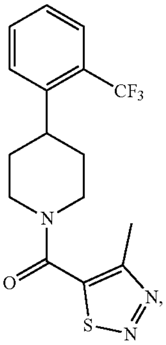
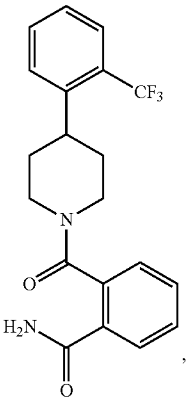
, -continued
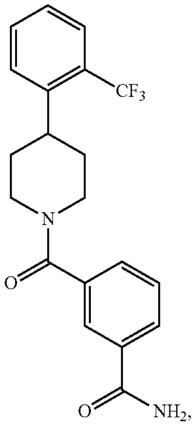
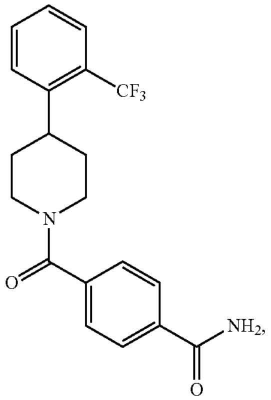
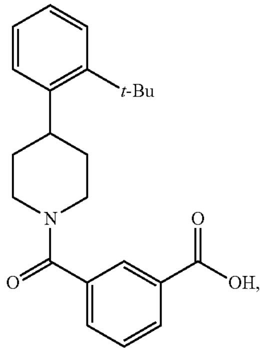
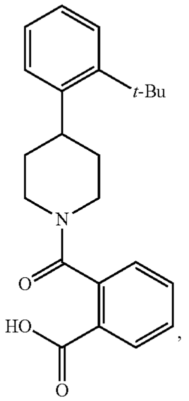
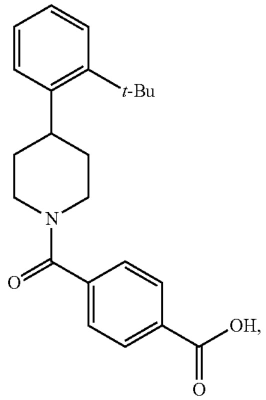
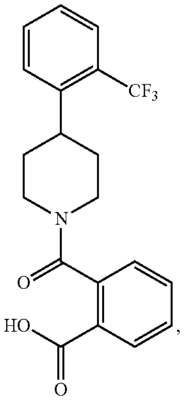
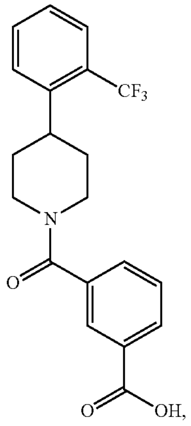
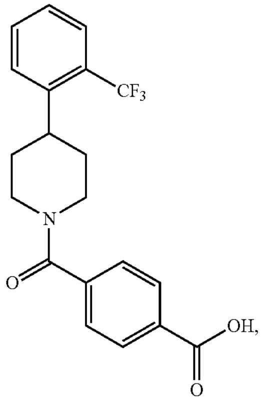
-continued
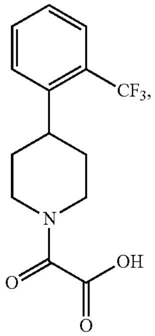
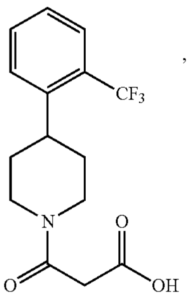
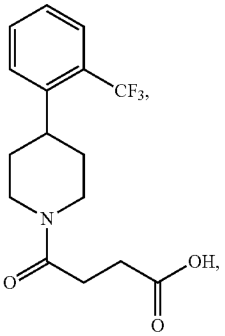
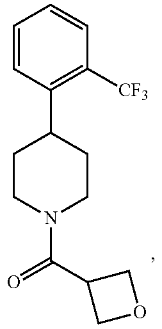
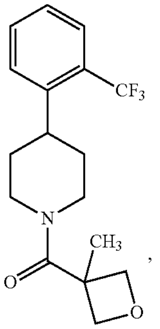
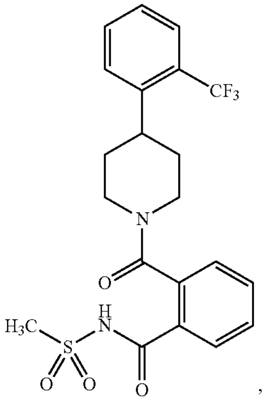
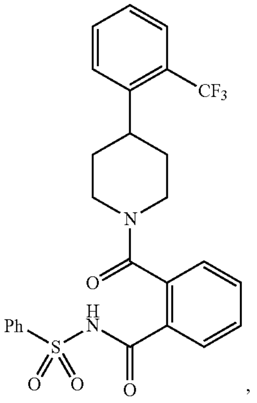
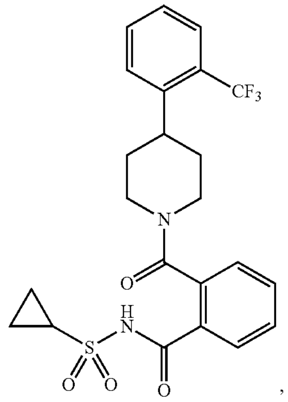
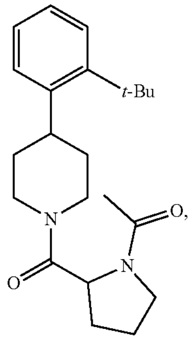

-continued
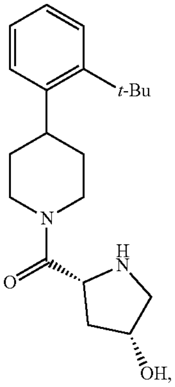
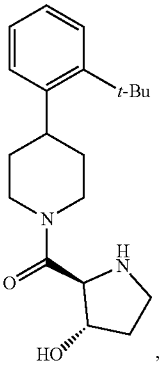
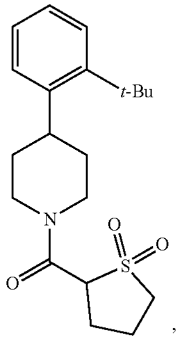
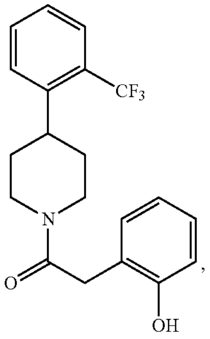
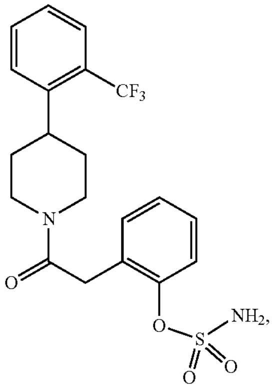
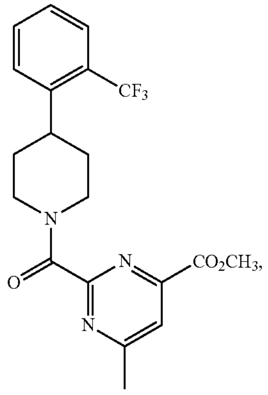
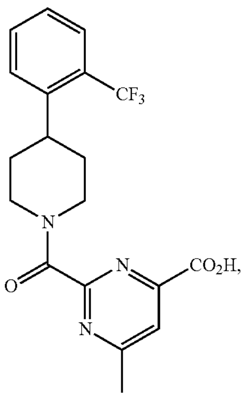
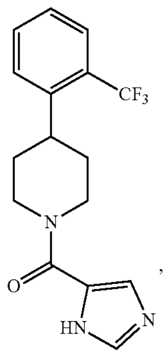
-continued
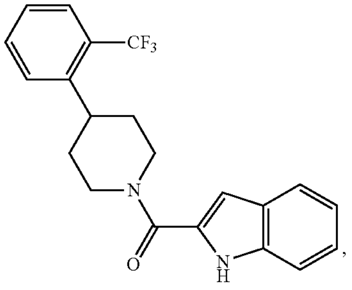
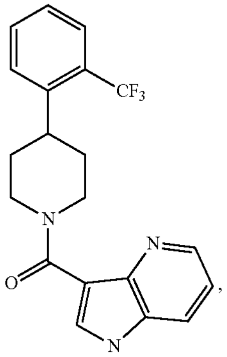
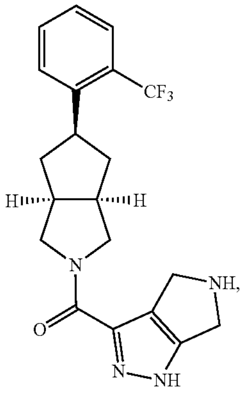
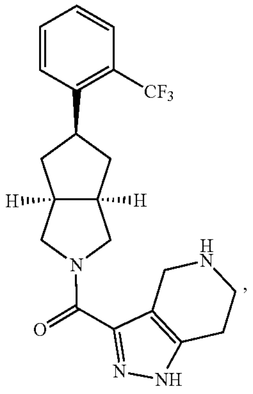
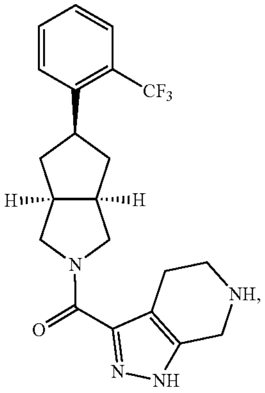
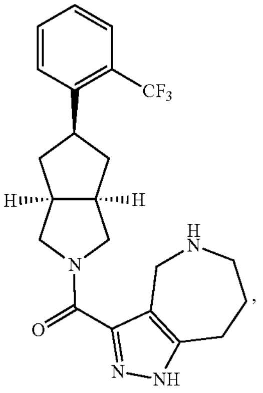
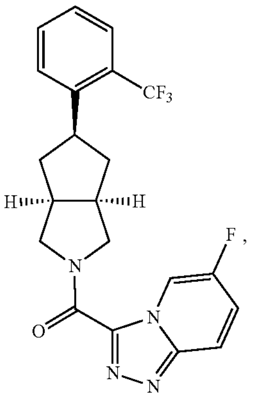
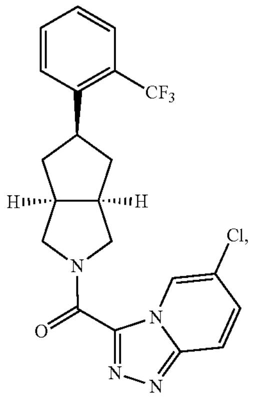

-continued
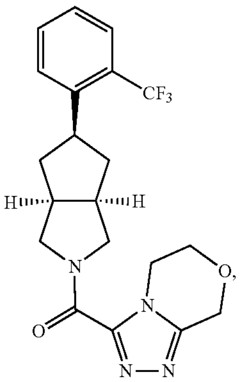
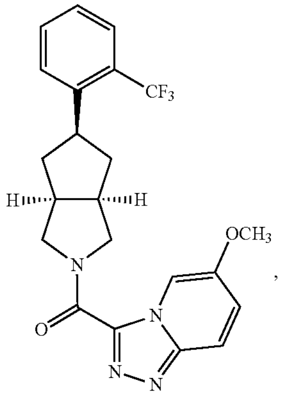
,
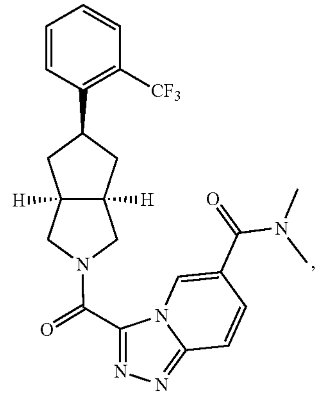
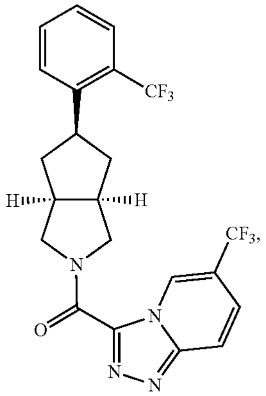
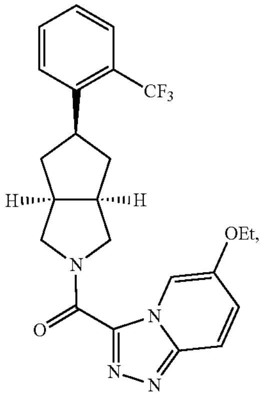
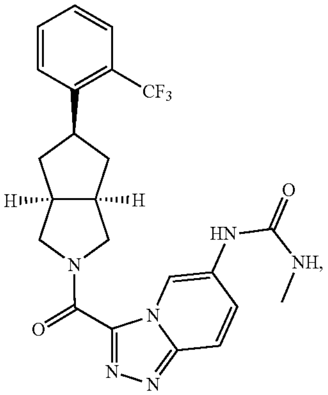
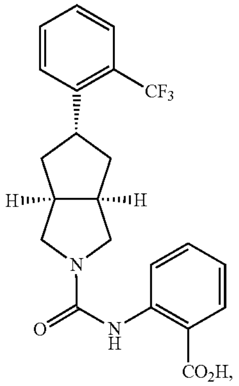
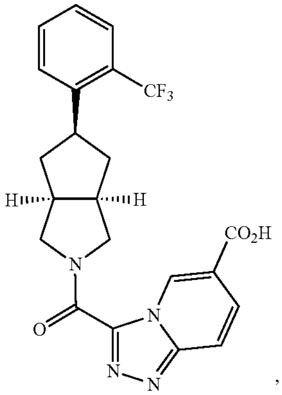
,
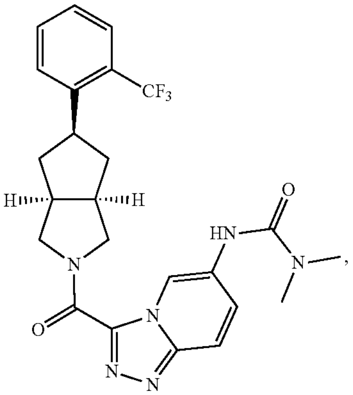
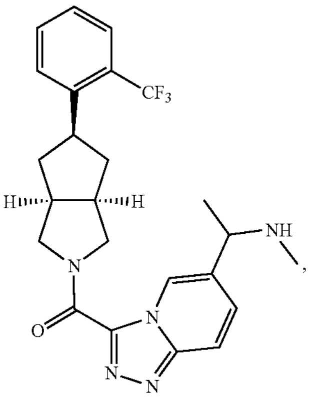
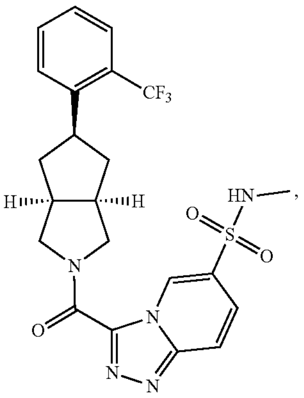

-continued
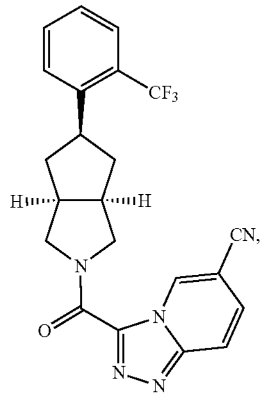
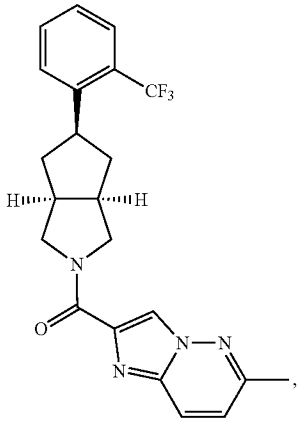
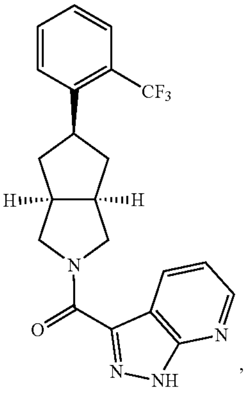
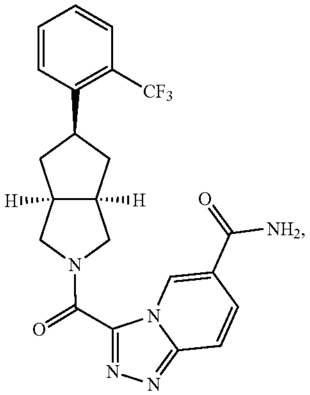
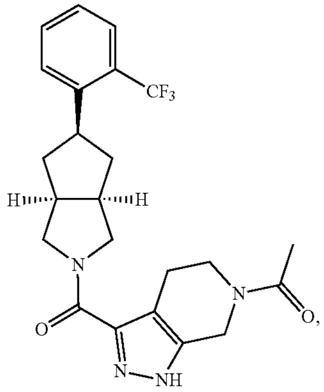
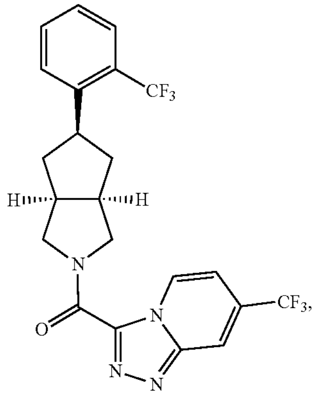
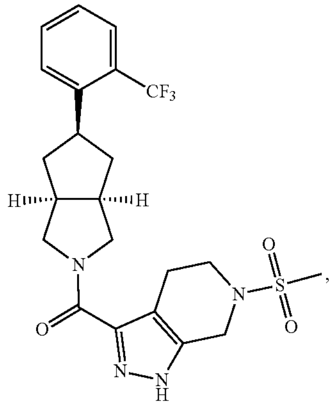
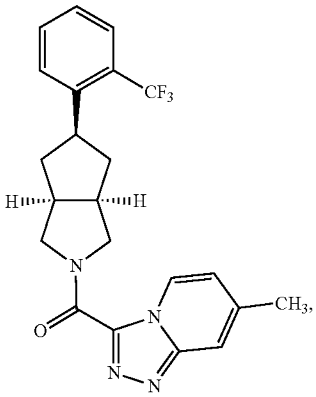
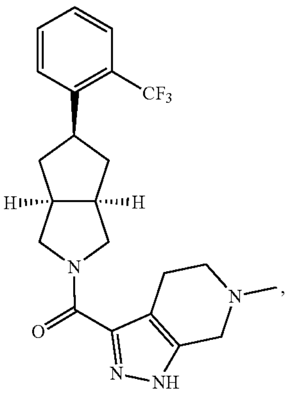

-continued
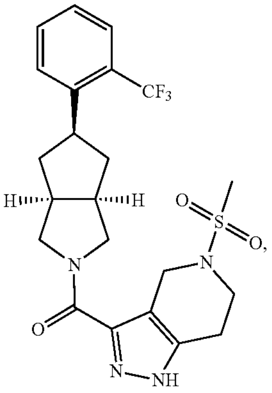
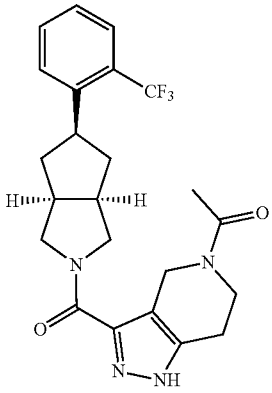
,
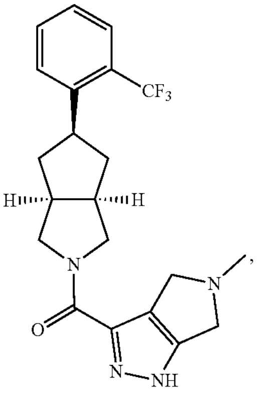
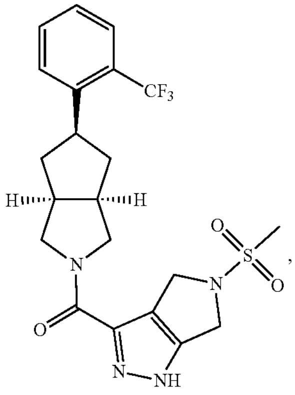
,
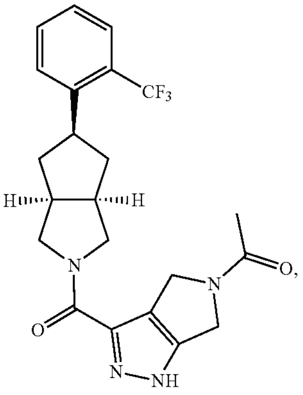
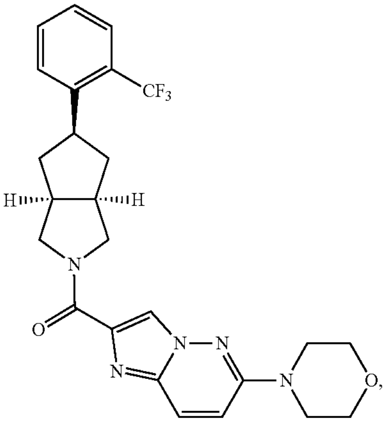
-continued
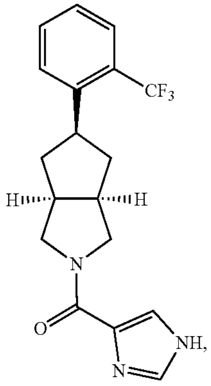
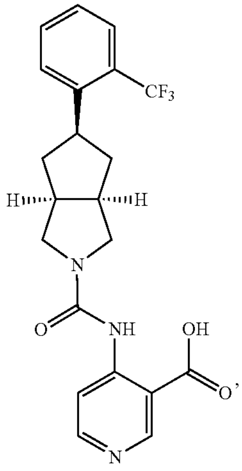
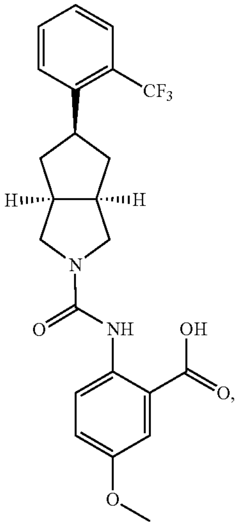
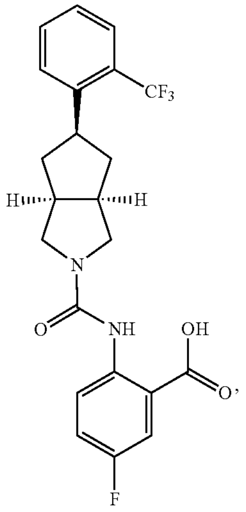
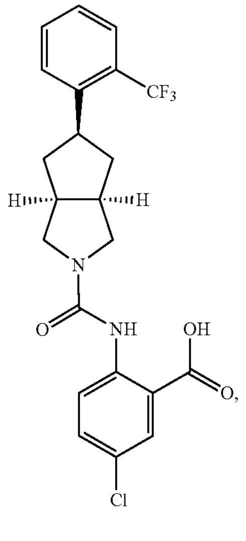
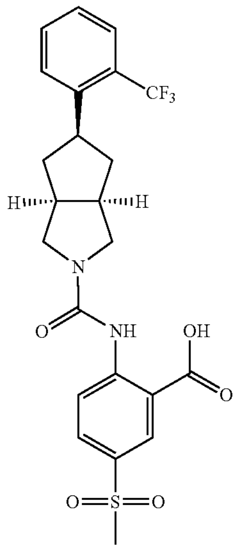
, -continued
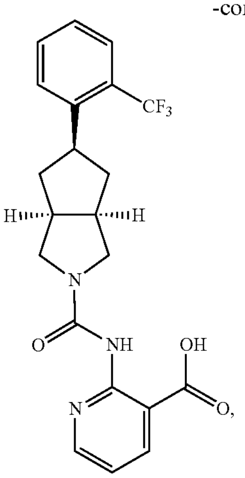
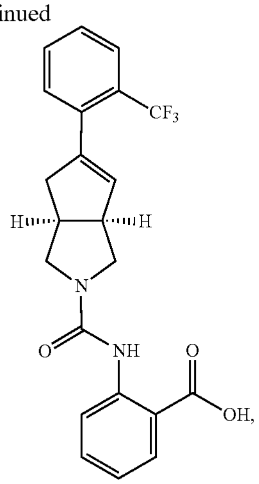
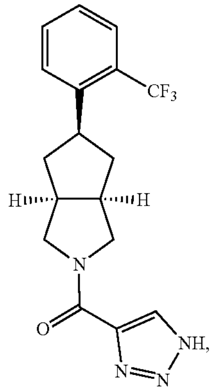
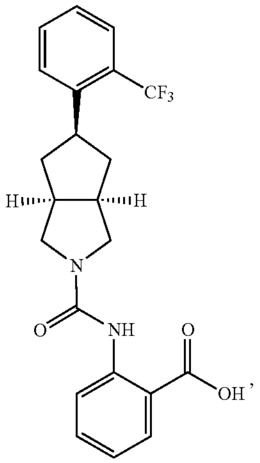
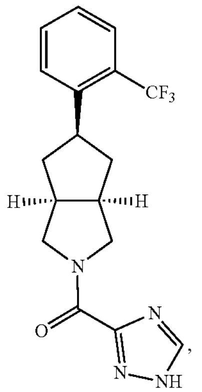
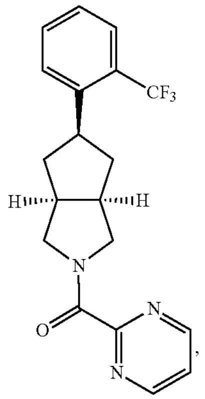
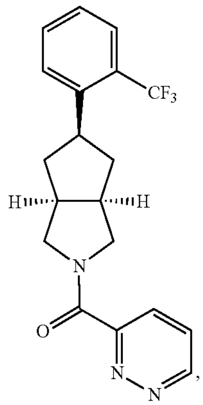
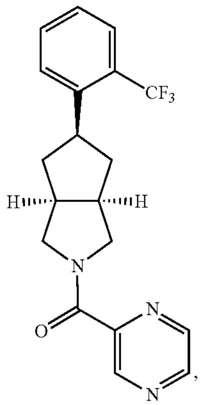
-continued
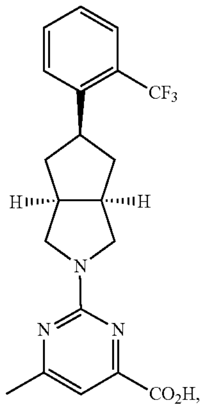
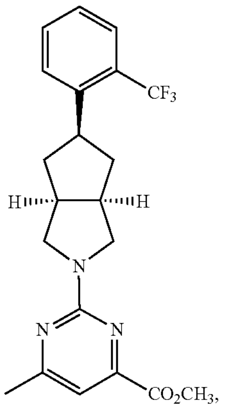
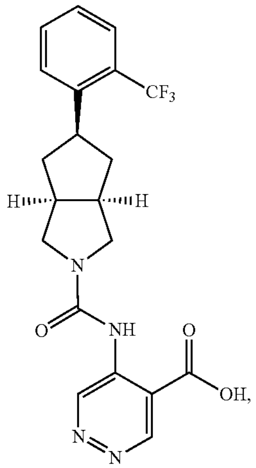
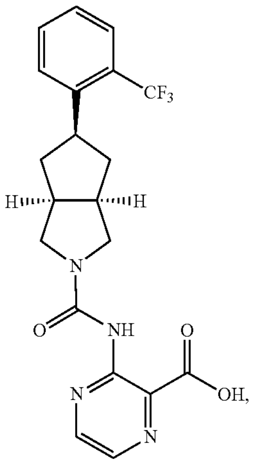
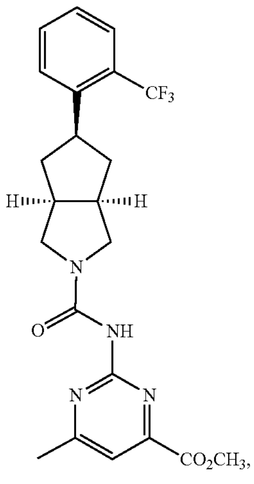
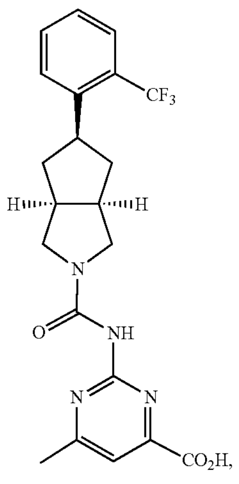

-continued
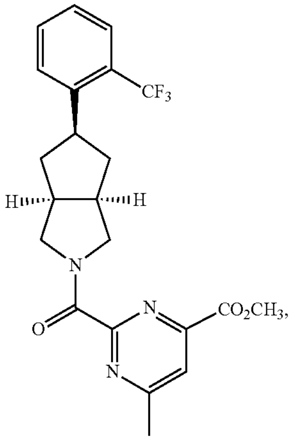
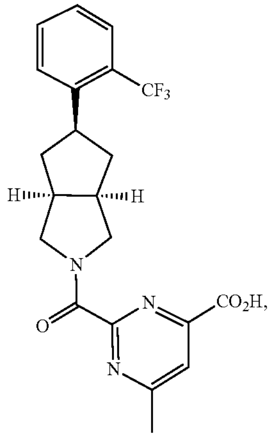
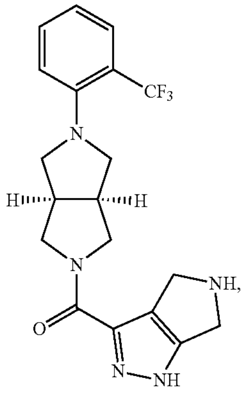
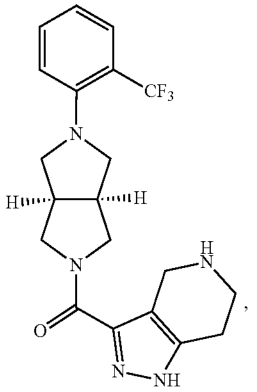
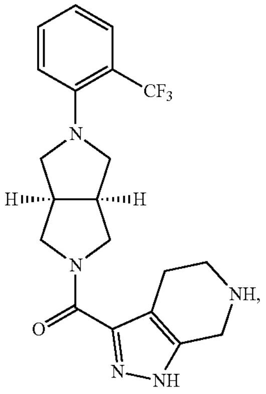
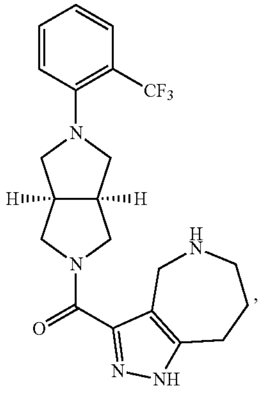
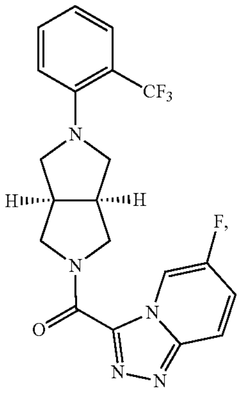
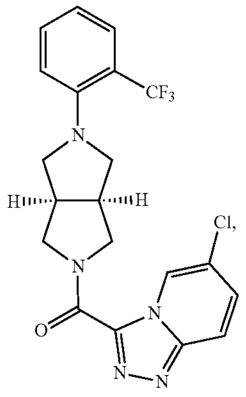
-continued
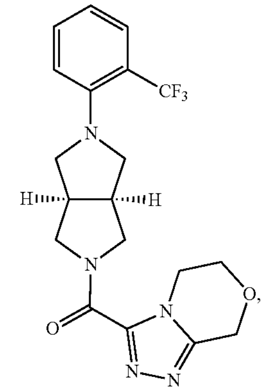
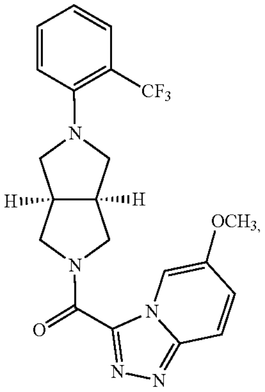
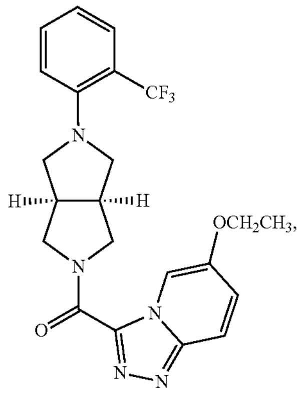
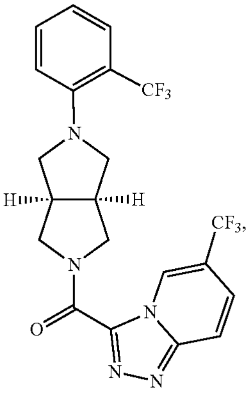
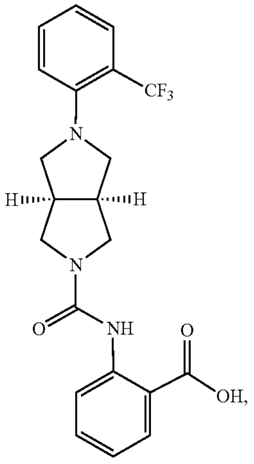
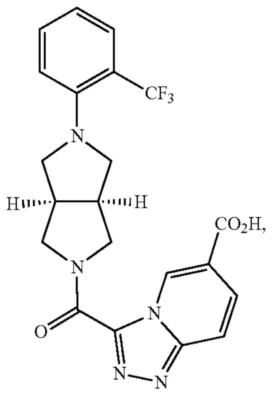

-continued
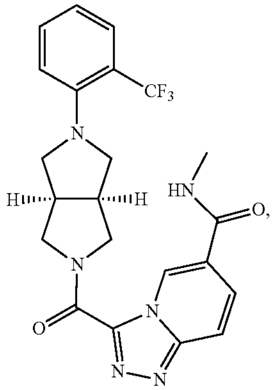
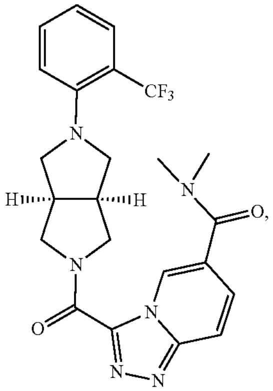
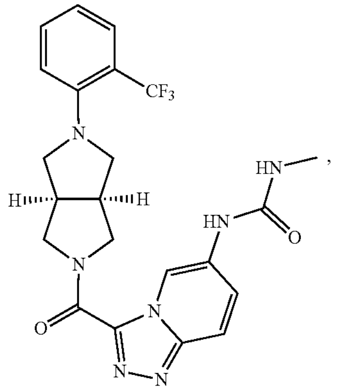
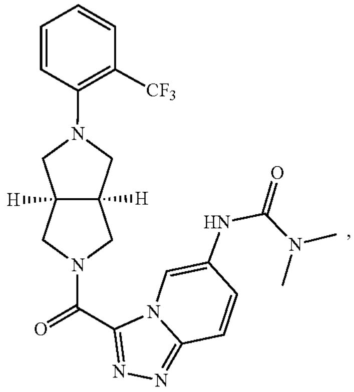
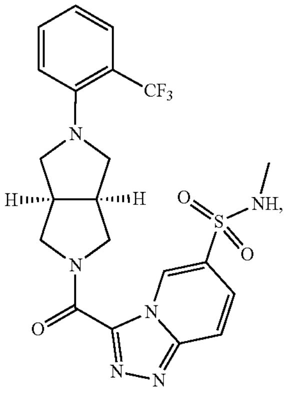
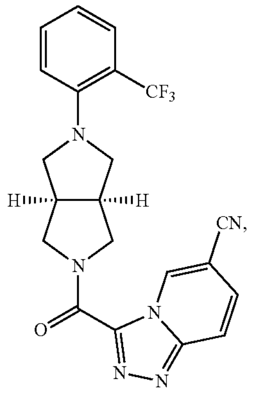
-continued
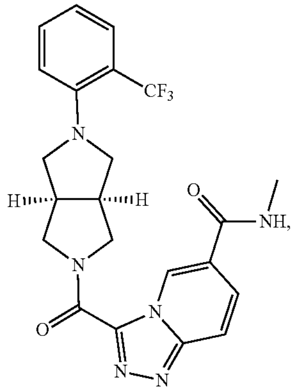
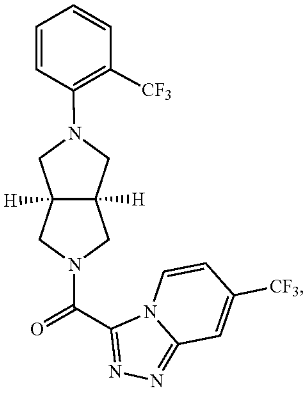
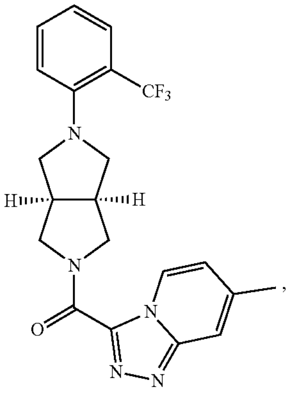
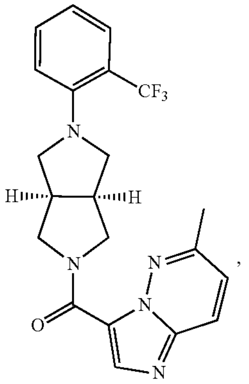
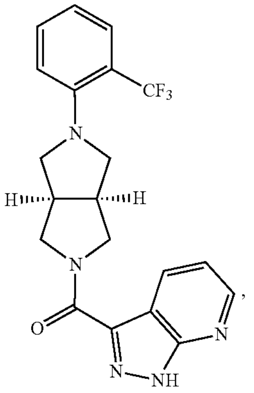
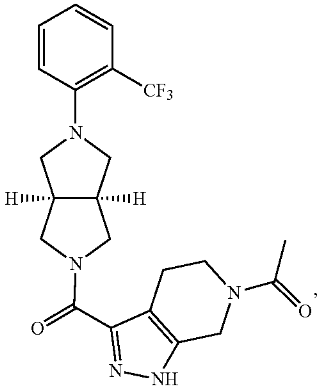

-continued
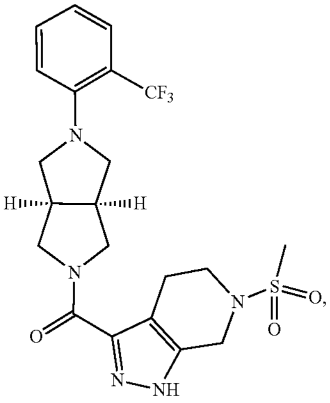
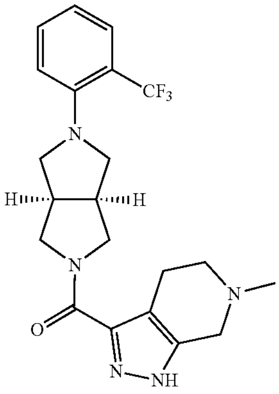
,
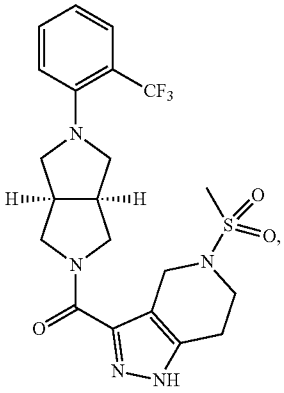
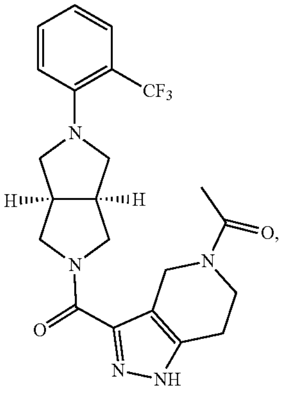
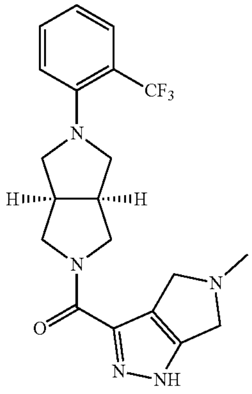
,
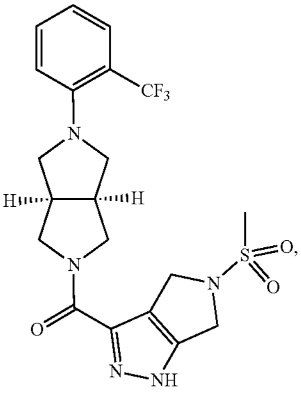
-continued
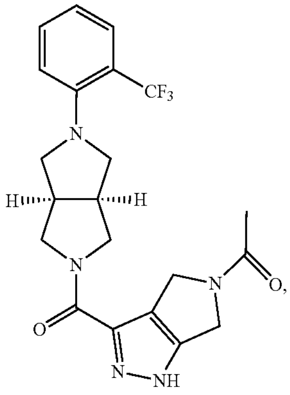
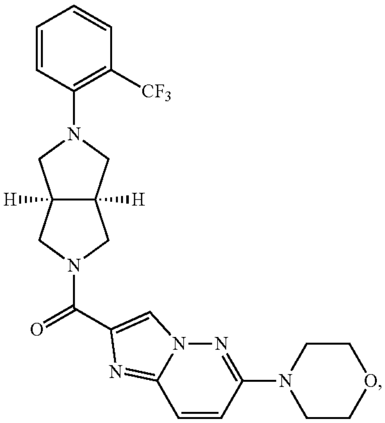
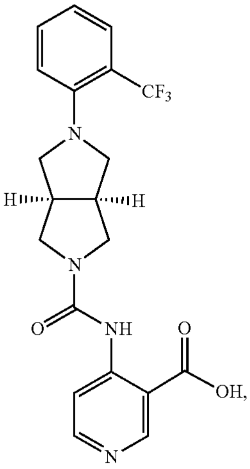
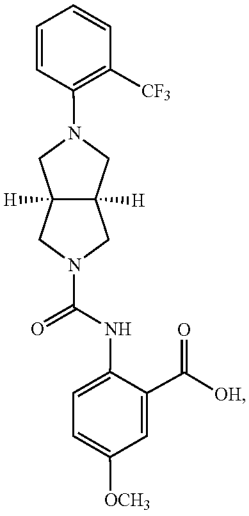

-continued
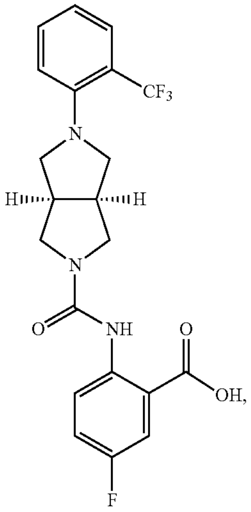
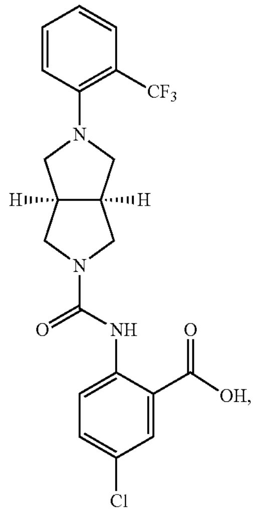
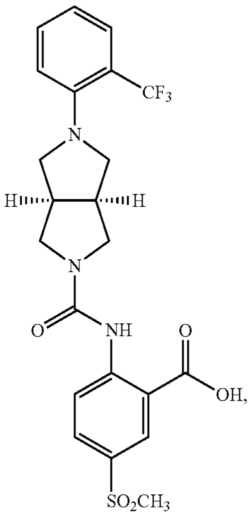
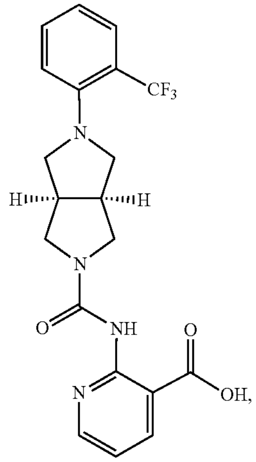
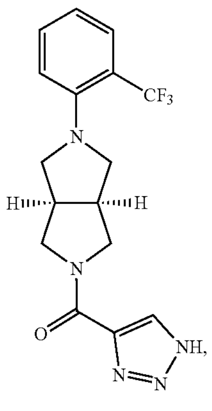
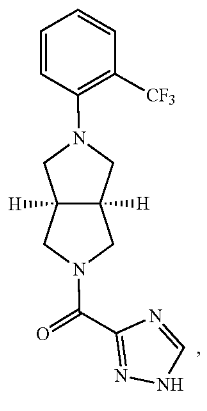
-continued
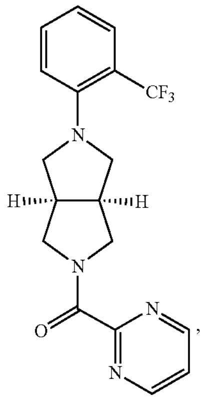
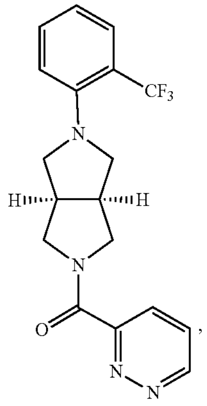
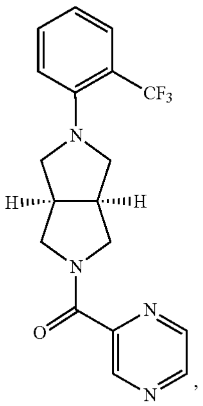
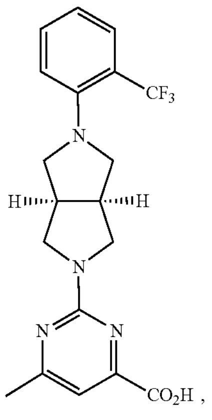
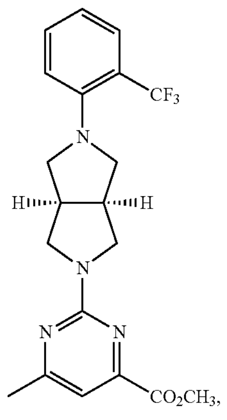
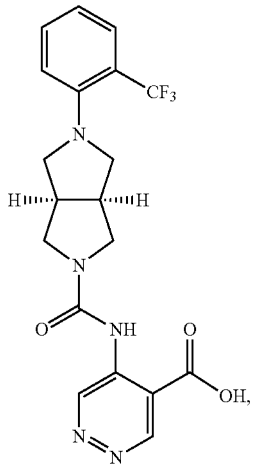

-continued
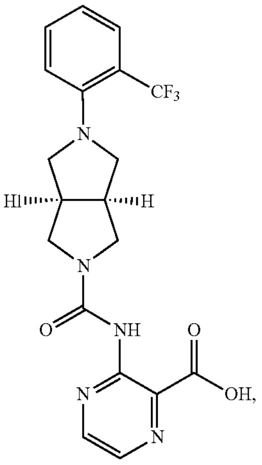
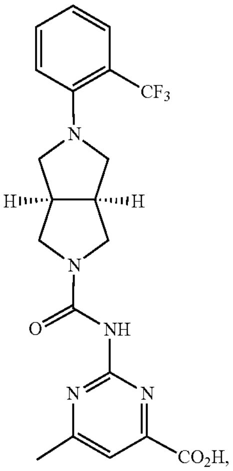
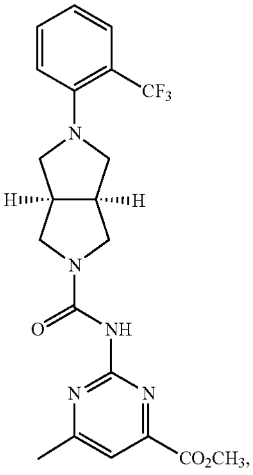
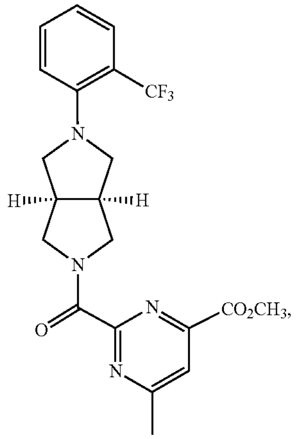
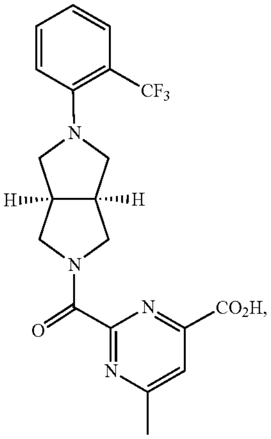
-continued
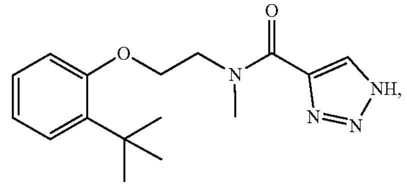
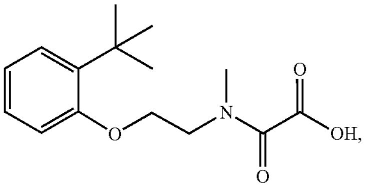
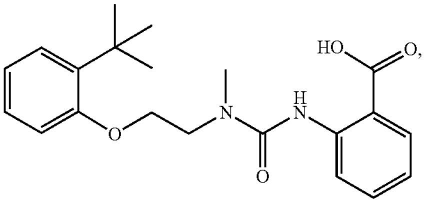
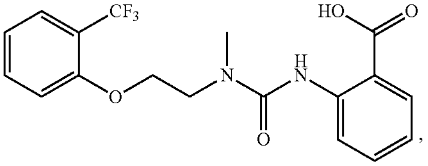
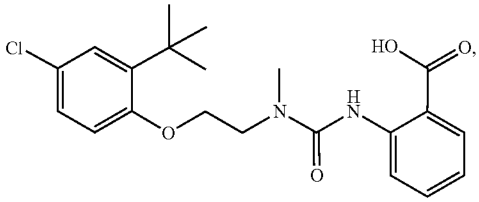
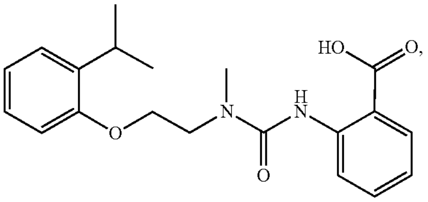
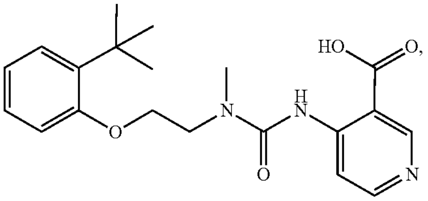
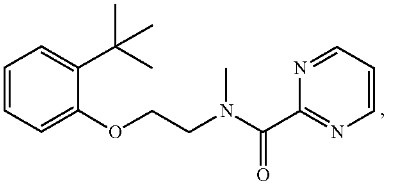
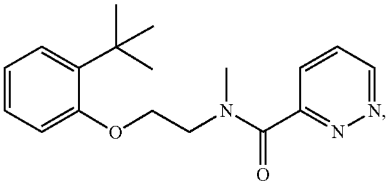

-continued
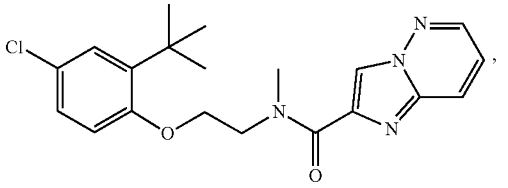
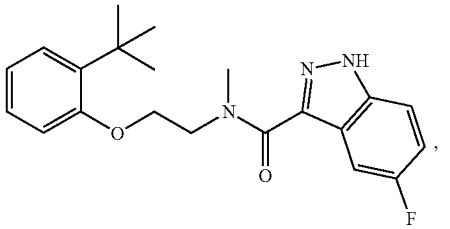
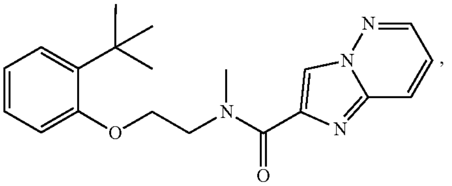
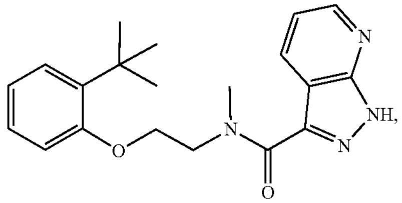
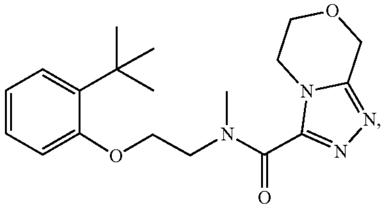
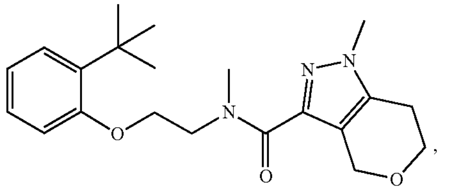
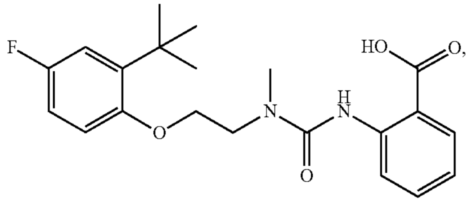
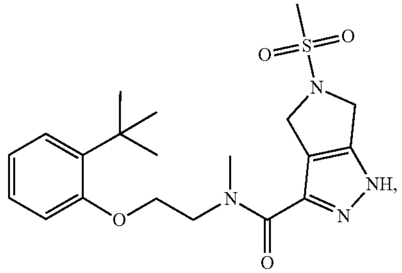
-continued
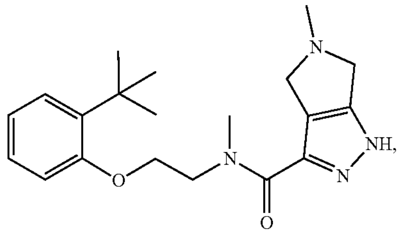
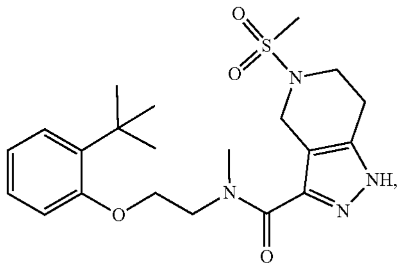
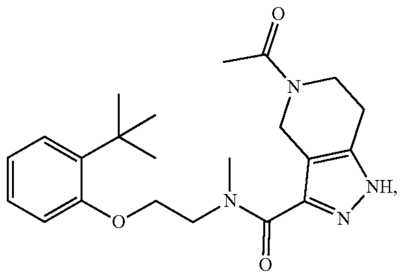
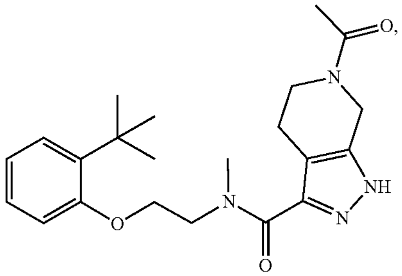
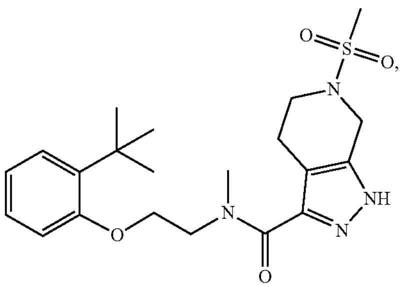
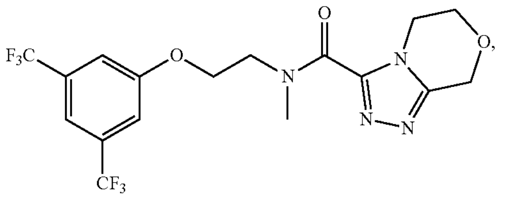

-continued
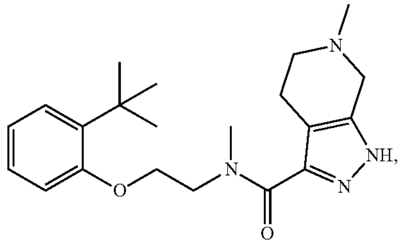
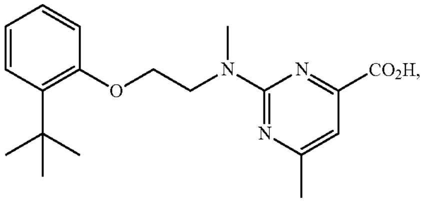
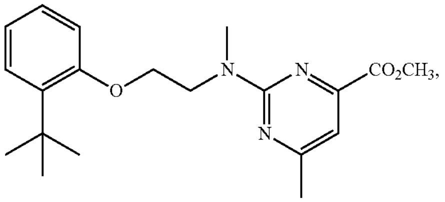
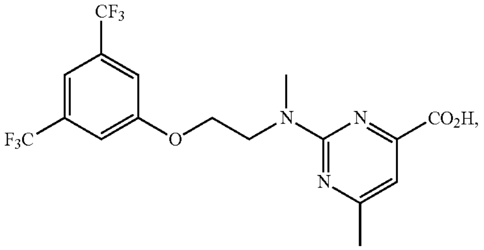
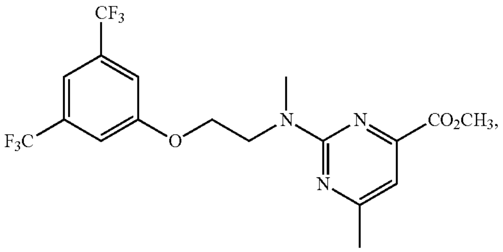
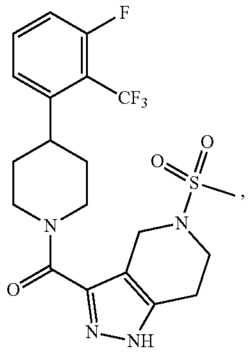
-continued
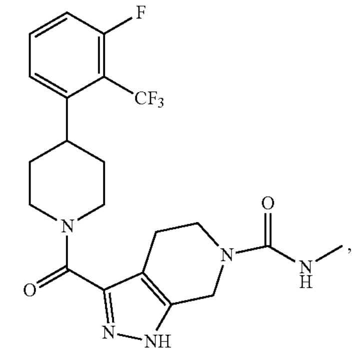
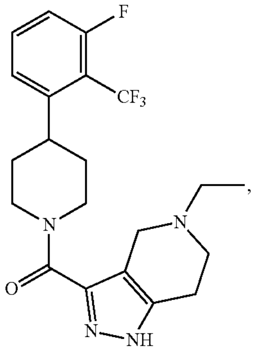
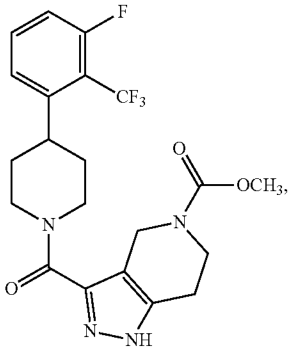
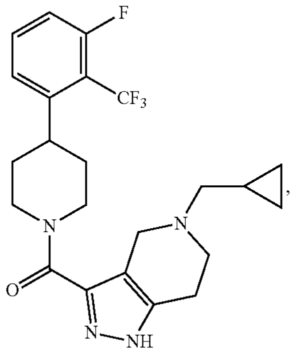
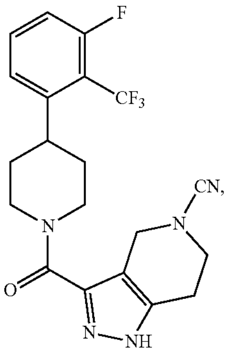
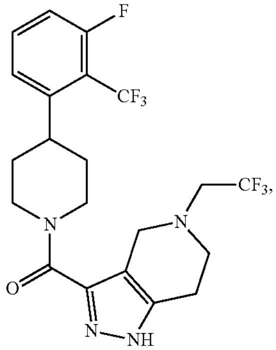

-continued
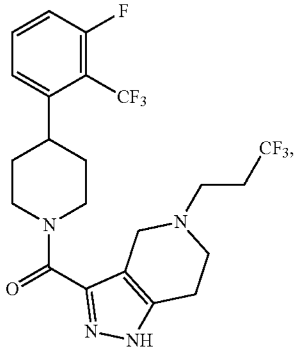
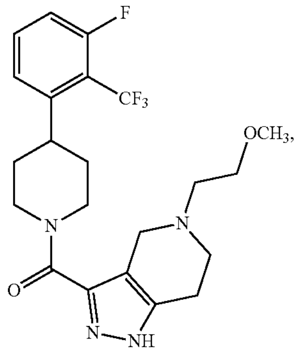
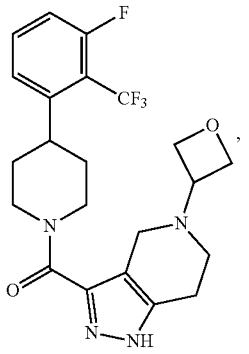
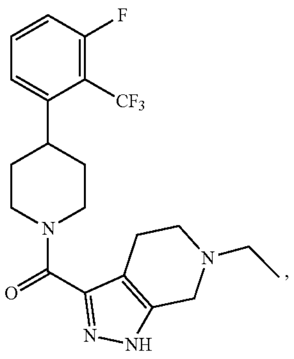
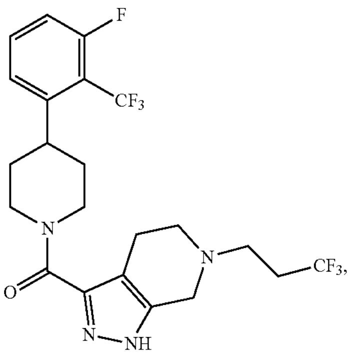
-continued
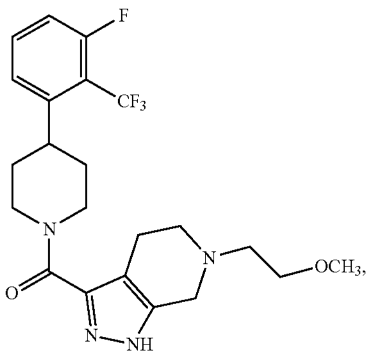
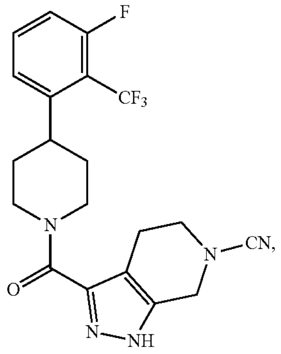
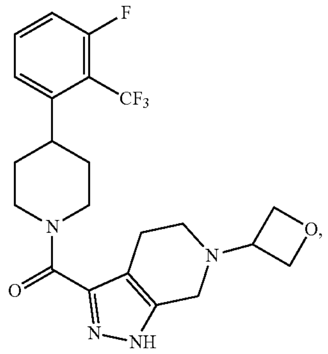
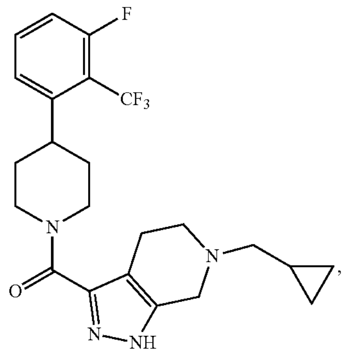

-continued
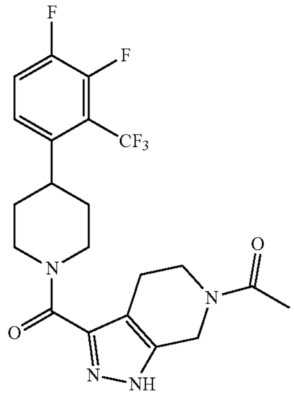
,
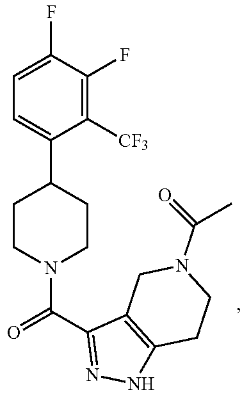
,
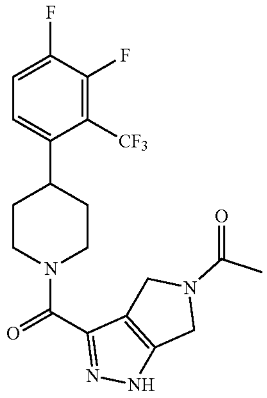
,
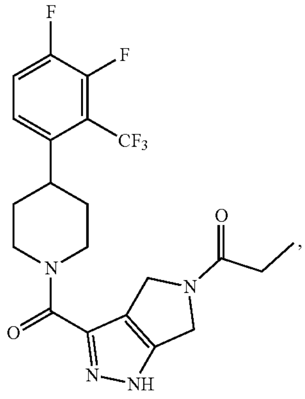
,
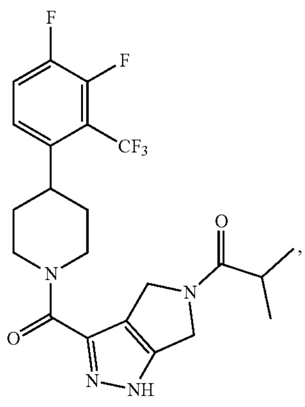
,
-continued
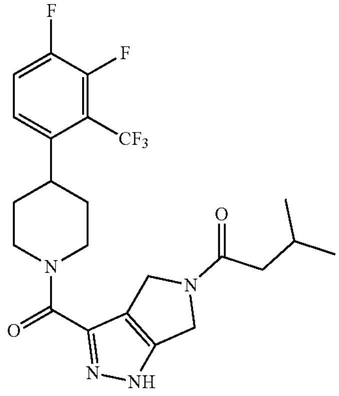
,
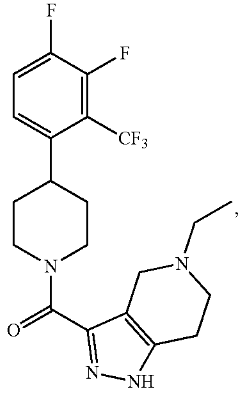
,
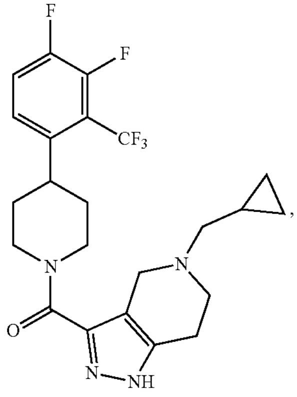
,
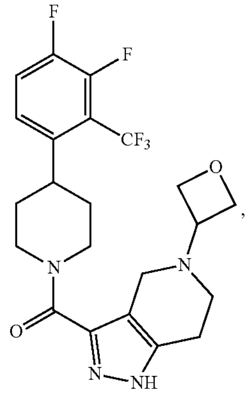
,
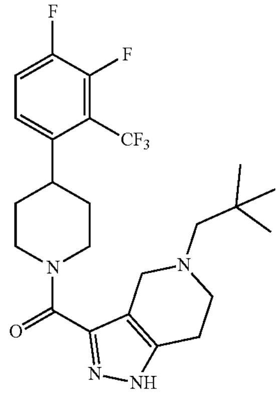
,
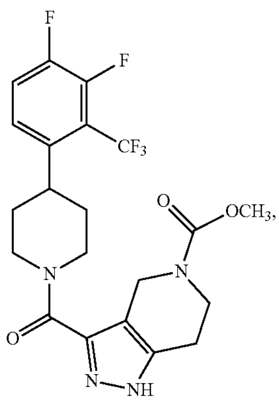
, -continued
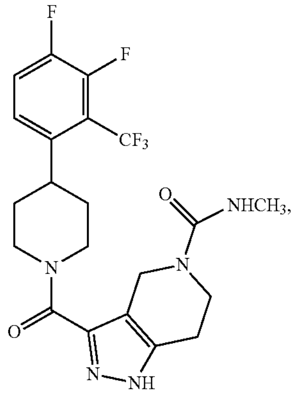
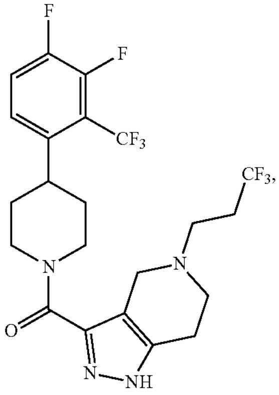
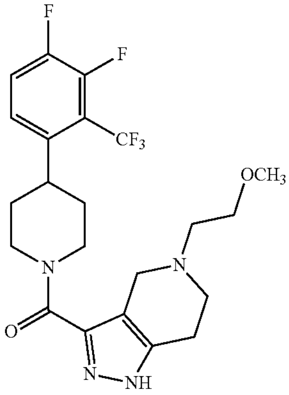
,
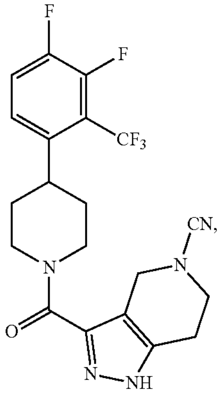
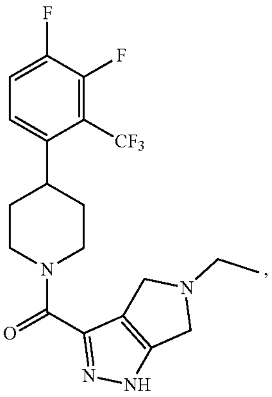
-continued
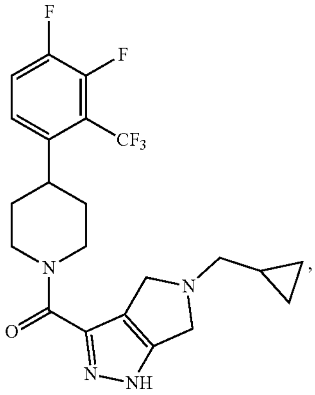
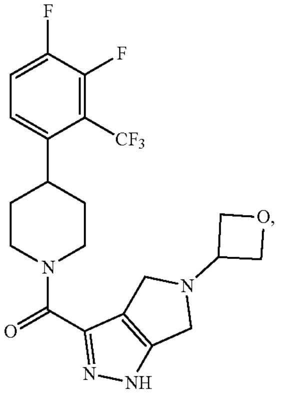
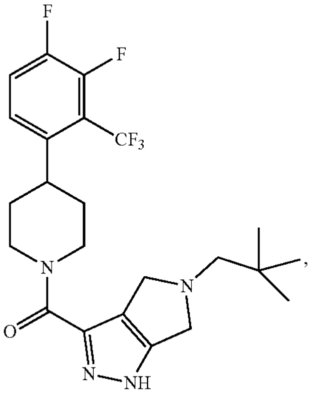
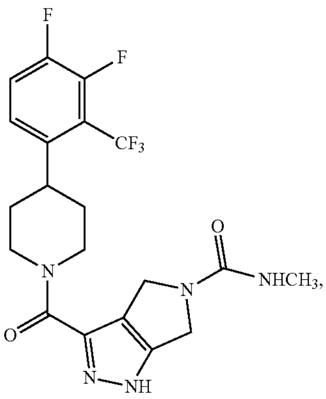

-continued
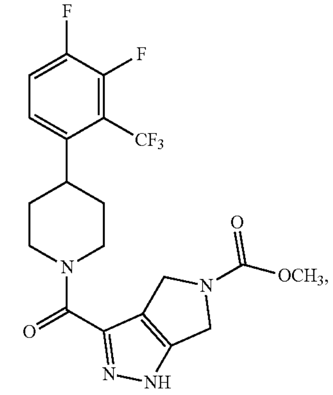
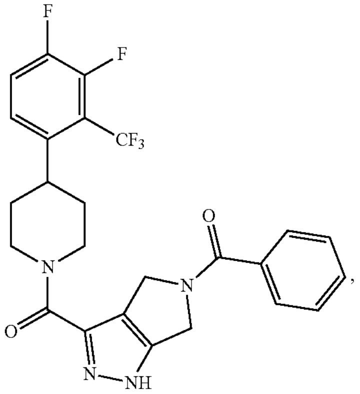
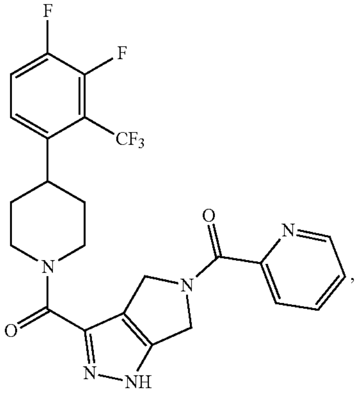
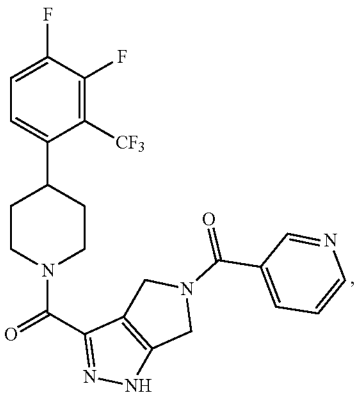
-continued
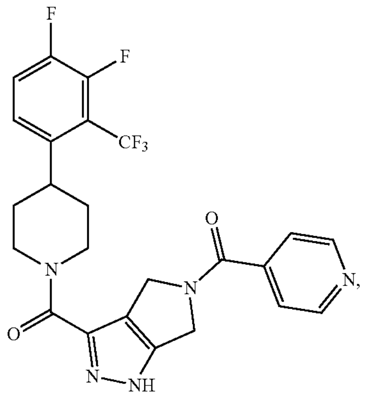
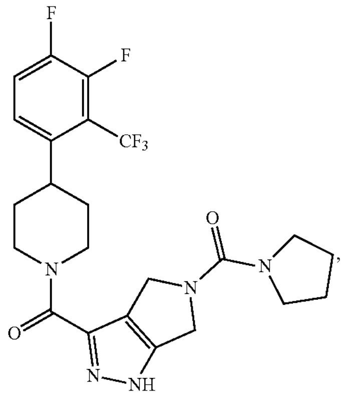
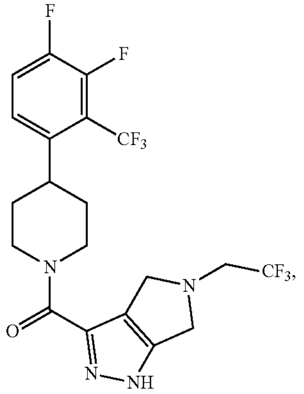
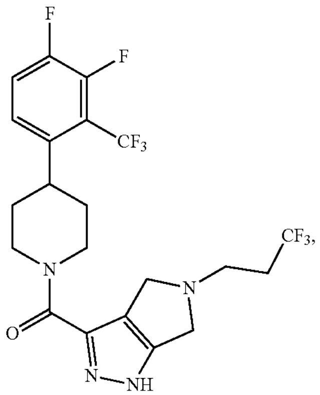

-continued
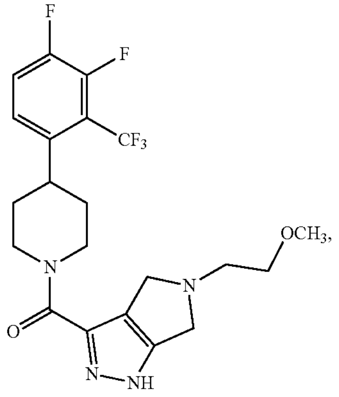
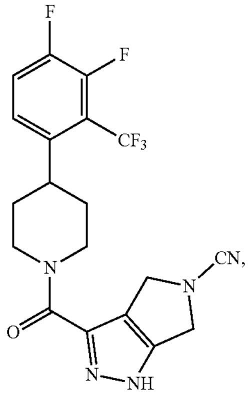
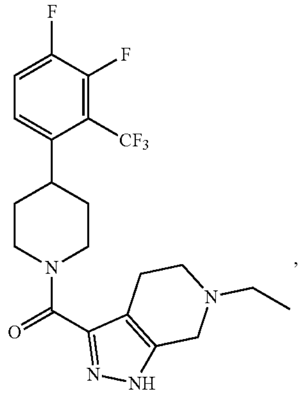
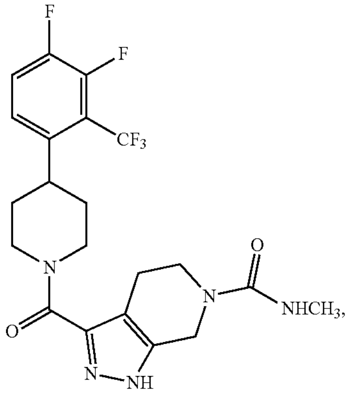
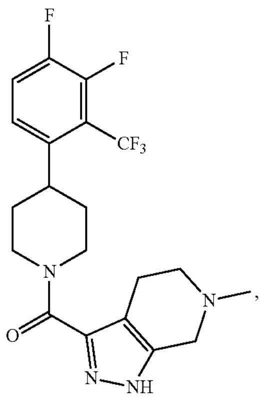
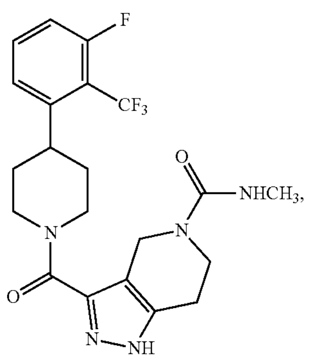
-continued
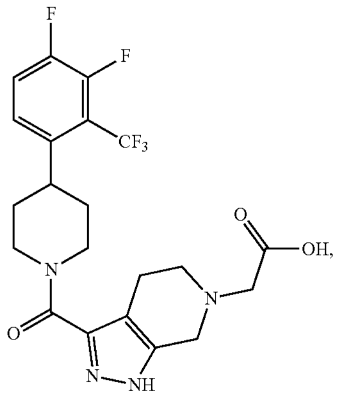
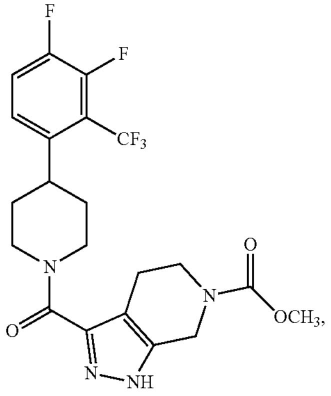
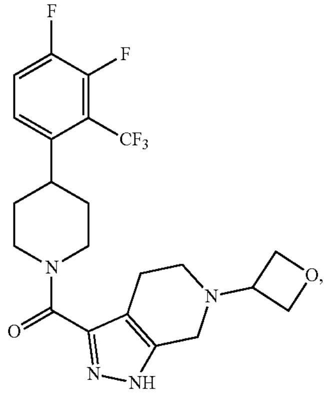
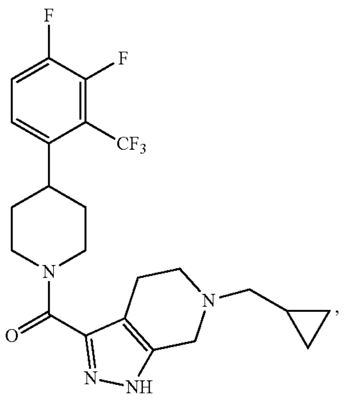

-continued
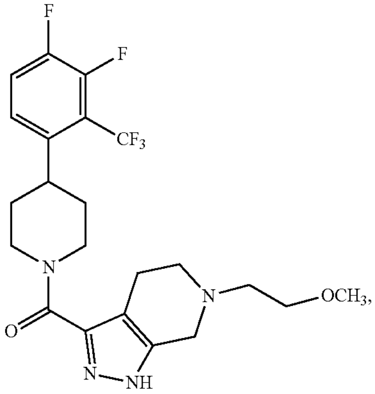
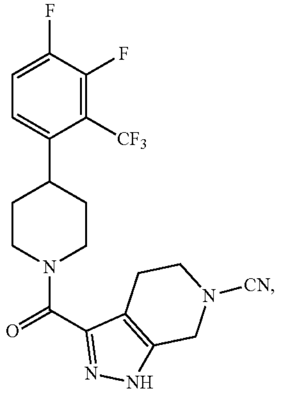
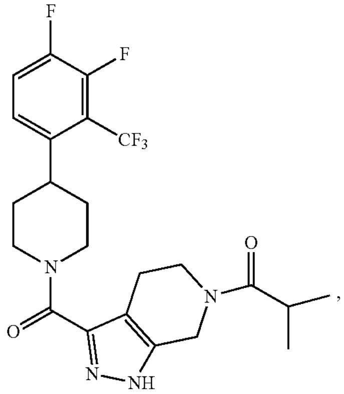
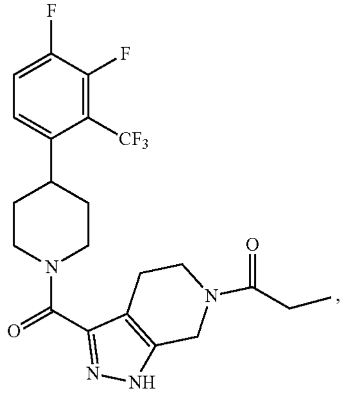
-continued
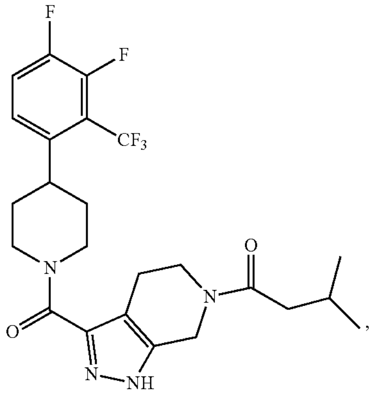
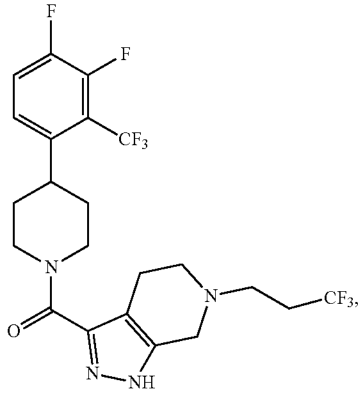
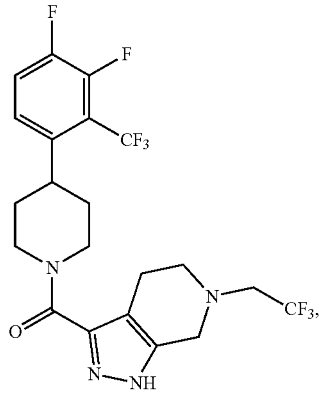
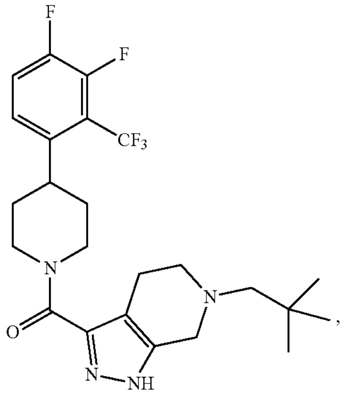

-continued
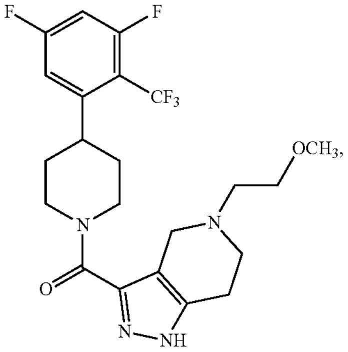
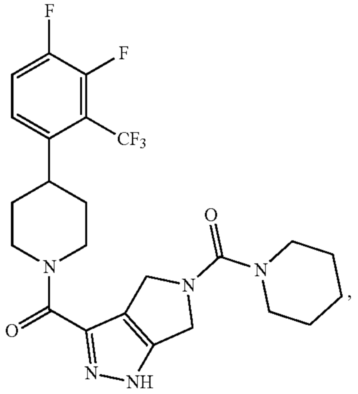
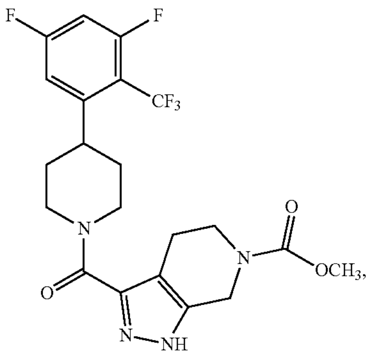
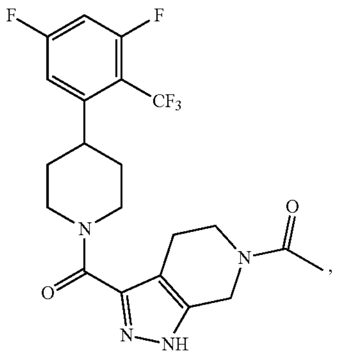
-continued
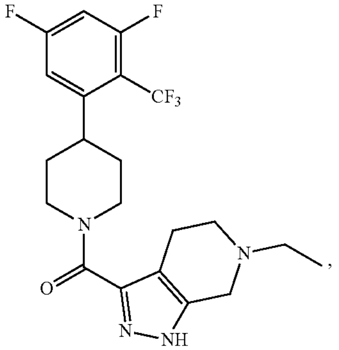
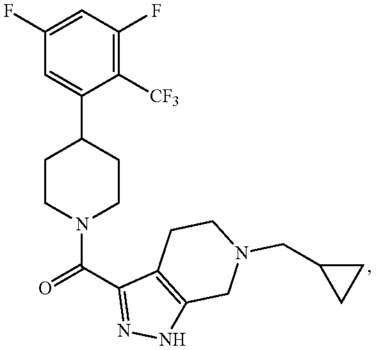
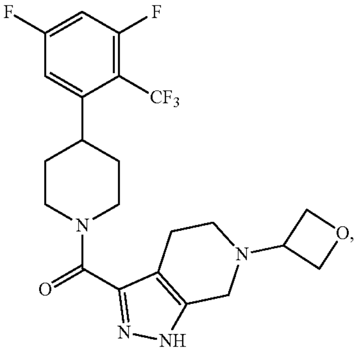
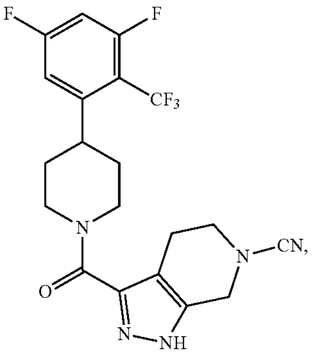

-continued
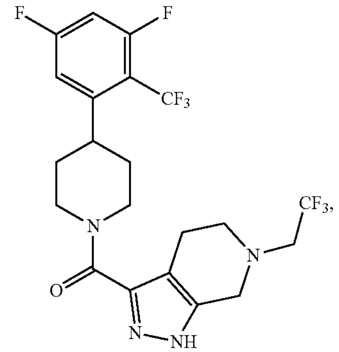
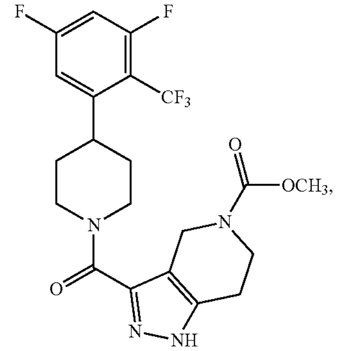
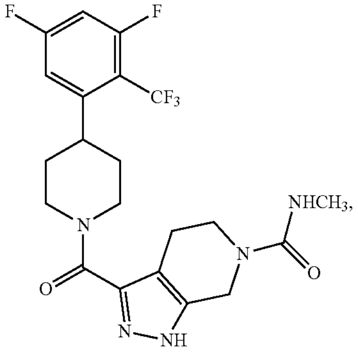
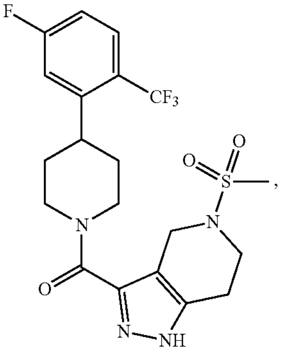
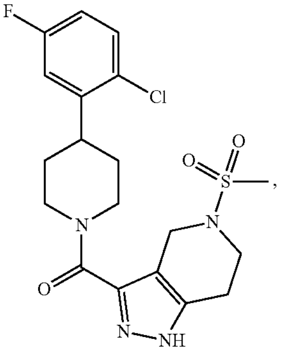
-continued
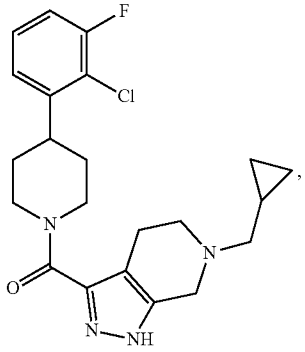
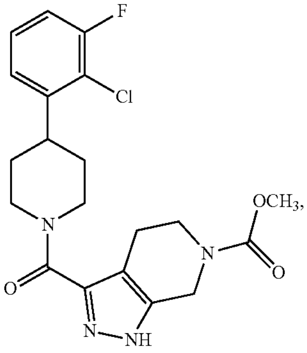
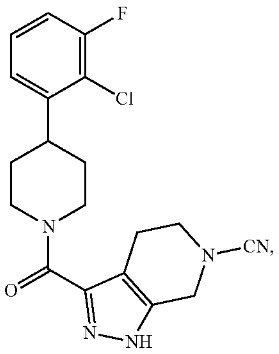
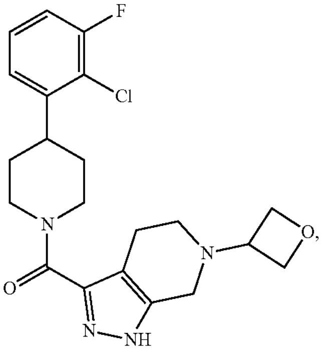

-continued
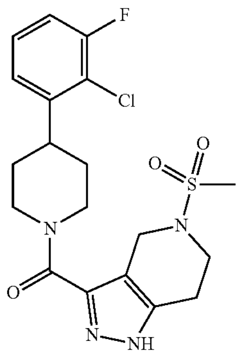,
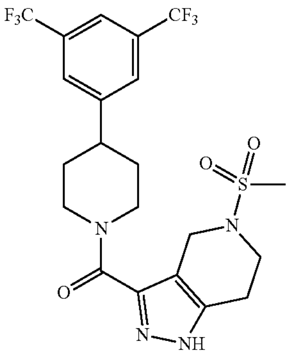,
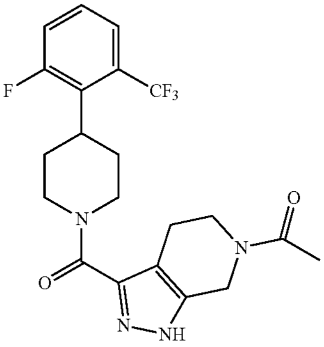,
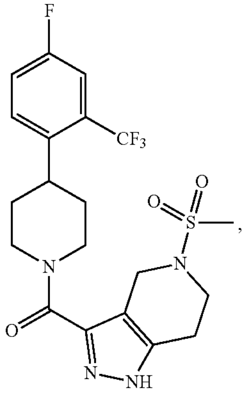,
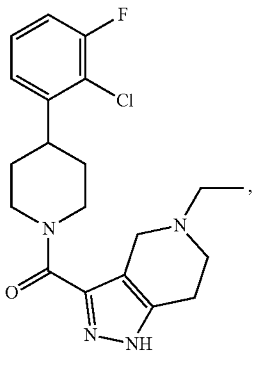,
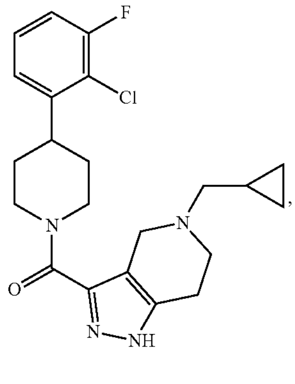,
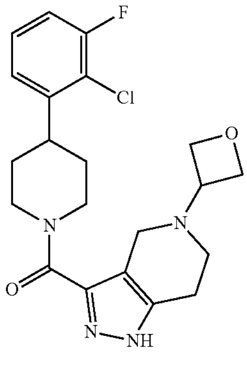,
-continued
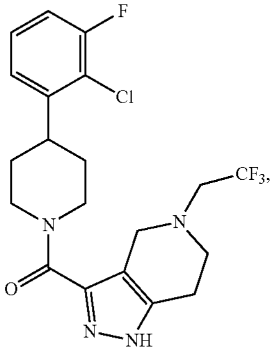,
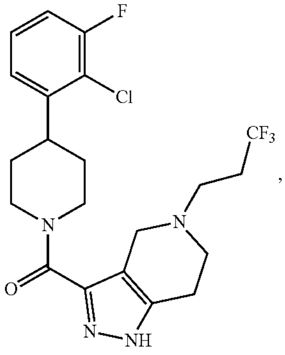,
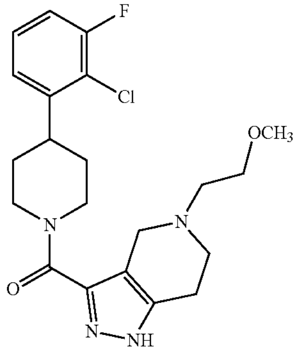,
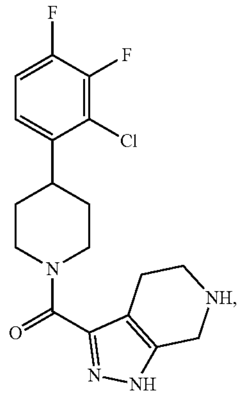,
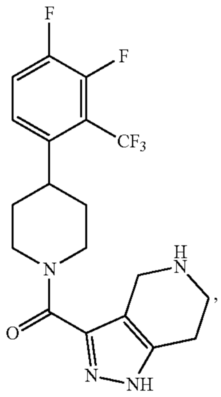,
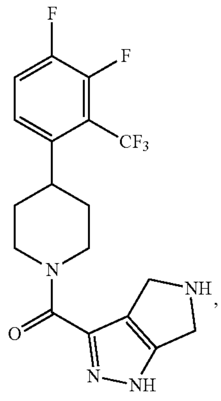,
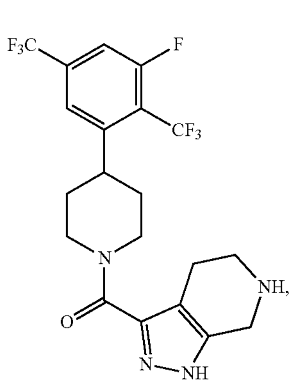, -continued
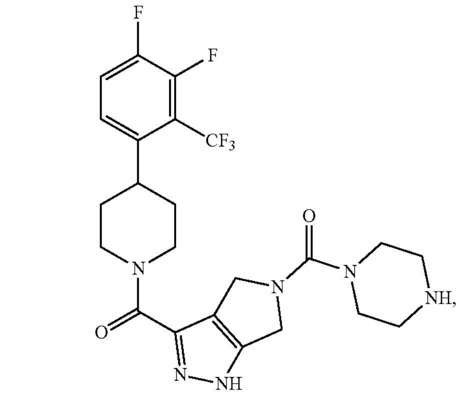
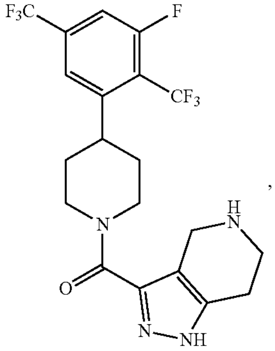
,
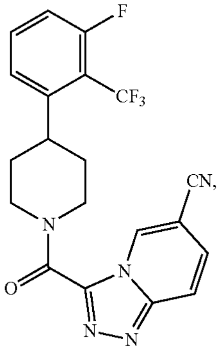
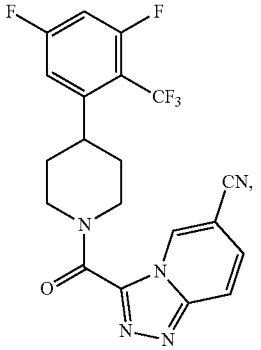
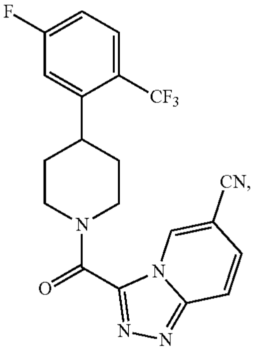
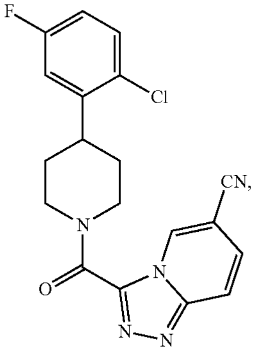
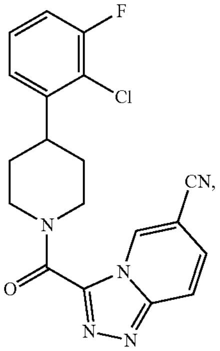
-continued
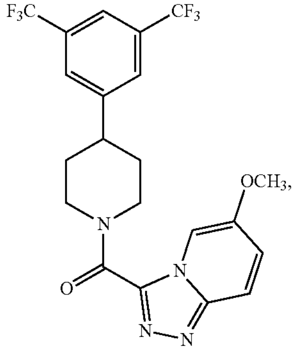
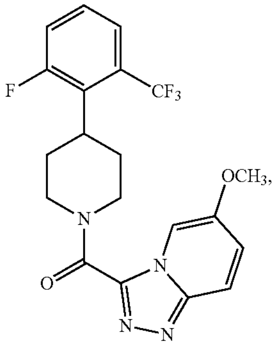
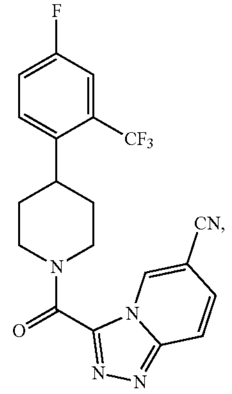
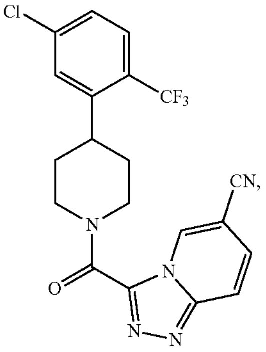
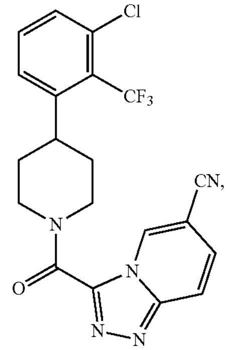
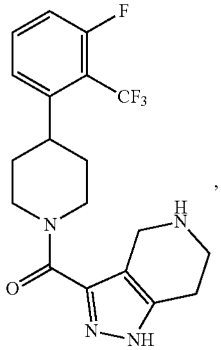
,
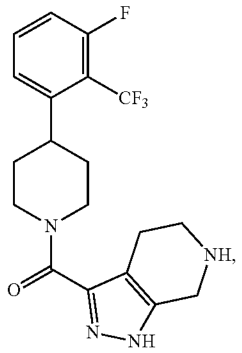
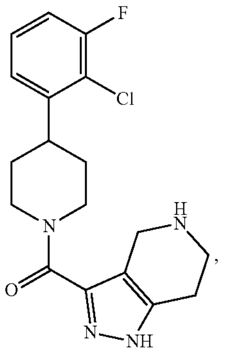

-continued
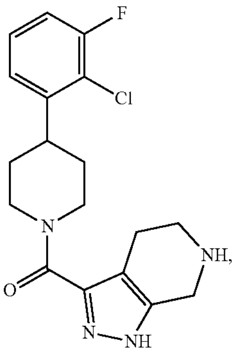
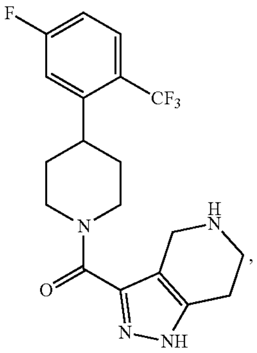
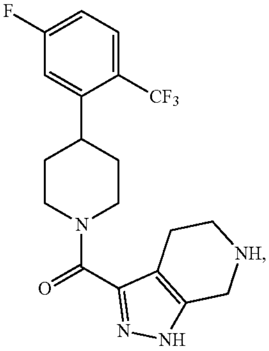
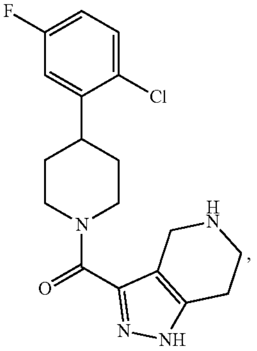
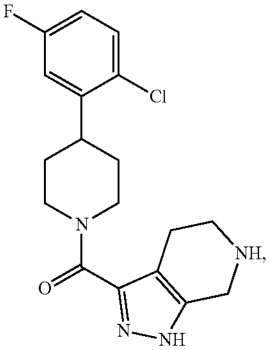
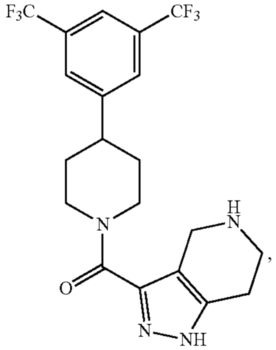
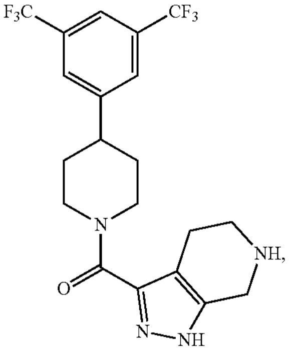
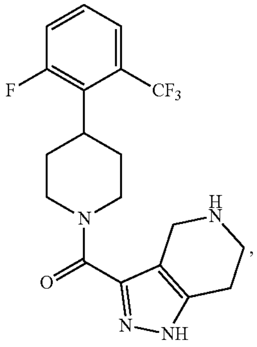
-continued
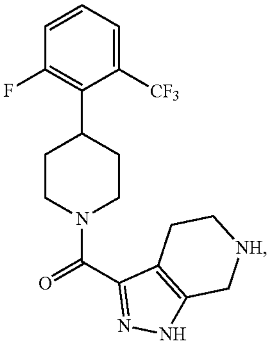
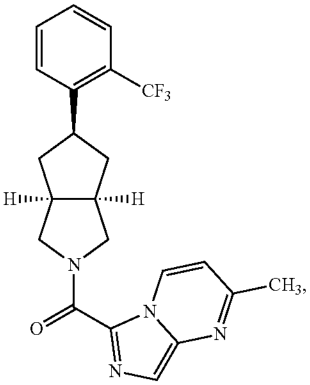
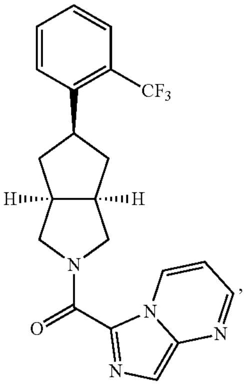
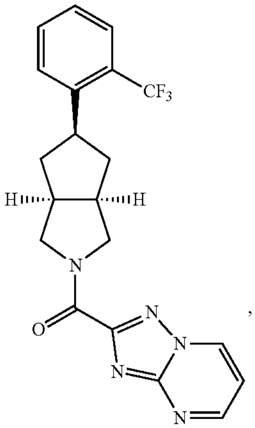
,
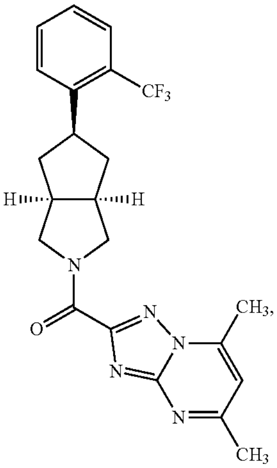
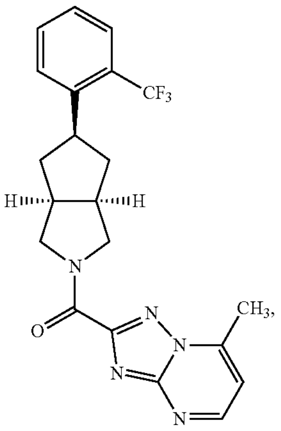

-continued
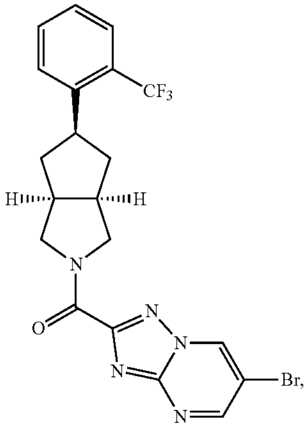
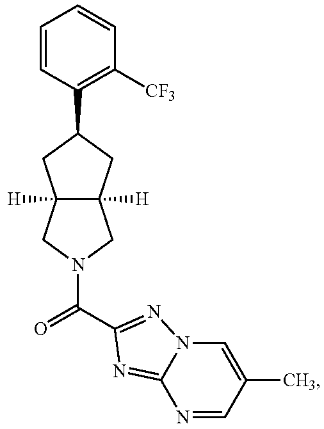
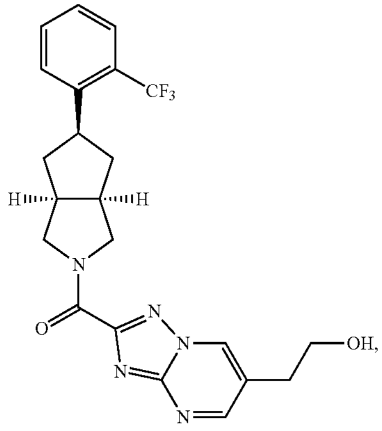
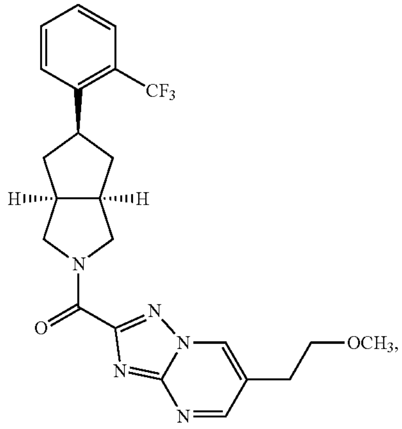
-continued
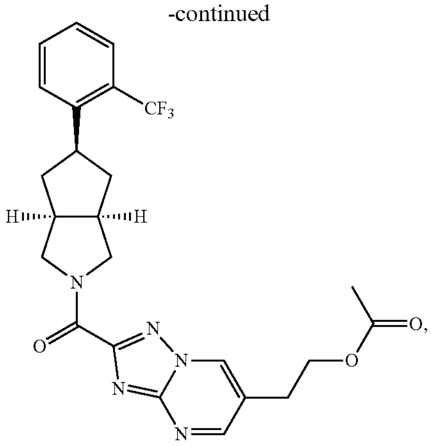
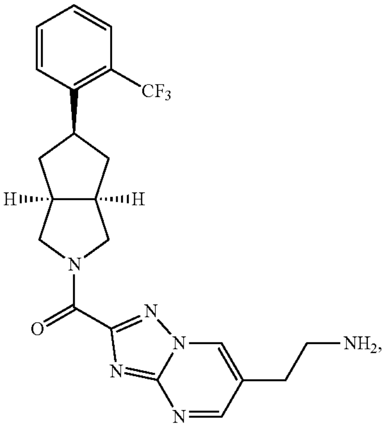
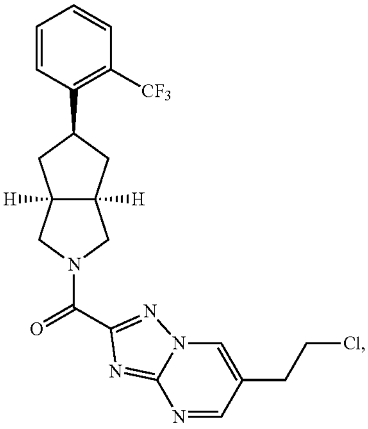
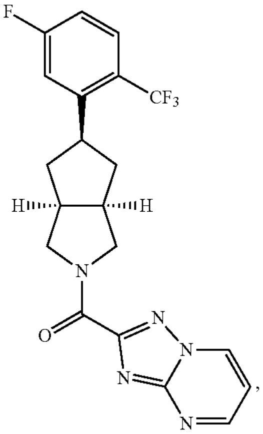

-continued
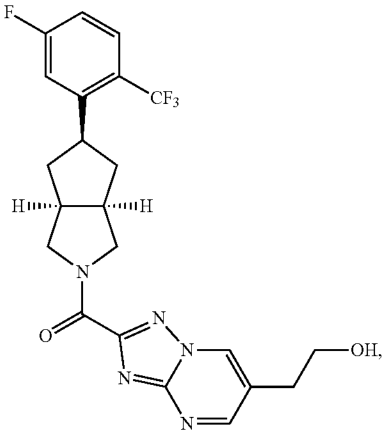
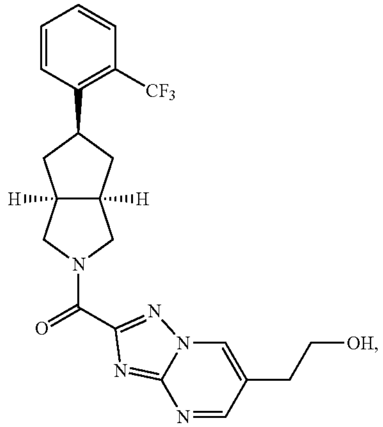
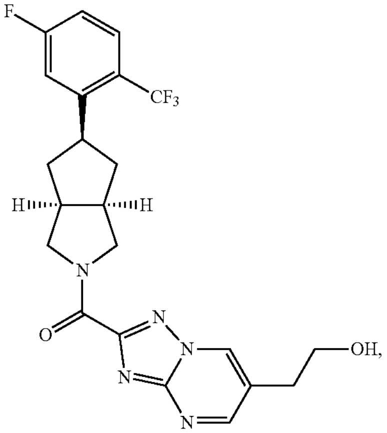
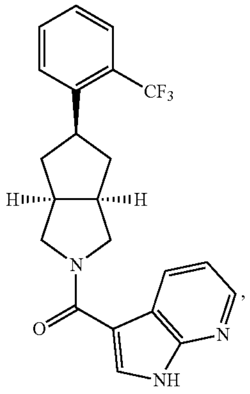
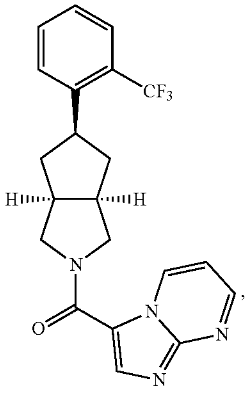
-continued
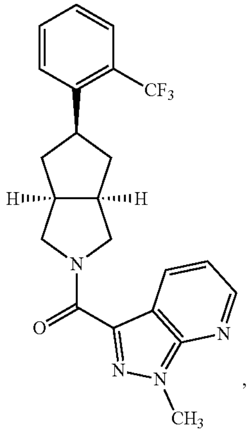
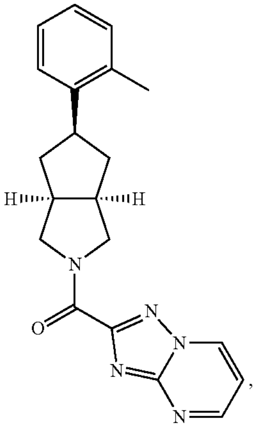
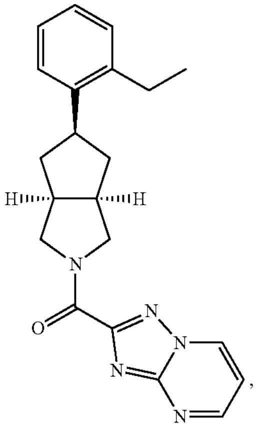
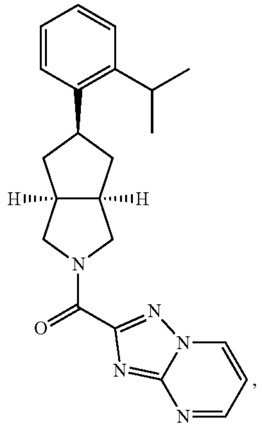
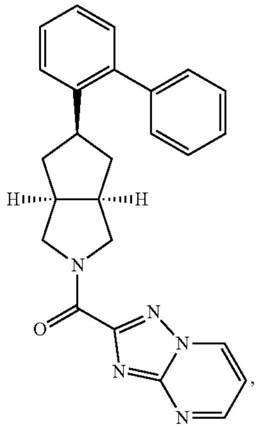
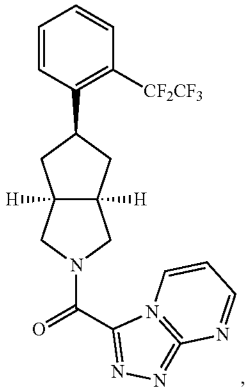
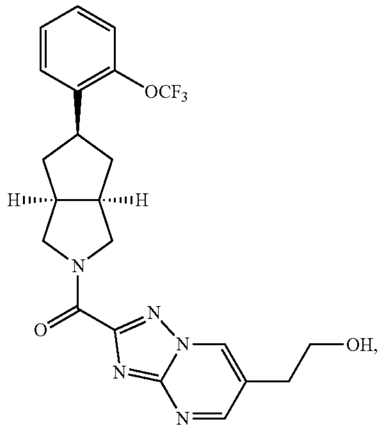

-continued
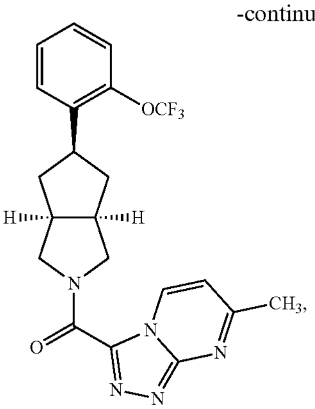
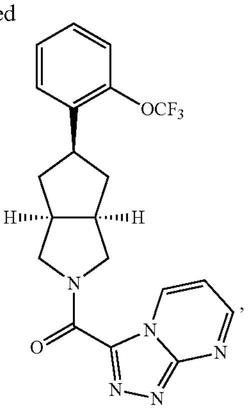
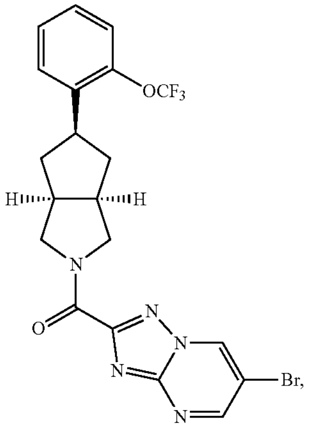
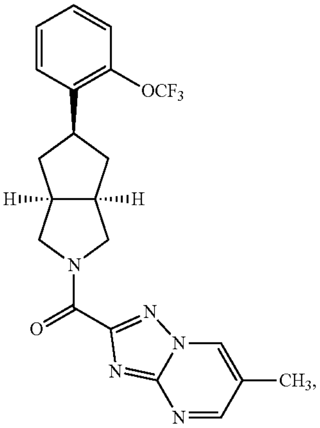
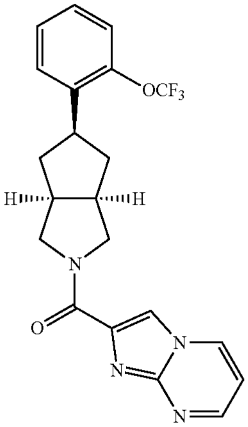
,
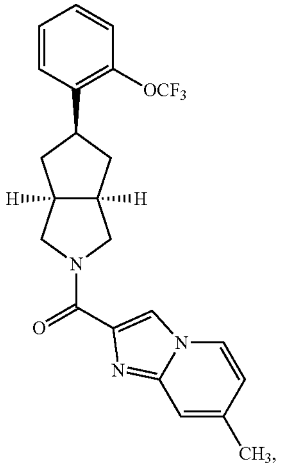
-continued
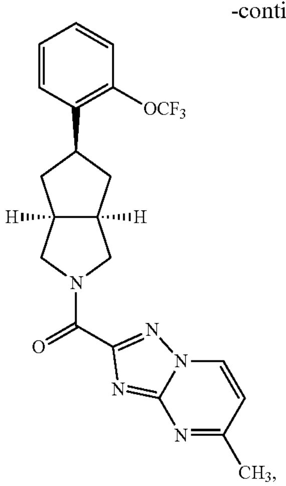
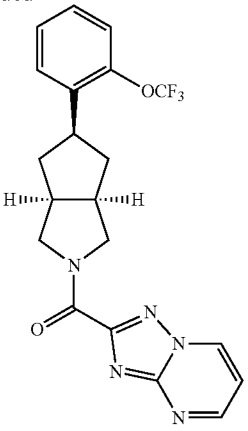
,
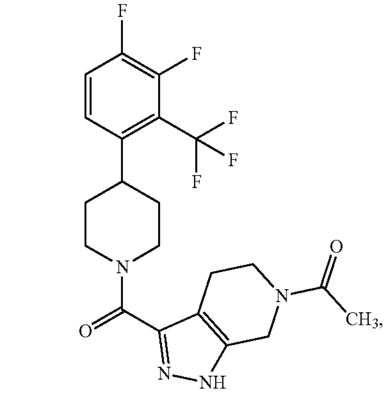
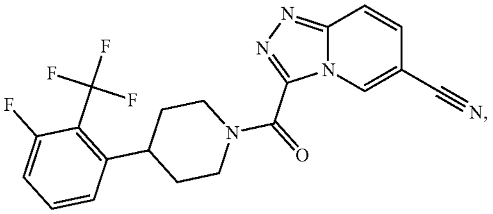
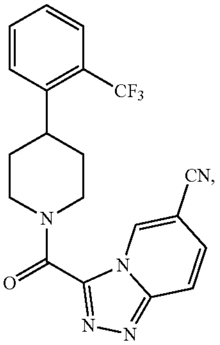
or
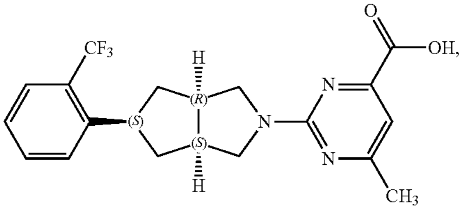
or a pharmaceutically acceptable salt thereof.
12. The method of claim 1, wherein the amount of the compound administered to the subject is 5-1000 mg, 5-800 mg, 5-200 mg, 45-200 mg, 45-1000 mg, 45-800 mg, 10-50 mg, 96 mg, 24 mg or 10 mg per day.

13. The method of claim 1, wherein the method further comprises administering an amount of a second agent which is (R)-(+)-(5,6-dichloro 2,3,9,9a-tetrahydro 3-oxo-9a-propyl-1H-fluoren-7-yl)oxy]acetic acid (DPOFA), a Nonsteroidal Anti-inflammatory Drug (NSAID, indomethacin, colchicine, lesinurad, corticosteroids, betamethasone, prednisone, dexamethasone, cortisone, cortisone, hydrocortisone, methylprednisone, prednisolone, biologic anti-IL-1alpha/beta agents, canakinumab, rilonacept, anakinra, allopurinol, benzbromarone, forms of uricase enzymes, pegloticase, topiroxostat (FYX-051), ulodesine (BCX4208), KUX-1151, RLBN1001, RDEA3170, arhalofenate (MBX-102), levotofisopam, UR-1102, PF-06743649, BCX4208, SHR4640, Lumiracoxib, Tranilast, Topiroxostat, LC350189, Bucillamine, AC-201, HuZhen Capsules, MPC-004, FYU-981, Sodium Bicarbonate, SEL-212, SEL-037, Apremilast, TMX-67, SSS11, D-0120, febuxostat or probenecid, or esters or salts thereof effective to treat the subject, thereby treating the subject.

14. The method of claim 1, wherein the subject is afflicted with gout; or wherein the subject is afflicted with chronic gout or acute gout.

15. The method of claim 14, wherein the amount of the compound is effective in reducing uric acid levels to 3.4-7.0 mg/dL in the blood of the subject.

16. The method of claim 1, wherein in the compound,

L is a linking group having the structure:

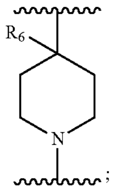

Z is a group having the structure:

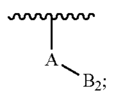

A is

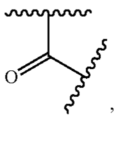 [SMILES: *C(*)=O]

and $B_2$ is

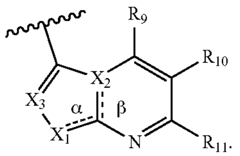

17. The method of claim 1, wherein in the compound, L is

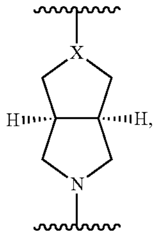

Z is

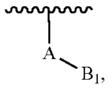

and A is absent.

18. The method of claim 1, wherein in the compound, L is,

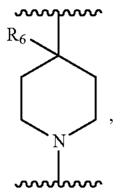

Z is

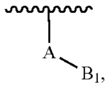

$R_6$ is H, and A is

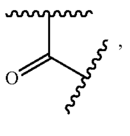 [SMILES: *C(*)=O ; ","]

19. The method of claim 1, wherein the compound is

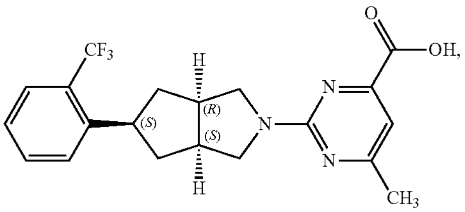

or a pharmaceutically acceptable salt thereof.

20. The method of claim 1, wherein the compound is

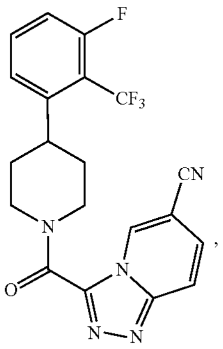 [SMILES: N#Cc1ccc2nnc(C(=O)N3CCC(c4cccc(F)c4C(F)(F)F)CC3)n2c1 ; ","]

or a pharmaceutically acceptable salt thereof.

21. The method of claim 1, wherein the compound is

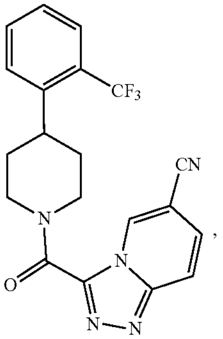 [SMILES: N#Cc1ccc2nnc(C(=O)N3CCC(c4ccccc4C(F)(F)F)CC3)n2c1 ; ","]

or a pharmaceutically acceptable salt thereof.

22. The method of claim 1, wherein the compound is

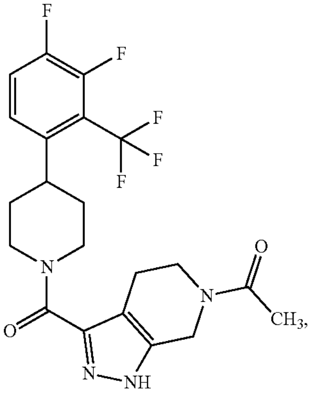 [SMILES: CC(=O)N1CCc2c(C(=O)N3CCC(c4ccc(F)c(F)c4C(F)(F)F)CC3)n[nH]c2C1]

or a pharmaceutically acceptable salt thereof.

* * * * *